United States Patent
Mortlock et al.

(10) Patent No.: US 7,235,559 B1
(45) Date of Patent: Jun. 26, 2007

(54) THERAPEUTIC QUINAZOLINE DERIVATIVES

(75) Inventors: Andrew Austen Mortlock, Macclesfield (GB); Nicholas John Keen, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 98 days.

(21) Appl. No.: 10/088,856

(22) PCT Filed: Sep. 19, 2000

(86) PCT No.: PCT/GB00/03593

§ 371 (c)(1),
(2), (4) Date: Mar. 21, 2002

(87) PCT Pub. No.: WO01/21597

PCT Pub. Date: Mar. 29, 2001

(30) Foreign Application Priority Data

Sep. 21, 1999 (GB) .................................. 9922171.5

(51) Int. Cl.
*A61P 35/00* (2006.01)
*A61K 31/517* (2006.01)
*C07D 239/94* (2006.01)
*C07D 401/12* (2006.01)
*C07D 403/12* (2006.01)

(52) U.S. Cl. .................................... 514/266.2; 544/284

(58) Field of Classification Search ........... 514/266.21, 514/266.22, 266.2; 544/284
See application file for complete search history.

(56) References Cited

U.S. PATENT DOCUMENTS 5,721,237 A * 2/1998 Myers et al. ............ 514/266.1
6,258,820 B1 * 7/2001 Uckun et al. ............ 514/266.4

FOREIGN PATENT DOCUMENTS

WO WO 95/15758 6/1995
WO WO 99/35132 7/1999

* cited by examiner

*Primary Examiner*—Brenda Coleman

(57) ABSTRACT

A compound of formula (I) or a salt, ester, amide or prodrug thereof; where X is O, or S, S(O), S(O)$_2$ or NR$^6$ where R$^6$ is hydrogen of C$_{1-6}$alkyl; R$^5$ is an optionally substituted 6-membered aromatic ring containing at least one nitrogen atom, and R$^1$, R$^2$, R$^3$, R$^4$ are independently selected from halogeno, cyano, nitro, C$_{1-3}$alkylsulphanyl, —N(OH)R$^7$— (wherein R$^7$ is hydrogen, or C$_{1-3}$alkyl), or R$^9$X$^1$— (wherein X$^1$ represents a direct bond, —O—, —CH$_2$—, —OC(O), —C(O)—, —S—, —SO—, —SO$_2$—, —NR$^{10}$C(O)—, —C(O)NR$^{11}$—, —SO$_2$NR$^{12}$—, —NR$^{13}$SO$_2$— or NR$^{14}$— (wherein R$^{10}$, R$^{11}$, R$^{12}$, R$^{13}$ and R$^{14}$ each independently represents hydrogen, C$_{1-3}$alkyl or C$_{1-3}$alkoxyC$_{2-3}$alkyl), and R$^9$ is hydrogen, optionally substituted hydrocarbyl, optionally substituted heterocyclyl or optionally substituted alkoxy; provided that at least one of R$^2$ or R$^3$ is other than hydrogen. These compounds inhibit aurora 2 kinase and are useful in the preparation of medicaments for the treatment of proliferative disease such as cancer.

14 Claims, No Drawings

THERAPEUTIC QUINAZOLINE DERIVATIVES

This application is a U.S. National Stage under 35 U.S.C § 371 of International Application No. PCT/GB00/03593 (filed Sep. 19, 2000) which claims priority under 35 U.S.C. § 119(a)–(d) to Application No. GB 9922171.5 filed on Sep. 21, 1999.

The present invention relates to certain quinazoline derivatives for use in the treatment of certain diseases in particular to proliferative disease such as cancer and in the preparation of medicaments for use in the treatment of proliferative disease, to novel quinazoline compounds and to processes for their preparation, as well as pharmaceutical compositions containing them as active ingredient.

Cancer (and other hyperproliferative disease) is characterised by uncontrolled cellular proliferation. This loss of the normal regulation of cell proliferation often appears to occur as the result of genetic damage to cellular pathways that control progress through the cell cycle.

In eukaryotes, the cell cycle is largely controlled by an ordered cascade of protein phosphorylation. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

The first identified, and most widely studied of these cell cycle regulators have been the cyclin dependent kinases (or CDKs). Activity of specific CDKs at specific times is essential for both initiation and coordinated progress through the cell cycle For example, the CDK4 protein appears to control entry into the cell cycle (the G0-G1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and cyclin D protein levels increased (and hence the activity of CDK4 increased) in many human tumours (Reviewed in Sherr, 1996, Science 274: 1672–1677; Pines, 1995, Seminars in Cancer Biology 6: 63–72). Other studies (Loda et al., 1997, Nature Medicine 3(2): 231–234; Gemma et al., 1996, International Journal of Cancer 68(5): 605–11; Elledge et al. 1996, Trends in Cell Biology 6; 388–392) have shown that negative regulators of CDK function are frequently down regulated or deleted in human tumours again leading to inappropriate activation of these kinases.

More recently, protein kinases that are structurally distinct from the CDK family have been identified which play critical roles in regulating the cell cycle and which also appear to be important in oncogenesis. These include the newly identified human homologues of the *Drosophila* aurora and *S. cerevisiae* Ip11 proteins. *Drosophila* aurora and *S. cerevisiae* Ip11, which are highly homologous at the amino acid sequence level, encode serine/threonine protein kinases. Both aurora and Ip11 are known to be involved in controlling the transition from the G2 phase of the cell cycle through mitosis, centrosome function, formation of a mitotic spindle and proper chromosome separation/segregation into daughter cells. The two human homologues of these genes, termed aurora1 and aurora2, encode cell cycle regulated protein kinases. These show a peak of expression and kinase activity at the G2/M boundary (aurora2) and in mitosis itself (aurora1). Several observations implicate the involvement of human aurora proteins, and particularly aurora2 in cancer. The aurora2 gene maps to chromosome 20q13, a region that is frequently amplified in human tumours including both breast and colon tumours. Aurora2 may be the major target gene of this amplicon, since aurora2 DNA is amplified and aurora2 mRNA overexpressed in greater than 50% of primary human colorectal cancers. In these tumours aurora2 protein levels appears greatly elevated compared to adjacent normal tissue. In addition, transfection of rodent fibroblasts with human aurora2 leads to transformation, conferring the ability to grow in soft agar and form tumours in nude mice (Bischoff et al., 1998, The EMBO Journal. 17(11): 3052–3065). Other work (Zhou et al., 1998, Nature Genetics. 20(2): 189–93) has shown that artificial overexpression of aurora2 leads to an increase in centrosome number and an increase in aneuploidy.

Importantly, it has also been demonstrated that abrogation of aurora2 expression and function by antisense oligonucleotide treatment of human tumour cell lines (WO 97/22702 and WO 99/37788) leads to cell cycle arrest in the G2 phase of the cell cycle and exerts an antiproliferative effect in these tumour cell lines. This indicates that inhibition of the function of aurora2 will have an antiproliferative effect that may be useful in the treatment of human tumours and other hyperproliferative diseases.

A number of quinazoline derivatives have been proposed hitherto for use in the inhibition of various kinases. Examples of such proposals are included in WO 92/20642 and EP-B-584222 which relates to bicyclic compounds which inhibit epidermal growth factor (EGF) and platelet-derived growth factor (PDGF) receptor tyrosine kinase, WO 95/15758 which describes the use of bis ring systems for the selective inhibition of CSF-1R tyrosine kinase activity, and WO 99/09016, WO 97/03069 and US 570158 which describe the use of certain quinazoline compounds as tyrosine kinase inhibitors in other contexts.

The applicants have found a series of compounds which inhibit the effect of the aurora2 kinase and which are thus of use in the treatment of proliferative disease such as cancer, in particular in such diseases such as colorectal or breast cancer where aurora 2 kinase is known to be active.

The present invention provides a compound of formula (I)

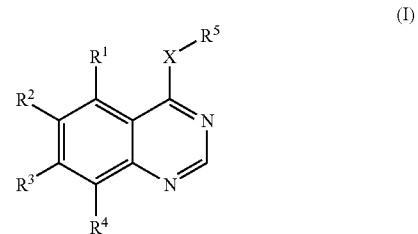

or a salt, ester, amide or prodrug thereof;
where X is O, or S, S(O), S(O)$_2$ or NR$^6$ where R$^6$ is hydrogen or C$_{1-6}$alkyl;
R$^5$ is an optionally substituted 6-membered aromatic ring containing at least one nitrogen atom, and
R$^1$, R$^2$, R$^3$, R$^4$ are independently selected from halogeno, cyano, nitro, C$_{1-3}$alkylsulphanyl, —N(OH)R$^7$— (wherein R$^7$ is hydrogen, or C$_{1-3}$alkyl), or R$^9$X$^1$— wherein X$^1$ represents a direct bond, —O—, —CH$_2$—, —OC(O)—, —C(O)—, —S—, —SO—, —SO$_2$—, —NR$^{10}$C(O)—, —C(O)NR$^{11}$—, —SO$_2$NR$^{12}$—, —NR$^{13}$SO$_2$— or —NR$^{14}$— (wherein R$^{10}$, R$^{11}$, R$^{12}$, R$^{13}$ and R$^{14}$ each independently represents hydrogen, C$_{1-3}$alkyl, hydroxyC$_{1-4}$alkyl or C$_{1-3}$alkoxyC$_{2-3}$alkyl), and R$^9$ is hydrogen, optionally substituted hydrocarbyl, optionally substituted heterocyclyl or optionally substituted alkoxy; provided that at least one of R$^2$ or R$^3$ is other than hydrogen.

In this specification the term 'alkyl' when used either alone or as a suffix includes straight chained, branched structures. Unless otherwise stated, these groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocyclic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl. Examples of non-aromatic heterocyclyl groups include morpholino, piperidino, azetidine, tetrahydrofuryl, tetrahydropyridyl. In the case of bicyclic rings, these may comprise an aromatic and non-aromatic portion.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. The moiety may be saturated or unsaturated. For example, these may be alkyl, alkenyl, alkynyl, aryl, aralkyl, cycloalkyl, cycloalkenyl or cycloalkynyl, or combinations thereof.

Examples of such combinations are alkyl, alkenyl or alkynl substituted with aryl, aralkyl, cycloalkyl, cycloalkenyl or cycloalkynyl, or an aryl, heterocyclyl, alkoxy, aralkyl, cycloalkyl, cycloalkenyl or cycloalkynyl substituted with alkyl, alkenyl, alkynyl or alkoxy, but others may be envisaged.

In particular hydrocarbyl groups include alkyl, alkenyl, alkynyl, aryl, aralkyl, cycloalkyl, cycloalkenyl or cycloalkynyl.

The term "functional group" refers to reactive substituents such as nitro, cyano, halo, oxo, =CR$^{78}$R$^{79}$, C(O)$_x$R$^{77}$, OR$^{77}$, S(O)$_y$R$^{77}$, NR$^{78}$R$^{79}$, C(O)NR$^{78}$R$^{79}$, OC(O)NR$^{78}$R$^{79}$, =NOR$^{77}$, —NR$^{77}$C(O)$_x$R$^{78}$, —NR$^{77}$CONR$^{78}$R$^{79}$, —N=CR$^{78}$R$^{79}$, S(O)$_y$NR$^{78}$R$^{79}$ or —NR$^{77}$S(O)$_y$R$^{78}$ where R$^{77}$, R$^{78}$ and R$^{79}$ are independently selected from hydrogen, optionally substituted hydrocarbyl, optionally substituted hetercyclyl or optionally substituted alkoxy, or R$^{78}$ and R$^{79}$ together form an optionally substituted ring which optionally contains further heteroatoms such as oxygen, nitrogen, S, S(O) or S(O)$_2$, where x is an integer of 1 or 2, y is 0 or an integer of 1–3.

Suitable optional substituents for hydrocarbyl, heterocyclyl or alkoxy groups R$^{77}$, R$^{78}$ and R$^{79}$ as well as rings formed by R$^{78}$ and R$^{79}$ include halo, perhaloalkyl such as trifluoromethyl, mercapto, thioalkyl, hydroxy, carboxy, alkoxy, heteroaryl, heteroaryloxy, cycloalkyl, cycloalkenyl, cycloalkynyl, alkenyloxy, alkynyloxy, alkoxyalkoxy, aryloxy (where the aryl group may be substituted by halo, nitro, or hydroxy), cyano, nitro, amino, mono- or di-alkyl amino, oximino or S(O)$_y$R$^{90}$ where y is as defined above and R$^{90}$ is a hydrocarbyl group such as alkyl.

In particular, optional substituents for hydrocarbyl, heterocyclyl or alkoxy groups R$^{77}$, R$^{78}$ and R$^{79}$ include halo, perhaloalkyl such as trifluoromethyl, mercapto, hydroxy, carboxy, alkoxy, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or S(O)$_y$R$^{90}$ where y is as defined above and R$^{90}$ is a hydrocarbyl group such as alkyl.

Certain compounds of formula (I) may include a chiral centre and the invention includes all enantiomeric forms thereof, as well as mixtures thereof including racemic mixtures.

In particular, R$^9$ is hydrogen or an alkyl group, optionally substituted with one or more groups selected from functional groups as defined above, or alkenyl, alkynyl, aryl, heterocyclyl, cycloalkyl, cycloalkenyl or cycloalkynyl, any of which may be substituted with a functional group as defined above, and where any aryl, heterocyclyl, cycloalkyl, cycloalkenyl, cycloalkynyl groups may also be optionally substituted with hydrocarbyl such as alkyl, alkenyl or alkynyl.

For example, R$^9$ is selected from one of the following twenty-two groups:

1) hydrogen or C$_{1-5}$alkyl which may be unsubstituted or which may be substituted with one or more functional groups;
2) —R$^a$X$^2$C(O)R$^{15}$ (wherein X$^2$ represents —O— or —NR$^{16}$— (in which R$^{16}$ represents hydrogen, or alkyl optionally substituted with a functional group) and R$^{15}$ represents C$_{1-3}$alkyl, —NR$^{17}$R$^{18}$ or —OR$^{19}$ (wherein R$^{17}$, R$^{18}$ and R$^{19}$ which may be the same or different each represents hydrogen, or alkyl optionally substituted with a functional group);
3) —R$^b$X$^3$R$^{20}$ (wherein X$^3$ represents —O—, —C(O)—, —S—, —SO—, —SO$_2$—, —OC(O)—, —NR$^{21}$C(O)$_s$—, —C(O)NR$^{22}$—, —SO$_2$NR$^{23}$—, —NR$^{24}$SO$_2$— or —NR$^{25}$— (wherein R$^{21}$, R$^{22}$, R$^{23}$, R$^{24}$ and R$^{25}$ each independently represents hydrogen, or alkyl optionally substituted with a functional group and s is 1 or 2) and R$^{20}$ represents hydrogen, hydrocarbyl (as defined herein) or a saturated heterocyclic group, wherein the hydrocarbyl or heterocyclic groups may be optionally substituted by one or more functional groups and the heterocyclic groups may additionally be substituted by a hydrocarbyl group);
4) —R$^c$X$^4$R$^{c'}$X$^5$R$^{26}$ (wherein X$^4$ and X$^5$ which may be the same or different are each —O—, —C(O)—, —S—, —SO—, —SO$_2$—, —OC(O)—, —NR$^{27}$C(O)$_s$—, —C(O)$_x$NR$^{28}$—, —SO$_2$NR$^{29}$—, —NR$^{30}$SO$_2$— or —NR$^{31}$— (wherein R$^{27}$, R$^{28}$, R$^{29}$, R$^{30}$ and R$^{31}$ each independently represents hydrogen or alkyl optionally substituted by a functional group and s is 1 or 2) and R$^{26}$ represents hydrogen, or alkyl optionally substituted by a functional group);
5) R$^{32}$ wherein R$^{32}$ is a C$_{3-6}$ cycloalkyl or saturated heterocyclic ring (linked via carbon or nitrogen), which cycloalkyl or heterocyclic group may be substituted by one or more functional groups or by a hydrocarbyl or heterocyclyl group which hydrocarbyl or heterocyclyl group may be optionally substituted by one or more functional groups;

6) —$R^dR^{32}$ (wherein $R^{32}$ is as defined hereinbefore);
7) —$R^eR^{32}$ (wherein $R^{32}$ is as defined hereinbefore);
8) —$R^fR^{32}$ (wherein $R^{32}$ is as defined hereinbefore);
9) $R^{33}$ (wherein $R^{33}$ represents a pyridone group, an aryl group or an aromatic heterocyclic group (linked via carbon or nitrogen) with 1–3 heteroatoms selected from O, N and S, which pyridone, aryl or aromatic heterocyclic group may be substituted by one or more functional groups or by a hydrocarbyl group optionally substituted by one or more functional groups or heterocyclyl groups, or by a heterocyclyl group optionally substituted by one or more functional groups or hydrocarbyl groups;
10) —$R^gR^{33}$ (wherein $R^{33}$ is as defined hereinbefore);
11) —$R^hR^{33}$ (wherein $R^{33}$ is as defined hereinbefore);
12) —$R^iR^{33}$ (wherein $R^{33}$ is as defined hereinbefore);
13) —$R^jX^6R^{33}$ (wherein $X^6$ represents —O—, —S—, —SO—, —SO$_2$—, —OC(O)—, —NR$^{38}$C(O)—, —C(O)NR$^{39}$—, —SO$_2$NR$^{40}$—, —NR$^{41}$SO$_2$— or —NR$^{42}$— (wherein $R^{38}$, $R^{39}$, $R^{40}$, $R^{41}$ and $R^{42}$ each independently represents hydrogen, or alkyl optionally substituted with a functional group) and $R^{37}$ is as defined hereinbefore);
14) —$R^kX^7R^{33}$ (wherein $X^7$ represents —O—, —C(O)—, —S—, —SO—, —SO$_2$—, —OC(O)—, —NR$^{43}$C(O)—, —C(O)NR$^{44}$—, —SO$_2$NR$^{45}$—, —NR$^{46}$SO$_2$— or —NR$^{47}$— (wherein $R^{43}$, $R^{44}$, $R^{45}$, $R^{46}$ and $R^{47}$ each independently represents hydrogen, or alkyl optionally substituted with a functional group) and $R^{33}$ is as defined hereinbefore);
15) —$R^mX^8R^{33}$ (wherein $X^8$ represents —O—, —C(O)—, —S—, —SO—, —SO$_2$—, —OC(O)—, —NR$^{48}$C(O)—, —C(O)NR$^{49}$—, —SO$_2$NR$^{50}$—, —NR$^{51}$SO$_2$— or —NR$^{52}$— (wherein $R^{48}$, $R^{49}$, $R^{50}$, $R^{51}$ and $R^{52}$ each independently represents hydrogen, hydrogen, or alkyl optionally substituted with a functional group) and $R^{33}$ is as defined hereinbefore);
16) —$R''X^9R'''R^{33}$ (wherein $X^9$ represents —O—, —C(O)—, —S—, —SO—, —SO$_2$—, —OC(O)—, —NR$^{53}$C(O)—, —C(O)NR$^{54}$—, —SO$_2$NR$^{55}$—, —NR$^{56}$SO$_2$— or —NR$^{57}$— (wherein $R^{53}$, $R^{54}$, $R^{55}$, $R^{56}$ and $R^{57}$ each independently represents hydrogen, hydrogen, or alkyl optionally substituted with a functional group) and $R^{33}$ is as defined hereinbefore);
17) —$R^pX^9$—$R^{p'}R^{32}$ (wherein $X^9$ and $R^{32}$ are as defined hereinbefore);
18) $C_{2-5}$alkenyl which may be unsubstituted or which may be substituted with one or more functional groups;
19) $C_{2-5}$alkynyl which may be unsubstituted or which may be substituted with one or more functional groups;
20) —$R^rX^9R^tR^{32}$ (wherein $X^9$ and $R^{32}$ are as defined hereinbefore);
21) —$R^uX^9R^{u'}R^{32}$ (wherein $X^9$ and $R^{32}$ are as defined hereinbefore); and
22) —$R^vR^{58}(R^{v'})_q(X^9)_rR^{59}$ (wherein $X^9$ is as defined hereinbefore, q is 0 or 1, r is 0 or 1, and $R^{58}$ is a $C_{1-3}$alkylene group or a cyclic group selected from divalent cycloalkyl or heterocyclic group, which $C_{1-3}$alkylene group may be substituted by one or more functional groups and which cyclic group may be substituted by one or more functional groups or by a hydrocarbyl group optionally substituted by one or more functional groups or heterocyclyl groups, or by a heterocyclyl group optionally substituted by one or more functional groups or hydrocarbyl groups; and $R^{59}$ is hydrogen, $C_{1-3}$alkyl, or a cyclic group selected from cycloalkyl or heterocyclic group, which $C_{1-3}$alkylene group may be substituted by one or more functional groups and which cyclic group may be substituted by one or more may be substituted by one or more functional groups or by a hydrocarbyl group optionally substituted by one or more functional groups or heterocyclyl groups, or by a heterocyclyl group optionally substituted by one or more functional groups or hydrocarbyl groups);

and wherein $R^a$, $R^b$, $R^{b'}$, $R^c$, $R^{c'}$, $R^d$, $R^g$, $R^j$, $R^n$, $R^{n'}$, $R^p$, $R^{p'}$, $R^{r'}$, $R^{u'}$, $R^v$ and $R^{v'}$ are independently selected from $C_{1-8}$alkylene groups optionally substituted by one or more substituents functional groups, $R^e$ $R^h$, $R^k$ and $R^t$ are independently selected from $C_{2-8}$alkenylene groups optionally substituted by one or more functional groups, and $R^f$, $R^i$, $R^m$ and $R^u$ are independently selected from by $C_{2-8}$alkynylene groups optionally substituted by one or more functional groups.

For example, $R^9$ is selected from one of the following twenty-two groups:

1) hydrogen or $C_{1-5}$alkyl which may be unsubstituted or which may be substituted with one or ore groups selected from hydroxy, oxiranyl, fluoro, chloro, bromo and amino (including $C_{1-3}$alkyl and trifluoromethyl);
2) —$R^aX^2C(O)R^{15}$ (wherein $X^2$ represents —O— or —NR$^{16}$— (in which $R^{16}$ represents hydrogen, $C_{1-3}$alkyl or $C_{1-3}$alkoxyC$_{2-3}$alkyl) and $R^{15}$ represents $C_{1-3}$alkyl, —NR$^{17}$R$^{18}$ or —OR$^{19}$ (wherein $R^{17}$, $R^{18}$ and $R^{19}$ which may be the same or different each represents hydrogen, $C_{1-5}$alkyl, hydroxyC$_{1-5}$alkyl or $C_{1-3}$alkoxyC$_{2-3}$alkyl));
3) —$R^bX^3R^{20}$ (wherein $X^3$ represents —O—, C(O) —S—, —SO—, —SO$_2$—, —OC(O)—, —NR$^{21}$C(O)$_s$—, —C(O)NR$^{22}$—, —SO$_2$NR$^{23}$—, —NR$^{24}$SO$_2$— or —NR$^{25}$— (wherein $R^{21}$, $R^{22}$, $R^{23}$, $R^{24}$ and $R^{25}$ each independently represents hydrogen, $C_{1-3}$alkyl, hydroxy $C_{1-4}$alkyl or $C_{1-3}$alkoxyC$_{2-3}$alkyl and s is 1 or 2) and $R^{20}$ represents hydrogen, $C_{1-6}$alkyl, $C_{2-6}$alkenyl, cyclopropyl, cyclobutyl, cyclopentyl, cyclohexyl, phenyl or a 5–6-membered saturated heterocyclic group with 1–2 heteroatoms, selected independently from O, S and N, which $C_{1-6}$alkyl group may bear 1, 2 or 3 substituents selected from oxo, hydroxy, halogeno, cyclopropyl, amino, $C_{1-4}$alkylamino, $C_{1-4}$alkanoyldi-C$_{1-4}$alkylamino, $C_{1-4}$alkylthio, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylaminoC$_{1-4}$alkyl, di($C_{1-4}$alkyl)aminoC$_{1-4}$alkyl, $C_{1-4}$alkylaminoC$_{1-4}$alkoxy, di($C_{1-4}$alkyl)aminoC$_{1-4}$alkoxy and a group —(—O—)$_f$(R$^{b'}$)$_g$D (wherein f is 0 or 1, g is 0 or 1 and D is a cyclic group selected from $C_{3-6}$cycloalkyl group, an aryl group or a 5–6-membered saturated heterocyclic group with 1–2 heteroatoms, selected independently from O, S and N, which cyclic group may bear one or more substituents selected from halo or $C_{1-4}$alkyl));
4) —$R^cX^4R^{c'}X^5R^{26}$ (wherein $X^4$ and $X^5$ which may be the same or different are each —O—, C(O), —S—, —SO—, —SO$_2$—, —NR$^{27}$C(O)$_s$—, —C(O)$_x$NR$^{28}$—, —SO$_2$NR$^{29}$—, —NR$^{30}$SO$_2$— or —NR$^{31}$— (wherein $R^{27}$, $R^{28}$, $R^{29}$, $R^{30}$ and $R^{31}$ each independently represents hydrogen, $C_{1-3}$alkyl or $C_{1-3}$alkoxyC$_{2-3}$alkyl and s is 1 or 2) and $R^{26}$ represents hydrogen, $C_{1-3}$alkyl, hydroxyC$_{1-3}$alkyl or $C_{1-3}$alkoxyC$_{2-3}$alkyl);
5) $R^{32}$ (wherein $R^{32}$ is a 4–6-membered cycloalkyl or saturated heterocyclic ring (linked via carbon or nitrogen) with 1–2 heteroatoms, selected independently from O, S and N, which cycloalkyl or heterocyclic group may bear 1 or 2 substituents selected from oxo, hydroxy, halogeno, cyano, $C_{1-4}$alkyl, hydroxy$C_{1-4}$alkyl, cyano$C_{1-4}$alkyl, cyclopropyl, $C_{1-4}$alkylsulphonyl$C_{1-4}$alkyl, $C_{1-4}$alkoxycarbonyl, carboxamido, $C_{1-4}$aminoalkyl, $C_{1-4}$alkylamino, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy nitro, amino, $C_{1-4}$alkoxy, $C_{1-4}$hydroxyalkoxy, carboxy, trifluoromethyl, —C(O)NR$^{38}$R$^{39}$, —NR$^{40}$C(O)R$^{41}$ (wherein R$^{38}$, R$^{39}$, R$^{40}$ and R$^{41}$, which may be the same or different, each represents hydrogen, $C_{1-4}$alkyl, hydroxy$C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$-alkyl);

6) —R$^d$R$^{32}$ (wherein R$^{32}$ is as defined hereinbefore);
7) —R$^e$R$^{32}$ (wherein R$^{32}$ is as defined hereinbefore);
8) —R$^f$R$^{32}$ (wherein R$^{32}$ is as defined hereinbefore);
9) R$^{33}$ (wherein R$^{33}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, nitro, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, oxo, cyano$C_{1-4}$alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$akylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxy, carboxamido, trifluoromethyl, cyano, —C(O)NR$^{38}$R$^{39}$, —NR$^{40}$C(O)R$^{41}$ (wherein R$^{38}$, R$^{39}$, R$^{40}$ and R$^{41}$, which may be the same or different, each represents hydrogen, $C_{1-4}$alkyl, hydroxy$C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl));
10) —R$^g$R$^{33}$ (wherein R$^{33}$ is as defined hereinbefore);
11) —R$^h$R$^{33}$ (wherein R$^{33}$ is as defined hereinbefore);
12) —R$^i$R$^{33}$ (wherein R$^{33}$ is as defined hereinbefore);
13) —R$^j$X$^6$R$^{33}$ (wherein X$^6$ represents —O—, —C(O)—, —S—, —SO—, —SO$_2$—, —OC(O)—, —NR$^{38}$C(O)—, —C(O)NR$^{39}$—, —SO$_2$NR$^{40}$—, —NR$^{41}$SO$_2$— or —NR$^{42}$— (wherein R$^{38}$, R$^{39}$, R$^{40}$, R$^{41}$ and R$^{42}$ each independently represents hydrogen, $C_{1-3}$alkyl, hydroxy$C_{1-3}$alkyl or $C_{1-3}$alkoxy$C_{2-3}$alkyl) and R$^{33}$ is as defined hereinbefore);
14) —R$^k$X$^7$R$^{33}$ (wherein X$^7$ represents —O—, C(O), —S—, —SO—, —SO$_2$—, —NR$^{43}$C(O)—, —C(O)NR$^{44}$—, —SO$_2$NR$^{45}$—, —NR$^{46}$SO$_2$— or —NR$^{47}$— (wherein R$^{43}$, R$^{44}$, R$^{45}$, R$^{46}$ and R$^{47}$ each independently represents hydrogen, $C_{1-3}$alkyl, hydroxy$C_{1-3}$alkyl or $C_{1-3}$alkoxy$C_{2-3}$alkyl) and R$^{33}$ is as defined hereinbefore);
15) —R$^m$X$^8$R$^{33}$ (wherein X$^8$ represents —O—, —C(O)—, —S—, —SO—, —SO$_2$—, —NR$^{48}$C(O)—, —C(O)NR$^{49}$—, —SO$_2$NR$^{50}$—, —NR$^{51}$SO$_2$— or —NR$^{52}$— (wherein R$^{48}$, R$^{49}$, R$^{50}$, R$^{51}$ and R$^{52}$ each independently represents hydrogen, $C_{1-3}$alkyl, hydroxy$C_{1-3}$alkyl or $C_{1-3}$alkoxy$C_{2-3}$alkyl) and R$^{33}$ is as defined hereinbefore);
16) —R″X$^9$R″R$^{33}$ (wherein X$^9$ represents —O—, —C(O)—, —S—, —SO—, —SO$_2$—, —NR$^{53}$C(O)—, —C(O)NR$^{54}$—, —SO$_2$NR$^{55}$—, —NR$^{56}$SO$_2$— or —NR$^{57}$— (wherein R$^{53}$, R$^{54}$, R$^{55}$, R$^{56}$ and R$^{57}$ each independently represents hydrogen, $C_{1-3}$alkyl, hydroxy$C_{1-3}$alkyl or $C_{1-3}$alkoxy$C_{2-3}$alkyl) and R$^{33}$ is as defined hereinbefore);
17) —R$^p$X$^9$—R$^{p'}$1R$^{32}$ (wherein X$^9$ and R$^{32}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;
20) —R$^t$X$^9$R$^{t'}$R$^{32}$ (wherein X$^9$ and R$^{32}$ are as defined hereinbefore);
21) —R$^u$X$^9$R$^{u'}$R$^{32}$ (wherein X$^9$ and R$^{32}$ are as defined hereinbefore); and
22) —R$^v$R$^{58}$(R$^{v'}$)$_q$(X$^9$)$_r$R$^{59}$ (wherein X$^9$ is as defined hereinbefore, q is 0 or 1, r is 0 or 1, and R$^{58}$ is a $C_{1-3}$alkylene group or a cyclic group selected from cyclopropyl, cyclobutyl, cyclopentylene, cyclohexylene or a 5–6-membered saturated heterocyclic group with 1–2 heteroatoms, selected independently from O, S and N, which $C_{1-3}$alkylene group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl); and R$^{59}$ is hydrogen, $C_{1-3}$alkyl, or a cyclic group selected from cyclopropyl, cyclobutyl, cyclopentyl, cyclohexyl and a 5–6-membered saturated heterocyclic group with 1–2 heteroatoms, selected independently from O, S and N, which $C_{1-3}$alkyl group may bear 1 or 2 substituents selected from oxo, hydroxy, halogeno, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl));

and wherein R$^a$, R$^b$, R$^{b'}$, R$^c$, R$^{c'}$, R$^d$, R$^g$, R$^j$, R$^n$, R$^{n'}$, R$^p$, R$^{p'}$, R$^{t'}$, R$^{u'}$, R$^v$ and R$^{v'}$ are independently selected from $C_{1-8}$alkylene groups optionally substituted by one or more substituents selected from hydroxy, halogeno, amino, $R^e$ $R^h$, $R^k$ and $R^t$ are independently selected from $C_{2-8}$alkenylene groups optionally substituted by one or more substituents selected from hydroxy, halogeno, amino, and $R^t$ may additionally be a bond; and $R^f$, $R^i$, $R^m$ and $R^u$ are independently selected from by $C_{2-8}$alkynylene groups optionally substituted by one or more substituents selected from hydroxy, halogeno, amino.

For instance, $R^1$, $R^2$, $R^3$, $R^4$ are independently selected from, halo, cyano, nitro, trifluoromethyl, $C_{1-3}$alkyl, —$NR^7R^8$ (wherein $R^7$ and $R^8$, which may be the same or different, each represents hydrogen or $C_{1-3}$alkyl), or other groups from formula —$X^1R^9$ wherein $X^1$ represents a direct bond, —O—, —$CH_2$—, —OCO—, carbonyl, —S—, —SO—, —$SO_2$—, —$NR^{10}CO$—, —$CONR^{11}$—, —$SO_2NR^{12}$—, —$NR^{13}SO_2$— or —$NR^{14}$— (wherein $R^{10}$, $R^{11}$, $R^{12}$, $R^{13}$ and $R^{14}$ each independently represents hydrogen, $C_{1-3}$alkyl or $C_{1-3}$alkoxy$C_{2-3}$alkyl), and $R^9$ is selected from one of the following groups:

1') hydrogen or $C_{1-5}$alkyl which may be unsubstituted or which may be substituted with one or more groups selected from hydroxy, fluoro or amino;

2') $C_{1-5}$alkyl$X^2C(O)R^{15}$ (wherein $X^2$ represents —O— or —$NR^{16}$— (in which $R^{15}$ represents hydrogen, $C_{1-3}$alkyl or $C_{1-3}$alkoxy$C_{2-3}$alkyl) and $R^5$ represents $C_{1-3}$alkyl, —$NR^{17}R^{18}$ or —$OR^{19}$ (wherein $R^{17}$, $R^{18}$ and $R^{19}$ which ay be the same or different each represents hydrogen, $C_{1-3}$alkyl or $C_{1-3}$alkoxy$C_{2-3}$alkyl));

3') $C_{1-5}$alkyl$X^3R^{20}$ (wherein $X^3$ represents —O—, —S—, —SO—, —$SO_2$—, —OCO—, —$NR^{21}CO$—, —$CONR^{22}$—, —$SO_2NR^{23}$—, —$NR^{24}SO_2$— or —$NR^{25}$— (wherein $R^{21}$, $R^{22}$, $R^{23}$, $R^{24}$ and $R^{25}$ each independently represents hydrogen, $C_{1-3}$alkyl or $C_{1-3}$alkoxy$C_{2-3}$alkyl) and $R^{20}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4') $C_{1-5}$alkyl$X^4C_{1-5}$alkyl$X^5R^{26}$ (wherein $X^4$ and $X^5$ which may be the same or different are each —O—, —S—, —SO—, —$SO_2$—, —$NR^{27}CO$—, —$CONR^{28}$—, —$SO_2NR^{29}$—, —$NR^{30}SO_2$— or —$NR^{31}$— (wherein $R^{27}$, $R^{28}$, $R^{29}$, $R^{30}$ and $R^{31}$ each independently represents hydrogen, $C_{1-3}$alkyl or $C_{1-3}$alkoxy$C_{2-3}$alkyl) and $R^{26}$ represents hydrogen or $C_{1-3}$alkyl);

5') $R^{32}$ (wherein $R^{32}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6') $C_{1-5}$alkyl$R^{32}$ (wherein $R^{32}$ is as defined in (5') above);
7') $C_{2-5}$alkenyl$R^{32}$ (wherein $R^{32}$ is as defined in (5') above);
8') $C_{2-5}$alkynyl$R^{32}$ (wherein $R^{32}$ is as defined in (5') above);
9') $R^{33}$ (wherein $R^{33}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{34}R^{35}$ and —$NR^{36}COR^{37}$ (wherein $R^{34}$, $R^{35}$, $R^{36}$ and $R^{37}$, which may be the same or different, each represents hydrogen, $C_{1-4}$alkyl or $C_{1-3}$alkoxy$C_{2-3}$alkyl));

10') $C_{1-5}$alkyl$R^{33}$ (wherein $R^{33}$ is as defined in (9') above);
11') $C_{2-5}$alkenyl$R^{33}$ (wherein $R^{33}$ is as defined in (9') above);
12') $C_{2-5}$alkynyl$R^{33}$ (wherein $R^{33}$ is as defined in (9') above);
13') $C_{1-5}$alkyl$X^6R^{33}$ (wherein $X^6$ represents —O—, —S—, —SO—, —$SO_2$—, —$NR^{38}CO$—, —$CONR^{39}$—, —$SO_2NR^{40}$—, —$NR^{41}SO_2$— or —$NR^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{33}$ is as defined hereinbefore);

14') $C_{2-5}$alkenyl$X^7R^{33}$ (wherein $X^7$ represents —O—, —S—, —SO—, —$SO_2$—, —$NR^{43}CO$—, —$CONR^{44}$—, —$SO_2NR^{45}$—, —$NR^{46}SO_2$— or —$NR^{47}$— (wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl) and $R^{33}$ is as defined hereinbefore);

15') $C_{2-5}$alkynyl$X^8R^{33}$ (wherein $X^8$ represents —O—, —S—, —SO—, —$SO_2$—, —$NR^{48}CO$—, —$C(O)NR^{49}$—, —$SO_2NR^{50}$—, —$NR^{51}SO_2$— or —$NR^{52}$— (wherein $R^{48}$, $R^{49}$, $R^{50}$, $R^{51}$ and $R^{52}$ each independently represents hydrogen, $C_{1-3}$alkyl or $C_{1-3}$alkoxy$C_{2-3}$alkyl) and $R^{33}$ is as defined hereinbefore);

16') $C_{1-3}$alkyl$X^9C_{1-3}$alkyl$R^{33}$ (wherein $X^9$ represents —O—, —S—, —SO—, —$SO_2$—, —$NR^{53}CO$—, —$C(O)NR^{54}$—, —$SO_2NR^{55}$—, —$NR^{56}SO_2$— or —$NR^{57}$— (wherein $R^{53}$, $R^{54}$, $R^{55}$, $R^{56}$ and $R^{57}$ each independently represents hydrogen, $C_{1-3}$alkyl or $C_{1-3}$alkoxy$C_{2-3}$alkyl) and $R^{33}$ is as defined hereinbefore); and 17') $C_{1-3}$alkyl$X^9C_{1-3}$alkyl$R^{32}$ (wherein $X^9$ and $R^{32}$ are as defined in (5') above); provided that at least one of $R^2$ or $R^3$ is other than hydrogen.

Preferably $R^1$ is hydrogen. Suitably $R^4$ is hydrogen or a small substituent such as halo, $C_{1-4}$ alkyl or $C_{1-4}$alkoxy such as methoxy.

Preferably both $R^1$ and $R^4$ are hydrogen.

In a preferred embodiment, at least one group $R^2$ or $R^3$, preferably $R^3$, comprises a chain of at least 3 and preferably at least 4 optionally substituted carbon atoms or heteroatoms such as oxygen, nitrogen or sulphur. Most preferably the chain is substituted by a polar group which assists in solubility.

Suitably $R^3$ is a group $X^1R^9$.

Preferably in this case, $X^1$ is oxygen and $R^9$ includes a methylene group directly adjacent $X^1$. Preferably where bridging alkylene, alkenylene or alkynylene groups $R^a$, $R^b$, $R^{b'}$, $R^c$, $R^{c'}$, $R^d$, $R^g$, $R^j$, $R^n$, $R^{n'}$, $R^p$, $R^{p'}$, $R^t$, $R^{u'}$, $R^v$, $R^{v'}$, $R^e$ $R^h$, $R^k$ $R^t$, $R^f$, $R^i$, $R^m$ and $R^u$ are present, at least one such group includes a substituent and in particular a hydroxy substituent.

In particular $R^9$ is selected from a group of formula (1), (3), (6) or (10) above and preferably selected from groups (1) or (10) above. Particular groups $R^9$ are those in group (1) above, especially alkyl such as methyl or halo substituted alkyl, or those in group (10) above. In one suitable embodiment, at least one of $R^2$ or $R^3$ is a group $OC_{1-5}$alkyl$R^{33}$ and $R^{33}$ is a heterocyclic ring such as an N-linked morpholine ring such as 3-morpholinopropoxy.

Other preferred groups for $R^3$ are groups of formula (3) above in particular those where $X^3$ is $NR^{25}$.

Suitably $R^2$ is selected from, halo, cyano, nitro, trifluoromethyl, $C_{1-3}$alkyl, —$NR^7R^8$ (wherein $R^7$ and $R^8$, which may be the same or different, each represents hydrogen or $C_{1-3}$alkyl), or a group —$X^1R^9$. Preferred examples of —$X^1R^9$ for $R^2$ include those listed above in relation to $R^3$.

Other examples for $R^2$ and $R^3$ include methoxy or 3,3,3-trifluoroethoxy.

Preferably X is NH or O and is most preferably NH.

Suitably $R^5$ is optionally substituted pyridine or optionally substituted pyrimidine and is preferably optionally substituted pyrimidine.

Most preferably, $R^5$ is a substituted pyridine or substituted pyrimidine group. Suitably, at least one substituent is positioned at the para position on the ring $R^5$. Thus suitable groups $R^5$ include compounds of sub-formulae

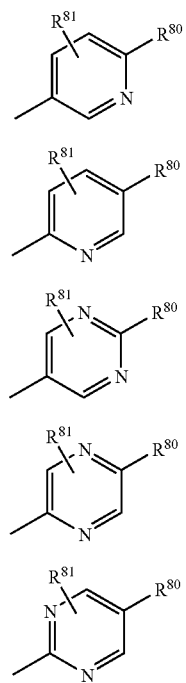

where $R^{80}$ is a substituent group and in particular $R^{80}$ is a large substituent of a chain of at least 4 atoms, in particular a group of sub-formula (II), (f) or sub-formula (VI) as defined below, and $R^{81}$ is hydrogen or a substituent and in particular a small substituent such as halo, $C_{1-4}$alkoxy such as methoxy, or ethoxy, cyano or trifluoromethyl, or phenyl.

In particular $R^5$ is a group of formula (i), (ii) or (iii) as defined above, and most preferably is a group of sub-formula (iii). Alternatively, $R^5$ is a group of sub-formula (i) or (ii) as defined above, and may preferably be a group of sub-formula (i).

Suitable substituents for the pyridine or pyrimidine groups $R^5$ include a functional group as defined above; hydrocarbyl optionally substituted by one or more functional groups as defined above; heterocyclyl optionally substituted by one or more functional groups or hydrocarbyl groups wherein the hydrocarbyl group may be substituted by a functional group or a heterocyclic group as defined above; alkoxy optionally substituted by a functional group, or a heterocyclic group which is optionally substituted by a functional group.

In particular, $R^5$ is substituted by one or more groups selected from halo, $C_{1-4}$alkyl, optionally substituted $C_{1-6}$alkoxy, $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5–6-membered heterocyclic group with 1–3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N-$C_{1-4}$alkylcarbamoyl, N,N-di($C_{1-4}$alkyl)carbamoyl, aminosulphonyl, N-$C_{1-4}$alkylaminosulphonyl, N,N-di($C_{1-4}$ alkyl) aminosulphonyl, $C_{1-4}$alkylsulphonylamino, and a saturated heterocyclic group selected from morpholino, thiomorpholino, pyrrolidinyl, piperazinyl, piperidinyl, imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl.

Other substituents groups for $R^5$ include carboxamido, carboxy and benzoyl.

Suitably $R^5$ is substituted with at least one group which has at least 4 atoms which may be carbon or heteroatoms forming a chain. A particular example of such a substituent is optionally substituted alkoxy. Suitable substituents for the alkoxy group include those listed above in relation to $R^{77}$, $R^{78}$ and $R^{79}$.

A further particular substituent group for $R^5$ is a group of sub-formula (II)

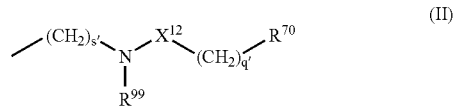

where q' is 0, 1, 2, 3 or 4;
s' is 0 or 1;
$X^{12}$ is C(O) or S($O_2$), and preferably C(O);
$R^{70}$ is hydrogen, hydroxy, $C_{1-6}$alkyl, $C_{1-6}$alkoxy, amino, N-$C_{1-6}$alkylamino, N,N-($C_{1-6}$alkyl)$_2$amino, hydroxy$C_{2-6}$alkoxy, $C_{1-6}$alkoxy$C_{2-6}$alkoxy, amino$C_{2-6}$alkoxy, N-$C_{1-6}$alkylamino$C_{2-6}$alkoxy, N,N-($C_{1-6}$alkyl)$_2$amino$C_{2-6}$alkoxy or $C_{3-7}$cycloalkyl, or $R^{70}$ is of the Formula (III):

wherein J is aryl, heteroaryl or heterocyclyl and K is a bond, oxy, imino, N-($C_{1-6}$alkyl)imino, oxy$C_{1-6}$alkylene, imino$C_{1-6}$alkylene, N-($C_{1-6}$alkyl)imino$C_{1-6}$alkylene, —NHC(O)—, —$SO_2$NH—, —$NHSO_2$— or —NHC(O)—$C_{1-6}$alkylene-, and any aryl, heteroaryl or heterocyclyl group in a $R^{70}$ group may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)—O—, $C_{1-6}$alkylS(O)$_n$— (wherein n is 0–2), N-$C_{1-6}$alkylamino, N,N-($C_{1-6}$alkyl)$_2$amino, $C_{1-6}$alkoxycarbonyl, N-$C_{1-6}$alkylcarbamoyl, N,N-($C_{1-}$ $_6$alkyl)$_2$carbamoyl, C$_{2-6}$alkanoyl, C$_{1-6}$alkanoyloxy, C$_{1-6}$alkanoylamino, N-C$_{1-6}$alkylsulphamoyl, N,N-(C$_{1-6}$alkyl)$_2$sulphamoyl, C$_{1-6}$alkylsulphonylamino and C$_{1-6}$alkylsulphonyl-N-(C$_{1-6}$alkyl)amino, and suitably also oxo, or any aryl, heteroaryl or heterocyclyl group in a R$^{70}$ group may be optionally substituted with one or more groups of the Formula (IV):

$$-B^1-(CH_2)_p-A^1 \qquad (IV)$$

wherein A$^1$ is halo, hydroxy, C$_{1-6}$alkoxy, cyano, amino, N-C$_{1-6}$alkylamino, N,N-(C$_{1-6}$alkyl)$_2$amino, carboxy, C$_{1-6}$alkoxycarbonyl, carbamoyl, N-C$_{1-6}$alkylcarbamoyl or N,N-(C$_{1-6}$alkyl)$_2$carbamoyl, p is 1–6, and B$^1$ is a bond, oxy, imino, N-(C$_{1-6}$alkyl)imino or —NHC(O)—, with the proviso that p is 2 or more unless B$^1$ is a bond or —NHC(O)—;

or any aryl, heteroaryl or heterocyclyl group in a R$^{70}$ group may be optionally substituted with one or more groups of the Formula (V):

$$-E^1-D^1 \qquad (V)$$

wherein D$^1$ is aryl, heteroaryl or heterocyclyl and E$^1$ is a bond, C$_{1-6}$alkylene, oxyC$_{1-6}$alkylene, oxy, imino, N-(C$_{1-6}$alkyl)imino, iminoC$_{1-6}$alkylene, N-(C$_{1-6}$alkyl)-iminoC$_{1-6}$alkylene, C$_{1-6}$alkylene-oxyC$_{1-6}$alkylene, C$_{1-6}$alkylene-iminoC$_{1-6}$alkylene, C$_{1-6}$alkylene-N-(C$_{1-6}$alkyl)-iminoC$_{1-6}$ alkylene, —NHC(O)—, —NHSO$_2$—, —SO$_2$NH— or —NHC(O)—C$_{1-6}$alkylene-, and any aryl, heteroaryl or heterocyclyl group in a substituent on R$^5$ may be optionally substituted with one or more groups selected from hydroxy, halo, C$_{1-6}$alkyl, C$_{1-6}$alkoxy, carboxy, C$_{1-6}$alkoxycarbonyl, carbamoyl, N-C$_{1-6}$alkylcarbamoyl, N-(C$_{1-6}$alkyl)$_2$carbamoyl, C$_{2-6}$alkanoyl, amino, N-C$_{1-6}$ alkylamino and N,N-(C$_{1-6}$alkyl)$_2$amino, and any C$_{3-7}$cycloalkyl or heterocyclyl group in a R$^{70}$ group may be optionally substituted with one or two oxo or thioxo substituents, and any of the R$^{70}$ groups defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, C$_{1-6}$alkoxy, N-C$_{1-6}$alkylamino, N,N-(C$_{1-6}$alkyl)$_2$amino and heterocyclyl;

and R$^{99}$ is hydrogen or a group C(O)R$^{70}$ where R$^{70}$ is as defined above and is preferably hydrogen.

In yet a further alternative, R$^{70}$ may be cycloalkenyl or cycloalkynyl such as cyclohexenyl, alkenyl optionally substituted by aryl such as styryl or alkyl substituted by cycloalkenyl such as cyclohexenylethyl Suitably, when q' is 0, R$^{70}$ is other than hydroxy.

Preferably s' is 0.

Preferably the group of sub-formula (II) is a group of sub-formula (IIA)

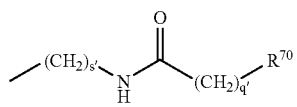

(IIA)

where s', q' and R$^{70}$ are as defined above.

A preferred example of a substituent of formula (II) or (IIA) is a group where q' is 0.

Examples of heterocyclyl groups for R$^{70}$ include pyridyl, methyledioxyphenyl, furyl, pyrrolyl, thiophene, quinolyl, isoquinolyl, thiazolyl, thiadiazolyl, pyrazolyl, tetrahydrothiophene-1,1-dioxide, dioxan, tetrahydrofuryl, pyrazinyl, imidazolyl, tetrahydropyran, indolyl, indanyl, pyrrolidine, or isoxazolyl.

A particular example of a group R$^{70}$ in formula (II) is phenyl. Preferably R$^{70}$ is halosubstituted phenyl and 2-chloro-4-fluorophenyl is a particularly preferred example.

More suitably R$^5$ is substituted by a group —X$^{10}$(CH$_2$)$_{p'}$, —X$^{11}$R$^{100}$ or —X$^{13}$R$^{100}$ where p' is 1–3, X$^{10}$ and X$^{11}$ are independently selected from a bond, —O—, —S— or NR$^{101}$— where R$^{101}$ is hydrogen or a C$_{1-3}$alkyl, provided that one of X$^{10}$ or X$^{11}$ is a bond; X$^{13}$ is —O—, —S— or NR$^{102}$— where R$^{102}$ is hydrogen or a C$_{1-4}$alkyl and R$^{100}$ is hydrogen or optionally substituted hydrocarbyl or optionally substituted heterocyclyl. Suitable optional substituents for hydrocarbyl and heterocyclyl groups R$^{100}$ include functional groups as defined above. Preferred groups R$^{100}$ are hydrocarbyl or heterocyclyl groups which are included in the definition of R$^{70}$ as defined hereinbefore. Preferably one of X$^{10}$ or X$^{11}$ is other than a bond.

Particular examples of R$^{70}$ in this instance include optionally substituted phenyl and especially, mono or di-halophenyl, or optionally substituted pyridyl such as nitropyridyl.

Another preferred substituent group for R$^5$ is a group of formula (VI)

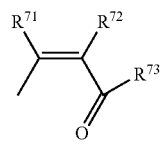

(VI)

where R$^{71}$ and R$^{72}$ are independently selected from hydrogen or C$_{1-4}$alkyl, or R$^{71}$ and R$^{72}$ together form a bond, and R$^{73}$ is a group OR$^{74}$, NR$^{75}$R$^{76}$ where R$^{74}$, R$^{75}$ and R$^{76}$ are independently selected from optionally substituted hydrocarbyl or optionally substituted heterocyclic groups, and R$^{75}$ and R$^{76}$ may additionally form together with the nitrogen atom to which they are attached, an aromatic or non-aromatic heterocyclic ring which may contain further heteroatoms.

Suitable optional substituents for hydrocarbyl or heterocyclic groups R$^{74}$, R$^{75}$ and R$^{76}$ include functional groups as defined above. Heterocyclic groups R$^{74}$, R$^{75}$ and R$^{76}$ may further be substituted by hydrocarbyl groups.

In particular, R$^{71}$ and R$^{72}$ in sub-formula (VI) are hydrogen.

Particular examples of R$^{73}$ are groups OR$^{74}$ where R$^{74}$ is C$_{1-4}$alkyl.

Further examples of R$^{73}$ are groups of formula NR$^{75}$R$^{76}$ where one of R$^{75}$ or R$^{76}$ is hydrogen and the other is optionally substituted C$_{1-6}$alkyl, optionally substituted aryl or optionally substituted heterocyclyl.

In particular, one of R$^{75}$ or R$^{76}$ is hydrogen and the other is C$_{1-6}$alkyl optionally substituted with trifluoromethyl, C$_{1-3}$ alkoxy such as methoxy, cyano, thioC$_{1-4}$alkyl such as methylthio, or heterocyclyl optionally substituted with hydrocarbyl, such as indane, furan optionally substituted with C$_{1-4}$ alkyl such as methyl.

In another embodiment, one of R$^{75}$ or R$^{76}$ is hydrogen and the other is an optionally substituted heterocyclic group such as pyridine, or a phenyl group optionally substituted with for example one or more groups selected from halo, nitro, alkyl such as methyl, or alkoxy such as methoxy.

Other suitable substituents groups for $R^5$ are groups of sub-formula (f)

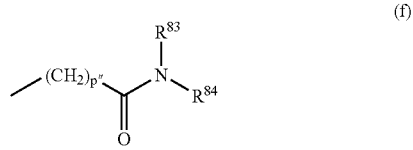

(f)

where p" is 0 or 1 and $R^{83}$ and $R^{84}$ are independently selected from hydrogen, optionally substituted hydrocarbyl or optionally substituted heterocyclyl, or $R^{83}$ and $R^{84}$ together with the nitrogen atom to which they are attached form an optionally substituted heterocyclic ring. Suitable optional substituents for hydrocarbyl or heterocyclic groups $R^{83}$ and $R^{84}$ include functional groups as defined above and heterocyclic groups $R^{83}$ or $R^{84}$ may further be substituted by a hydrocarbyl group.

Examples of groups for $R^{83}$ and $R^{84}$ include $C_{1-4}$alkyl substituted by cycloalkyl such as 2-cyclopropylethyl; $C_{1-6}$alkylthio such a methylthio; $C_{1-6}$alkoxy; or a group $-(CH^2)_qR^{70}$ where q and $R^{70}$ are as defied above in relation to formula (II).

Suitably one of $R^{83}$ or $R^{84}$ is hydrogen, or methyl, ethyl or propyl optionally substituted with hydroxy and preferably one of $R^{83}$ or $R^{84}$ is hydrogen. In this case, the other is suitably a larger substituent for example of at least 4 carbon or heteroatoms, and is optionally substituted hydrocarbyl or optionally substituted heterocyclyl. Particular optionally substituted hydrocarbyl groups for $R^{83}$ or $R^{84}$ include alkyl, cycloalkyl, alkenyl, or aryl any of which is optionally substituted with a functional group as defined above, or in the case of aryl groups, with an alkyl group and in the case of alkyl group, with an aryl or heterocyclic group either of which may themselves be optionally substituted with alkyl or a functional group. Examples of optionally substituted aryl groups $R^{83}$ or $R^{84}$ include phenyl optionally substituted with one or more groups selected from $C_{1-6}$ alkyl group such as methyl or ethyl (either of which may be optionally substituted with a functional group such as hydroxy), or a functional group as defined above (such as halo like fluoro, chloro or bromo, hydroxy, alkoxy such as methoxy, trifluoromethyl, nitro, cyano, trifluoromethoxy, $CONH_2$, $C(O)CH_3$, amino, or dimethylamino).

When $R^{83}$ or $R^{84}$ is an optionally substituted alkyl group, it is suitably a $C_{1-6}$alkyl group, optionally substituted with one or more functional groups (such as cyano, hydroxy, alkoxy in particular methoxy or ethoxy, alkylthio in particular methylthio, COOalkyl such as $COOCH_3$), or aryl optionally substituted with a functional group as defined above (in particular in relation to $R^{83}$ or $R^{84}$ themselves, or an optionally substituted heterocyclic group such as N-methyl pyrrole).

When $R^{83}$ and $R^{84}$ is optionally substituted cycloalkyl, it is suitable cyclohexyl optionally substituted with a functional group such as hydroxy.

When $R^{83}$ and $R^{84}$ is optionally substituted alkenyl, it is suitably prop-2-enyl.

When $R^{83}$ or $R^{84}$ is optionally substituted heterocyclyl, or $R^{83}$ and $R^{84}$ together form a heterocyclic group, then this may be aromatic or non-aromatic and includes in particular, piperadine, piperazine, morpholino, pyrrolidine or pyridine any of which may be optionally substituted with a functional group such as hydroxy, alkoxy such as methoxy, or alkyl such as methyl which may itself be substituted with for instance a hydroxy group.

Where possible, the group $R^5$ may have a second substituent in particular halo, $C_{1-4}$alkoxy such as methoxy, or ethoxy, cyano, trifluoromethyl, or phenyl. Preferably any second substituent is a small group.

Suitable prodrugs of compounds of formula (I) are groups which enhance solubility and include phoshates and sulphates, in particular phosphates as well as alkyl, aryl or aralkyl derivatives thereof such as dibenzylphosphate. The prodrug moiety may be attached at any suitable position in the molecule, for example as a derivative of a hydroxy group, but in particular, may be advantageously present on one or more of groups $R^1$, $R^2$, $R^3$ or $R^4$, and preferably at $R^2$ or $R^3$.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. There may be more than one cation or anion depending on the number of charged functions and the valency of the cations or anions. Where the compound of formula (I) includes an acid functionality, salts may be base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. A preferred pharmaceutically acceptable salt is a sodium salt.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkyl esters such as methyl or ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxy-carbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Suitable amides are derived from compounds of formula (I) which have a carboxy group which is derivatised into an amide such as a N-$C_{1-6}$alkyl and N,N-di($C_{1-6}$alkyl)amide such as N-methyl, N-ethyl, N-propyl, N,N-dimethyl, N-ethyl-N-methyl or N,N-diethylamide.

Esters which are not in vivo hydrolysable may be useful as intermediates in the production of the compounds of formula (I).

Particular examples of compounds of formula (I) are set out in Tables 1–14

TABLE 1

[Structure: quinazoline with CH₃O at 6-position, R³ at 7-position, NH linked to pyrimidine with N(R¹⁰⁵)(R¹⁰⁶) at 5-position]

| N°. | R³ | R¹⁰⁵ | R¹⁰⁶ |
|---|---|---|---|
| 1 | OCH₃ | H | CO—Ph |
| 2 | OCH₂CH₂CH₂-(4-morpholine) | H | CO—Ph |
| 3 | OCH₂CH₂CH₂-(4-morpholine) | =R¹⁰⁶ | CO-(4-dimethylaminophenyl) |
| 4 | OCH₂CH₂CH₂-(4-morpholine) | H | CO-(4-nitrophenyl) |
| 5 | OCH₂CH₂CH₂-(4-morpholine) | H | SO₂-(4-nitrophenyl) | where Ph = phenyl

TABLE 2

[Structure: quinazoline with R², R³, R⁴ substituents, NH linked to pyrimidine-2-NHCO-Ph]

| N°. | R² | R³ | R⁴ |
|---|---|---|---|
| 6 | OCH₃ | OCH₃ | H |
| 7 | OCH₃ | OCH₂CF₃ | H |
| 8 | OCH₃ | OCH₂CH₂CH₂-(4-morpholine) | H |
| 9 | OCH₃ | OCH₂-(4-(1-methyl)piperidine) | H |
| 10 | OCH₃ | OCH₃ | OCH₃ |
| 11 | F | H | H |
| 12 | OCH₃ | benzyloxy | H |
| 13 | OCH₃ | OH | H |
| 14 | OCH₃ | [epoxide-CH₂-O-* group] | H |
| 15 | OCH₃ | [epoxide-CH₂-O-* group] | H |
| 16 | OCH₃ | (S)—OCH₂CH(OH)CH₂-(3-hydroxy-1-pyrrolidine) | H |
| 17 | OCH₃ | (S)—OCH₂CH(OH)CH₂-(1-azetidine) | H |
| 18 | OCH₃ | (S)—OCH₂CH(OH)CH₂-(1-pyrrolidine) | H |
| 19 | OCH₃ | (S)—OCH₂CH(OH)CH₂-(1-piperidine) | H |
| 20 | OCH₃ | (S)—OCH₂CH(OH)CH₂NH-(cyclobutyl) | H |
| 21 | OCH₃ | (S)—OCH₂CH(OH)CH₂NH-(cyclopentyl) | H |

TABLE 2-continued

| N°. | R² | R³ | R⁴ |
|---|---|---|---|
| 22 | OCH₃ | (S)—OCH₂CH(OH)CH₂—NHCH₂(5-methyl-2-furyl) | H |
| 23 | OCH₃ | (S)—OCH₂CH(OH)CH₂—NHCH₂(2-thiophene) | H |
| 24 | OCH₃ | (S)—OCH₂CH(OH)CH₂NH-(2-hydroxyethyl) | H |
| 25 | OCH₃ | (S)—OCH₂CH(OH)CH₂NH-(2-(thioethyl)ethyl) | H |
| 26 | OCH₃ | OCH₂CH₂NHCH₂CH₂N(CH₃)₂ | H |
| 27 | OCH₃ | OCH₂CH₂NH-(4-hydroxy-n-butyl) | H |
| 28 | OCH₃ | OCH₂CH₂NHC(CH₃)₂CH₂OH | H |
| 29 | OCH₃ | OCH₂CH₂NHCH₂-(cyclopropyl) | H |
| 30 | OCH₃ | OCH₂CH₂NHCH₂-(2-tetrahydrofuryl) | H |
| 31 | OCH₃ | OCH₂CH₂-(1-piperidine) | H |
| 32 | OCH₃ | OCH₂CH₂CH₂NH-(4-hydroxy-n-butyl) | H |
| 33 | OCH₃ | OCH₂CH₂CH₂NHC(CH₃)₂CH₂OH | H |
| 34 | OCH₃ | OCH₂CH₂CH₂NHCH₂-(cyclopropyl) | H |
| 35 | OCH₃ | OCH₂CH₂CH₂NHCH₂-(2-tetrahydrofuryl) | H |
| 36 | OCH₃ | OCH₂CH₂CH₂-(1-pyrrolidine) | H |
| 37 | OCH₃ | OCH₂CH₂CH₂-(4-hydroxy-1-piperidine) | H |
| 38 | OCH₃ | OCH₂-(2-(4-benzylmorpholine)) | H |
| 39 | OCH₃ | (S)—OCH₂CH(OH)CH₂-(4-carboxamido-1-piperidine) | H |
| 40 | OCH₃ | (S)—OCH₂CH(OH)CH₂NHC(CH₂CH₃)(CH₂OH)₂ | H |
| 41 | OCH₃ | (S)—OCH₂CH(OH)CH₂NHC(CH₃)₂CH₂CH₂OH | H |
| 42 | OCH₃ | (S)—OCH₂CH(OH)CH₂NHC(CH₃)₂CH₂OH | H |
| 43 | OCH₃ | (S)—OCH₂CH(OH)CH₂NH-(cyclohexyl) | H |
| 44 | OCH₃ | (S)—OCH₂CH(OH)CH₂NH-(1-methyl-2-hydroxyethyl) | H |
| 45 | OCH₃ | (S)—OCH₂CH(OH)CH₂NHCH₂C(CH₃)₂CH₂OH | H |
| 46 | OCH₃ | (S)—OCH₂CH(OH)CH₂NHCH₂-(1-ethyl-2-pyrrolidinyl) | H |
| 47 | OCH₃ | (S)—OCH₂CH(OH)CH₂NHCH₂-(cyclohexyl) | H |
| 48 | OCH₃ | OCH₂CH₂-(1-(2-methyl-4,5-dihydroimidazole)) | H |
| 49 | OCH₃ | OCH₂CH₂-(1-(2-ethyl-4,5-dihydroimidazole)) | H |
| 50 | OCH₃ | OCH₂CH₂-(1-(1,4,5,6-tetrahydropyrimidine)) | H |
| 51 | OCH₃ | OCH₂CH₂-(1-(4,5-dihydroimidazole)) | H |
| 52 | OCH₃ | OCH₂CH₂NHCO-(tert-butoxy) | H |
| 53 | OCH₃ | 3-chloropropoxy | H |
| 54 | OCH₃ | (S)—OCH₂C(CH₃)(OH)CH₂O-(4-nitrobenzoyl) | H |
| 55 | OCH₃ | OCH₂-(3-(4-benzylmorpholine)) | H |
| 56 | OCH₃ | (S)—OCH₂CH(OH)CH₂-(4-morpholine) | H |
| 57 | OCH₃ | OCH₂CH₂CH₂-(1-(4,5-dihydroimidazole)) | H |
| 58 | OCH₃ | (S)—OCH₂C(CH₃)(OH)CH₂-(1-piperidine) | H |
| 59 | OCH₃ | (S)—OCH₂C(CH₃)(OH)CH₂NH-(cyclopentyl) | H |
| 60 | OCH₃ | (S)—OCH₂C(CH₃)(OH)CH₂NH-(cyclohexyl) | H |
| 61 | OCH₃ | (S)—OCH₂C(CH₃)(OH)CH₂-(4-morpholine) | H |
| 62 | OCH₃ | (S)—OCH₂C(CH₃)(OH)CH₂-(1-pyrrolidine) | H |
| 63 | OCH₃ | (S)—OCH₂C(CH₃)(OH)CH₂NH-(2-(thioethyl)ethyl) | H |
| 64 | OCH₃ | OCH₂CH₂CH₂-(1-piperidine) | H |

TABLE 2-continued

Structure: quinazoline with R2, R3, R4 substituents and 4-(pyrimidin-2-yl benzamide-NH) group

| N°. | R² | R³ | R⁴ |
|---|---|---|---|
| 65 | OCH₃ | (dibenzyl phosphate of 1-piperidinyl-3-methoxy-propan-2-yl) | H |
| 66 | OCH₃ | (phosphate of 1-piperidinyl-3-methoxy-propan-2-yl) | H | where * indicates the point of attachment to the quinazoline ring.

TABLE 3

Structure: 6-methoxy-quinazoline with R³ at position 7, linked through pyrimidine-NH-CO-R¹⁰⁷

| N°. | R³ | R¹⁰⁷ |
|---|---|---|
| 67 | OCH₂CH₂CH₂-(4-morpholine) | 4-chlorophenyl |
| 68 | benzyloxy | 4-chlorophenyl |
| 69 | OH | 4-chlorophenyl |
| 70 | (glycidyloxymethyl *) | 4-chlorophenyl |
| 71 | (R)—OCH₂CH(OH)CH₂-(1-pyrrolidine) | 4-chlorophenyl |
| 72 | (R)—OCH₂CH(OH)CH₂-(1-piperidine) | 4-chlorophenyl |
| 73 | (R)—OCH₂CH(OH)CH₂NH-(cyclopentyl) | 4-chlorophenyl |
| 74 | (R)—OCH₂CH(OH)CH₂NH-(cyclohexyl) | 4-chlorophenyl |
| 75 | 2-bromoethoxy | 4-chlorophenyl |
| 76 | OCH₂CH₂-(1-pyrrolidine) | 4-chlorophenyl |
| 77 | OCH₂CH₂-(1-piperidine) | 4-chlorophenyl |
| 78 | OCH₂CH₂—NH(cyclopentyl) | 4-chlorophenyl |
| 79 | OCH₂CH₂—NH(cyclohexyl) | 4-chlorophenyl |
| 80 | OCH₂CH₂—NHCH₂-(cyclopropyl) | 4-chlorophenyl |
| 81 | OCH₂CH₂—NHCH₂-(2-tetrahydrofuryl) | 4-chlorophenyl |
| 82 | (glycidyloxymethyl *) | 3-chlorophenyl |
| 83 | (glycidyloxymethyl *) | 4-fluorophenyl |
| 84 | (S)—OCH₂CH(OH)CH₂-(1-piperidine) | 3-chlorophenyl |
| 85 | OCH₂-(4-(1-methyl)piperidine) | 3-chloro-4-fluorophenyl |
| 86 | benzyloxy | 3-chloro-4-fluorophenyl |

TABLE 4

Structure: 6-methoxy-7-(3-morpholinopropoxy)-quinazoline linked through pyrimidin-2-yl-NH-R¹⁰⁸

| N°. | R¹⁰⁸ |
|---|---|
| 87 | H |
| 88 | CO-(4-pyridyl) |
| 89 | CO-(2,4-difluorophenyl) |
| 90 | CO-(3-bromo-4-fluorophenyl) |
| 91 | CO-(3-bromo-4-tolyl) |
| 92 | CO-(3-(trifluoromethyl)phenyl) |
| 93 | CO-(3-chlorophenyl) |
| 94 | CO-(3,4-dichlorophenyl) |
| 95 | CO-(3-chloro-4-fluorophenyl) |
| 96 | CO-(3,5-dichlorophenyl) |
| 97 | CO-(3-cyanophenyl) |
| 98 | CO-(3-fluorophenyl) |
| 99 | CO-(3,5-dichloro-4-nitrophenyl) |
| 100 | CO-(3,5-dimethylphenyl) |
| 101 | CO-(3-nitro-4-chlorophenyl) |
| 102 | CO-(3,4-methylenedioxyphenyl) |
| 103 | CO-(3-methoxyphenyl) |
| 104 | CO-(3-phenoxyphenyl) |
| 105 | CO-(4-bromophenyl) |
| 106 | CO-(4-ethylphenyl) |

TABLE 4-continued

| Nº. | R¹⁰⁸ |
|---|---|
| 107 | CO-(4-fluorophenyl) |
| 108 | CO-(4-nitrophenyl) |
| 109 | CO-(4-methoxyphenyl) |
| 110 | CO-(4-(methylthio)phenyl) |
| 111 | CO-(2-furyl) |
| 112 | CO-(1-methyl-2-pyrrolyl) |
| 113 | CO-(2-thiophene) |
| 114 | CO—CH₂CH₂—Ph |
| 115 | CO-(4-tolyl) |
| 116 | CO—CH₂CH₂CH₂-cyclohexyl |
| 117 | CO-n-butyl |
| 118 | CO-cyclopentyl |
| 119 | CO-cyclohexyl |
| 120 | CO-(2-chlorophenyl) |
| 121 | CO-(4-(N,N-di-n-propylsulphamoyl)phenyl) |
| 122 | CO-(2-(trifluoromethyl)-4-fluoro-phenyl) |
| 123 | CO-(2-chloro-4,5-difluorophenyl) |

TABLE 5

| Nº. | R¹⁰⁹ |
|---|---|
| 124 | OH |
| 125 | NH—Ph |
| 126 | NH-cyclohexyl |
| 127 | NH-(4-chlorophenyl) |
| 128 | NH-(4-tolyl) |
| 129 | NH-(2-quinolyl) |
| 130 | NH-(2,3-dichlorophenyl) |
| 131 | NH-(1-methyl-5-pyrazolyl) |
| 132 | NH-(3-methyl-4-nitro-5-isoxazolyl) |
| 133 | NH-(2-chlorophenyl) |
| 134 | NH-(2-chloro-5-nitrophenyl) |
| 135 | NH-(2-nitrophenyl) |
| 136 | NH-(2-(methylthio)phenyl) |
| 137 | NH-(3-cyanophenyl) |
| 138 | NH-(3-fluorophenyl) |
| 139 | NH-(3,4-dichlorophenyl) |
| 140 | NH-(3-methoxyphenyl) |
| 141 | NH-(3-(trifluoromethyl)phenyl) |
| 142 | NH-(4-nitrophenyl) |
| 143 | NH-(3-methylbutyl) |
| 144 | NH-(5-carbomethoxy-2-furyl) |
| 145 | NHCH₂-(3-(trifluoromethyl)phenyl) |
| 146 | NH-n-heptyl |
| 147 | NHCH₂-(4-fluorophenyl) |

TABLE 5-continued

| Nº. | R¹⁰⁹ |
|---|---|
| 148 | NH-(2-carbomethoxy-4-methyl-3-thiophene) |
| 149 | NHCH₂CH₂-(1-cyclohexenyl) |
| 150 | NH-(3,5-dimethyl-2-pyrazinyl) |
| 151 | NHCH₂CH₂-(2-thiophene) |
| 152 | NH-(2-fluoro-5-nitrophenyl) |
| 153 | NH-cyclopropyl |
| 154 | NHCH₂-cyclopropyl |
| 155 | NH-cyclobutyl |
| 156 | NH-cyclopentyl |
| 157 | NH-2-indanyl |
| 158 | NHCH₂-cyclohexyl |
| 159 | NH-(6-chloro-3-pyridyl) |
| 160 | NHCH₂-(4-nitrophenyl) |
| 161 | NHCH₂-(2-tetrahydrofuryl) |
| 162 | NHCH₂CH₂(5-methyl-3-indolyl) |
| 163 | NH-2-pyridyl |
| 164 | NH-3-pyridyl |
| 165 | NH-4-pyridyl |
| 166 | NH-(1-isoquinolyl) |
| 167 | NH-(2,4-dinitrophenyl) |
| 168 | NH-(3-(trifluoromethyl)-4-nitrophenyl) |
| 169 | NH-(2-cyanophenyl) |
| 170 | NH-(2-fluorophenyl) |
| 171 | NH-(2,4-difluorophenyl) |
| 172 | NHCH₂-(3-chloro-4-fluorophenyl) |
| 173 | NHCH₂-(2,2-dimethyl-tetrahhydropyran) |
| 174 | NH-(3-(methylthio)propyl) |
| 175 | NH-(3-(3-methyl-4-pyrazolyl)propyl) |
| 176 | NH-(5-methyl-2-thiazolyl) |
| 177 | NH-(4-fluorophenyl) |
| 178 | NH-(4-(methylthio)phenyl) |
| 179 | NHCH₂—Ph |
| 180 | NHCH₂-(2-tolyl) |
| 181 | NHCH₂-(3,4-dichlorophenyl) |
| 182 | NH-(3-ethoxypropyl) |
| 183 | NH-(3-(1-imidazolyl)propyl) |
| 184 | NHCH₂-(2,4-difluorophenyl) |
| 185 | NH-(3-(1-pyrrolidinyl)propyl) |
| 186 | NHCH₂-(3-thiophene) |
| 187 | NH-(3-tetrahydrothiophene-1,1-dioxide) |
| 188 | NHCH₂-(2-(1,4-dioxan)) |
| 189 | NHCH₂-(4-(dimethylamino)phenyl) |
| 190 | NH-(3-phenylpropyl) |
| 191 | NHCH₂CH₂-(4-pyridyl) |
| 192 | NHCH₂-(3-chlorophenyl) |
| 193 | NH-(3-bromo-4-methylphenyl) |
| 194 | NH-(5-ethyl-2-thiadiazolyl) |
| 195 | NH-(2-pyrazinyl) |
| 196 | NH-(3-chlorophenyl) |
| 197 | NH-(3,5-dichlorophenyl) |
| 198 | NHCH₂-(2-chlorophenyl) |
| 199 | NHCH₂-(3-tolyl) |
| 200 | NHCH₂CH₂—Ph |
| 201 | NHCH₂-(2,5-difluorophenyl) |
| 202 | NHCH₂-(3,4-difluorophenyl) |
| 203 | NH-(3-methoxyphenyl) |
| 204 | NH-(2-thiadiazolyl) |
| 205 | NHCH₂-(2-furyl) |

TABLE 5-continued

Structure: 6-methoxy-quinazoline with R³ at 7-position, 4-position bearing NH-pyrimidin-5-yl, pyrimidin-2-yl substituted with NH-C(=O)-R¹⁰⁷

| N°. | R¹⁰⁹ |
|---|---|
| 206 | NH-(3-chloro-4-fluorophenyl) |
| 207 | NHCH₂-(3,5-dimethylphenyl) |
| 208 | NH-(4-methoxyphenyl) |
| 209 | NHCH₂-(2-fluorophenyl) |
| 210 | NHCH₂-(2-methoxyphenyl) |
| 211 | NHCH₂-(3-fluorophenyl) |
| 212 | NHCH₂-(4-chlorophenyl) |
| 213 | NHCH₂-(4-tolyl) |
| 214 | NH-(4-bromophenyl) |
| 215 | NH-(iso-propyl) |
| 216 | NH-((R)—sec-butyl) |
| 217 | NH-((S)—sec-butyl) |
| 218 | NH-(4-(dimethylamino)phenyl) |
| 219 | NH—CH₂CH₂-cyclopropyl |

TABLE 6

Structure: 6-methoxy-quinazoline with R³, 4-NH-pyrimidin-5-yl, pyrimidin-2-yl-C(=O)NH-R¹¹⁰

| N°. | R³ | R¹¹⁰ |
|---|---|---|
| 220 | benzyloxy | 3-chloro-4-fluorophenyl |
| 221 | benzyloxy | 2,4-difluorophenyl |
| 222 | OH | 2,4-difluorophenyl |
| 223 | OH | 3-chloro-4-fluorophenyl |
| 224 | 3-chloropropoxy | 3-chloro-4-fluorophenyl |
| 225 | 3-chloropropoxy | 2,4-difluorophenyl |
| 226 | glycidyloxymethyl* | 3-chloro-4-fluorophenyl |
| 227 | glycidyloxymethyl* | 2,4-difluorophenyl |
| 228 | benzyloxy | 2-(cyclopropyl)ethyl |
| 229 | (R)—OCH₂CH(OH)CH₂-(1-piperidine) | 3-chloro-4-fluorophenyl |
| 230 | OCH₂CH₂CH₂—NHCH₂(cyclopropyl) | 2,4-difluorophenyl | where * is the point of attachment to the quinazoline ring

TABLE 7

Structure: 6-methoxy-7-(3-morpholinopropoxy)-quinazoline, 4-NH-pyrimidin-5-yl, pyrimidin-2-yl-R¹¹¹

| N°. | R¹¹¹ |
|---|---|
| 231 | CN |
| 232 | 4-pyridyl |
| 233 | 4-carboxamidophenyl |
| 234 | CH₂NH—CO-(benzyloxy) |
| 235 | CH₂NH₂ |
| 236 | CH₂NH(4-chlorophenyl) |
| 237 | CH₂NH(2-(methylthio)phenyl) |
| 238 | CH₂NH(2,3-difluorophenyl) |
| 239 | CH₂NH(3-chloro-4-fluorophenyl) |
| 240 | CH₂NHCO-(iso-butyl) |
| 241 | CH₂NH—CO-(4-chlorophenyl) |
| 242 | CH₂NH—CO—CH₂-(4-chlorophenyl) |
| 243 | CH₂NH—CO—CH₂CH₂-(4-chlorophenyl) |
| 244 | CH₂NH(3-methylbutyl) |
| 245 | CH₂NH—CH₂CH₂(1-cyclohexenyl) |
| 246 | CH₂NH(5-nitro-2-pyridyl) |
| 247 | CH₂NH(3-nitro-2-pyridyl) |
| 248 | CH₂NH(3,4-difluorophenyl) |
| 249 | CH₂NH(2,4-difluorophenyl) |
| 250 | CH₂NH(4-fluorophenyl) |
| 251 | CH₂NH(2-chloro-4-fluorophenyl) |

TABLE 8

Structure: 6-methoxy-quinazoline with R³, 4-NH-pyrimidin-5-yl, pyrimidin-2-yl-R¹¹²

| N°. | R³ | R¹¹² |
|---|---|---|
| 252 | benzyloxy | CH₂NH-(3-chloro-4-fluorophenyl) |
| 253 | OH | CH₂NH-(3-chloro-4-fluorophenyl) |
| 254 | (R)—OCH₂CH(OH)CH₂-(1-piperidine) | CH₂NH-(3-chloro-4-fluorophenyl) |
| 255 | OCH₂CH₂CH₂-(4-morpholine) | OCH₂-(3-chloro-4-fluorophenyl) |

TABLE 9

| N°. | R² | R³ |
|---|---|---|
| 256 | OCH₂CH₂CH₂-(4-morpholine) | OCH₃ |
| 257 | NO₂ | F |
| 258 | NO₂ | benzyloxy |
| 259 | NO₂ | OCH₂-(4-(1-methyl)piperidine) |
| 260 | NH₂ | F |
| 261 | 2-methoxyethoxy | 2-methoxyethoxy |
| 262 | NH—(OH) | OCH₂-(4-(1-methyl)piperidine) |

TABLE 10

| N°. | R¹¹³ |
|---|---|
| 263 | Ph |
| 264 | 5-methyl-2-pyrazinyl |
| 265 | 2-pyridiyl |
| 266 | 2-quinolinyl |
| 267 | 2-chloro-5-nitrophenyl |
| 268 | 2-nitro-3-methoxyphenyl |
| 269 | 2,4-dinitrophenyl |
| 270 | 2-(methylthio)phenyl |
| 271 | cyclopentyl |
| 272 | E-styrenyl |
| 273 | 4-methoxybenzyl |
| 274 | 3-thiophene |

TABLE 11

| N°. | R¹¹⁴ |
|---|---|
| 275 | NH—CO-(2-thiophene) |
| 276 | NH—CO—CH₂-(2-thiophene) |
| 277 | Cl |
| 278 | NH—CO-(3,5-dichlorophenyl) |
| 279 | NH—CO—Ph |
| 280 | NH—CO-(4-chlorophenyl) |
| 281 | NH—CO-(3,4-dichlorophenyl) |
| 282 | NH—CO-(3-chloro-4-fluorophenyl) |

TABLE 12

| N°. | R¹¹⁵ |
|---|---|
| 283 | CO—Ph |
| 284 | n-butoxy |
| 285 | Br |
| 286 | 1-pyrrolidinyl |
| 287 | NH-n-hexyl |
| 288 | 1-(4-(4-cyanophenyl)piperazinyl |
| 289 | 1-piperidinyl |
| 290 | NH-cyclopropyl |
| 291 | NH-cyclohexyl |
| 292 | NH-n-propyl |
| 293 | NHCH₂—Ph |
| 294 | NHSO₂-(4-tolyl) |
| 295 | 4-chlorophenoxy |
| 296 | benzyloxy |

TABLE 13

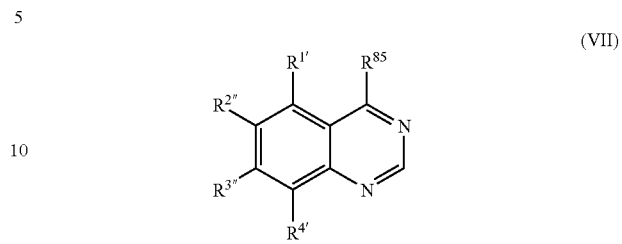

| N°. | R116 | R117 |
|---|---|---|
| 297 | trifluoromethyl | H |
| 298 | 3-pyridyloxy | H |
| 299 | 4-chlorophenoxy | H |
| 300 | 3-pyridylmethoxy | H |
| 301 | 3,4-dichlorobenzyloxy | H |
| 302 | 3,5-dichlorobenzyloxy | H |
| 303 | 3-fluorobenzyloxy | H |
| 304 | 4-(trifluomethyl)benzyloxy | H |
| 305 | 4-chlorobenzyloxy | H |
| 306 | benzyloxy | H |
| 307 | 3-chlorobenzyloxy | H |
| 308 | 2,3-difluorobenzyloxy | H |
| 309 | 4-fluorobenzyloxy | H |
| 310 | 2-chlorobenzyloxy | H |
| 311 | 2-chloro-4-fluorobenzyloxy | H |
| 312 | 3-chloro-4-fluorobenzyloxy | H |
| 313 | 4-chlorobenzyloxy | CH$_3$ |
| 314 | benzyloxy | CH$_3$ |
| 315 | 4-fluorobenzyloxy | CH$_3$ |
| 316 | 4-methylbenzyloxy | CH$_3$ |
| 317 | 3-chlorobenzyloxy | CH$_3$ |
| 318 | 2,3-difluorobenzyloxy | CH$_3$ |
| 319 | 2-chloro-4-fluorobenzyloxy | CH$_3$ |
| 320 | SCH$_2$—Ph | H |
| 321 | SCH$_2$-(3,4-dichlorophenyl) | H |
| 322 | SCH$_2$-(4-fluorophenyl) | H |
| 323 | NHCH$_2$-(4-fluorophenyl) | H |
| 324 | NHCH$_2$-(3,4-dichlorophenyl) | H |
| 325 | NHCH$_2$-(3,5-dichlorophenyl) | H |
| 326 | NHCH$_2$—Ph | CH$_3$ |

TABLE 14

| N°. | R$^3$ | R118 |
|---|---|---|
| 327 | benzyloxy | 4-chlorophenyl |
| 328 | benzyloxy | 3-pyridyl |
| 329 | OCH$_2$CH$_2$CH$_2$—NHCH$_2$CH$_2$CH$_2$-(4-morpholine) | 3-chlorobenzyl |
| 330 | OCH$_2$CH$_2$CH$_2$—NHCH$_2$CH$_2$CH$_2$N(CH$_3$)$_2$ | 3-chlorobenzyl |
| 331 | OCH$_2$CH$_2$CH$_2$—N(CH$_3$)CH$_2$CH$_2$OH | 3-chlorobenzyl |
| 332 | OCH$_2$CH$_2$CH$_2$-(4-morpholine) | 3-chlorobenzyl |
| 333 | OCH$_2$CH$_2$CH$_2$-(1-piperazine) | 3-chlorobenzyl |
| 334 | OCH$_2$CH$_2$CH$_2$-(1-pyrrolidine) | 3-chlorobenzyl |
| 335 | OCH$_2$CH$_2$CH$_2$—NHC(CH$_3$)$_2$CH$_2$OH | 3-chlorobenzyl |

Compounds of formula (I) may be prepared by various methods which would be apparent from the literature. For example compounds of formula (I)

(VII)

where $R^{1'}$, $R^{2''}$, $R^{3'''}$, and $R^{4'}$ are equivalent to a group $R^1$, $R^2$, $R^3$ and $R^4$ as defined in relation to formula (I) or a precursor thereof, and $R^{85}$ is a leaving group, with a compound of formula (VIII)

$$H—X—R^5 \quad (VIII)$$

where X and $R^5$ are as defined in relation to formula (I): and thereafter if desired or necessary converting a group $R^{1'}$, $R^{2''}$, $R^{3'''}$ or $R^{4'}$ to a group $R^1$, $R^2$, $R^3$ and $R^4$ respectively or to a different such group.

Suitable leaving groups for $R^{85}$ include halo such as chloro, mesylate and tosylate. The reaction is suitably effected in an organic solvent such as an alcohol like isopropanol, at elevated temperatures, conveniently at the reflux temperature of the solvent.

The conversion of a group $R^{1'}$, $R^{2''}$, $R^{3'''}$ or $R^{4'}$ to a group $R^1$, $R^2$, $R^3$ and $R^4$ respectively or to a different such group, may be particularly useful in connection with the preparation of compounds of formula (I) where these groups are complex in nature and examples of these preparations are provided hereinafter.

In a particular embodiment, $R^{1'}$, $R^{2''}$, $R^{3'''}$ or $R^{4'}$ are groups $R^1$, $R^2$, $R^3$ and $R^4$ respectively.

Compounds of formula (VII) and (VIII) are either known compounds or they can be derived from known compounds by conventional methods. For example, where in the compound of formula (VIII), $R^5$ carries a substituent group $R^{80}$, this may be introduced into the ring using known chemistry. For example, compounds of formula (IX) where X is an NH group may be prepared by reduction of a compound of formula (IX)

$$O_2N—R^5 \quad (IX)$$

for example by reaction with hydrogen in the presence of a catalyst such as a palladium catalyst or by reaction with a reducing agent such as sodium hydrosulphite.

Compounds of formula (IX) where $R^5$ is a group of formula (i), (ii), (iii), (iv) or (v) above and $R^{80}$ is a group of formula (II) above can be prepared by reacting a compound of formula (X)

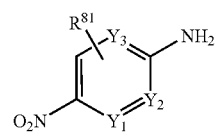

(X)

where $R^{81}$ is as defined above and $Y_1$, $Y_2$ and $Y_3$ are selected from N, CH or $CR^{81}$ as appropriate, with a compound of formula (XI)

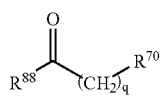
(XI)

where $R^{70}$ and q are as defined in relation to sub-formula (II) and $R^{88}$ is a leaving group such as halo. The reaction is suitably effected in the presence of a base such as pyridine at elevated temperatures, conveniently at the reflux temperature of the solvent.

Compounds of formula (I) are inhibitors of aurora 2 kinase. As a result, these compounds can be used to treat disease mediated by these agents, in particular proliferative disease.

According to a further aspect of the invention there is provided a compound of the formula (I) as defined herein, or a pharmaceutically acceptable salt or an in vivo hydrolysable ester thereof, for use in a method of treatment of the human or animal body by therapy. In particular, the compounds are used in methods of treatment of proliferative disease such as cancer and in particular cancers such as colorectal or breast cancer where aurora 2 is upregulated.

According to a further aspect of the present invention there is provided a method for inhibiting aurora 2 kinase in a warm blooded animal, such as man, in need of such treatment, which comprises administering to said animal an effective amount of a compound of formula (I), or a pharmaceutically acceptable salt, or an in vivo hydrolysable ester thereof.

The invention also provides a pharmaceutical composition comprising a compound of formula (I) as defined herein, or a pharmaceutically acceptable salt, or an in vivo hydrolysable ester thereof, in combination with at pharmaceutically acceptable carrier. Preferred compounds of formula (I) for use in the compositions of the invention are as described above.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid.

Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain alphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate), anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the return to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30µ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of aurora 2 kinase.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

A further aspect of the invention comprises a compound of formula (I) as defined above, or a pharmaceutically acceptable salt or in vivo hydrolysable ester thereof, for use in the preparation of a medicament for the treatment of proliferative disease. Preferred compounds of formula (I) for this purpose are as described above.

The treatment defined hereinbefore may be applied as a sole therapy or may involve, in addition to the compounds of the invention, one or more other substances and/or treatments. Such conjoint treatment may be achieved by way of simultaneous, sequential or separate administration of the individual components of the treatment. In the field of medical oncology it is normal practice to use a combination of different forms of treatment to treat each patient with cancer. The other components of such conjoint treatment may be, for example, surgery, radiotherapy or chemotherapy. Such chemotherapy may include one or more of the following categories of therapeutic agents:

(i) anti-invasion agents (for example metalloproteinase inhibitors like marimastat and inhibitors of urokinase plasminogen activator receptor function);

(ii) anti-proliferative/anti-neoplastic drugs and combinations thereof, as used in medical oncology, such as platinum derivatives (for example cis-platin, carboplatin); alkylating agents (for example cyclophosphamide, nitrogen mustard, melphalan, chlorambucil, busulphan and nitrosoureas); anti-metabolites (for example anti-folates such as fluoropyrimidines like 5-fluorouracil and tegafur, raltitrexed, methotrexate, cytosine arabinoside and hydroxyurea); anti-tumour antibiotics (for example anthracyclines like adriamycin, bleomycin, doxorubicin, daunomycin, epirubicin, idarubicin, mitomycin-C, dactinomycin and mithramycin); anti-mitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as anti-oestrogens (for example tamoxifen, toremifene, raloxifene, droloxifene and iodoxyfene); anti-androgens (for example bicalutamide, flutamide, nilutamide and cyproterone acetate); LHRH antagonists or LHRH agonists (for example goserelin, leuprorelin and buserelin); progestogens (for example megestrol acetate); aromatase inhibitors (for example as anastrozole, letrazole, vorazole and exemestane) and inhibitors of 5-reductase such as finasteride;

(iv) inhibitors of growth factor function, for example such inhibitors include growth factor antibodies, growth factor receptor antibodies, tyrosine kinase inhibitors and serine/threonine kinase inhibitors, for example inhibitors of the epidermal growth factor family (for example EGFR tyrosine kinase inhibitors) for example inhibitors of the platelet-derived growth factor family and for example inhibitors of the hepatocyte growth factor family; and (v) antiangiogenic agents such as those which inhibit vascular endothelial growth factor such as the compounds disclosed in International Patent Applications WO 97/22596, WO 97/30035, WO 97/32856 and WO 98/13354 and those that work by other mechanisms (for example linomide, inhibitors of integrin αvβ3 function and angiostatin).

Such combination products employ the compounds of this invention within the dosage range described hereinbefore and the other pharmaceutically-active agent within its approved dosage range.

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) operations were carried out at ambient temperature, typically in the range 18–25° C. and in air unless stated, or unless the skilled person would otherwise operate under an atmosphere of an inert gas such as argon;

(iii) column chromatography (by the flash procedure) and medium pressure liquid chromatography (MPLC) were performed on Merck Kieselgel silica (Art. 9385) or on Merck Lichroprep RP-18 (Art. 9303) reversed-phase silica, obtained from E. Merck, Darmstadt, Germany; bond elute chromatography was performed using Varian Mega Bond Elut cartridges (10 g, order code 1225-6034), obtained from Varian Sample Preparation Products, California, USA;

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated DMSOd$_6$ (unless otherwise stated) on the delta scale (ppm downfield from tetramethylsilane) using a Varian Gemini 2000 spectrometer operating at a field strength of 300 MHz, or a Bruker DPX300 spectrometer operating at a field strength of 300 MHz; and peak multiplicities are shown as follows: s, singlet; d, doublet; dd, double doublet; t, triplet; q, quartet; qu, quintet; m, multiplet; bs, broad singlet; mass spectrometry (MS) was performed by electrospray on a VG platform;

(vi) robotic synthesis was carried out using a Zymate XP robot, with solution additions via a Zymate Master Laboratory Station and stirred via a Stem RS5000 Reacto-Station at 25° C.;

(vii) work up and purification of reaction mixtures from robotic synthesis was carried out as follows: evaporations were carried out in vacuo using a Savant AES 2000; column chromatography was performed using either an Anachem Sympur MPLC or Jones Flashmaster MPLC systems on silica using Varian Mega Bond Elut cartridges; the structures of the final products were confirmed by LCMS on a Micromass OpenLynx system using the following and are quoted as retention time (RT) in minutes:

Column: 4.6 mm×3 cm Hichrom RPB
Solvent A: 5% Methanol in Water+0.1% formic acid
Solvent B: 5% Methanol in Acetonitrile+0.1% formic acid
Flow rate: 1.4 ml/min
Run time: 5 minutes with a 4.5 minute gradient from 0–100% B
Wavelength: 254 nm, bandwidth 10 nm
Mass detector: Micromass Platform LC
Injection volume 0.002 ml (vii) Analytical LCMS for compounds which had not been prepared by robotic synthesis was performed on a a Waters Alliance HT system using the following and are quoted as retention time (RT) in minutes:

Column: 2.0 mm×5 cm Phenomenex Max-RP 80A
Solvent A: Water
Solvent B: Acetonitrile
Solvent C: Methanol+1% formic acid
Flow rate: 1.1 ml/min
Run time: 5 minutes with a 4.5 minute gradient from 0–95% B+constant 5% solvent C
Wavelength: 254 nm, bandwidth 10 nm
Injection volume 0.005 ml
Mass detector: Micromass ZMD (viii) Preparative high performance liquid chromatography (HPLC) was performed on a Gilson instrument using the following and are quoted as retention time (RT) in minutes:

Column: 21 mm×10 cm Hichrom RPB
Solvent A: Water+0.1% trifluoracetic acid,
Solvent B: Acetonitrile+0.1% trifluoracetic acid
Flow rate: 18 ml/min
Run time: 15 minutes with a 10 minute gradient from 5–100% B
Wavelength: 254 nm, bandwidth 10 nm
Injection volume 2.0–4.0 ml (ix) intermediates were not generally fully characterised and purity was assessed by thin layer chromatography (TLC), HPLC, infra-red (IR), MS or NMR analysis;

Particular examples of compounds of formula (I) are set out in Table 1

The following Examples illustrate the invention.

EXAMPLE 1

Preparation of Compound 1 in Table 1

Benzoyl chloride (0.175 ml, 1.5 mmol) was added to a solution of 4-(2-amino-5-pyrimidinamino)-6,7-dimethoxyquinazoline (300 mg, 1.0 mmol) in pyridine (10 ml). The reaction was stirred at 0° C. for 1 hour, then the solvent was removed in vacuo. Purification by flash chromatography on silica gel, eluting with 5% methanol in dichloromethane containing 1% triethylamine yielded the title compound (260 mg, 64% yield) as an orange solid:

$^1$H-NMR (DMSO-d$_6$): 10.63 (s, 1H), 9.12 (s, 2H), 8.61 (s, 1H), 8.01 (d, 2H), 7.96 (s, 1H), 7.50–7.66 (m, 3H), 7.27 (s, 1H), 3.96 (s, 3H), 3.94 (s, 3H):

MS (−ve ESI): 401 (M−H)$^-$,
MS (+ve ESI): 403 (M+H)$^+$.

4-chloro-6,7-dimethoxyquinazoline used as the starting material was obtained as follows:

a) A mixture of 4,5-dimethoxyanthranilic acid (19.7 g, 100 mmol) and formamide (10 ml) was heated at 190° C. for 5 hours. The mixture was allowed to cool to approximately 80° C. and water (50 ml) was added. The mixture was then allowed to stand at ambient temperature for 3 hours. Collection of the solid by suction filtration, followed by washing with water (2×50 ml) and drying in vacuo, yielded 6,7-dimethoxy-3,4-dihydroquinazolin-4-one (3.65 g, 18% yield) as a white solid:

¹H-NMR (DMSO-d₆): 12.10 (s, 1H), 7.95 (s, 1H), 7.42 (s, 1H), 7.11 (s, 1H), 3.88 (s, 3H), 3.84 (s, 3H):

MS (−ve ESI): 205 (M−H)⁻.

b) Dimethylformamide (0.2 ml) was added dropwise to a solution of 6,7-dimethoxy-3,4-dihydroquinazolin-4-one (10.0 g, 48.5 mmol) in thionyl chloride (200 ml) and the reaction was heated at reflux for 6 hours. The reaction was cooled, excess thionyl chloride was removed in vacuo and the residue was azeotroped with toluene (2×50 ml) to remove the last of the thionyl chloride. The residue was taken up in dichloromethane (550 ml), the solution was washed with saturated aqueous sodium hydrogen carbonate solution (2×250 ml) and the organic phase was dried over magnesium sulphate. Solvent evaporation in vacuo yielded 4-chloro-6,7-dimethoxyquinazoline (10.7 g, 98% yield) as a white solid:

¹H-NMR (DMSO-d₆): 8.86 (s, 1H), 7.42 (s, 1H), 7.37 (s, 1H), 4.00 (s, 3H), 3.98 (s, 3H):

MS (+ve ESI): 225 (M−H)⁺.

c) 60% Sodium hydride in oil (0.4 g, 10 mmol) was slowly added to a solution of 4-chloro-6,7-dimethoxyquinazoline (1.12 g, 5 mmol) and 2-amino-5-nitropyrimidine (1.05 g, 7.5 mmol) in dimethylacetamide (50 ml) at 100° C. under an inert atmosphere for 30 minutes. The mixture was cooled then water (10 ml) was added and the solvents evaporated in vacuo. Purification by flash chromatography on silica gel, eluting with 1–3% methanol in dichloromethane yielded 4-(2-amino-5-nitropyrimidino)-6,7-dimethoxyquinazoline (1.38 g, 84% yield) as an orange solid:

¹H-NMR (DMSO-d₆): 9.34 (s, 2H), 8.78 (s, 1H), 7.65 (s, 1H), 7.35 (s, 1H), 3.98 (s, 3H), 3.90 (s, 3H):

MS (+ve ESI): 329 (M−H)+.

d) 10% Palladium on carbon (100 mg, 0.094 mmol) was added to a stirred suspension of 4-(2-amino-5-nitropyrimidino)-6,7-dimethoxyquinazoline (1.37 g, 4.19 mmol) in ethanol (100 ml) at ambient temperature and the reaction stirred for 6 hours under an atmosphere of hydrogen. The reaction was filtered through a pad of celite and the solvent was evaporated in vacuo. Purification by flash chromatography on silica gel, eluting with 5–15% methanol in dichloromethane yielded 4-(2-amino-5-pyrimidinamino)-6,7-dimethoxyquinazoline (721 mg, 58% yield) as an orange solid:

¹H-NMR (DMSO-d₆): 8.37 (s, 1H), 8.10 (s, 2H), 7.80 (s, 1H), 7.15 (s, 1H), 5.40 (s, 2H), 3.92 (s, 3H), 3.90 (s, 3H):

MS (+ve ESI): 299 (M−H)+.

EXAMPLE 2

Preparation of Compound 2 in Table 1

An analogous reaction to that described in example 1, but starting with 4-(2-amino-5-pyrimidinamino)-6-methoxy-7-(3-morpholinopropoxy)quinazoline (206 mg, 0.5 mmol) and benzoyl chloride (0.088 mg, 0.75 mmol), yielded the title compound (75 mg, 30% yield) as a white solid:

¹H-NMR (DMSO-d₆): 10.73 (s, 1H), 9.21 (s, 1H), 8.75 (s, 1H), 8.18 (s, 1H), 8.01 (d, 2H), 7.70–7.54 (m, 3H), 7.40 (s, 1H), 4.32 (t, 2H):

MS (−ve ESI): 514 (M−H)⁻,
MS (+ve ESI): 516 (M+H)⁺.

4-(2-amino-5-pyrimidinamino)-6-methoxy-7-(3-morpholinopropoxy)quinazoline, used as the starting material, was obtained as follows:

a) A mixture of morpholine (261 ml, 3.00 mol) and 1-bromo-3-chloropropane (148 ml, 1.50 mol) in toluene (900 ml) was stirred for 18 hours at ambient temperature. Additional 1-bromo-3-chloropropane (25 ml, 0.25 mol) was added, the reaction was stirred for a further 1 hour and then filtered to remove the precipitated solid before the filtrate was concentrated in vacuo. Distillation of the crude oil yielded N-(3-chloropropyl)-morpholine (119.3 g, 49% yield) as the fraction boiling at 70–80° C./2.6 mmHg:

¹H-NMR (DMSO-d₆): 3.65 (t, 2H), 3.55 (m, 4H), 2.40 (t, 2H), 2.39 (m, 4H), 1.85 (m, 2H):

MS (+ve ESI): 164 (M+H)⁺.

b) N-(3-Chloropropyl)morpholine (90 g, 0.55 mol) was added dropwise, over 30 minutes, to a solution of ethyl vanillate (98 g, 0.50 mol) and powdered potassium carbonate (104 g, 0.75 mol) in dimethylformamide (300 ml) at 80° C. The reaction was heated at 80° C. for 90 minutes, cooled to ambient temperature, filtered and the filtrate concentrated in vacuo. The crude product was taken up in diethyl ether (1000 ml), filtered and washed with water (2×200 ml) and brine (200 ml). Solvent evaporation yielded ethyl 3-methoxy-4-(3-morpholinopropoxy)benzoate (161.5 g, 100% yield) as a pale yellow oil which crystallised on standing to afford a pale yellow solid:

¹H-NMR (DMSO-d₆): 7.55 (dd, 1H), 7.40 (d, 1H), 7.05 (d, 1H), 4.30 (q, 2H), 4.05 (t, 2H), 3.80 (s, 3H), 3.55 (m, 4H), 2.40 (t, 2H), 2.35 (m, 4H), 1.90 (m, 2H), 1.30 (t, 3H):

MS (−ve ESI): 324 (M−H)⁻.

c) Concentrated sulphuric acid (110 ml) and concentrated nitric acid (19.0 ml, 0.289 mol) were added cautiously, over a 50 minute period, to a two-phase system containing a stirred solution of ethyl 3-methoxy-4-(3-morpholinopropoxy)benzoate (76.5 g, 0.237 mol) in dichloromethane (600 ml), acetic acid (300 ml) and water (70 ml) at 5° C. The reaction was allowed to warm to ambient temperature over 18 hours, the aqueous phase was separated, and the aqueous phase was taken to pH 9 by addition of 40% aqueous sodium hydroxide solution (775 ml). Extraction of the aqueous phase with dichloromethane (3×600 ml) and subsequent solvent evaporation in vacuo yielded ethyl 3-methoxy-4-(3-morpholinopropoxy)-6-nitrobenzoate (141.3 g, 86% yield) as a yellow gum:

¹H-NMR (CDCl₃): 7.50 (s, 1H), 7.10 (s, 1H), 4.40 (q, 2H), 4.20 (t, 2H), 4.00 (s, 3H), 3.70 (m, 4H), 2.50 (t, 2H), 2.45 (m, 4H), 2.05 (m, 2H), 1.40 (t, 3H):

MS (+ve ESI): 369 (M+H)⁺.

d) A suspension of ethyl 3-methoxy-4-(3-morpholinopropoxy)-6-nitrobenzoate (132.2 g, 359 mmol) and 10% palladium on carbon (3.0 g) in a mixture of ethanol (200 ml) and ethyl acetate (2000 ml) was stirred under an atmosphere of hydrogen for 18 hours. Removal of the catalyst by filtration, followed by solvent evaporation in vacuo yielded ethyl 3-methoxy-4-(3-morpholinopropoxy)-6-aminobenzoate (122 g, 100% yield) as a brown oil:

¹H-NMR (DMSO-d₆): 7.15 (s, 1H), 6.40 (s, 2H), 6.35 (s, 1H), 4.20 (q, 2H), 3.95 (t, 2H), 3.65 (s, 3H), 3.55 (m, 4H), 2.40 (t, 2H), 2.35 (m, 4H), 1.85 (m, 2H), 1.25 (t, 3H):

MS (−ve ESI): 337 (M−H)⁻,
MS (+ve ESI): 339 (M+H)⁺.

e) A solution of ethyl 3-methoxy-4-(3-morpholinopropoxy)-6-aminobenzoate (130 g, 384 mmol) in formamide (280 ml) was heated at 180° C. for 3 hours, during which time a small amount (25 ml) of liquid distilled out of the reaction. The reaction was cooled to 125° C. and the excess formamide was evaporated in vacuo. Trituration of the solid residue with isopropanol (100 ml), followed by drying in vacuo, yielded 6-methoxy-7-(3-morpholinopropoxy)-3,4-dihydroquinazolin-4-one (83.0 g, 68% yield) as a pale brown solid:

$^1$H-NMR (DMSO-$d_6$): 12.01 (s, 1H), 7.95 (s, 1H), 7.45 (s, 1H), 7.10 (s, 1H), 4.15 (t, 2H), 3.85 (s, 3H), 3.60 (m, 4H), 2.45 (t, 2H), 2.35 (m, 4H), 1.90 (m, 2H):

MS (−ve ESI): 318 (M−H)$^−$,
MS (+ve ESI): 320 (M+H)$^+$.

f) Dimethylformamide (2.0 ml) was added dropwise to a solution of 6-methoxy-7-(3-morpholinopropoxy)-3,4-dihydro-quinazolin-4-one (83.0 g, 261 mmol) in thionyl chloride (700 ml) and the reaction was heated at reflux for 3.5 hours. The reaction was cooled, excess thionyl chloride was removed in vacuo, the residue was taken up in water (500 ml) and this aqueous solution was taken to pH 9 by addition of saturated aqueous sodium bicarbonate solution (300 ml). The aqueous phase was extracted with dichloromethane (2×400 ml), the organic solution was washed with brine (400 ml) and the solvents were removed in vacuo. Trituration of the solid residue with ethyl acetate (150 ml), followed by drying in vacuo, yielded 4-chloro-6-methoxy-7-(3-morpholinopropoxy)quinazoline (53 g, 60% yield) as a pale brown solid:

$^1$H-NMR (CDCl$_3$): 8.85 (s, 1H), 7.39 (s, 1H), 7.38 (s, 1H), 4.30 (t, 2H), 4.05 (s, 3H), 3.70 (m, 4H), 2.60 (t, 2H), 2.50 (m, 4H), 2.10 (m, 2H):

MS (+ve ESI): 338 (M+H)$^+$.

g) 60% Sodium hydride in oil (3.2 g, 80 mmol) was slowly added to a solution of 4-chloro-6-methoxy-7-(3-morpholinopropoxy)quinazoline (13.5 g, 40 mmol) and 2-amino-5-nitropyrimidine (8.4 g, 60 mmol) in dimethylacetamide (200 ml) at 100° C. under an inert atmosphere for 30 minutes. The mixture was cooled, water (100 ml) was added and the solvents were evaporated in vacuo. The residue was dissolved in water (250 ml) and washed with dichloromethane (150 ml). The aqueous solution was neutralised with 5.0 N hydrochloric acid and the resulting solid was collected by suction filtration, washed with water and then with acetone. Drying in vacuo yielded 4-(2-amino-5-nitropyrimidino)-6-methoxy-7-(3-morpholinopropoxy) quinazoline (15.1 g, 86% yield) as a light brown solid:

$^1$H-NMR (DMSO-$d_6$): 9.33 (s, 2H), 8.75 (s, 1H), 7.65 (s, 1H), 7.30 (s, 1H), 4.22 (t, 2H), 3.95 (s, 3H), 3.58 (m, 4H), 2.42 (m, 2H), 2.39 (m, 4H), 1.98 (m, 2H):

MS (+ve ESI): 442 (M+H)$^+$.

h) 10% Palladium on carbon (500 mg, 0.475 mmol) was added to a stirred suspension of 4-(2-amino-5-nitropyrimidino)-6-methoxy-7-(3-morpholinopropoxy)quinazoline (5.4 g, 12.2 mmol) in ethanol (250 ml) at ambient temperature and the reaction stirred for 6 hours under an atmosphere of hydrogen. The reaction was filtered through a pad of celite and the solvent evaporated in vacuo to yield crude 4-(2-amino-5-pyrimidinamino)-6,7-dimethoxyquinazoline (4.9 g, 97% yield) as a brown solid:

$^1$H-NMR (DMSO-$d_6$): 8.20 (s, 1H), 8.1 (s, 2H), 7.70 (s, 1H), 7.15 (s, 1H), 5.30 (s, 2H), 4.20 (t, 2H), 3.95 (s, 3H), 3.58 (m, 4H), 2.42 (m, 2H), 2.39 (m, 4H), 1.98 (m, 2H):

MS (+ve ESI): 412 (M−H)$^+$.

EXAMPLE 3

Preparation of Compound 3 in Table 1

An analogous reaction to that described in example 2, but starting with 4-(dimethylamino)benzoyl chloride (138 mg, 0.75 mmol), yielded the title compound (62 mg, 22% yield) as a white solid:

$^1$H-NMR (DMSO-$d_6$): 10.35 (s, 1H), 9.20 (s, 2H), 8.78 (s, 1H), 8.21 (s, 1H), 7.92 (d, 2H), 7.72 (d, 2H), 7.40 (s, 1H), 6.80 (d, 2H), 6.70 (d, 2H), 4.30 (t, 2H), 4.05 (m, 2H), 3.99 (s, 3H), 3.68 (m, 2H), 3.50 (m, 2H), 3.30 (m, 2H), 3.15 (m, 2H), 3.05 (s, 6H), 2.98 (s, 6H), 2.25 (m, 2H):

MS (+ve ESI): 559 (M+H)$^+$.

EXAMPLE 4

Preparation of Compound 4 in Table 1

An analogous reaction to that described in example 2, but starting with 4-nitrobenzoyl chloride (140 mg, 0.75 mmol), yielded the title compound (120 mg, 43% yield) as a white solid:

$^1$H-NMR (DMSO-$d_6$): 11.00 (s, 1H), 9.06 (s, 2H), 8.70 (s, 1H), 8.41 (d, 2H), 8.23 (d, 2H), 8.04 (s, 1H), 7.36 (s, 1H), 4.30 (t, 2H), 4.00 (s, 3H), 3.00–4.01 (m, 10H), 2.17–2.32 (m, 2H):

MS (−ve ESI): 559 (M−H)$^−$,
MS (+ve ESI): 561 (M+H)$^+$.

EXAMPLE 5

Preparation of Compound 5 in Table 1

An analogous reaction to that described in example 2, but starting with 4-nitrobenzene sulphonyl chloride (166 mg, 0.75 mmol), yielded the title compound (105 mg, 35% yield) as a white solid:

$^1$H-NMR (DMSO-$d_6$): 8.63 (s, 1H), 8.42 (s, 2H), 8.40 (d, 2H), 8.03 (d, 2H), 7.92 (s, 1H), 7.31 (s, 1H), 4.28 (t, 2H), 3.92 (s, 3H), 3.00–4.01 (m, 10H), 2.15–2.30 (m, 2H):

MS (+ve ESI): 597 (M+H)$^+$.

EXAMPLE 6

Preparation of Compound No. 6 in Table 2

A solution of 2-(N-benzoyl)-amino-5-aminopyrimidine (91 mg, 0.43 mmol) and 4-chloro-6,7-dimethoxyquinazoline (97 mg, 0.43 mmol), in isopropanol (200 ml) was heated at reflux for 3 hours before the reaction was allowed to cool to ambient temperature. The solid which had precipitated was collected by suction filtration and washed with diethyl ether (2×50 ml). Drying of this material yielded the title compound (109 mg, 58% yield) as a white solid:

$^1$H-NMR (DMSO-$d_6$): 11.79 (s, 1H), 11.11 (s, 1H), 9.11 (s, 1H), 8.88 (s, 1H), 8.41 (s, 1H), 7.98 (d, 2H, J=8 Hz), 7.48–7.64 (m, 3H), 7.36 (s, 1H), 4.04 (s, 3H), 3.99 (s, 3H):

MS (−ve ESI): 403 (M−H)$^−$,
MS (+ve ESI): 401 (M+H)$^+$.

2-(N-Benzoyl)amino-5-aminopyrimidine, used as the starting material was obtained as follows:

a) Benzoyl chloride (0.92 ml, 7.93 mmol) was added dropwise to a stirred solution of 2-amino-5-nitropyrimidine (1.00 g, 7.14 mmol) in pyridine (20 ml) and the reaction was heated at reflux for 4 hours under an inert atmosphere. The reaction was allowed to cool to ambient temperature, poured into water (200 ml) and allowed to stand for 16 hours. The solid was collected by suction filtration, washed with water (3×20 ml) and dried in vacuo. An oil residue on the surface of the aqueous phase was dissolved in dichloromethane (50 ml) and then purified by flash chromatography on silica gel, eluting with 1–3% methanol in dichloromethane. The two materials were identical and yielded 2-(N-benzoyl)amino-5-nitropyrimidine (826 mg, 47% yield) as a white solid:

$^1$H-NMR (DMSO-$d_6$): 11.73 (s, 1H), 9.43 (s, 1H), 7.96 (d, 2H, J=8 Hz), 7.47–7.65 (m, 3H):

MS (−ve ESI): 243 (M−H)$^-$,
MS (+ve ESI): 245 (M+H)$^+$.

b) 10% Platinum on carbon (71 mg, 0.036 mmol) was added to a solution 2-(N-benzoyl)amino-5-nitropyrimidine (733 mg, 3.00 mmol) in ethanol (100 ml) at ambient temperature and the reaction stirred for 1 hour under an atmosphere of hydrogen. The reaction was filtered through a pad of celite and the solvents were evaporated in vacuo. Purification by flash chromatography on silica gel, eluting with 5% methanol in dichloromethane yielded 2-(N-benzoyl)amino-5-aminopyrimidine (91 mg, 14% yield) as white solid:

$^1$H-NMR (DMSO-$d_6$): 8.63 (s, 1H), 8.14 (s, 2H), 7.90 (d, 2H, J=8 Hz), 7.42–7.56 (m, 3H), 3.76 (s, 1H):

MS (−ve ESI): 213 (M−H)$^-$,
MS (+ve ESI): 215 (M+H)$^+$.

EXAMPLE 7

Preparation of Compound 7 in Table 2

An analogous reaction to that described in example 6, but starting with 4-chloro-6-methoxy-7-(2,2,2-trifluoroethoxy)quinazoline (44 mg, 0.176 mmol), yielded the title compound (54 mg, 70% yield) as a white solid:

$^1$H-NMR (DMSO-$d_6$): 12.29 (s, 1H), 11.14 (s, 1H), 9.15 (s, 2H), 8.90 (s, 1H), 8.65 (s, 1H), 8.00 (d, 2H), 7.60 (m, 2H), 7.50 (m, 3H), 7.45 (s, 1H), 5.05 (dd, 2H), 4.05 (s, 3H):

MS (+ve ESI): 471 (M+H)$^+$.

4-Chloro-6-methoxy-7-(2,2,2-trifluoroethoxy)quinazoline, used as starting material was obtained as follows:

a) Potassium carbonate (62.2 g, 450 mmol) was added to a solution of ethyl vanillate (58.9 g, 300 mmol) in dimethylformamide (400 ml) and the reaction heated to 120° C. 2,2,2-Trifluoroethyl methanesulphonate (63.4 g, 360 mmol) was added over 15 minutes and the reaction heated at 120° C. for 15 hours. The reaction was cooled to ambient temperature, diethyl ether (400 ml) was added and the reaction was filtered. The filtrate was evaporated in vacuo and the residue was taken up in a mixture of diethyl ether (375 ml) and isohexane (375 ml). The organic layer was concentrated in vacuo to a total volume of 250 ml and the solid which crystallised out was collected by suction filtration. Drying of the solid in vacuo yielded ethyl 4-(2,2,2-trifluoroethoxy)-3-methoxybenzoate (43.0 g, 52% yield) as a white crystalline solid:

$^1$H-NMR (DMSO-$d_6$): 7.57 (dd, 1H, J=2, 8 Hz), 7.49 (d, 1H, J=2 Hz), 7.18 (d, 1H, J=8 Hz), 5.81 (q, 2H, J=7 Hz), 5.29 (q, 2H, J=7 Hz), 3.82 (s, 3H), 1.30 (t, 3H, J=7 Hz):

MS (+ve ESI): 279 (M+H)$^+$.

b) Concentrated sulphuric acid (64 ml) and concentrated nitric acid (10.0 ml, 0.152 mol) were added cautiously, over 1 hour, to a two-phase system containing a stirred solution of ethyl 4-(2,2,2-trifluoroethoxy)-3-methoxybenzoate (35.3 g, 0.127 mol) in dichloromethane (340 ml), acetic acid (173 ml) and water (40 ml) at 5° C. The reaction was allowed to warm to ambient temperature over 60 hours (with vigorous mechanical stirring), the aqueous phase was separated, and the organic phase washed with water (6×250 ml). The organic phase was concentrated to a total volume of ~200 ml, isohexane (150 ml) was added and the solid which precipitated was collected by suction filtration. Drying of the solid in vacuo yielded ethyl-3-methoxy-4-(2,2,2-trifluoroethoxy)-6-nitrobenzoate (21.7 g, 52% yield) as a yellow solid. The mother liquors contained a mixture of product (28%) and starting material (72%) which was recycled in a latter reaction:

$^1$H-NMR (DMSO-$d_6$): 7.80 (s, 1H), 7.42 (s, 1H), 4.90 (q, 2H, J=7 Hz), 4.20–4.35 (m, 2H), 4.00 (s, 3H), 1.32 (t, 3H, J=7 Hz):

MS (+ve ESI): 324 (M+H)$^+$.

c) A suspension of ethyl 3-methoxy-4-(2,2,2-trifluoroethoxy)-6-nitrobenzoate (24.0 g, 74.3 mmol) and 10% palladium on carbon (3.0 g) in a mixture of ethanol (100 ml) and ethyl acetate (750 ml) was stirred under an atmosphere of hydrogen for 18 hours. Removal of the catalyst by filtration, followed by solvent evaporation in vacuo yielded ethyl 3-methoxy-4-(2,2,2-trifluoroethoxy)-6-aminobenzoate (20.2 g, 93% yield) as a pale brown solid:

$^1$H-NMR (DMSO-$d_6$): 7.20 (s, 1H), 6.45 (s, 1H), 6.40 (s, 2H), 5.70 (q, 2H, J=7 Hz), 4.20 (q, 2H, J=7 Hz), 3.65 (s, 3H), 1.32 (t, 3H, J=7 Hz):

MS (−ve ESI): 292 (M−H)$^-$.
MS (+ve ESI): 294 (M+H)$^+$.

d) A mixture of ethyl 2-amino-4-(2,2,2-trifluoroethoxy)-5-methoxybenzoate (20.2 g, 69.1 mmol) and formamide (50 ml) was heated at 175° C. for 6 hours. The mixture was allowed to cool to ambient temperature, ethanol (150 ml) was added and the reaction allowed to stand for 18 hours. Collection of the solid which had precipitated by suction filtration, followed by washing with ethanol (2×50 ml) and drying in vacuo, yielded 6-methoxy-7-(2,2,2-trifluoroethoxy)-3,4-dihydroquinazolin-4-one (15.8 g, 84% yield) as a pale brown crystalline solid:

$^1$H-NMR (DMSO-$d_6$): 12.10 (s, 1H), 8.00 (s, 1H), 7.51 (s, 1H), 7.30 (s, 1H), 4.90 (q, 2H, J=7 Hz), 3.90 (s, 3H):

MS (−ve ESI): 273 (M−H)$^-$,
MS (+ve ESI): 275 (M+H)$^+$.

e) Dimethylformamide (0.1 ml) was added dropwise to a solution of 6-methoxy-7-(2,2,2-trifluoroethoxy)-3,4-dihydroquinazolin-4-one (15.8 g, 57.7 mmol) in thionyl chloride (200 ml) and the reaction was heated at reflux for 6 hours. The reaction was cooled, excess thionyl chloride was removed in vacuo and the residue was azeotroped with toluene (2×50 ml) to remove the last of the thionyl chloride. The residue was taken up in dichloromethane (550 ml), the solution was washed with saturated aqueous sodium hydrogen carbonate solution (2×250 ml) and the organic phase was dried over magnesium sulphate. Solvent evaporation in vacuo yielded 4-chloro-6-methoxy-7-(2,2,2-trifluoroethoxy)quinazoline (16.3 g, 97% yield) as a cream solid:

$^1$H-NMR (DMSO-$d_6$): 8.95 (s, 1H), 7.65 (s, 1H), 7.25 (s, 1H), 5.05 (q, 2H, J=7 Hz), 4.00 (s, 3H):

MS (+ve ESI): 293, 295 (M+H)$^+$.

EXAMPLE 8

Preparation of Compound 8 in Table 2

An analogous reaction to that described in example 6, but starting with 4-chloro-6-methoxy-7-(3-morpholinopropoxy)quinazoline (50 mg, 0.15 mmol), yielded the title compound (26 mg, 30% yield) as a white solid:

$^1$H-NMR (DMSO-$d_6$): 11.08 (s, 1H), 9.08 (s, 1H), 8.79 (s, 1H), 7.96–8.01 (m, 3H), 7.61 (t, 1H, J=7 Hz), 7.52 (t, 2H, J=7 Hz), 7.36 (s, 1H), 4.29 (t, 2H, J=7 Hz), 4.00 (s, 3H), 3.60–3.71 (m, 2H), 3.49–3.58 (m, 2H), 3.33 (t, 2H, J=7 Hz), 3.07–3.19 (m, 2H), 2.40–2.47 (m, 2H), 2.21–2.30 (m, 2H):

MS (+ve ESI): 516 (M+H)$^+$.

EXAMPLE 9

Preparation of Compound 9 in Table 2

An analogous reaction to that described in example 6, but starting with 2-(N-benzoyl)amino-5-aminopyrimidine (66.6 mg, 0.31 mmol) and 4-chloro-6-methoxy-7-((1-methyl-4-piperazinyl)methoxy)quinazoline (100 mg, 0.31 mmol), yielded the title compound (66 mg, 43% yield) as a pale brown solid:

$^1$H-NMR (DMSO-$d_6$): 10.96 (s, 1H), 9.73 (s, 1H), 9.10 (s, 2H), 8.48 (s, 1H), 7.97 (d, 2H, J=7 Hz), 7.81 (s, 1H), 7.46–7.64 (m, 3H), 7.20 (d, 1H), 4.01 (d, 2H), 3.98 (s, 3H), 2.72–2.85 (m, 2H), 2.15 (s, 3H), 1.70–1.94 (m, 5H), 1.25–1.45 (m, 2 Hz):

MS (+ve ESI): 500 (M+H)$^+$.

4-Chloro-6-methoxy-7-((1-methyl-4-piperazinyl)methoxy)quinazoline, used as the starting material was obtained as follows:

a) A solution of di-tert-butyl dicarbonate (41.7 g, 0.19 mol) in ethyl acetate (75 ml) was added dropwise to a solution of ethyl 4-piperidinecarboxylate (30 g, 0.19 mol) in ethyl acetate (150 ml) while maintaining the temperature below 5° C. The reaction was stirred at ambient temperature for 48 hours, poured onto water (300 ml) and the organic layer was separated and washed with i) water (200 ml), ii) 0.1N aqueous hydrochloric acid (200 ml), iii) saturated sodium hydrogen carbonate (200 ml) and iv) brine (200 ml). Evaporation and drying in vacuo yielded ethyl 4-(1-tert-butyloxycarbonyl-piperidine)carboxylate (48 g, 98% yield) as a white solid:

$^1$H NMR (CDCl$_3$): 4.15 (q, 2H), 3.91–4.10 (s, 2H), 2.70–2.95 (t, 2H), 2.35–2.50 (m, 1H), 1.80–2.00 (d, 2H), 1.55–1.70 (m, 2H), 1.45 (s, 9H), 1.25 (t, 3H):

b) A solution of 1.0 N lithium aluminum hydride in tetrahydrofuran (133 ml, 0.133 mol) was added dropwise to a solution of ethyl 4-(1-tert-butyloxycarbonyl-piperidine)carboxylate (48 g, 0.19 mol) in dry tetrahydrofuran (180 ml) at 0° C. The reaction was stirred at 0° C. for 2 hours, water (30 ml) and 2.0N sodium hydroxide (10 ml) were added and the precipitate was filtered through diatomaceous earth and washed with ethyl acetate. The filtrate was washed with water and brine before being evaporated to yield 4-hydroxymethyl-1-tert-butyloxycarbonylpiperidine (36.3 g, 89% yield) as a white solid:

$^1$H NMR (CDCl$_3$): 4.10 (s, 2H), 3.40–3.60 (t, 2H), 2.60–2.80 (t, 2H), 1.60–1.80 (m, 2H), 1.35–1.55 (m, 10H), 1.05–1.20 (m, 2H):

MS (+ve EI): 215 (M+H)$^+$.

c) 1,4-Diazabicyclo[2.2.2]octane (42.4 g, 0.378 mol) was added to a solution of 4-hydroxymethyl-1-tert-butyloxycarbonylpiperidine (52.5 g, 0.244 mol) in tert-butyl methyl ether (525 ml) and the reaction stirred at ambient temperature for 15 minutes. The reaction was cooled to 5° C. and a solution of 4-toluenesulphonyl chloride (62.8 g, 0.33 mmol) in tert-butyl methyl ether (525 ml) was added dropwise over 2 hours while maintaining the temperature at 0° C. The reaction was stirred at ambient temperature for 1 hour, isohexane was added and the resultant precipitate was collected by suction filtration. Solvent evaporation in vacuo afforded a solid which was dissolved in diethyl ether (250 ml) and washed successively with 0.5N aqueous hydrochloric acid (2×500 ml), water, saturated sodium hydrogen carbonate and brine. Solvent evaporation and drying in vacuo yielded 4-(4-methylphenylsulphonyloxy-methyl)-1-tert-butyloxy-carbonylpiperidine (76.7 g, 85% yield) as a white solid:

$^1$H NMR (CDCl$_3$): 7.80 (d, 2H), 7.35 (d, 2H), 4.00–4.20 (s, 2H), 3.85 (d, 1H), 2.55–2.75 (m, 2H), 2.45 (s, 3H), 1.75–1.90 (m, 2H), 1.65 (d, 2H), 1.45 (s, 9H), 1.00–1.20 (m, 2H):

MS (+ve ESI): 392 (M+Na)$^+$.

d) 4-(4-Methylphenylsulphonyloxymethyl)-1-tert-butyloxycarbonylpiperidine (40 g, 0.11 mol) was added to a suspension of ethyl 3-methoxy-4-hydroxybenzoate (19.6 g, 0.1 mol) and potassium carbonate (28 g, 0.2 mol) in dry dimethylformamide (200 ml) and the reaction was heated at 95° C. for 2.5 hours. The reaction was cooled to ambient temperature, partitioned between water and ethyl acetate/diethyl ether, before the organic layer was washed with water and brine. Solvent evaporation in vacuo afforded a clear oil which crystallised on standing. Washing with isohexane and drying in vacuo yielded ethyl 3-methoxy-4-(1-tert-butyloxycarbonylpiperidin-4-ylmethoxy)benzoate (35 g, 89%) as a white solid:

m.p. 81–83° C.:

$^1$H NMR (CDCl$_3$): 7.65 (d, 1H), 7.55 (s, 1H), 6.85 (d, 1H), 4.35 (q, 2H), 4.05–4.25 (s, 2H), 3.95 (s, 3H), 3.9 (d, 2H), 2.75 (t, 2H), 2.00–2.15 (m, 2H), 1.80–1.90 (d, 2H), 1.48 (s, 9H), 1.40 (t, 3H), 1.20–1.35 (m, 2H):

MS (+ve ESI): 416 (M+Na)$^{30}$ :

e) Formaldehyde (35 ml of a 37% solution in water, 420 mmol) was added to a solution of ethyl 3-methoxy-4-(1-tert-butyloxycarbonylpiperidin-4-ylmethoxy)benzoate (35 g, 89 mmol) in formic acid (35 ml) and the reaction was heated at 95° C. for 3 hours. The reaction was cooled, the volatiles we removed in vacuo and the residue was dissolved in dichloromethane. 3.0 N Hydrogen chloride in diethyl ether (40 ml, 120 mmol) was added, together with a little diethyl ether and a solid was precipitated. Collection of the solid by suction filtration followed by drying in vacuo yielded ethyl 3-methoxy-4-(1-methylpiperidin-4-ylmethoxy)benzoate (30.6 g, 100% yield) as a white solid:

$^1$H-NMR (DMSO-$d_6$): 7.60 (d, 1H), 7.48 (s, 1H), 7.10 (d, 1H), 4.30 (q, 2H), 3.90–4.05 (s, 2H), 3.85 (s, 3H), 3.35–3.50 (s, 2H), 2.90–3.10 (m, 2H), 2.72 (s, 3H), 2.00–2.15 (s, 1H), 1.95 (d, 2H), 1.50–1.70 (m, 2H), 1.29 (t, 3H):

MS (+ve ESI): 308 (M+H)$^+$.

f) Trifluoroacetic acid (37.5 ml) was added to a solution of ethyl 3-methoxy-4-(1-methylpiperidin-4-ylmethoxy)benzoate (30.6 g, 89 mmol) in dichloromethane (75 ml) at 0–5° C. before dropwise addition of a solution of fuming nitric acid (7.42 ml, 178 mmol) in dichloromethane (15 ml) over 15 minutes. The reaction was stirred at ambient temperature for 2 hours, the volatiles were removed in vacuo and the residue was dissolved in dichloromethane (50 ml). The solution was cooled to 0–5° C., diethyl ether was added (50 ml) and the resultant precipitate was collected by suction filtration, and dried in vacuo. The solid was taken up in dichloromethane (500 ml), 3.0N hydrogen chloride in diethyl ether (30 ml) was added followed by diethyl ether (500 ml) which cause precipitation of a solid. Collection of the solid by suction filtration followed by drying in vacuo yielded ethyl 3-methoxy-4-(1-methylpiperidin-4-ylmethoxy)-6-nitrobenzoate (28.4 g, 82% yield) as a white solid:

$^1$H-NMR (DMSO-$d_6$): 7.66 (s, 1H), 7.32 (s, 1H), 4.30 (q, 2H), 4.05 (d, 2H), 3.95 (s, 3H), 3.40–3.50 (d, 2H), 2.90–3.05 (m, 2H), 2.75 (s, 3H), 1.75–2.10 (m, 3H), 1.45–1.65 (m, 2H), 1.30 (t, 3H):

MS (+ve ESI): 353 (M+H)$^+$.

g) A suspension of ethyl 3-methoxy-4-(1-methylpiperidin-4-ylmethoxy)-6-nitrobenzoate (3.89 g, 10 mmol) in methanol (80 ml) containing 10% platinum on activated carbon (50% wet) (389 mg) was hydrogenated at 1.8 atmospheres pressure until uptake of hydrogen ceased. The reaction was filtered through celite, the filtrate was evaporated and the residue was taken up in water (30 ml) and adjusted to pH 10 with a saturated solution of sodium hydrogen carbonate. The mixture was diluted with ethyl acetate/diethyl ether (1:1) and the organic layer was separated. The aqueous layer was further extracted with ethyl acetate/ether and the organic layers were combined prior to washing with water and brine. Solvent evaporation in vacuo, followed by trituration with a mixture of diethyl ether/isohexane yielded ethyl 6-amino-3-methoxy-4-(1-methylpiperidin-4-ylmethoxy)benzoate (2.58 g, 80% yield) as a white solid after drying in vacuo:

m.p. 111–112° C.:

$^1$H NMR (CDCl$_3$): 7.33 (s, 1H), 6.13 (s, 1H), 5.55 (s, 2H), 4.30 (q, 2H), 3.85 (d, 2H), 3.80 (s, 3H), 2.90 (d, 2H); 2.29 (s, 3H), 1.95 (t, 2H), 1.85 (m, 3H), 1.40–1.50 (m, 2H), 1.35 (t, 3H):

MS (+ve ESI): 323 (M+H)$^+$:

h) A solution of ethyl 6-amino-3-methoxy-4-(1-methylpiperidin-4-ylmethoxy)benzoate (16.1 g, 50 mmol) in 2-methoxyethanol (160 ml) containing formamidine acetate (5.2 g, 50 mmol) was heated at 115° C. for 2 hours. Formamidine acetate (10.4 g, 100 mmol) was added in portions every 30 minutes over a period of 4 hours and the reaction was heated for 30 minutes after the last addition. The reaction was cooled, the volatiles were removed in vacuo, and the residue was dissolved in ethanol (100 ml) and dichloromethane (50 ml). The reaction was filtered and the filtrate was concentrated to a final volume of 100 ml. Collection of the precipitated solid by suction filtration (at 5° C.) followed by drying in vacuo yielded 6-methoxy-7-((1-methylpiperidin-4-yl)methoxy)-3,4-dihydroquinazolin-4-one (12.7 g, 70% yield) as a white solid:

$^1$H-NMR (DMSO-d$_6$): 7.97 (s, 1H), 7.44 (s, 1H), 7.11 (s, 1H), 4.00 (d, 2H), 3.90 (s, 3H), 2.80 (d, 2H), 2.16 (s, 2H), 1.90 (s, 3H), 1.90 (t, 1H), 1.75 (d, 2H), 1.25–1.40 (m, 2H):

MS (+ve ESI): 304 (M+H)$^+$.

i) A solution of 6-methoxy-7-((1-methylpiperidin-4-yl)methoxy)-3,4-dihydroquinazolin-4-one (2.8 g, 9.24 mmol) in thionyl chloride (28 ml) containing dimethylformamide (0.28 ml) was heated at reflux for 1 hour. The reaction was cooled, the volatiles were removed in vacuo and the resultant solid was triturated with diethyl ether, filtered, washed with diethyl ether and dried in vacuo. The solid was dissolved in dichloromethane and washed with saturated aqueous sodium hydrogen carbonate, water and brine. Evaporation of the solvent and drying in vacuo yielded 4-chloro-6-methoxy-7-((1-methylpiperidin-4-yl)methoxy)quinazoline (2.9 g, 98% yield):

$^1$H-NMR (DMSO-d$_6$): 8.90 (s, 1H), 7.46 (s, 1H), 7.41 (s, 1H), 4.12 (d, 2H), 4.02 (s, 3H), 2.85 (d, 2H), 2.25 (s, 3H), 2.00 (t, 1H), 1.75–1.90 (m, 3H), 1.30–1.50 (m, 2H):

MS (+ve ESI): 322 (M+H)$^+$.

EXAMPLE 10

Preparation of Compound 10 in Table 2

An analogous reaction to that described in example 6, but starting with 2-(N-benzoyl)amino-5-aminopyrimidine (32 mg, 0.15 mmol) and 4-chloro-6,7,8-trimethoxyquinazoline (38.2 mg, 0.15 mmol—for synthesis see *J. Med. Chem.* (1993), 36(24), 3765–70), yielded the title compound (53.4 mg, 76% yield) as a pale brown solid:

$^1$H-NMR (DMSO-d$_6$): 11.12 (s, 1H), 9.11 (s, 2H), 8.77 (s, 1H), 8.3 (s, 1H), 7.97 (d, 2H), 7.6 (t, 1H), 7.5 (t, 2H), 4.06 (s, 3H), 4.01 (s, 6H):

MS (+ve ESI): 433 (M+H)$^+$.

EXAMPLE 11

Preparation of Compound 11 in Table 2

An analogous reaction to that described in example 10, but starting with 4-chloro-6-fluoroquinazoline (27.4 mg, 0.15 mmol—for synthesis see patent WO 9609294 A1), yielded the title compound (34.4 mg, 58% yield) as a light brown solid:

$^1$H-NMR (DMSO-d$_6$): 11.11 (s, 1H), 9.13 (s, 2H), 8.91 (s, 1H), 8.78 (d, 1H), 8.0 (m, 4H), 7.58 (t, 1H), 7.50 (t, 3H):

MS (+ve ESI): 361 (M+H)$^+$.

EXAMPLE 12

Preparation of Compound 12 in Table 2

An analogous reaction to that described in example 6, but starting with 2-(N-benzoyl)amino-5-aminopyrimidine (14.0 g, 65.4 mmol) and 4-chloro-6-methoxy-7-benzoyloxyquinazoline (19.6 g, 65.4 mmol), yielded the title compound (33.0 g, 98% yield) as a pale yellow solid:

$^1$H-NMR (DMSO-d$_6$): 12.14 (s, 1H), 11.12 (s, 1H), 9.10 (s, 2H), 8.90 (s, 1H), 8.60 (s, 1H), 8.00 (d, 2H, J=7 Hz), 7.55–7.65 (m, 1H), 7.45–7.50 (m, 4H), 7.30–7.43 (m, 4H), 5.35 (s, 2H), 4.02 (s, 3H):

MS (+ve ESI): 479 (M+H)$^+$.

4-Chloro-6-methoxy-7-benzyloxyquinazoline, used as the starting material, was obtained as follows:

a) A mixture of 2-amino-4-benzoyloxy-5-methoxybenzamide (10 g, 0.04 mol), (prepared according to *J. Med. Chem.* 1977, 20, 146–149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The volatiles were removed by evaporation, water was added to the residue, the solid was collected by filtration, washed with water and dried. Recrystallisation from acetic acid yielded 7-benzyloxy-6-methoxy-3,4-dihydroquinazolin-4-one (8.7 g, 84% yield) as a white solid.

b) Dimethylformamide (0.2 ml) was added dropwise to a solution of 6-methoxy-7-benzyloxy-3,4-dihydroquinazolin-4-one (5.00 g, 17.9 mmol) in thionyl chloride (100 ml) and the reaction was heated at reflux for 1 hour. The reaction was cooled, excess thionyl chloride was removed in vacuo and the residue was azeotroped with toluene (3×50 ml) to remove the last of the thionyl chloride. The residue was taken up in dichloromethane (550 ml), the solution was washed with saturated aqueous sodium hydrogen carbonate solution (100 ml) and water (100 ml) and the organic phase was dried over magnesium sulphate. Solvent evaporation in vacuo yielded 4-chloro-6,7-dimethoxyquinazoline (4.80 g, 90% yield) as a pale brown solid:

$^1$H-NMR (DMSO-d$_6$): 8.85 (s, 1H), 7.58 (s, 1H), 7.50 (d, 2H), 7.40 (m, 4H), 5.35 (s, 2H), 4.00 (s, 3H):

MS (+ve ESI): 301 (M+H)$^+$.

EXAMPLE 13

Preparation of Compound 13 in Table 2

A solution of 4-(((2-(N-benzoyl)amino)-5-pyrimidine)amino)-6-methoxy-7-benzyloxyquinazoline hydrochloride (12.36 g, 25.2 mmol) in trifluoroacetic acid (150 ml) was heated at 75° C. for 4 hours. The reaction was cooled, evaporated in vacuo and the resultant was neutralised by addition of aqueous sodium hydrogen carbonate solution. The grey solid which precipitated was collected and purified by flash chromatography on silica gel, eluting with 1–15% methanol in dichloromethane containing 1% triethylamine. The fractions from the column were concentrated in vacuo, the product was crystallised by addition of ethyl acetate and isohexane and the resultant solid collected by suction filtration. Drying of this material yielded the title compound (3.72 g, 38% yield) as a pale-yellow solid:

$^1$H-NMR (DMSO-$d_6$): 10.95 (s, 1H), 10.42 (s, 1H), 9.65 (s, 1H), 9.10 (s, 2H), 8.40 (s, 1H), 8.00 (d, 2H, J=7 Hz), 7.80 (s, 1H), 7.55–7.65 (m, 1H), 7.45–7.50 (m, 2H), 7.05 (s, 1H), 3.99 (s, 3H):

MS (−ve ESI): 387 (M−H)$^−$,

MS (+ve ESI): 389 (M+H)$^+$.

EXAMPLE 14

Preparation of Compound 14 in Table 2

A mixture of 4-(((2-(N-benzoyl)amino)-5-pyrimidine)amino)-6-methoxy-7-hydroxyquinazoline trifluoroacetate (200 mg, 0.515 mmol), (2R)-(−)-glycidyl tosylate (129 mg, 0.567 mmol) and potassium carbonate (213 mg, 1.55 mmol) in dimethylformamide was heated to 60° C. for 5 hours. The reaction was cooled and poured into aqueous sodium bicarbonate solution (10 ml) and the resulting solid collected by suction filtration. Purification by flash chromatography on silica gel, eluting with 2–10% methanol in dichloromethane yielded the title compound (56 mg, 24% yield) as a pale yellow solid:

$^1$H-NMR (DMSO-$d_6$): 10.95 (s, 1H), 9.68 (s, 1H), 9.10 (s, 2H), 8.50 (s, 1H), 8.00 (d, 2H), 7.80 (s, 1H), 7.55–7.60 (m, 1H), 7.45–7.50 (m, 2H), 7.22 (s, 1H), 4.50–4.60 (m, 1H), 4.00 (s, 3H), 3.98–4.01 (m, 1H), 3.35–3.45 (m, 1H), 2.82–2.87 (m, 1H), 2.75–2.78 (m, 1H):

MS (−ve ESI): 443 (M−H)$^−$,

MS (+ve ESI): 445 (M+H)$^+$.

EXAMPLE 15

Preparation of Compound 15 in Table 2

An analogous reaction to that described in example 14, but starting with (2S)-(+)-glycidyl tosylate (5.23 g, 22.9 mmol), yielded the title compound (3 g, 32% yield) as a pale yellow solid:

$^1$H-NMR (DMSO-$d_6$): 10.95 (s, 1H), 9.68 (s, 1H), 9.10 (s, 2H), 8.50 (s, 1H), 8.00 (d, 2H), 7.80 (s, 1H), 7.55–7.60 (m, 1H), 7.45–7.50 (m, 2H), 7.22 (s, 1H), 4.50–4.60 (m, 1H), 4.0 (s, 3H), 3.98–4.01 (m, 1H), 3.35–3.45 (m, 1H), 2.82–2.87 (m, 1H), 2.75–2.78 (m, 1H):

MS (−ve ESI): 443 (M−H)$^−$,

MS (+ve ESI): 445 (M+H)$^+$.

EXAMPLE 16

Preparation of Compound 16 in Table 2

A mixture of N-(5-(((6-methoxy-7-((2S)oxiranylmethoxy)-4-quinazolinyl)amino)-2-pyrimidinyl)benzamide (150 mg, 0.338 mmol) and (±) pyrrolidinol (44 mg, 0.51 mmol) in dimethylacetamide (1 ml) was heated at 60° C. for 2 days. The reaction mixture was cooled and brine (10 ml) added and the resulting solids collected by suction filtration. Purification was by reverse phase preparative hplc, eluting with 25% acetonitrile in water containing 0.1% trifluoroacetic acid. Neutralisation with ammonia followed by concentration to a small volume and collection of the resulting solids by suction filtration yielded the title compound (50 mg, 28% yield) as a white solid:

$^1$H-NMR (DMSO-$d_6$): 10.95 (s, 1H), 9.70 (s, 1H), 9.10 (s, 2H), 8.50 (s, 1H), 8.00 (d, 2H), 7.80 (s, 1H), 7.55–7.60 (m, 1H), 7.45–7.50 (m, 2H), 7.22 (s, 1H), 4.90 (s, 1H), 4.60 (t, 1H), 4.05–4.20 (m, 2H), 3.99–4.02 (m, 2H), 3.98 (s, 3H), 2.70–2.80 (m, 1H), 2.55–2.65 (m, 2H), 2.35–2.45 (m, 2H), 1.90–2.00 (m, 1H), 1.45–1.65 (m, 1H):

MS (+ve ESI): 532 (M+H)$^+$

MS (−ve ESI): 530 (M−H)$^−$.

EXAMPLE 17

Preparation of Compound 17 in Table 2

An analogous reaction to that described in example 16, but starting with azetidine (29 mg, 0.51 mmol), yielded the title compound (11 mg, 6.5% yield) as a white solid:

$^1$H-NMR (DMSO-$d_6$): 10.95 (s, 1H), 9.70 (s, 1H), 9.10 (s, 2H), 8.50 (s, 1H), 8.00 (d, 2H), 7.80 (s, 1H), 7.55–7.60 (m, 1H), 7.45–7.50 (m, 2H), 7.22 (s, 1H), 4.90 (s, 1H), 4.05–4.15 (m, 1H), 4.01 (m, 1H), 3.99 (s, 3H), 3.75–3.80 (m, 1H), 3.10–3.20 (m, 4H), 2.40–2.50 (m, 2H), 1.90–2.00 (m, 2H):

MS (−ve ESI): 500 (M−H)$^−$,

MS (+ve ESI): 502 (M+H)$^+$.

EXAMPLE 18

Preparation of Compound 18 in Table 2

An analogous reaction to that described in example 16, but starting with pyrolidone (36 mg, 0.51 mmol), yielded the title compound (71 mg, 41% yield) as a white solid:

$^1$H-NMR (DMSO-$d_6$): 10.95 (s, 1H), 9.70 (s, 1H), 9.10 (s, 2H), 8.45 (s, 1H), 8.00 (d, 2H), 7.80 (s, 1H), 7.55–7.60 (m, 1H), 7.45–7.50 (m, 2H), 7.22 (s, 1H), 4.90 (d, 1H), 4.10–4.20 (m, 1H), 3.99–4.05 (m, 2H), 3.98 (s, 3H), 2.60–2.70 (m, 1H), 2.40–2.50 (m, 5H), 1.60–1.70 (m, 4H):

MS (+ve ESI): 516 (M+H)$^+$.

EXAMPLE 19

Preparation of Compound 19 in Table 2

An analogous reaction to that described in example 16, but starting with piperidine (21 mg, 0.25 mmol), yielded the title compound (60 mg, 50% yield) as a yellow solid:

$^1$H-NMR (DMSO-$d_6$): 10.95 (s, 1H), 9.75 (s, 1H), 9.10 (s, 2H), 8.42 (s, 1H), 7.98 (d, 2H), 7.80 (s, 1H), 7.55–7.60 (m, 1H), 7.45–7.50 (m, 2H), 7.22 (s, 1H), 4.10–4.22 (m, 1H), 3.99–4.05 (m, 2H), 3.98 (s, 3H), 2.30–2.50 (m, 6H), 1.50–1.60 (m, 4H), 1.30–1.40 (m, 2H):

MS (−ve ESI): 528 (M−H)⁻,
MS (+ve ESI): 530 (M+H)⁺.

EXAMPLE 20

Preparation of Compound 20 in Table 2

An analogous reaction to that described in example 16, but starting with cyclobutylamine (36 mg, 0.51 mmol), yielded the title compound (14 mg, 8% yield) as a white solid:
$^1$H-NMR (DMSO-d$_6$): 11.01 (s, 1H), 9.75 (s, 1H), 9.10 (s, 2H), 8.50 (s, 1H), 8.00 (d, 2H), 7.80 (s, 1H), 7.55–7.60 (m, 1H), 7.45–7.50 (m, 2H), 7.20 (s, 1H), 5.00 (d, 1H), 4.10–4.15 (m, 1H), 4.00–4.05 (m, 1H), 3.99 (s, 3H), 3.85–3.95 (m, 1H), 3.15–3.25 (m, 1H), 2.50–2.80 (m, 2H), 2.10–2.15 (m, 2H), 1.55–1.70 (m, 4H):
MS (−ve ESI): 514 (M−H)⁻.

EXAMPLE 21

Preparation of Compound 21 in Table 2

An analogous reaction to that described in example 16, but starting with cyclopentylamine (43 mg, 0.51 mmol), yielded the title compound (24 mg, 13% yield) as a white solid:
$^1$H-NMR (DMSO-d$_6$): 9.15 (s, 2H), 8.50 (s, 1H), 8.00 (d, 2H), 7.90 (s, 1H), 7.55–7.60 (m, 1H), 7.45–7.50 (m, 2H), 7.20 (s, 1H), 4.00–4.20 (m, 3H), 3.98 (s, 3H), 2.85–2.95 (m, 1H), 2.70–2.82 (m, 1H), 1.75–1.90 (m, 2H), 1.55–1.70 (m, 2H), 1.35–1.50 (m, 4H):
MS (−ve ESI): 528 (M−H)⁻,
MS (+ve ESI): 530 (M+H)⁺.

EXAMPLE 22

Preparation of Compound 22 in Table 2

An analogous reaction to that described in example 16, but starting with 5-methylfurfurylamine (56 mg, 0.51 mmol), yielded the title compound (65 mg, 35% yield) as a white solid:
$^1$H-NMR (DMSO-d$_6$): 10.95 (s, 1H), 9.80 (s, 1H), 9.10 (s, 2H), 8.50 (s, 1H), 7.99 (d, 2H), 7.80 (s, 1H), 7.55–7.60 (m, 1H), 7.45–7.50 (m, 2H), 7.12 (s, 1H), 6.25 (d, 1H), 6.01 (d, 1H), 4.05–4.20 (m, 3H), 4.00 (s, 3H), 3.90 (s, 2H), 2.70–2.90 (m, 2H), 2.20 (s, 3H):
MS (−ve ESI): 554 (M−H)⁻,
MS (+ve ESI): 556 (M+H)⁺.

EXAMPLE 23

Preparation of Compound 23 in Table 2

An analogous reaction to that described in example 16, but starting with 2-thiophenemethylamine (57 mg, 0.51 mmol), yielded the title compound (18 mg, 10% yield) as a white solid:
$^1$H-NMR (DMSO-d$_6$): 10.95 (s, 1H), 9.72 (s, 1H), 9.10 (s, 2H), 8.50 (s, 1H), 7.99 (d, 2H), 7.80 (s, 1H), 7.55–7.60 (m, 1H), 7.45–7.50 (m, 2H), 7.35 (d, 1H), 7.20 (s, 1H), 6.90–6.95 (m, 2H), 5.03 (d, 1H), 4.10–4.20 (m, 1H), 3.99–4.05 (m, 2H), 3.98 (s, 3H), 3.90 (s, 2H), 2.60–2.80 (m, 2H):
MS (−ve ESI): 556 (M−H)⁻,
MS (+ve ESI): 558 (M+H)⁺.

EXAMPLE 24

Preparation of Compound 24 in Table 2

An analogous reaction to that described in example 16, but starting with ethanolamine (31 mg, 0.51 mmol), yielded the title compound (26 mg, 15% yield) as a white solid:
$^1$H-NMR (DMSO-d$_6$): 9.80 (s, 1H), 9.10 (s, 2H), 8.45 (s, 1H), 8.01 (d, 2H), 7.85 (s, 1H), 7.55–7.60 (m, 1H), 7.45–7.50 (m, 2H), 7.20 (s, 1H), 4.45 (s, 1H), 4.05–4.20 (m, 2H), 3.98 (s, 3H), 3.40–3.50 (m, 2H), 2.70–2.80 (m, 1H), 2.60–2.65 (m, 3H):
MS (−ve ESI): 504 (M−H)⁻,
MS (+ve ESI): 506 (M+H)⁺.

EXAMPLE 25

Preparation of Compound 25 in Table 2

An analogous reaction to that described in example 16, but starting with ethylthioethylamine (53 mg, 0.51 mmol), yielded the title compound (36 mg, 19% yield) as a white solid:
$^1$H-NMR (DMSO-d$_6$): 10.95 (s, 1H), 9.80 (s, 1H), 9.10 (s, 2H), 8.50 (s, 1H), 8.00 (d, 2H), 7.80 (s, 1H), 7.55–7.60 (m, 1H), 7.45–7.50 (m, 2H), 7.20 (s, 1H), 4.00–4.20 (m, 3H), 3.98 (s, 3H), 2.75–2.80 (m, 3H), 2.67–2.73 (m, 1H), 2.60–2.65 (m 2H), 2.50–2.55 (m, 2H), 1.15 (3H, t):
MS (−ve ESI): 548 (M−H)⁻,
MS (+ve ESI): 550 (M+H)⁺.

EXAMPLE 26

Preparation of Compound 26 in Table 2

A solution of 4-(((2-(N-benzoyl)amino)-5-pyrimidine)amino)-6-methoxy-7-(2-bromoethoxy)quinazoline (223 mg, 0.45 mmol) and N,N-dimethylethylenediamine (0.247 ml, 2.25 mmol) were heated in a mixture of tetrahydrofuran (10 ml) and dimethylacetamide (1 ml) at 70° C. for 20 hours. The reaction was cooled, poured into diethyl ether (35 ml) and the resultant solid was collected by suction filtration. Purification of this solid by flash chromatography on silica gel, eluting with 5–10% methanol in dichloromethane yielded the title compound (23 mg, 10% yield) as white solid:
$^1$H-NMR (DMSO-d$_6$): 10.95 (s, 1H), 9.75 (s, 1H), 9.10 (s, 2H), 8.47 (s, 1H), 7.98 (d, 2H, J=7 Hz), 7.80 (s, 1H), 7.55–7.65 (m, 1H), 7.45–7.52 (m, 2H), 7.22 (s, 1H), 4.20 (t, 2H, J=7 Hz), 3.99 (s, 3H), 2.95 (t, 2H, J=7 Hz), 2.65 (t, 2H, J=7 Hz), 2.30 (t, 2H, J=7 Hz), 2.10 (s, 6H):
MS (−ve ESI): 501 (M−H)⁻,
MS (+ve ESI): 503 (M+H)⁺.

4-(((2-(N-benzoyl)amino)-5-pyrimidine)amino)-6-methoxy-7-(2-bromoethoxy)quinazoline, used as the starting material was obtained as follows:
Potassium carbonate (2.33 g, 16.9 mmol) was added to a solution of 4-(((2-(N-benzoyl)amino)-5-pyrimidine)amino)-6-methoxy-7-hydroxyquinazoline (1.40 g, 3.60 mmol) and 1,2-dibromoethane (6.75 g, 36.0 mmol) in dimethylformamide (120 ml) and the reaction heated at 85° C. for 20 hours. At the end of this period, additional potassium carbonate (1.24 g, 9.0 mmol) and 1,2-dibromoethane (3.82 g, 18.0 mmol) were added and the reaction heated at 85° C. for 4 hours and then at ambient temperature for 16 hours. The reaction was poured into saturated brine (200 ml) and the solid which precipitated was collected by suction filtration. Purification by flash chromatography on silica gel, eluting with 5–10% methanol in dichloromethane yielded 4-(((2-(N-benzoyl)amino)-5-pyrimidine)amino)-6-methoxy-7-(2-bromoethoxy)quinazoline (537 mg, 38% yield) as a white solid:

$^1$H-NMR (DMSO-d$_6$): 10.96 (s, 1H), 9.75 (s, 1H), 9.11 (s, 2H), 8.49 (s, 1H), 7.98 (d, 2H, J=7 Hz), 7.84 (s, 1H), 7.57–7.62 (m, 1H), 7.48–7.53 (m, 2H), 7.25 (s, 1H), 4.51 (t, 2H, J=7 Hz), 3.99 (s, 3H), 3.88 (t, 2H, J=7 Hz):

MS (–ve ESI): 493, 495 (M–H)$^-$,
MS (+ve ESI): 495, 497 (M+H)$^+$.

EXAMPLE 27

Preparation of Compound 27 in Table 2

An analogous reaction to that described in example 26, but starting with 4-amino-1-butanol (121 mg, 1.36 mmol), yielded the title compound (6 mg, 4% yield) as an off white solid:

$^1$H-NMR (DMSO-d$_6$): 10.80 (s, 1H), 9.70 (s, 1H), 9.10 (s, 2H), 8.50 (s, 1H), 8.00 (d, 2H), 7.80 (s, 1H), 7.60–7.65 (m, 1H), 7.50–7.55 (m, 2H), 7.20 (s, 1H), 4.20 (t, 2H), 3.90 (s, 3H), 3.40 (t, 2H), 2.80 (t, 2H), 2.50 (t, 2H), 1.20–1.30 (4H, m):

MS (–ve ESI): 502 (M–H)$^-$,
MS (+ve ESI): 504 (M+H)$^+$.

EXAMPLE 28

Preparation of Compound 28 in Table 2

An analogous reaction to that described in example 26, but starting with 2-amino-2-methyl-1-propanol (121 mg, 1.36 mmol), yielded the title compound (65 mg, 47% yield) as an off white solid:

$^1$H-NMR (DMSO-d$_6$): 9.02 (s, 2H), 8.31 (s, 1H), 7.90 (d, 2H), 7.80 (s, 1H), 7.55–7.60 (m, 1H), 7.45–7.50 (m, 2H), 7.10 (s, 1H), 4.10 (t, 2H), 3.92 (s, 3H), 3.20 (s, 2H), 2.85–2.95 (m, 2H), 1.60–1.70 (m, 1H), 0.98 (s, 6H):

MS (–ve ESI): 502 (M–H)$^-$,
MS (+ve ESI): 504 (M+H)$^+$.

EXAMPLE 29

Preparation of Compound 29 in Table 2

An analogous reaction to that described in example 26, but starting with cyclopropanemethylamine (96 mg, 1.36 mmol), yielded the title compound (50 mg, 38% yield) as an off white solid:

$^1$H-NMR (DMSO-d$_6$): 9.01 (s, 2H), 8.30 (s, 1H), 7.90 (d, 2H), 7.75 (s, 1H), 7.45–7.52 (1H, m), 7.38–7.42 (m, 2H), 7.15 (s, 1H), 4.10 (t, 2H), 3.82 (s, 3H), 2.90 (t, 2H), 0.75–0.90 (m, 1H), 0.25–0.35 (m, 2H), 0.01–0.10 (m, 2H):

MS (–ve ESI): 484 (M–H)$^-$,
MS (+ve ESI): 486 (M+H)$^+$.

EXAMPLE 30

Preparation of Compound 30 in Table 2

An analogous reaction to that described in example 26, but starting with tetrahydrofurfurylamine (138 mg, 1.36 mmol), yielded the title compound (27 mg, 19% yield) as an off white solid:

$^1$H-NMR (DMSO-d$_6$): 10.95 (s, 1H), 9.70 (s, 1H), 9.10 (s, 2H), 8.45 (s, 1H), 7.98 (d, 2H), 7.80 (s, 1H), 7.55–7.60 (m, 1H), 7.45–7.50 (m, 2H), 7.20 (s, 1H), 4.20 (t, 2H), 4.00 (s, 3H), 3.80–3.90 (m, 1H), 3.70–3.78 (m, 1H), 3.55–3.62 (m, 1H), 3.00 (t, 2H), 2.62 (d, 2H), 1.70–2.00 (m, 4H), 1.42–1.60 (m, 1H):

MS (–ve ESI): 514 (M–H)$^-$,
MS (+ve ESI): 516 (M+H)$^+$.

EXAMPLE 31

Preparation of Compound 31 in Table 2

An analogous reaction to that described in example 26, but starting with piperidine (116 mg, 1.36 mmol), yielded the title compound (80 mg, 59% yield) as an off white solid:

$^1$H-NMR (DMSO-d$_6$): 9.10 (s, 2H), 8.45 (s, 1H), 7.98 (d, 2H), 7.80 (s, 1H), 7.59–7.62 (m, 1H), 7.45–7.57 (m, 2H), 7.20 (s, 1H), 4.20 (t, 2H), 3.98 (s, 3H), 2.70 (t, 2H), 2.40–2.50 (m, 4H), 1.42–1.57 (m, 4H), 1.30–1.40 (m, 2H):

MS (–ve ESI): 498 (M–H)$^-$,
MS (+ve ESI): 500 (M+H)$^+$.

EXAMPLE 32

Preparation of Compound 32 in Table 2

A mixture of 4-(((2-(N-benzoyl)amino)-5-pyrimidine)amino)-6-methoxy-7-(3-chloropropoxy)-quinazoline (200 mg, 0.43 mmol), 4-aminobutan-1-ol (192 mg, 2.15 mmol) and sodium iodide (65 mg, 0.43 mmol) in dimethyacetamide (5 ml) was heated at 80° C. for 5 hours. The solvent was removed in vacuo and the residue dissolved in methanol (2 ml). Water (10 ml) was added and the resulting solid was collected by suction filtration and washed with water, sodium bicarbonate solution then water. Drying of the solid yielded the title compound (78 mg, 35% yield) as an off white solid:

$^1$H-NMR (DMSO-d$_6$): 9.10 (s, 2H), 8.41 (s, 1H), 7.96–8.00 (m, 2H), 7.81 (s, 1H), 7.43–7.60 (m, 3H), 7.15 (s, 1H), 4.21 (t, 3H), 3.99 (s, 3H), 3.40 (m, 2H), 2.40–2.65 (m, 4H), 1.90–1.98 (m, 2H), 1.40 (m, 4H):

MS (+ve ESI): 518 (M+H)$^+$.

4-(((2-(N-benzoyl)amino)-5-pyrimidine)amino)-6-methoxy-7-(3-chloropropoxy)quinazoline, used as the starting material was obtained as outlined in example 53.

EXAMPLE 33

Preparation of Compound 33 in Table 2

An analogous reaction to that described in example 32, but starting with 2-amino-2-methyl-propan-1-ol (192 mg, 2.15 mmol), yielded the title compound (88 mg, 40% yield) as an off white solid:

$^1$H-NMR (DMSO-d$_6$): 9.10 (s, 2H), 8.41 (s, 1H), 7.96–8.00 (d, 2H, J=6.9 Hz), 7.81 (s, 1H), 7.43–7.60 (m,

3H), 7.15 (s, 1H), 4.40 (bs, 1H), 4.21 (t, 3H, J=6 Hz), 3.99 (s, 3H), 3.15 (s, 2H), 2.60 (m, 2H), 1.98 (m, 2H), 0.95 (s, 6H):

MS (+ve ESI): 518 (M+H)$^+$.

EXAMPLE 34

Preparation of Compound 34 in Table 2

An analogous reaction to that described in example 32, but starting with cyclopropylmethylamine (153 mg, 2.15 mmol), yielded the title compound (117 mg, 54% yield) as an off white solid:

$^1$H-NMR (CDCl$_3$): 8.60 (m, 2H), 8.05 (m, 1H), 7.55–7.80 (m, 3H), 7.20–7.25 (m, 1H), 7.10–7.15 (m, 1H), 7.15 (s, 1H), 4.21 (t, 3H), 4.05 (s, 3H), 3.75 (m, 4H), 2.45–2.61 (m, 6H), 2.20 (m, 2H):

MS (+ve ESI): 521 (M+H)$^+$.

EXAMPLE 35

Preparation of Compound 35 in Table 2

An analogous reaction to that described in example 32, but starting with tetrahydrofurfurylamine (218 mg, 2.15 mmol), yielded the title compound (51 mg, 22% yield) as an off white solid:

$^1$H-NMR (DMSO-d$_6$): 9.10 (s, 2H), 8.41 (s, 1H), 7.96–8.00 (m, 2H), 7.81 (s, 1H), 7.43–7.60 (m, 3H), 7.15 (s, 1H), 4.21 (t, 3H), 3.99 (s, 3H), 3.55–3.95 (m, 3H), 2.80–2.85 (m, 2H), 2.55–2.60 (m, 2H), 1.41–1.98 (m, 6H):

MS (+ve ESI): 530 (M+H)$^+$.

EXAMPLE 36

Preparation of Compound 36 in Table 2

An analogous reaction to that described in example 32, but starting with pyrolidine (153 mg, 2.15 mmol), yielded the title compound (34 mg, 16% yield) as an off-white solid:

$^1$H-NMR (DMSO-d$_6$): 9.10 (s, 2H), 8.41 (s, 1H), 7.96–8.00 (d, 2H, J=7 Hz), 7.81 (s, 1H), 7.43–7.60 (m, 3H), 7.15 (s, 1H), 4.21 (t, 3H), 3.99 (s, 3H), 2.40–2.61 (m, 6H), 1.90–1.98 (m, 2H), 1.80 (m, 4H):

MS (+ve ESI): 500 (M+H)$^+$.

EXAMPLE 37

Preparation of Compound 37 in Table 2

An analogous reaction to that described in example 32, but starting with 4-hydroxypiperidine (218 mg, 2.15 mmol), yielded the title compound (15 mg, 7% yield) as an off white solid:

$^1$H-NMR (DMSO-d$_6$): 9.10 (s, 2H), 8.41 (s, 1H), 7.96–8.00 (m, 2H), 7.81 (s, 1H), 7.43–7.60 (m, 3H), 7.15 (s, 1H), 4.45 (s, 1H), 4.21 (t, 3H), 3.99 (s, 3H), 3.90 (m, 1H), 2.35–2.44 (b, 6H), 1.90–2.05 (m, 4H), 1.35–1.45 (m, 2H):

MS (+ve ESI): 530 (M+H)$^+$.

EXAMPLE 38

Preparation of Compound 38 in Table 2

A mixture of 4-(((2-(N-benzoyl)amino)-5-pyrimidine) amino)-6-methoxy-7-hydroxyquinazoline (223 mg, 0.515 mmol), 2-(4-methylphenylsulphonyloxymethyl)-4-benzyl-morpholine (279 mg, 0.773 mmol) and caesium carbonate (502 mg, 1.55 mmol) in dimethylacetamide (1 ml) were heated in at 60° C. for 20 hours. The reaction was cooled, aqueous sodium hydrogen carbonate solution (10 ml) was added and the resultant solid was collected by suction filtration. Purification by flash chromatography on silica gel, eluting with 5–10% methanol in dichloromethane yielded the title compound (81 mg, 27% yield) as a pale yellow solid:

$^1$H-NMR (DMSO-d$_6$): 10.95 (s, 1H), 9.70 (s, 1H), 9.10 (s, 2H), 8.45 (s, 1H), 8.00 (d, 2H), 7.80 (s, 1H), 7.55–7.60 (m, 1H), 7.45–7.50 (m, 2H), 7.30–7.40 (m, 4H), 7.22–7.25 (m, 1H), 7.20 (s, 1H), 4.15 (d, 2H), 3.98 (s, 3H), 3.80–3.95 (m, 2H), 3.45–3.60 (m, 1H), 3.42 (s, 2H), 2.85 (d, 1H), 2.60 (d, 1H), 2.00–2.20 (m, 2H):

MS (–ve ESI): 576 (M–H)$^-$,

MS (+ve ESI): 578 (M+H)$^+$.

EXAMPLE 39

Preparation of Compound 39 in Table 2

An analogous reaction to that described in example 16, but starting with isonipectoamine (64 mg, 0.51 mmol), yielded the title compound (25 mg, 19% yield) as a white solid:

$^1$H-NMR (DMSO-d$_6$): 11.0 (s, 1H), 9.90 (s, 1H), 9.15 (s, 2H), 8.50 (s, 1H), 8.01 (d, 2H), 7.90 (s, 1H), 7.60–7.70 (m, 1H), 7.50–7.60 (m, 2H), 7.30 (s, 2H), 6.80 (s, 1H), 4.00–4.20 (m, 3H), 3.98 (s, 3H), 2.90–3.20 (m, 2H), 1.90–2.20 (m, 3H), 1.50–1.80 (m, 4H):

MS (–ve ESI): 571 (M–H)$^-$,

MS (+ve ESI): 573 (M+H)$^+$.

EXAMPLE 40

Preparation of Compound 40 in Table 2

An analogous reaction to that described in example 16, but starting with 2-amino-2-ethylpropane-1,3-diol (59 mg, 0.51 mmol), yielded the title compound (35 mg, 28% yield) as a white solid:

$^1$H-NMR (DMSO-d$_6$): 10.95 (s, 1H), 9.85 (s, 1H), 9.12 (s, 2H), 8.48 (s, 1H), 7.97 (d, 2H), 7.90 (s, 1H), 7.55–7.60 (m, 1H), 7.45∝7.50 (m, 2H), 7.20 (s, 1H), 5.00 (d, 1H), 4.20–4.25 (m, 1H), 4.00–4.18 (m, 2H), 3.98 (s, 3H), 3.80–3.90 (m, 1H), 3.10–3.20 (m, 3H), 2.60–2.80 (m, 1H), 2.40–2.50 (m, 2H), 1.20–1.30 (m, 2H), 0.70–0.95 (m, 3H):

MS (–ve ESI): 562 (M–H)$^-$,

MS (+ve ESI): 564 (M+H)$^+$.

EXAMPLE 41

Preparation of Compound 41 in Table 2

An analogous reaction to that described in example 16, but starting with 3-amino-3-methyl-1-butanol (52 mg, 0.51 mmol), yielded the title compound (28 mg, 23% yield) as a white solid:

$^1$H-NMR (DMSO-d$_6$): 10.95 (s, 1H), 9.83 (s, 1H), 9.13 (s, 2H), 8.48 (s, 1H), 7.97 (d, 2H), 7.88 (s, 1H), 7.55–7.60 (m, 1H), 7.45–7.50 (m, 2H), 7.22 (s, 1H), 4.00–4.20 (m, 2H), 3.98 (s, 3H), 3.80–3.95 (m, 1H), 3.50 (t, 2H), 2.55–2.75 (m, 2H), 1.50 (t, 2H), 1.02 (s, 6H):

MS (–ve ESI): 546 (M–H)$^-$,

MS (+ve ESI): 548 (M+H)$^+$.

EXAMPLE 42

Preparation of Compound 42 in Table 2

An analogous reaction to that described in example 16, but starting with 2-amino-2-methylpropanol (44 mg, 0.51 mmol), yielded the title compound (52 mg, 43% yield) as a white solid:

$^1$H-NMR (DMSO-d$_6$): 10.95 (s, 1H), 9.76 (s, 1H), 9.12 (s, 2H), 8.48 (s, 1H), 7.97 (d, 2H), 7.84 (s, 1H), 7.55–7.60 (m, 1H), 7.45–7.50 (m, 2H), 7.20 (s, 1H), 4.5 (s, 1H), 4.00–4.20 (m, 2H), 3.97 (s, 3H), 3.90–3.80 (m, 1H), 3.15–3.20 (m, 2H), 2.50–2.70 (m, 2H), 0.93 (s, 6H):

MS (–ve ESI): 532 (M–H)$^-$,
MS (+ve ESI): 534 (M+H)$^+$.

EXAMPLE 43

Preparation of Compound 43 in Table 2

An analogous reaction to that described in example 16, but starting with cyclohexylamine (51 mg, 0.51 mmol), yielded the title compound (66 mg, 54% yield) as a white solid:

$^1$H-NMR (DMSO-d$_6$): 9.70 (s, 1H), 9.10 (s, 2H), 8.50 (s, 1H), 7.97 (d, 2H), 7.81 (s, 1H), 7.55–7.60 (m, 1H), 7.45–7.50 (m, 2H), 7.22 (s, 1H), 5.01 (s, 1H), 4.00–4.20 (m, 2H), 3.97 (s, 3H), 3.85–3.96 (m, 1H), 2.60–2.80 (m, 2H), 2.30–2.40 (m, 1H), 1.75–1.85 (m, 2H), 1.60–1.70 (m, 2H), 1.50–1.58 (m, 1H), 0.98–1.25 (m, 5H):

MS (–ve ESI): 542 (M–H)$^-$,
MS (+ve ESI): 544 (M+H)$^+$.

EXAMPLE 44

Preparation of Compound 44 in Table 2

An analogous reaction to that described in example 16, but starting racemic 2-aminopropanol (38 mg, 0.51 mmol), yielded the title compound (29 mg, 25% yield) as a white solid:

$^1$H-NMR (DMSO-d$_6$): 10.95 (s, 1H), 9.80 (s, 1H), 9.20 (s, 2H), 8.50 (s, 1H), 7.97 (d, 2H), 7.88 (s, 1H), 7.55–7.60 (m, 1H), 7.45–7.50 (m, 2H), 7.23 (s, 1H), 5.00 (d, 1H), 4.20–4.35 (m, 1H), 4.02–4.20 (m, 2H), 3.98 (s, 3H), 3.96 (m, 1H), 3.20–3.30 (m, 2H), 2.70–2.73 (m, 1H), 2.55–2.65 (m, 2H), 0.95–0.98 (m, 3H), 0.80–0.85 (m, 1H):

MS (–ve ESI): 518 (M–H)$^-$,
MS (+ve ESI): 520 (M+H)$^+$.

EXAMPLE 45

Preparation of Compound 45 in Table 2

An analogous reaction to that described in example 16, but starting with neopentylamine (52 mg, 0.51 mmol), yielded the title compound (25 mg, 20% yield) as a white solid:

$^1$H-NMR (DMSO-d$_6$): 10.95 (s, 1H), 9.73 (s, 1H), 9.11 (s, 2H), 8.48 (s, 1H), 8.00 (d, 2H), 7.82 (s, 1H), 7.55–7.60 (m, 1H), 7.45–7.50 (m, 2H), 7.22 (s, 1H), 5.00 (s, 1H), 4.00–4.20 (m, 2H), 3.97 (s, 3H), 3.94 (m, 1H), 3.17 (s, 2H), 2.60–2.70 (m, 2H), 2.35–2.40 (m, 2H), 0.80 (s, 6H):

MS (–ve ESI): 546 (M–H)$^-$,
MS (+ve ESI): 548 (M+H)$^+$.

EXAMPLE 46

Preparation of Compound 46 in Table 2

An analogous reaction to that described in example 16, but starting with (2-aminomethyl)-1-ethylpyrrolidine (64 mg, 0.51 mmol), yielded the title compound (49 mg, 38% yield) as a white solid:

$^1$H-NMR (DMSO-d$_6$): 9.84 (s, 1H), 9.10 (s, 2H), 8.48 (s, 1H), 7.97 (d, 2H), 7.88 (s, 1H), 7.55–7.60 (m, 1H), 7.45–7.50 (m, 2H), 7.20 (s, 1H), 4.00–4.20 (m, 2H), 3.98 (s, 3H), 3.90–3.95 (m, 1H), 3.00–3.05 (m, 1H), 2.50–2.80 (m, 5H), 2.30–2.40 (m, 2H), 2.00–2.20 (m, 2H), 1.70–1.82 (m, 1H), 1.55–1.65 (m, 3H), 1.00 (t, 3H):

MS (–ve ESI): 571 (M–H)$^-$,
MS (+ve ESI): 573 (M+H)$^+$.

EXAMPLE 47

Preparation of Compound 47 in Table 2

An analogous reaction to that described in example 16, but starting with cyclohexymethylamine (58 mg, 9.51 mmol), yielded the title compound (54 mg, 43% yield) as a white solid:

$^1$H-NMR (DMSO-d$_6$): 10.95 (s, 1H), 9.73 (s, 1H), 9.10 (s, 2H), 8.50 (s, 1H), 8.00 (d, 2H), 7.80 (s, 1H), 7.55–7.60 (m, 1H), 7.45–7.50 (m, 2H), 7.20 (s, 1H), 5.00 (s, 1H), 4.00–4.20 (m, 2H), 4.00 (s, 3H), 3.90–3.98 (m, 2H), 2.55–2.70 (m, 3H), 2.40 (d, 2H), 1.55–1.80 (m, 6H), 1.05–1.20 (m, 3H), 0.80–0.90 (m, 2H):

MS (–ve ESI): 556 (M–H)$^-$,
MS (+ve ESI): 558 (M+H)$^+$.

EXAMPLE 48

Preparation of Compound 48 in Table 2

A mixture of 4-(((2-(N-benzoyl)amino)-5-pyrimidine)amino)-6-methoxy-7-(2-bromoethoxy)-quinazoline (350 mg, 0.707 mmol), 1-methyl-2-imidazolin hexafluorophosphate (350 mg, 0.707 mmol) and potassium carbonate (293 mg, 2.12 mmol) in dimethylformamide (8 ml) was heated at 80° C. for 4 hours. The solvent was removed in vacuo, water (10 ml) was added to the residue and the resultant solid was collected by suction filtration. Purification of this solid by flash chromatography on silica gel, eluting with 5–10% methanol containing ammonia in dichloromethane yielded the title compound (153 mg, 53% yield) as white solid:

$^1$H-NMR (DMSO-d$_6$): 9.14 (s, 2H), 8.52 (s, 1H), 8.01 (d, 2H), 7.86 (s, 1H), 7.63 (t, 1H), 7.54 (t, 2H), 7.28 (s, 1H), 4.28 (t, 2H), 3.99 (s, 3H), 3.60 (t, 2H), 3.51 (t, 2H), 3.40 (t, 2H), 1.96 (s, 3H):

MS (+ve ESI): 499 (M+H)$^+$.

EXAMPLE 49

Preparation of Compound 49 in Table 2

An analogous reaction to that described in example 48, but starting with 2-ethyl-2-imidazolin hexafluorophosphate (446 mg, 1.82 mmol) yielded the title compound (131 mg, 42% yield) as a white solid:

$^1$H-NMR (DMSO-d$_6$): 9.12 (s, 2H), 8.52 (s, 1H), 8.00 (d, 2H), 7.88 (s, 1H), 7.60 (t, 1H), 7.50 (t, 2H), 7.30 (s, 1H), 4.40 (t, 2H), 4.05 (t, 2H), 3.98 (s, 3H), 3.95 (t, 2H), 3.81 (t, 2H), 2.78 (q, 2H), 1.22 (t, 3H):
MS (+ve ESI): 513 (M+H)$^+$.

EXAMPLE 50

Preparation of Compound 50 in Table 2

An analogous reaction to that described in example 48, but starting with 1,4,5,6-tetrahydropyrimidine hexafluorophosphate (488 mg, 2.12 mmol) yielded the title compound (15 mg, 4% yield) as a white solid:
$^1$H-NMR (DMSO-d$_6$, CF$_3$COOD): 9.07 (s, 2H), 8.99 (s, 1H), 8.26 (s, 1H), 8.14 (s, 1H), 8.01 (d, 2H), 7.64 (t, 1H), 7.55 (t, 2H), 7.40 (s, 1H), 4.49 (t, 2H), 4.05 (s, 3H), 3.98 (t, 2H), 3.58 (t, 2H), 3.31 (t, 2H), 1.96 (m, 2H):
MS (+ve ESI): 499 (M+H)$^+$.

EXAMPLE 51

Preparation of Compound 51 in Table 2

An analogous reaction to that described in example 48, but starting 2-imidazolin hexafluorophosphate (393 mg, 1.82 mmol) yielded the title compound (75 mg, 38% yield) as a white solid:
$^1$H-NMR (DMSO-d$_6$, CF$_3$COOD): 9.07 (s, 2H), 8.99 (s, 1H), 8.14 (s, 1H), 8.0 (d, 2H), 7.58 (t, 1H), 7.54 (m, 2H), 7.43 (s, 1H), 4.98 (t, 2H), 4.03 (m, 9H);
MS (+ve ESI): 485 (M+H)$^+$.

EXAMPLE 52

Preparation of Compound 52 in Table 2

A mixture of 4-(((2-(N-benzoyl)amino)-5-pyrimidine)amino)-6-methoxy-7-hydroxyquinoline (200 mg, 0.51 mmol), 1-tert-butyloxycarbonyl-2-bromo ethylamine (578 mg, 2.98 mmol) and potassium carbonate (536 mg, 2.58 mmol) dimethylformamide (10 ml) in were heated at 80° C. for 2 hours. The solvent was removed in vacuo, water (10 ml) was added to the residue and the resultant solid was collected by suction filtration. Purification by flash chromatography on silica gel, eluting with 5–10% methanol containing ammonia in dichloromethane yielded the title compound (181 mg, 66% yield) as pale yellow solid:
$^1$H-NMR (DMSO-d$_6$): 9.07 (s, 2H), 8.41 (s, 1H), 7.98 (d, 2H), 7.81 (s, 1H), 7.60 (t, 1H), 7.51 (t, 2H), 7.17 (s, 1H), 7.02 (t, 1H), 4.15 (t, 2H), 3.95 (s, 3H), 3.37 (t, 2H), 1.39 (s, 9H):
MS (+ve ESI): 532 (M+H)$^+$.

1-tert-Butyloxycarbonyl-2-bromo ethylamine, used as the starting material was obtained as follows:
A mixture of 2-bromoethylamine hydrobromide (5.00 g, 24.4 mmol), di(tert-butyl)-dicarbonate (6.12 g, 28.1 mmol), triethylamine (7.14 ml, 51.2 mmol) and dimethylaminopyridine (0.3 g, 2.44 mmol) in dichloromethane (50 ml) was stirred at room temperature for 5 hours. The reaction was poured into water, extracted with ethyl acetate, washed with a saturated solution of sodium chloride, dried, filtered and concentrated to give an oil. Purified by flash chromatography on silica gel, eluting with 10% ethyl acetate in hexane yielded 1-tert-butyloxycarbonyl-2-bromo ethylamine (2.3 g, 42% yield):
$^1$H-NMR (CDCl$_3$): 4.95 (s, 1H), 3.52 (m, 2H), 3.46 (m, 2H), 1.45 (s, 9H).

EXAMPLE 53

Preparation of Compound 53 in Table 2

A mixture of 4-(((2-(N-benzoyl)amino)-5-pyrimidine)amino)-6-methoxy-7-hydroxyquinazoline (2.00 g, 5.15 mmol), 1-bromo-3-chloropropane (5.1 ml, 51.5 mmol) and potassium carbonate (2.14 g, 15.5 mmol) in dimethylacetamide (50 ml) was stirred at ambient temperature for 2 days. The mixture was filtered to remove salts then the solvents were removed in vacuo. Trituration of the residue with ethyl acetate, collection of the resultant solid by suction filtration and drying of the solid in vacuo yielded 4-(((2-(N-benzoyl)amino)-5-pyrimidine)amino)-6-methoxy-7-(3-chloropropoxy)-quinazoline (1.56 g, 65% yield) as a yellow solid:
$^1$H-NMR (DMSO-d$_6$): 10.96 (s, 1H), 9.79 (s, 1H), 9.60 (s, 2H), 8.49 (s, 1H), 7.96 (dd, 2H), 7.86 (s, 1H), 7.55 (m, 3H), 7.25 (s, 1H), 4.27 (t, 2H), 3.98 (s, 3H), 3.81 (t, 2H), 2.28 (m, 2H):
MS (+ve ESI): 465 (M+H)$^+$.

EXAMPLE 54

Preparation of Compound 54 in Table 2

A mixture of 4-(((2-(N-benzoyl)amino)-5-pyrimidine)amino)-6-methoxy-7-hydroxyquinazoline trifluoroacetate (200 mg, 0.515 mmol), (2S)-(+)-2-methylglycidyl-4-nitrobenzoate (134 mg, 0.567 mmol) and potassium carbonate (101 mg, 0.773 mmol) in dimethylformamide was heated to 70° C. for 20 hours. The reaction was cooled and poured into aqueous sodium bicarbonate solution (10 ml) and the resulting solid collected by suction filtration. Purification by flash chromatography on silica gel, eluting with 5% methanol in dichloromethane yielded the title compound (44 mg, 14% yield) as a pale yellow solid:
$^1$H-NMR (DMSO-d$_6$): 10.95 (s, 1H), 9.70 (s, 2H), 8.45 (s, 1H), 8.30 (d, 2H), 8.20 (d, 2H), 8.00 (dd, 2H), 7.8 (s, 1H), 7.55–7.60 (m, 1H); 7.45–7.50 (m, 2H), 7.15 (s, 1H), 4.30–4.40 (m, 2H), 4.10–4.20 (m, 2H), 3.99 (s, 3H), 1.40 (s, 3H):
MS (+ve ESI): 626 (M+H)$^+$
MS (−ve ESI): 624 (M−H)$^-$.

EXAMPLE 55

Preparation of Compound 55 in Table 2

To a solution of the 4-benzyl-3-morpholinemethanol (160 mg, 0.78 mmol—prepared according to *J. Chem. Soc., Perkin Trans.* 1 1985, 12, 2577–80) and triethylamine (0.143 ml, 1.02 mmol) in tetrahydrofuran (2 ml), was added methanesulphonylchloride (60 ul, 0.773 mmol) at 0° C. The reaction mixture was stirred at this temperature for 2 hours before removal of the triethylamine salts by filtration. The filtrate was concentrated and potassium carbonate (142 mg, 1.03 mmol) and a solution of 4-(((2-(N-benzoyl)amino)-5-pyrimidine)amino)-6-methoxy-7-hydroxyquinazoline trifluoroacetate (200 mg, 0.515 mmol) in dimethylacetamide (3 ml) were added. The reaction mixture was heated at 70° C. for 16 hours. The reaction was cooled, poured into aqueous sodium hydrogen carbonate solution (10 ml) and the resulting solid was collected by suction filtration. Purification by flash chromatography on silica gel, eluting with 5% methanol in dichloromethane yielded the title compound (60 mg, 20% yield) as a white solid:

¹H-NMR (DMSO-d₆): 10.95 (s, 1H), 9.70 (s, 1H), 9.10 (s, 2H), 8.50 (s, 1H), 8.00 (d, 2H), 7.80 (s, 1H), 7.55–7.60 (m, 1H); 7.45–7.50 (m, 2H), 7.15–7.40 (m, 6H), 4.40–4.50 (m, 1H), 4.20–4.25 (m, 1H), 4.00–4.05 (m, 1H), 3.99 (s, 3H), 3.80–3.90 (m, 1H), 3.45–3.650 (m, 4H), 2.85–3.00 (m, 1H), 2.65–2.70 (m, 1H), 2.20–2.30 (m, 1H):
MS (+ve ESI): 578 (M+H)⁺
MS (−ve ESI): 576 (M−H)⁻.

EXAMPLE 56

Preparation of Compound 56 in Table 2

An analogous reaction to that described in example 16, but starting with morpholine (0.50 ml, 5.7 mmol), yielded the title compound (57 mg, 32% yield) as a yellow solid:
¹H-NMR (DMSO-d₆): 10.95 (s, 1H), 9.80 (s, 1H), 9.15 (s, 2H), 8.50 (s, 1H), 8.00 (d, 2H), 7.90 (s, 1H), 7.55–7.60 (m, 1H), 7.45–7.50 (m, 2H), 7.25 (s, 1H), 4.90–4.95 (m, 1H), 4.15–4.20 (m, 1H), 4.05–4.10 (m, 1H), 4.00 (s, 3H), 3.60 (t, 4H), 2.40–2.50 (m, 4H):
MS (+ve ESI): 532 (M+H)⁺
MS (−ve ESI): 530 (M−H)⁻.

EXAMPLE 57

Preparation of Compound 57 in Table 2

A mixture of 4-(((2-(N-benzoyl)amino)-5-pyrimidine)amino)-6-methoxy-7-hydroxyquinazoline trifluoroacetate (480 mg, 1.23 mmol), 1-(3-bromopropyl)-1H-imidazole (500 mg, 1.48 mmol) and potassium carbonate (513 mg, 3.71 mmol) in dimethylformamide (15 ml) was heated to 80° C. for 4 hours. The reaction was concentrated, water (15 ml) was added to the residue and the resulting solid collected by suction filtration. Purification by flash chromatography on silica gel, eluting with 10–15% methanol, 1% ammonia in dichloromethane yielded the title compound (180 mg, 30% yield) as a pale yellow solid:
¹H-NMR (DMSO-d₆): 9.12 (s, 2H), 8.50 (s, 1H), 8.00 (m, 3H), 7.84 (m, 1H), 7.60 (t, 1H), 7.52 (t, 2H), 7.22 (m, 1H), 4.23 (t, 1H), 4.18 (m, 1H), 4.00 (m, 3H), 3.42 (m, 2H), 3.28 (m, 1H), 2.72 (m, 2H), 2.62 (t, 1H), 2.03 (m, 1H), 1.92 (t, 1H):
MS (+ve ESI): 499 (M+H)⁺.

1-(3-bromopropyl)-1H-imidazole), used as the starting material was obtained as follows:
A mixture of 1H-imidazole-1-propanol (1.00 g, 3.65 mmol—prepared according to patent: WO 9722596 A1), carbon tetrabromide (1.80 g, 5.47 mmol) and triphenyl phosphine (1.43 g, 5.47 mmol) was stirred at ambient temperature for 18 hours. The solvent was evaporated and the residue purified by flash chromatography on silica gel. Elution with 10% methanol in dichloromethane yielded the title compound (425 mg, 35% yield) as a pale yellow solid:
¹H-NMR (DMSO-d₆): 8.45 (s, 1H), 3.83 (m, 4H), 3.58 (m, 4H), 2.14 (q, 2H).

EXAMPLE 58

Preparation of Compound 58 in Table 2

Piperidine (1.0 ml, 0.86 mmol) was added to a solution of N-(5-((6-methoxy-7-((2S)-2-methyloxiranylmethoxy)-4-quinazolinyl)amino)-2-pyrimidinyl)benzamide and heated to 70° C. for 2 hours. The mixture was cooled and aqueous sodium bicarbonate solution (10 ml) added. The resulting solid was collected by suction filtration. Purification was by reverse phase preparative hplc, eluting with 25% acetonitrile in water containing 0.1% trifluoroacetic acid. Neutralisation with aqueous sodium bicarbonate and collection of the solid by suction filtration yielded the title compound (65 mg, 9% yield) as yellow solid:
¹H-NMR (DMSO-d₆): 10.50 (s, 1H), 9.50 (s, 1H), 9.10 (s, 2H), 8.50 (s, 1H), 8.00 (d, 2H), 7.85 (s, 1H), 7.70 (m, 1H), 7.55 (m, 2H), 7.40 (s, 1H), 4.10 (m, 2H), 3.98 (s, 3H), 3.96 (m, 1H), 2.70 (m, 6H), 1.65 (m, 4H), 1.45 (m, 2H), 1.30 (s, 3H):
MS (+ve ESI): 544 (M+H)⁺
MS (−ve ESI): 542 (M−H)⁻.

N-(5-((6-methoxy-7-((2S)-2-methyloxiranylmethoxy)-4-quinazolinyl)amino)-2-pyrimidinyl)benzamide solution, used as the starting material was obtained as follows: a) Methanesulphonyl chloride (233 mg, 2.05 mmol) was added to an ice cold solution of (R)-2-methylglycidol (170 mg, 1.93 mmol) and triethylamine (391 mg, 3.87 mmol) in diethylether (3 ml). The mixture was stirred at 0° C. for 30 minutes then at ambient temperature for 1 hour. The reaction was filtered to remove triethylamine hydrochloride. To the filtrate was added potassium carbonate (534 mg, 3.87 mmol) and 4-(((2-(N-benzoyl)amino)-5-pyrimidine)amino)-6-methoxy-7-hydroxyquinazoline (500 mg, 1.29 mmol) in dimethylacetamide (3 ml) and the mixture heated to 70° C. for 20 hours, then cooled, resulting in a solution of N-(5-((6-methoxy-7-((2S)-2-methyloxiranylmethoxy)-4-quinazolinyl)amino-2- b) pyrimidinyl)benzamide which was used without isolation.
MS (+ve ESI): 459 (M+H)⁺.

EXAMPLE 59

Preparation of Compound 59 in Table 2

An analogous reaction to that described in example 58, but starting with cyclopentylamine (175 mg, 2.06 mmol), yielded the title compound (63 mg, 11% yield) as a yellow solid:
¹H-NMR (DMSO-d₆): 10.95 (s, 1H), 10.12 (s, 1H), 9.20 (s, 2H), 8.48 (s, 1H), 8.05 (s, 1H), 7.97 (d, 2H), 7.57 (m, 1H), 7.50 (m, 2H), 7.20 (s, 1H), 4.04 (m, 1H), 3.98 (s, 3H), 3.90 (m, 1H), 2.70 (m, 3H), 1.75 (m, 2H), 1.60 (m, 2H), 1.40 (m, 4H), 1.24 (s, 3H):
MS (+ve ESI): 544 (M+H)⁺
MS (−ve ESI): 542 (M−H)⁻.

EXAMPLE 60

Preparation of Compound 60 in Table 2

An analogous reaction to that described in example 58, but starting with cyclohexylamine (204 mg, 2.06 mmol), yielded the title compound (40 mg, 7% yield) as a yellow solid:
¹H-NMR (DMSO-d₆): 10.95 (s, 1H), 9.72 (s, 1H), 9.10 (s, 2H), 8.48 (s, 1H), 7.97 (d, 2H), 7.81 (s, 1H), 7.57 (m, 1H), 7.48 (m, 2H), 7.20 (s, 1H), 4.65 (s, 1H), 4.02 (m, 1H), 3.97 (s, 3H), 3.90 (m, 1H), 2.65 (m, 2H), 2.30 (m, 2H), 1.80 (m, 2H), 1.65 (m, 2H), 1.50 (m, 1H), 1.21 (s, 3H), 1.15 (m, 2H), 1.00 (m, 2H):
MS (+ve ESI): 558 (M+H)⁺
MS (−ve ESI): 556 (M−H)⁻.

EXAMPLE 61

Preparation of Compound 61 in Table 2

An analogous reaction to that described in example 58, but starting with morpholine (179 mg, 2.06 mmol), yielded the title compound (34 mg, 6% yield) as a yellow solid:
$^1$H-NMR (DMSO-$d_6$): 9.10 (s, 2H), 8.45 (s, 1H), 7.97 (d, 2H), 7.85 (s, 1H), 7.57 (m, 1H), 7.47 (m, 2H), 7.20 (s, 1H), 4.50 (s, 1H), 4.05 (d, 1H), 3.97 (s, 3H), 3.90 (d, 1H), 3.47 (m, 4H), 2.45 (m, 4H), 1.22 (s, 3H):
MS (+ve ESI): 546 (M+H)$^+$
MS (−ve ESI): 544 (M−H)$^-$.

EXAMPLE 62

Preparation of Compound 62 in Table 2

An analogous reaction to that described in example 58, but starting with pyrrolidine (146 mg, 2.06 mmol), yielded the title compound (20 mg, 4% yield) as a yellow solid:
$^1$H-NMR (DMSO-$d_6$): 10.95 (s, 1H), 9.78 (s, 1H), 9.13 (s, 2H), 8.48 (s, 1H), 7.97 (d, 2H), 7.85 (s, 1H), 7.58 (m, 1H), 7.47 (m, 2H), 7.21 (s, 1H), 4.03 (m, 1H), 3.98 (s, 3H), 3.92 (m, 1H), 2.65 (m, 4H), 1.70 (m, 4H), 1.24 (s, 3H):
MS (+ve ESI): 530 (M+H)$^+$
MS (−ve ESI): 528 (M−H)$^-$.

EXAMPLE 63

Preparation of Compound 63 in Table 2

An analogous reaction to that described in example 58, but starting with 2-(ethylthio)ethylamine (216 mg, 2.06 mmol), yielded the title compound (40 mg, 7% yield) as a yellow solid:
$^1$H-NMR (DMSO-$d_6$): 9.80 (s, 1H), 9.12 (s, 2H), 8.48 (s, 1H), 7.97 (d, 2H), 7.83 (s, 1H), 7.58 (m, 1H), 7.48 (m, 2H), 7.20 (s, 1H), 4.65 (s, 1H), 4.02 (d, 1H), 3.98 (s, 3H), 3.92 (d, 1H), 2.55–2.80 (m, 6H), 2.45 (m, 2H), 1.22 (s, 3H), 1.10 (t, 3H):
MS (+ve ESI): 564 (M+H)$^+$
MS (−ve ESI): 562 (M−H)$^-$.

EXAMPLE 64

Preparation of Compound 64 in Table 2

An analogous reaction to that described in example 32, but starting with 5-amino-2-piperidine (230 mg, 2.70 mmol), yielded the title compound (10 mg, 4% yield):
$^1$H-NMR (DMSO-$d_6$): 9.80 (s, 1H), 9.10 (s, 2H), 8.41 (s, 1H), 7.96–8.00 (m, 2H), 7.81 (s, 1H), 7.43–7.0 (m, 3H), 7.15 (s, 1H), 4.21 (t, 3H), 3.99 (s, 3H), 2.10–2.58 (m, 6H), 1.90–1.98 (m, 2H), 1.35–1.60 (m, 6H):
MS (+ve ESI): 514 (M+H)$^+$.

EXAMPLE 65

Preparation of Compound 65 in Table 2

Dibenzyl-N,N-diethylphosphoramidine (233 mg, 0.736 mmol) was added slowly to a solution of N-(5-((7-(((2S)-2-hydroxy-3-piperidinopropyl)oxy)-6-methoxy-4-quinazolinyl)amino)-2-pyrimidinyl)benzamide (300 mg, 0.566 mmol) and tetrazole (119 mg, 1.698 mmol) in dimethylformamide (12 ml). The reaction was stirred under an inert atmosphere at ambient temperature for 4 hours during which a further two portions of dibenzyl-N,N-diethylphosphoramidine (115 mg, 0.36 mmol) were added. The reaction was cooled to −40° C. and metachloroperbenzoic acid (279 mg, 1.13 mmol) was added and the reaction stirred for 1 hour. The reaction was quenched with aqueous sodium metabisulphite and extracted into dichloromethane. Purification by flash chromatography on silica gel, eluting with 5% methanol in dichloromethane containing ammonia yielded the title compound (85 mg, 19% yield) as a yellow glassy solid:
$^1$H-NMR (DMSO-$d_6$): 10.95 (s, 1H), 9.72 (s, 1H), 9.12 (s, 2H), 8.50 (s, 1H), 7.98 (dd, 2H), 7.82 (s, 1H), 7.59 (d, 1H), 7.51 (t, 2H), 7.37 (m, 5H), 7.28 (m, 6H), 5.12 (m, 4H), 4.83 (s, 1H), 4.38 (m, 2H), 3.85 (s, 3H), 2.20–2.70 (m, 6H), 1.22–1.51 (m, 6H):
MS (+ve ESI): 790 (M+H)$^+$.

N-(5-((7-(((2S)-2-hydroxy-3-piperidinopropyl)oxy)-6-methoxy-4-quinazolinyl)amino)-2-pyrimidinyl)benzamide, used as the starting material was obtained as described in example 19.

EXAMPLE 66

Preparation of Compound 66 in Table 2

Trimethylsilyl bromide (140 mg, 0.91 mmol) was added slowly to a solution of (1S)-2-[(4-{[2-(benzoylamino)-5-pyrimidinyl]amino}-6-methoxy-7-quinazolinyl)oxy]-1-(piperidinomethyl)ethyl dibenzyl phosphate (72 mg, 0.09 mmol) in dichloromethane (5 ml) at −60° C. The reaction was stirred for 10 minutes then warmed to ambient temperature and stirred for 1 hour. Methanol was added and the reaction concentrated in vacuo. Trituration with diethylether and collection of the solid by suction filtration yielded the title compound (53 mg, 75% yield) as the di hydrobromide salt:
$^1$H-NMR (DMSO-$d_6$+CD$_3$COOD): 9.10 (s, 2H), 8.78 (s, 1H), 8.20 (s, 1H), 8.00 (d, 2H), 7.61 (m, 1H), 7.51 (m, 2H), 7.40 (s, 1H), 5.03 (m, 1H), 4.49 (d, 2H), 4.07 (s, 3H), 3.52 (m, 2H), 3.35 (m, 4H), 1.81 (m, 4H), 1.60 (m, 2H):
MS (+ve ESI): 610 (M+H)$^+$.

Particular examples of compounds of formula (I) are set out in Table 3

EXAMPLE 67

Preparation of Compound 67 in Table 3

A mixture of 4-chlorobenzoic anhydride (89 mg, 0.3 mmol) and 4-(2-amino-5-pyrimidinamino)-6-methoxy-7-(3-morpholinopropoxy)quinazoline (62 mg, 0.15 mmol) in diphenylether (1 ml) was stirred for 20 hours at 150° C. The mixture was cooled, diluted with diethylether (10 ml) and the solid was collected by suction filtration. Purification by reverse phase preparative hplc, eluting with 25% acetonitrile in water containing 0.1% trifluoroacetic acid yielded the title compound (48 mg, 58% yield) as a white solid:
$^1$H-NMR (DMSO-$d_6$): 11.20 (s, 1H), 11.05 (s, 1H), 9.05 (s, 2H), 8.80 (s, 1H), 8.03 (s, 1H), 7.98 (d, 2H), 7.58 (d, 2H), 7.38 (s, 1H), 4.30 (m, 2H), 4.01 (m, 2H), 4.00 (s, 3H), 3.70 (m, 2H), 3.50 (m, 2H), 3.30 (m, 2H), 3.10 (m, 2H), 2.30 (m, 2H):
MS (−ve ESI): 548 (M−H)$^-$,
MS (+ve ESI): 550 (M+H)$^+$.

4-(2-amino-5-pyrimidinamino)-6-methoxy-7-(3-morpholinopropoxy)quinazoline, used as starting material was obtained as in example 8.

EXAMPLE 68

Preparation of Compound 68 in Table 3

An analogous reaction to that described in example 67, but starting with 4-(2-amino-5-pyrimidinamino)-6-methoxy-7-benzyloxyquinazoline (2.36 mg, 6.31 mmol), and 4-chlorobenzoic anhydride (3.72 g, 12.62 mmol), yielded the title compound (2.9 g, 89% yield) as a white solid:

$^1$H-NMR (DMSO-d$_6$): 11.01 (s, 1H), 10.0 (s, 1H), 9.11 (s, 2H), 8.42 (s, 1H), 7.95 (m, 3H), 7.53 (d, 2H), 7.45 (m, 2H), 7.38 (m, 3H), 7.30 (s, 1H), 5.22 (s, 2H), 3.95 (s, 3H):

MS (–ve ESI): 513 (M–H)$^-$,

MS (+ve ESI): 513 (M+H)$^+$.

4-(2-amino-5-pyrimidinamino)-6-methoxy-7-benzyloxyquinazoline, used as the starting material was obtained as follows:

a) 10% Platinum on carbon (500 mg, 0.25 mmol) was added to a stirred suspension on 2-amino-5-nitropyrimidine (7.41 g, 52.89 mmol) in ethanol (250 ml) and water (100 ml) at ambient temperature and the reaction stirred for 36 hours under an atmosphere of hydrogen. The reaction was filtered through a pad of celite and the solvent evaporated in vacuo to yield crude 2,5-diaminopyrimidine (5.77 g, 99% yield) as a brown solid:

$^1$H-NMR (DMSO-d$_6$): 7.73 (s, 2H), 5.57 (s, 2H), 4.36 (s, 2H):

MS (+ve ESI): 110 (M+H)$^+$.

b) A solution of 2,5-diaminopyrimidine (1.34 g, 12.2 mmol), 4-chloro-6-methoxy-7-benzyloxyquinazoline (3.66 g, 12.2 mmol) and 1.0N solution of hydrogen chloride in diethylether (25 ml, 24.4 mmol), in isopropanol (100 ml) was heated and the diethylether allowed to evaporate then heated at reflux for 1.5 hours before the reaction was allowed to cool to ambient temperature. The solid which had precipitated was collected by suction filtration and washed with diethyl ether (2×20 ml). The solid was dissolved in methanol/dichloromethane/ammonia then solvents removed in vacuo. The solid was triturated with water and the solid collected by suction filtration. Drying of this material yielded 4-(2-amino-5-pyrimidinamino)-6-methoxy-7-benzyloxyquinazoline (2.32 g, 51% yield) as a brown solid:

$^1$H-NMR (DMSO-d$_6$): 8.51 (s, 1H), 8.43 (s, 2H), 8.00 (s, 1H), 7.51 (m, 2H), 7.41 (m, 3H), 7.32 (s, 1H), 6.63 (s, 2H), 5.32 (s, 2H), 3.95 (s, 3H):

MS (–ve ESI): 373 (M–H)$^-$,

MS (+ve ESI): 375 (M+H)$^+$.

EXAMPLE 69

Preparation of Compound 69 in Table 3

An analogous reaction to that described in example 13, but starting with 4-(((2-(N-4-chlorobenzoyl)amino)-5-pyrimidine)amino)-6-methoxy-7-benzyloxy-quinazoline (2.85 g, 5.57 mmol), yielded the title compound (0.88 mg, 37% yield) as a white solid:

$^1$H-NMR (DMSO-d$_6$): 11.14 (s, 1H), 10.90 (bs, 1H), 8.98 (s, 2H), 8.72 (s, 1H), 7.92 (d, 2H), 7.53 (d, 2H), 7.15 (s, 1H), 3.95 (s, 3H):

MS (+ve ESI): 423 (M+H)$^+$.

EXAMPLE 70

Preparation of Compound 70 in Table 3

An analogous reaction to that described in example 14, but starting with 4-(((2-(N-4-chlorobenzoyl)amino)-5-pyrimidine)amino)-6-methoxy-7-hydroxyquinazoline (417 g, 0.99 mmol) and (2R)-(–)-glycidyl tosylate (250 g, 1.09 mmol), yielded the title compound (426 g, 90% yield) as a beige solid:

$^1$H-NMR (DMSO-d$_6$): 8.98 (s, 2H), 8.32 (s, 1H), 8.00 (d, 2H), 7.81 (s, 1H), 7.55 (d, 2H), 7.10 (s, 1H), 4.50 (m, 1H), 3.95 (m, 4H), 3.40 (m, 1H), 2.85 (m, 1H), 2.75 (m, 1H):

MS (–ve ESI): 477 (M–H)$^-$,

MS (+ve ESI): 479 (M+H)$^+$.

EXAMPLE 71

Preparation of Compound 71 in Table 3

An analogous reaction to that described in example 16, but starting with 4-(((2-(N-4-chlorobenzoyl)amino)-5-pyrimidine)amino)-6-methoxy-7-((2R)-oxiranylmethoxy)quinazoline (96 g, 0.2 mmol) and pyrrolidine (71.6 g, 1.0 mmol), yielded the title compound (23 g, 21% yield) as a white solid:

$^1$H-NMR (DMSO-d$_6$): 11.11 (s, 1H), 9.75 (s, 1H), 9.12 (s, 2H), 8.50 (s, 1H), 8.00 (d, 2H), 7.82 (s, 1H), 7.58 (d, 2H), 7.23 (s, 1H), 4.98 (s, 1H), 4.18 (m, 1H), 4.05 (m, 2H), 4.00 (s, 3H), 2.60 (m, 6H), 1.71 (m, 4H):

MS (–ve ESI): 548 (M–H)$^-$,

MS (+ve ESI): 550 (M+H)$^+$.

EXAMPLE 72

Preparation of Compound 72 in Table 3

An analogous reaction to that described in example 16, but starting with piperidine (85.2 g, 1.0 mmol), yielded the title compound (32 g, 28.4% yield) as a white solid:

$^1$H-NMR (DMSO-d$_6$): 11.10 (s, 1H), 9.75 (s, 1H), 9.12 (s, 2H), 8.42 (s, 1H), 7.95 (d, 2H), 7.75 (s, 1H), 7.61 (d, 2H), 7.18 (s, 1H), 4.10 (m, 1H), 3.98 (m, 2H), 3.95 (s, 3H), 2.41 (m, 6H), 1.45 (m, 4H), 1.30 (m, 2H):

MS (–ve ESI): 562 (M–H)$^-$,

MS (+ve ESI): 564 (M+H)$^+$.

EXAMPLE 73

Preparation of Compound 73 in Table 3

An analogous reaction to that described in example 16, but starting with cyclopentylamine (85.4 g, 1.0 mmol), yielded the title compound (29 g, 25.7% yield) as a white solid:

$^1$H-NMR (DMSO-d$_6$): 10.10 (s, 1H), 9.75 (s, 1H), 9.11 (s, 2H), 8.45 (s, 1H), 7.95 (d, 2H), 7.75 (s, 1H), 7.52 (d, 2H), 7.18 (s, 1H), 4.10 (m, 1H), 4.00 (m, 1H), 3.95 (s, 4H), 3.0 (m, 1H), 2.65 (m, 1H), 2.55 (m, 1H), 1.65 (m, 2H), 1.55 (m, 2H), 1.41 (m, 2H), 1.25 (m, 2H):

MS (+ve ESI): 564 (M+H)$^+$.

EXAMPLE 74

Preparation of Compound 74 in Table 3

An analogous reaction to that described in example 16, but starting with cyclohexylamine (99.6 g, 1.0 mmol), yielded the title compound (27 g, 23.4% yield) as a white solid:

$^1$H-NMR (DMSO-$d_6$): 11.05 (s, 1H), 9.78 (s, 1H), 9.08 (s, 2H), 8.45 (s, 1H), 7.95 (d, 2H), 7.80 (s, 1H), 7.52 (d, 2H), 7.20 (s, 1H), 4.10 (m, 3H), 3.90 (s, 3H), 2.50–3.20 (m, 5H), 1.90 (m, 2H), 1.65 (m, 2H), 1.50 (m, 1H), 1.15 (m, 5H):
MS (–ve ESI): 576 (M–H)$^-$,
MS (+ve ESI): 578 (M+H)$^+$.

EXAMPLE 75

Preparation of Compound 75 in Table 3

Caesium carbonate (1.30 g, 4.0 mmol) was added to a solution of 4-(((2-(N-4-chlorobenzoyl)amino)-5-pyrimidine)amino)-6-methoxy-7-hydroxyquinazoline (422 mg, 1.0 mmol) and 1,2-dibromoethane (1.88 g, 10.0 mmol) in dimethylformamide (5 ml) and tetrahydrofuran (5 ml) and the reaction heated at 60° C. for 3 hours. The mixture was concentrated in vacuo then poured into ice-water (50 ml) and the resulting solid was collected by suction filtration. Drying of the solid yielded the title compound (400 mg, 76% yield) as light brown solid:

$^1$H-NMR (DMSO-$d_6$): 10.96 (s, 1H), 9.75 (s, 1H), 9.11 (s, 2H), 8.49 (s, 1H), 7.98 (d, 2H, J=7 Hz), 7.84 (s, 1H), 7.57–7.62 (m, 1H), 7.48–7.53 (m, 2H), 7.25 (s, 1H), 4.51 (t, 2H, J=7 Hz), 3.99 (s, 3H), 3.88 (t, 2H, J=7 Hz):
MS (–ve ESI): 493, 495 (M–H)$^-$,
MS (+ve ESI): 495, 497 (M+H)$^+$.

EXAMPLE 76

Preparation of Compound 76 in Table 3

A solution of 4-(((2-(N-4-chlorobenzoyl)amino)-5-pyrimidine)amino)-6-methoxy-7-(2-bromoethoxy)quinazoline (124 mg, 0.24 mmol) and pyrrolidine (84.4 mg, 1.18 mmol) were heated in dimethylformamide (3 ml) at 60° C. for 5 hours. The reaction was cooled, poured into ice water (15 ml) containing concentrated aqueous ammonia solution (0.5 ml) and the resultant solid was collected by suction filtration. Drying of the solid in vacuo yielded the title compound (76 mg, 62% yield) as white solid:

$^1$H-NMR (DMSO-$d_6$): 11.0 (s, 1H), 9.65 (s, 1H), 9.05 (s, 2H), 8.42 (s, 1H), 7.95 (d, 2H), 7.75 (s, 1H), 7.51 (d, 2H), 7.18 (s, 1H), 4.20 (t, 2H), 3.92 (s, 3H), 2.80 (t, 2H), 2.50 (m, 4H), 1.61 (m, 4H):
MS (–ve ESI): 518 (M–H)$^-$,
MS (+ve ESI): 520 (M+H)$^+$.

EXAMPLE 77

Preparation of Compound 77 in Table 3

An analogous reaction to that described in example 76, but starting with piperidine (72.3 mg, 0.85 mmol). Purification by reverse phase preparative, eluting with 25% acetonitrile in water containing 0.1% trifluoroacetic acid, followed by neutralisation with ammonia, yielded the title compound (33 mg, 36.4% yield) as a white solid:

$^1$H-NMR (DMSO-$d_6$): 11.05 (s, 1H), 9.71 (s, 1H), 9.05 (s, 2H), 8.45 (s, 1H), 7.95 (d, 2H), 7.75 (s, 1H), 7.50 (d, 2H), 7.21 (s, 1H), 4.15 (t, 2H), 3.95 (s, 3H), 2.68 (m, 2H), 2.42 (m, 4H), 1.41 (m, 4H), 1.30 (m, 2H):
MS (–ve ESI): 532 (M–H)$^-$,
MS (+ve ESI): 534 (M+H)$^+$.

EXAMPLE 78

Preparation of Compound 78 in Table 3

An analogous reaction to that described in example 76, but starting with cyclopentylamine (101 mg, 1.18 mmol), yielded the title compound (71 mg, 56.4% yield) as a white solid:

$^1$H-NMR (DMSO-$d_6$): 9.71 (s, 1H), 9.08 (s, 2H), 8.42 (s, 1H), 7.95 (d, 2H), 7.75 (s, 1H), 7.50 (d, 2H), 7.17 (s, 1H), 4.15 (t, 2H), 3.92 (s, 3H), 3.02 (m, 1H), 2.91 (t, 2H), 1.72 (m, 2H), 1.55 (m, 2H), 1.41 (m, 2H), 1.25 (m, 2H):
MS (–ve ESI): 532 (M–H)$^-$,
MS (+ve ESI): 534 (M+H)$^+$.

EXAMPLE 79

Preparation of Compound 79 in Table 3

An analogous reaction to that described in example 76, but starting with cyclohexylamine (66 mg, 1.18 mmol), yielded the title compound (95 mg, 74% yield) as a white solid:

$^1$H-NMR (DMSO-$d_6$): 9.65 (s, 1H), 9.05 (s, 2H), 8.42 (s, 1H), 7.95 (d, 2H), 7.77 (s, 1H), 7.51 (d, 2H), 7.18 (s, 1H), 4.10 (t, 2H), 3.95 (s, 3H), 2.91 (t, 2H), 2.38 (m, 1H), 1.80 (m, 2H), 1.62 (m, 2H), 1.51 (m, 1H), 0.90–1.21 (m, 5H):
MS (–ve ESI): 546 (M–H)$^-$,
MS (+ve ESI): 548 (M+H)$^+$.

EXAMPLE 80

Preparation of Compound 80 in Table 3

An analogous reaction to that described in example 76, but starting with cyclopropanemethylamine (61 mg, 0.85 mmol), yielded the title compound (36 mg, 41% yield) as a white solid:

$^1$H-NMR (DMSO-$d_6$): 10.95 (s, 1H), 9.62 (s, 1H), 8.95 (s, 2H), 8.35 (s, 1H), 7.85 (d, 2H), 7.68 (s, 1H), 7.43 (d, 2H), 7.12 (s, 1H), 4.10 (t, 2H), 3.81 (s, 3H), 2.92 (t, 2H), 2.38 (m, 2H), 0.75 (m, 1H), 0.30 (m, 2H), 0.01 (m, 2H):
MS (–ve ESI): 518 (M–H)$^-$,
MS (+ve ESI): 520 (M+H)$^+$.

EXAMPLE 81

Preparation of Compound 81 in Table 3

An analogous reaction to that described in example 76, but starting with tetrahydrofurfurylamine (86.24 mg, 0.85 mmol), yielded the title compound (15 mg, 16.1% yield) as a white solid:

$^1$H-NMR (DMSO-$d_6$): 11.05 (s, 1H), 9.70 (s, 1H), 9.05 (s, 2H), 8.45 (s, 1H), 7.92 (d, 2H), 7.75 (s, 1H), 7.50 (d, 2H), 7.18 (s, 1H), 4.15 (t, 2H), 3.95 (s, 3H), 3.82 (m, 1H), 3.65 (m, 1H), 3.55 (m, 1H), 2.91 (m, 2H), 2.60 (d, 2H), 1.80 (m, 4H), 1.45 (m, 1H):
MS (+ve ESI): 550 (M+H)$^+$.

EXAMPLE 82

Preparation of Compound 82 in Table 3

An analogous reaction to that described in example 14, but starting with 4-(((2-(N-3-chlorobenzoyl)amino)-5-pyrimidine)amino)-6-methoxy-7-hydroxyquinazoline (100 mg, 0.237 mmol) and (2S)-(+)-glycidyl tosylate (59 mg, 0.261 mmol), yielded the title compound (28 mg, 25% yield) as a yellow solid:

$^1$H-NMR (DMSO-$d_6$): 11.10 (s, 1H), 9.81 (s, 1H), 9.11 (s, 2H), 8.52 (s, 1H), 8.00 (s, 1H), 7.90 (d, 1H), 7.80 (s, 1H), 7.65 (d, 1H), 7.55 (m, 1H), 7.21 (s, 1H), 4.55 (m, 1H), 4.02 (m, 1H), 3.99 (s, 3H), 3.43 (m, 1H), 2.91 (m, 1H), 2.75 (m, 1H):

MS (+ve ESI): 479 (M+H)$^+$

MS (−ve ESI): 477 (M−H)$^−$.

4-(((2-(N-3-chlorobenzoyl)amino)-5-pyrimidine)amino)-6-methoxy-7-hydroxyquinazoline, used as starting material was obtained as follows:

a) Triphosgene (5.63 g, 19 mmol) was added to an ice cold solution of 3-chlorobenzoic acid (17.76 g, 114 mmol) and triethylamine (16 ml, 114 mmol) in ethyl acetate (250 ml). The reaction was stirred for 15 min then 1 hour at ambient temperature. The mixture was filtered to remove triethylamine hydrochloride then concentrated in vacuo. Diphenyl ether (16 g) and 2-amino-5-nitropyrimidine (4 g, 28.6 mmol) were added, mixed and heated 20 hours at 150° C. The mixture was cooled and diluted with diethylether (100 ml). Collected of the solid by suction filtration yielded, 2-(N-3-chlorobenzoyl)amino-5-nitropyrimidine (7.94 g, 100% yield) as a beige solid:

$^1$H-NMR (DMSO-$d_6$): 11.82 (s, 1H), 9.40 (s, 2H), 8.00 (s, 1H), 7.91 (d, 1H), 7.72 (d, 1H), 7.55 (m, 1H):

MS (+ve ESI): 279 (M+H)$^+$

MS (−ve ESI): 277 (M−H)$^−$.

b) An analogous reaction to example 122 (part b), but starting with 2-(N-3-chlorobenzoyl)amino-5-nitropyrimidine (7.94 g, 28.6 mmol), yielded 2-(N-3-chlorobenzoyl)amino-5-aminopyrimidine (5.5 g, 77% yield):

$^1$H-NMR (DMSO-$d_6$): 8.25 (s, 1H), 8.05 (s, 2H), 7.95 (s, 1H), 7.85 (d, 1H), 7.65 (d, 1H), 7.55 (m, 1H):

MS (+ve ESI): 249 (M+H)$^+$.

c) An analogous reaction to example 12, but starting with 2-(N-3-chlorobenzoyl)amino-5-aminopyrimidine (3.3 g 13.3 mmol), yielded 4-(((2-(N-3-chlorobenzoyl)amino)-5-pyrimidine)amino)-6-methoxy-7-benzyloxyquinazoline (6.02 g, 88% yield):

$^1$H-NMR (DMSO-$d_6$): 11.75 (s, 1H), 11.23 (s, 1H), 9.11 (s, 2H), 8.80 (s, 1H), 8.42 (s, 1H), 8.00 (d, 1H), 7.91 (dd, 1H), 7.65 (dd, 1H), 7.55 (m, 3H), 7.41 (m, 4H), 5.40 (s, 2H), 4.00 (s, 3H):

MS (+ve ESI): 513 (M+H)$^+$

MS (−ve ESI): 511 (M−H)$^−$.

d) An analogous reaction to example 13, but starting with 4-(((2-(N-3-chlorobenzoyl)amino)-5-pyrimidine)amino)-6-methoxy-7-benzyloxyquinazoline (6.02 g, 11.8 mmol), yielded 4-(((2-(N-3-chlorobenzoyl)amino)-5-pyrimidine)amino)-6-methoxy-7-hydroxyquinazoline (3.7 g, 74% yield):

$^1$H-NMR (DMSO-$d_6$): 11.10 (s, 1H), 10.42 (s, 1H), 9.81 (s, 1H), 9.10 (s, 2H), 8.42 (s, 1H), 8.00 (s, 1H), 7.91 (d, 1H), 7.80 (s, 1H), 7.61 (d, 1H), 7.50 (m, 1H), 7.20 (s, 1H), 4.00 (s, 3H):

MS (+ve ESI): 423 (M+H)$^+$

MS (−ve ESI): 421 (M−H)$^−$.

EXAMPLE 83

Preparation of Compound 83 in Table 3

An analogous reaction to that described in example 14, but starting with 4-(((2-(N-4-fluorobenzoyl)amino)-5-pyrimidine)amino)-6-methoxy-7-hydroxyquinazoline (5.24 g, 12.9 mmol) and (2S)-(+)-glycidyl tosylate (3.23 g, 14.2 mmol), yielded the title compound (346 mg, 6% yield) as a yellow solid:

$^1$H-NMR (DMSO-$d_6$): 11.00 (s, 1H), 9.81 (s, 1H), 9.10 (s, 2H), 8.50 (s, 1H), 8.05 (m, 2H), 7.18 (s, 1H), 7.35 (m, 2H), 7.21 (s, 1H), 4.55 (m, 1H), 4.00 (m, 1H), 3.97 (s, 3H), 3.42 (m, 1H), 2.85 (m, 1H):

MS (+ve ESI): 463 (M+H)$^+$,

MS (−ve ESI): 461 (M−H)$^−$.

4-(((2-(N-4-fluorobenzoyl)amino)-5-pyrimidine)amino)-6-methoxy-7-hydroxyquinazoline, used as starting material was obtained as follows:

a) An analogous reaction to example 82 (part a), but starting with 3-fluorobenzoic acid (12.12 g, 86.6 mmol), yielded 2-(N-4-fluorobenzoyl)amino-5-nitropyrimidine (3.75 g, 66% yield), after crystallisation from ethanol:

$^1$H-NMR (DMSO-$d_6$): 9.41 (s, 1H), 9.00 (s, 1H), 8.20 (s, 1H), 8.05 (m, 2H), 7.35 (m, 2H):

MS (+ve ESI): 263 (M+H)$^+$,

MS (−ve ESI): 261 (M−H)$^−$.

b) An analogous reaction to example 122 part b, but starting with 2-(N-4-fluorobenzoyl)amino-5-nitropyrimidine (3.75 g, 14.3 mmol), yielded 2-(N-4-fluorobenzoyl)amino-5-aminopyrimidine (3.31 g, 90% yield):

$^1$H-NMR (DMSO-$d_6$): 8.05 (s 2H), 7.95 (m, 2H), 7.25 (m, 2H), 5.40 (s, 2H):

MS (+ve ESI): 233 (M+H)$^+$.

c) An analogous reaction to example 12, but starting with 2-(N-4-fluorobenzoyl)amino-5-aminopyrimidine (3.3 g 14.3 mmol), yielded 4-(((2-(N-4-fluorobenzoyl)amino)-5-pyrimidine)amino)-6-methoxy-7-benzyloxyquinazoline (5.28 g, 77% yield):

$^1$H-NMR (DMSO-$d_6$): 11.90 (s, 1H), 11.15 (s, 1H), 9.11 (s, 2H), 8.85 (s, 1H), 8.45 (s, 1H), 8.05 (m, 2H), 7.25–7.55 (m, 8H), 5.31 (s, 2H), 4.02 (s, 3H):

MS (+ve ESI): 497 (M+H)$^+$,

MS (−ve ESI): 495 (M−H)$^−$.

d) An analogous reaction to example 13, but starting with 4-(((2-(N-4-fluorobenzoyl)amino)-5-pyrimidine)amino)-6-methoxy-7-benzyloxyquinazoline (5.28 g, 9.9 mmol), yielded 4-(((2-(N-4-fluorobenzoyl)amino)-5-pyrimidine)amino)-6-methoxy-7-hydroxyquinazoline (3.02 g, 75% yield):

$^1$H-NMR (DMSO-$d_6$): 11.25 (s, 1H), 9.10 (s, 2H), 8.51 (s, 1H), 8.05 (m, 2H), 7.92 (s, 1H), 7.35 (m, 2H), 7.20 (s, 1H), 4.0 (s, 3H):

MS (+ve ESI) 408 (M+H)$^+$.

EXAMPLE 84

Preparation of Compound 84 in Table 3

An analogous reaction to that described in example 16, but starting with piperidine (18 mg, 0.22 mmol) and N-(5-((6-methoxy-7-((2S)-oxiranylmethoxy)-4-quinazolinyl)amino)-2-pyrimidinyl)-3-chlorobenzamide (70 mg, 0.146 mmol), yielded the title compound (40 mg, 49% yield) as a yellow solid:

¹H-NMR (DMSO-d₆): 11.10 (s, 1H), 9.81 (s, 1H), 9.11 (s, 2H), 8.51 (s, 1H), 8.00 (s, 1H), 7.95 (d, 1H), 7.82 (s, 1H), 7.65 (d, 1H), 7.57 (m, 1H), 7.21 (s, 1H), 4.14 (m, 1H), 4.0 (m, 2H), 3.98 (s, 3H), 2.45 (m, 4H), 1.55 (m, 3H), 1.49 (m, 2H):
MS (+ve ESI): 564 (M+H)⁺,
MS (−ve ESI): 562 (M−H)⁻.

EXAMPLE 85

Preparation of Compound 85 in Table 3

An analogous reaction to that described in example 6, but starting with 2-(N-3-chloro-4-fluorobenzoyl)-amino-5-aminopyrimidine (100 mg, 0.375 mmol) and 4-chloro-6-methoxy-7-((1-methyl-4-piperazinyl)methoxy)quinazoline (121 mg, 0.375 mmol). Neutralisation with aqueous sodium bicarbonate and collection of the solid by suction filtration. Purification by reverse phase preparative hplc, eluting with 25% acetonitrile in water containing 0.1% trifluoroacetic acid, followed by neutralisation with sodium bicarbonate, yielded the title compound (35 mg, 17% yield):
¹H-NMR (DMSO-d₆): 9.10 (s, 2H), 8.45 (s, 1H), 8.21 (m, 1H), 8.00 (m, 1H), 7.81 (s, 1H), 7.55 (t, 1H), 7.20 (s, 1H), 4.00 (m, 2H), 3.97 (s, 3H), 2.75 (m, 2H), 2.15 (s, 3H), 1.71–1.92 (m, 5H), 1.20 (m, 2H):
MS (+ve ESI): 552 (M+H)⁺
MS (−ve ESI): 550 (M−H)⁻.

EXAMPLE 86

Preparation of Compound 86 in Table 3

An analogous reaction to that described in example 6, but starting with 2-(N-3-chloro-4-fluorobenzoyl)-amino-5-aminopyrimidine (100 mg, 0.375 mmol) and 4-chloro-6-methoxy-7-benzyloxyquinazoline (100 mg, 0.33 mmol), yielded the title compound (148 mg, 74% yield):
¹H-NMR (DMSO-d₆): 11.59 (s, 1H), 11.27 (s, 1H), 9.11 (s, 2H), 8.85 (s, 1H), 8.37 (s, 1H), 8.20 (m, 1H), 8.0 (m, 1H), 7.30–7.64 (m, 7H), 5.35 (s, 2H), 4.02 (s, 3H):
MS (+ve ESI): 531 (M+H)⁺
MS (−ve ESI): 529 (M−H)⁻.

Particular examples of compounds of formula (I) are set out in Table 4

EXAMPLE 87

Preparation of Compound 87 in Table 4

A solution of 2,5-diaminopyrimidine (5.7 g, 51.8 mmol), 4-chloro-6-methoxy-7-(3-morpholinopropoxy)quinazoline (15 g, 44.4 mmol) and 1.0 N solution of hydrogen chloride in diethylether (100 ml, 100 mmol), in isopropanol (300 ml) was heated (to allow the diethylether allowed to evaporate) and then heated at reflux for 3 hours before the reaction was allowed to cool to ambient temperature. The solid which had precipitated was collected by suction filtration and washed with diethyl ether (2×50 ml). The solid was dissolved in water (200 ml) and neutralised with 0.88 ammonia in water. The resulting solid was collected by suction filtration, washed with water then acetone. Drying of this material yielded the title compound (8.33 g, 46% yield) as a brown solid:
¹H-NMR (DMSO-d₆): 9.31 (s, 1H), 8.45 (s, 2H), 8.35 (s, 1H), 7.15 (s, 1H), 6.50 (s, 2H), 4.18 (t, 2H), 3.95 (s, 3H), 3.58 (m, 4H), 2.45 (t, 2H), 2.41 (m, 4H), 1.95 (m, 2H):
MS (−ve ESI): 410 (M−H)⁻,
MS (+ve ESI): 412 (M+H)⁺.

EXAMPLE 88

Preparation of Compound 88 in Table 4

An analogous reaction to that described in example 67, but starting with 4-pyridinecarboxylic anhydride (126 mg, 0.55 mmol), yielded the title compound (105 mg, 66% yield) as a white solid:
¹H-NMR (DMSO-d₆): 11.41 (s, 1H), 10.81 (s, 1H), 9.10 (s, 2H), 8.79 (m, 3H), 8.03 (s, 1H), 7.88 (m, 2H), 7.38 (s, 1H), 4.31 (m, 2H), 3.99 (m, 2H), 3.98 (s, 3H), 3.65 (m, 2H), 3.53 (m, 2H), 3.31 (m, 2H), 3.15 (m, 2H), 2.27 (m, 2H):
MS (−ve ESI): 515 (M−H)⁻,
MS (+ve ESI): 517 (M+H)⁺.

EXAMPLE 89

Preparation of Compound 89 in Table 4

An analogous reaction to that described in example 67, but starting with 2,4-difluorobenzoic anhydride (164 mg, 0.55 mmol), yielded the title compound (37 mg, 22% yield) as a pale brown solid:
¹H-NMR (DMSO-d₆): 10.33 (s, 1H), 9.55 (s, 1H), 8.30 (s, 2H), 8.25 (s, 1H), 7.95 (m, 1H), 7.65 (m, 1H), 7.58 (m, 1H), 7.45 (s, 1H), 7.25 (s, 1H), 4.25 (t, 2H), 3.98 (m, 2H), 3.88 (s, 3H), 3.65 (m, 2H), 3.51 (m, 2H), 3.31 (m, 2H), 3.15 (m, 2H), 2.25 (m, 2H):
MS (−ve ESI): 548 (M−H)⁻,
MS (+ve ESI): 550 (M+H)⁺.

EXAMPLE 90

Preparation of Compound 90 in Table 4

Triphosgene (38 mg, 0.13 mmol) was added to an ice cold solution of 3-bromo-4-fluorobenzoic acid (169 mg, 0.77 mmol) and triethylamine (0.112 ml, 0.81 mmol) in ethyl acetate (10 ml). The reaction was stirred for 15 minutes at 5° C. and then for 1 hour at ambient temperature before the reaction was washed with water (50 ml) and the solvents were removed in vacuo. Diphenyl ether (1 g) and 4-(2-amino-5-pyrimidinamino)-6-methoxy-7-(3-morpholinopropoxy)quinazoline (72 mg, 0.17 mmol) were added and the reaction heated at 150° C. for 20 hours. The mixture was cooled and diluted with diethylether (10 ml) and the solid collected by suction filtration. Purification by reverse phase preparative hplc, eluting with 25% acetonitrile in water containing 0.1% trifluoroacetic acid followed by neutralisation with ammonia yielded the title compound (45 mg, 42% yield) as a beige solid:
¹H-NMR (DMSO-d₆): 11.11 (s, 1H), 10.70 (s, 1H), 9.05 (s, 2H), 8.45 (s, 1H), 8.25 (m, 1H), 7.98 (m, 1H), 7.75 (s, 1H), 7.47 (t, 1H), 7.17 (s, 1H), 4.22 (t, 2H), 3.95 (s, 3H), 3.51 (m, 4H), 2.40 (t, 2H), 2.33 (m, 4H), 1.90 (m, 2H):
MS (−ve ESI): 612 (M−H)⁻,
MS (+ve ESI): 614 (M+H)⁺.

EXAMPLE 91

Preparation of Compound 91 in Table 4

An analogous reaction to that described in example 90, but starting with 3-bromo-4-methylbenzoic acid (166 mg, 0.77 mmol), yielded the title compound (38 mg, 35% yield) as a white solid:

$^1$H-NMR (DMSO-$d_6$): 11.03 (s, 1H), 9.71 (s, 1H), 9.05 (s, 2H), 8.45 (s, 1H), 8.13 (s, 1H), 7.85 (d, 1H), 7.75 (s, 1H), 7.45 (d, 1H), 7.17 (s, 1H), 4.12 (t, 2H), 3.9 (s, 3H), 3.52 (m, 4H), 2.40 (m, 2H), 2.37 (s, 3H), 2.31 (m, 4H), 1.92 (m, 2H):

MS (−ve ESI): 608 (M−H)$^-$,

MS (+ve ESI): 610 (M+H)$^+$.

EXAMPLE 92

Preparation of Compound 92 in Table 4

An analogous reaction to that described in example 90, but starting with 3-trifluoromethylbenzoic acid (293 mg, 1.54 mmol), yielded the title compound (40 mg, 20% yield) as a white solid:

$^1$H-NMR (DMSO-$d_6$): 11.35 (s, 1H), 9.85 (s, 1H), 9.07 (s, 2H), 8.65 (s, 1H), 8.28 (s, 1H), 8.20 (d, 1H), 8.93 (d, 1H), 8.91 (s, 1H), 7.71 (t, 1H), 7.30 (s, 1H), 4.23 (t, 2H), 3.95 (m, 5H), 3.61 (m, 2H), 3.48 (m, 2H), 3.25 (m, 2H), 3.07 (m, 2H), 2.22 (m, 2H):

MS (−ve ESI): 582 (M−H)$^-$,

MS (+ve ESI): 584 (M+H)$^+$.

EXAMPLE 93

Preparation of Compound 93 in Table 4

An analogous reaction to that described in example 90, but starting with 3-chlorobenzoic acid (121 mg, 0.38 mmol), yielded the title compound (48 mg, 50% yield) as a white solid:

$^1$H-NMR (DMSO-$d_6$): 11.10 (s, 1H), 9.70 (s, 1H), 9.07 (s, 2H), 8.43 (s, 1H), 7.95 (s, 1H), 7.88 (d, 1H), 7.75 (s, 1H), 7.61 (d, 1H), 7.52 (t, 1H), 7.18 (s, 1H), 4.13 (t, 2H), 3.95 (s, 3H), 3.51 (m, 4H), 2.42 (m, 2H), 2.31 (m, 4H), 1.90 (m, 2H):

MS (−ve ESI): 548 (M−H)$^-$,

MS (+ve ESI): 550 (M+H)$^+$.

EXAMPLE 94

Preparation of Compound 94 in Table 4

An analogous reaction to that described in example 67, but starting with 3,4-dichlorobenzoic anhydride (144 mg, 0.55 mmol), yielded the title compound (52 mg, 31% yield) as a pale yellow solid:

$^1$H-NMR (DMSO-$d_6$): 11.30 (s, 1H), 10.60 (s, 1H), 9.10 (s, 2H), 8.73 (s, 1H), 8.22 (d, 1H), 7.99 (s 1H), 7.95 (m, 1H), 7.80 (d, 1H), 7.32 (s, 1H), 4.30 (t, 2H), 4.05 (m, 2H), 3.99 (s, 3H), 3.65 (m, 2H), 3.55 (m, 2H), 3.30 (m, 2H), 3.15 (m, 2H), 2.25 (m, 2H):

MS (−ve ESI): 582 (M−H)$^-$,

MS (+ve ESI): 584 (M+H)$^+$.

EXAMPLE 95

Preparation of Compound 95 in Table 4

An analogous reaction to that described in example 90, but starting with 3-chloro-4-fluorobenzoic acid (384 mg, 1.1 mmol), yielded the title compound (174 mg, 61% yield) as a white solid:

$^1$H-NMR (DMSO-$d_6$): 11.08 (s, 1H), 9.68 (s, 1H), 9.07 (s, 2H), 8.43 (s, 1H), 8.15 (d, 1H), 7.03 (m, 1H), 7.73 (s, 1H), 7.52 (t, 1H), 7.15 (s, 1H), 4.13 (t, 2H), 3.95 (s, 3H), 3.51 (m, 4H), 2.38 (n, 2H), 2.30 (m, 4H), 1.88 (m, 2H):

MS (−ve ESI): 566 (M−H)$^-$,

MS (+ve ESI): 568 (M+H)$^+$.

EXAMPLE 96

Preparation of Compound 96 in Table 4

An analogous reaction to that described in example 90, but starting with 3,5-dichlorobenzoic acid (294 mg, 1.54 mmol), yielded the title compound (61 mg, 30% yield) as a beige solid:

$^1$H-NMR (DMSO-$d_6$): 11.25 (s, 1H), 10.15 (s, 1H), 9.08 (s, 2H), 8.55 (s, 1H), 8.93 (m, 2H), 8.83 (m, 2H), 7.25 (s, 1H), 4.20 (m, 2H), 3.95 (m, 5H), 3.61 (m, 2H), 3.45 (m, 2H), 3.25 (m, 2H), 3.08 (m, 2H), 2.18 (m, 2H):

MS (−ve ESI): 582 (M−H)$^-$,

MS (+ve ESI): 584 (M+H)$^+$.

EXAMPLE 97

Preparation of Compound 97 in Table 4

An analogous reaction to that described in example 67, but starting with 3-cyanobenzoic anhydride (190 mg, 0.7 mmol), yielded the title compound (10 mg, 7.4% yield) as a white solid:

$^1$H-NMR (DMSO-$d_6$): 11.31 (s, 1H), 10.60 (s, 1H), 9.10 (s, 2H), 8.75 (s, 1H), 8.40 (s, 1H), 8.25 (d, 1H), 8.08 (d, 1H), 7.99 (s, 1H), 7.75 (t, 1H), 7.35 (s, 1H), 4.31 (m, 2H), 4.00 (m, 5H), 3.65 (m, 2H), 3.50 (m, 2H), 3.32 (m, 2H), 3.13 (m, 2H), 2.25 (m, 2H):

MS (−ve ESI): 539 (M−H)$^-$,

MS (+ve ESI): 541 (M+H)$^+$.

EXAMPLE 98

Preparation of Compound 98 in Table 4

An analogous reaction to that described in example 67, but starting with 3-fluorobenzoic anhydride (144 mg, 0.55 mmol), yielded the title compound (131 mg, 82% yield) as a pale yellow solid:

$^1$H-NMR (DMSO-$d_6$): 11.20 (s, 1H), 10.71 (s, 1H), 9.11 (s, 2H), 8.75 (s, 1H), 8.00 (s, 1H), 7.82 (m, 2H), 7.58 (m, 1H), 7.47 (m, 1H), 7.35 (s, 1H), 4.30 (t, 2H), 4.05 (m, 2H), 4.00 (s, 3H), 3.65 (m, 2H), 3.52 (m, 2H), 3.35 (m, 2H), 3.15 (m, 2H), 2.28 (m, 2H):

MS (−ve ESI): 532 (M−H)$^-$,

MS (+ve ESI): 534 (M+H)$^+$.

EXAMPLE 99

Preparation of Compound 99 in Table 4

An analogous reaction to that described in example 90, but starting with 3,5-dimethyl-4-nitrobenzoic acid (150 mg, 0.385 mmol), yielded the title compound (33 mg, 32% yield) as a pale yellow solid:

$^1$H-NMR (DMSO-d$_6$): 11.10 (s, 1H), 10.71 (s, 1H), 9.07 (s, 2H), 8.45 (s, 1H), 7.83 (m, 2H), 7.75 (s, 1H), 7.17 (s, 1H), 4.13 (t, 2H), 3.94 (s, 3H), 3.51 (m, 4H), 2.41 (t, 2H), 2.32 (m, 4H), 2.27 (s, 6H), 1.93 (m, 2H):

MS (−ve ESI): 587 (M−H)$^−$,

MS (+ve ESI): 589 (M+H)$^+$.

EXAMPLE 100

Preparation of Compound 100 in Table 4

An analogous reaction to that described in example 90, but starting with 3,5-dimethylbenzoic acid (231 mg, 1.54 mmol), yielded the title compound (96 mg, 50% yield) as a white solid:

$^1$H-NMR (DMSO-d$_6$): 10.83 (s, 1H), 10.35 (s, 1H), 9.02 (s, 2H), 8.62 (s, 1H), 7.91 (s, 1H), 7.55 (s, 1H), 7.25 (s, 1H), 7.18 (s, 1H), 4.22 (t, 2H), 3.95 (m, 5H), 3.63 (m, 2H), 3.52 (m, 2H), 3.31 (m, 2H), 3.10 (m, 2H), 2.30 (s, 6H), 2.21 (m, 2H):

MS (−ve ESI): 542 (M−H)$^−$,

MS (+ve ESI): 544 (M+H)$^+$.

EXAMPLE 101

Preparation of Compound 101 in Table 4

An analogous reaction to that described in example 90, but starting with 4-chloro-3-nitrobenzoic acid (155 mg, 0.385 mmol), yielded the title compound (19 mg, 18% yield) as a pale yellow solid:

$^1$H-NMR (DMSO-d$_6$): 11.35 (s, 1H), 9.71 (s, 1H), 9.06 (s, 2H), 8.58 (d, 1H), 8.43 (s, 1H), 8.20 (dd, 1H), 7.90 (d, 1H), 7.76 (s, 1H), 7.17 (s, 1H), 4.13 (t, 2H), 3.92 (s, 3H), 3.51 (m, 4H), 2.42 (t, 2H), 2.31 (m, 4H), 1.88 (m, 2H):

MS (−ve ESI): 593 (M−H)$^−$,

MS (+ve ESI): 595 (M+H)$^+$.

EXAMPLE 102

Preparation of Compound 102 in Table 4

An analogous reaction to that described in example 90, but starting with piperonylic acid (256 mg, 1.54 mmol), yielded the title compound (70 mg, 36% yield) as a beige solid:

$^1$H-NMR (DMSO-d$_6$): 10.80 (s, 1H), 9.71 (s, 1H), 9.05 (s, 2H), 8.45 (s, 1H), 7.78 (s, 1H), 7.57 (d, 1H), 7.48 (s, 1H), 7.17 (s, 1H), 6.97 (d, 1H), 6.08 (s, 2H), 4.15 (t, 2H), 3.94 (s, 3H), 3.61 (m, 4H), 3.27 (m, 6H), 2.00 (m, 2H):

MS (−ve ESI): 558 (M−H)$^−$,

MS (+ve ESI): 560 (M+H)$^+$.

EXAMPLE 103

Preparation of Compound 103 in Table 4

An analogous reaction to that described in example 67, but starting with 3-methoxybenzoic anhydride (157 mg, 0.55 mmol), yielded the title compound (104 mg, 76% yield) as a white solid:

$^1$H-NMR (DMSO-d$_6$): 11.07 (s, 1H), 10.78 (s, 1H), 9.07 (s, 2H), 8.77 (s, 1H), 8.00 (s, 1H), 7.55 (m, 2H), 7.42 (t, 1H), 7.35 (s, 1H), 7.15 (dd, 1H), 4.30 (t, 2H), 4.00 (m, 5H), 3.83 (s, 3H), 3.71 (m, 2H), 3.50 (m, 2H), 3.35 (t, 2H), 3.12 (m, 2H), 2.15 (m, 2H):

MS (−ve ESI): 544 (M−H)$^−$,

MS (+ve ESI): 546 (M+H)$^+$.

EXAMPLE 104

Preparation of Compound 104 in Table 4

An analogous reaction to that described in example 90, but starting with 3-phenoxybenzoic acid (165 mg, 0.77 mmol), yielded the title compound (28 mg, 26% yield) as a white solid:

$^1$H-NMR (DMSO-d$_6$): 11.00 (s, 1H), 9.68 (s, 1H), 9.05 (s, 2H), 8.43 (s, 1H), 7.75 (s, 1H), 7.71 (d, 1H), 7.52 (m, 2H), 7.37 (m, 2H), 7.15 (m, 3H), 7.02 (d, 1H), 4.12 (t, 2H), 3.91 (s, 3H), 3.52 (m, 4H), 2.40 (t, 2H), 2.30 (m, 4H), 1.91 (m, 2H):

MS (−ve ESI): 606 (M−H)$^−$,

MS (+ve ESI): 608 (M+H)$^+$.

EXAMPLE 105

Preparation of Compound 105 in Table 4

An analogous reaction to that described in example 90, but starting with 4-bromobenzoic acid (155 mg, 0.77 mmol), yielded the title compound (23 mg, 22% yield) as a beige solid:

$^1$H-NMR (DMSO-d$_6$): 11.05 (s, 1H), 9.71 (s, 1H), 9.05 (s, 2H), 8.45 (s, 1H), 7.85 (d, 2H), 7.75 (s, 1H), 7.65 (d, 2H), 7.15 (s, 1H), 4.13 (t, 2H), 3.94 (s, 3H), 3.52 (m, 4H), 2.40 (t, 2H), 2.30 (m, 4H), 1.91 (m, 2H):

MS (−ve ESI): 594 (M−H)$^−$,

MS (+ve ESI): 596 (M+H)$^+$.

EXAMPLE 106

Preparation of Compound 106 in Table 4

An analogous reaction to that described in example 90, but starting with 4-ethylbenzoic acid (116 mg, 0.77 mmol), yielded the title compound (26 mg, 27% yield) as a white solid:

$^1$H-NMR (DMSO-d$_6$): 10.88 (s, 1H), 9.68 (s, 1H), 9.05 (s, 2H), 8.42 (s, 1H), 7.85 (d, 2H), 7.75 (s, 1H), 7.28 (d, 2H), 7.15 (s, 1H), 4.12 (t, 2H), 3.94 (s, 3H), 3.51 (m, 4H), 2.60 (q, 2H), 2.42 (m, 2H), 2.31 (m, 4H), 1.93 (m, 2H), 1.15 (t, 3H):

MS (−ve ESI): 542 (M−H)$^−$,

MS (+ve ESI): 544 (M+H)$^+$.

EXAMPLE 107

Preparation of Compound 107 in Table 4

An analogous reaction to that described in example 90, but starting with 4-fluorobenzoic acid (108 mg, 0.77 mmol), yielded the title compound (35 mg, 38% yield) as a white solid:

$^1$H-NMR (DMSO-$d_6$): 11.0 (s, 1H), 9.68 (s, 1H), 9.04 (s, 2H), 8.45 9s, 1H), 8.00 (m, 2H), 7.78 (s, 1H), 7.30 (t, 2H), 7.17 (s, 1H), 4.13 (t, 2H), 3.90 (s, 3H), 3.50 (m, 4H), 2.40 (m, 2H), 2.30 (m, 4H), 1.90 (m, 2H):

MS (−ve ESI): 532 (M−H)$^−$,

MS (+ve ESI): 534 (M+H)$^+$.

EXAMPLE 108

Preparation of Compound 108 in Table 4

An analogous reaction to that described in example 67, but starting with 4-nitrobenzoic anhydride (108 mg, 0.30 mmol), yielded the title compound (23 mg, 41% yield) as a pale yellow solid:

$^1$H-NMR (DMSO-$d_6$): 11.45 (s, 1H), 10.81 (s, 1H), 9.10 (s, 2H), 8.78 (s, 1H), 8.35 (d, 2H), 8.17 (d, 2H), 8.00 (s, 1H), 7.38 (s, 2H), 4.31 (t, 2H), 4.00 (m, 2H), 4.00 (s, 3H), 3.72 (m, 2H), 3.51 (m, 2H), 3.32 (t, 2H), 3.15 (m, 2H), 2.28 (m, 2H):

MS (−ve ESI): 559 (M−H)$^−$,

MS (+ve ESI): 561 (M+H)$^+$.

EXAMPLE 109

Preparation of Compound 109 in Table 4

An analogous reaction to that described in example 90, but starting with 4-methoxybenzoic acid (117 mg, 0.77 mmol), yielded the title compound (17 mg, 18% yield) as a white solid:

$^1$H-NMR (DMSO-$d_6$): 10.81 (s, 1H), 9.68 (s, 1H), 9.03 (s, 2H), 8.44 (s, 1H), 7.93 (d, 2H), 7.75 (s, 1H), 7.15 (s, 1H), 6.97 (s, 1H), 4.11 (m, 2H), 3.94 (s, 3H), 3.78 (s, 3H), 3.52 (m, 4H), 2.40 (m, 2H), 2.30 (m, 4H), 1.91 (m, 2H):

MS (−ve ESI): 544 (M−H)$^−$,

MS (+ve ESI): 546 (M+H)$^+$.

EXAMPLE 110

Preparation of Compound 110 in Table 4

An analogous reaction to that described in example 90, but starting with 4-methylthiobenzoic acid (129 mg, 0.77 mmol), yielded the title compound (32 mg, 33% yield) as a pale yellow solid:

$^1$H-NMR (DMSO-$d_6$): 10.92 (s, 1H), 9.68 (s, 1H), 9.05 (s, 2H), 8.45 (s, 1H), 7.88 (d, 2H), 7.75 (s, 1H), 7.31 (d, 2H), 7.17 (s, 1H), 4.15 (t, 2H), 3.94 (s, 3H), 3.52 (m, 4H), 2.52 (s, 3H), 2.41 (m, 2H), 2.30 (m, 4H), 1.91 (m, 2H):

MS (−ve ESI): 560 (M−H)$^−$,

MS (+ve ESI): 562 (M+H)$^+$.

EXAMPLE 111

Preparation of Compound 111 in Table 4

An analogous reaction to that described in example 90, but starting with furan-2-carboxylic acid (86 mg, 0.77 mmol), yielded the title compound (5 mg, 5.5% yield) as a white solid:

$^1$H-NMR (DMSO-$d_6$): 10.80 (s, 1H), 9.75 (s, 1H), 9.10 (s, 2H), 8.48 (s, 1H), 7.95 (s, 1H), 7.82 (s, 1H), 7.51 (d, 1H), 7.22 (s, 1H), 6.71 (d, 1H), 4.20 (t, 2H), 3.98 (s, 3H), 3.60 (m, 4H), 2.61 (m, 2H), 2.42 (m, 4H), 1.95 (m, 2H):

MS (−ve ESI): 504 (M−H)$^−$,

MS (+ve ESI): 506 (M+H)$^+$.

EXAMPLE 112

Preparation of Compound 112 in Table 4

An analogous reaction to that described in example 90, but starting with 1-methyl-2-pyrrolecarboxylic acid (96 mg, 0.385 mmol), yielded the title compound (8 mg, 9% yield) as a white solid:

$^1$H-NMR (DMSO-$d_6$): 10.42 (s, 1H), 9.71 (s, 1H), 9.05 (s, 2H), 8.48 (s, 1H), 7.82 (s, 1H), 7.20 (s, 1H), 7.15 (m, 1H), 7.03 (s, 1H), 6.07 (m, 1H), 4.23 (t, 2H), 3.97 (s, 2H), 3.87 (s, 3H), 3.59 (m, 4H), 2.45 (t, 2H), 2.37 (m, 4H), 1.95 (m, 2H):

MS (−ve ESI): 517 (M−H)$^−$,

MS (+ve ESI): 519 (M+H)$^+$.

EXAMPLE 113

Preparation of Compound 113 in Table 4

An analogous reaction to that described in example 90, but starting with thiophene-2-carboxylic acid (99 mg, 0.77 mmol), yielded the title compound (27 mg, 30% yield) as a white solid:

$^1$H-NMR (DMSO-$d_6$): 11.05 (s, 1H), 9.71 (s, 1H), 9.10 (s, 2H), 8.53 (s, 1H), 8.12 (d, 1H), 7.87 (d, 1H), 7.84 (s, 1H), 7.22 (m, 2H), 4.21 (t, 2H), 4.00 (s, 3H), 3.54 (m, 4H), 2.48 (m, 2H), 2.38 (m, 4H), 1.92 (m, 2H):

MS (−ve ESI): 520 (M−H)$^−$,

MS (+ve ESI): 522 (M+H)$^+$.

EXAMPLE 114

Preparation of Compound 114 in Table 4

An analogous reaction to that described in example 90, but starting with 3-phenylpropionic acid (116 mg, 0.77 mmol), yielded the title compound (38 mg, 40% yield) as a white solid:

$^1$H-NMR (DMSO-$d_6$): 10.54 (s, 1H), 10.08 (s, 1H), 9.10 (s, 2H), 8.43 (s, 1H), 8.03 (s, 1H), 7.25 (m, 4H), 7.18 (m, 2H), 4.21 (t, 2H), 3.98 (s, 3H), 3.63 (m, 4H), 2.92 (m, 2H), 2.81 (m, 2H), 2.50 (m, 6H), 2.02 (m, 2H):

MS (−ve ESI): 542 (M−H)$^−$,

MS (+ve ESI): 544 (M+H)$^+$.

EXAMPLE 115

Preparation of Compound 115 in Table 4

An analogous reaction to that described in example 67, but starting with 4-methylbenzoic anhydride (76.2 mg, 0.3 mmol), yielded the title compound (23 mg, 29% yield) as a white solid:

$^1$H-NMR (DMSO-d$_6$): 10.95 (s, 1H), 10.90 (s, 1H), 9.00 (s, 2H), 8.75 (s, 1H), 7.98 (s, 1H), 7.85 (d, 2H), 7.33 (s, 1H), 7.25 (d, 2H), 4.25 (t, 2H), 3.97 (m, 5H), 3.61 (m, 2H), 3.45 (m, 2H), 3.25 (t, 2H), 3.10 (m, 2H), 2.35 (s, 3H), 2.21 (m, 2H):

MS (−ve ESI): 528 (M−H)$^−$,
MS (+ve ESI): 530 (M+H)$^+$.

EXAMPLE 116

Preparation of Compound 116 in Table 4

An analogous reaction to that described in example 90, but starting with cyclohexanebutyric acid (131 mg, 0.77 mmol), yielded the title compound (11 mg, 11% yield) as a white solid:

$^1$H-NMR (DMSO-d$_6$): 10.00 (s, 1H), 9.05 (s, 2H), 8.40 (s, 1H), 7.95 (s, 1H), 7.20 (s, 1H), 4.20 (t, 2H), 3.95 (s, 3H), 3.60 (m, 4H), 2.30–2.45 (m, 8H), 1.98 (m, 2H), 1.45–1.63 (m, 8H), 1.25 (m, 6H), 0.80 (m, 2H):

MS (−ve ESI): 562 (M−H)$^−$,
MS (+ve ESI): 564 (M+H)$^+$.

EXAMPLE 117

Preparation of Compound 117 in Table 4

An analogous reaction to that described in example 6, but starting with 2-(N-pentanoyl)amino-5-aminopyrimidine (231 mg, 1.1 mmol) and 4-chloro-6-methoxy-7-(3-morpholinopropoxy)quinazoline (337.5 mg, 1.0 mmol), yielded the title compound (94 mg, 19% yield) as a white solid:

$^1$H-NMR (DMSO-d$_6$): 10.44 (s, 1H), 9.80 (s, 1H), 9.00 (s, 2H), 8.43 (s, 1H), 7.82 (s, 1H), 7.17 (s, 1H), 4.17 (t, 2H), 3.96 (s, 3H), 3.57 (t, 4H), 2.44 (m, 4H), 2.36 (t, 4H), 1.94 (m, 2H), 1.56 (m, 2H), 1.32 (m, 2H), 0.89 (t, 3H):

MS (+ve ESI): 496 (M+H)$^+$.

2-(N-pentanoyl)amino-5-aminopyrimidine, used as the starting material was obtained as follows:

a) Valeroyl chloride (861 mg, 7.14 mmol) was added dropwise to a stirred suspension of 2-amino-5-nitropyrimidine (500 mg, 3.57 mmol) in pyridine (10 ml) and the reaction was heated at reflux for 4 hours under an inert atmosphere. The solvent was removed in vacuo and the residue stirred in 2N hydrochloric acid (100 ml) and extracted with ethyl acetate. Solvent evaporation in vacuo yielded 2-(N-pentanoyl)amino-5-nitropyrimidine (658 mg, 82% yield) as a brown solid:

$^1$H-NMR (DMSO-d$_6$): 11.26 (s, 1H), 9.37 (s, 2H), 2.55 (t, 2H), 1.55 (m, 2H), 1.30 (m, 2H), 0.88 (t, 2H):

MS (+ve ESI): 225 (M+H)$^+$.

b) Platinum oxide (50 mg, 0.22 mmol) was added to a solution of 2-(N-pentanoyl)amino-5-nitropyrimidine (650 mg, 2.9 mmol) in ethanol (100 ml) at ambient temperature and the reaction stirred for 1 hour under an atmosphere of hydrogen. The reaction was filtered through a pad of celite and the solvents were evaporated in vacuo. Trituration with diethylether and drying yielded 2-(N-pentanoyl)amino-5-aminopyrimidine (307 mg, 55% yield) as brown solid:

$^1$H-NMR (DMSO-d$_6$): 9.91 (s, 1H), 7.98 (s, 2H), 5.23 (s, 2H), 2.32 (t, 2H), 1.70 (m, 2H), 1.50 (m, 2H), 1.12 (m, 3H):

MS (+ve ESI): 195 (M+H)$^+$.

EXAMPLE 118

Preparation of Compound 118 in Table 4

An analogous reaction to that described in example 117, but starting with 2-(N-cyclopentanoyl)amino-5-aminopyrimidine (134 mg, 0.65 mmol), yielded the title compound (193 mg, 64% yield) as a white solid:

$^1$H-NMR (DMSO-d$_6$): 11.79 (s, 1H), 10.63 (s, 1H), 9.02 (s, 2H), 8.84 (s, 1H), 8.46 (s, 1H), 7.40 (s, 1H), 4.31 (t, 2H, J=7 Hz), 4.04 (s, 3H), 3.98 (m, 2H), 3.81 (m, 2H), 3.49 (m, 2H), 3.29 (m, 2H), 3.09 (m, 3H), 2.32 (m, 2H), 1.49–1.92 (m, 8H):

MS (−ve ESI): 506 (M−H)$^−$.

2-(N-cyclopentanoyl)amino-5-aminopyrimidine, used as the starting material was obtained as follows:

a) Cyclopentanoyl chloride (946 mg, 7.14 mmol) was added dropwise to a stirred suspension of 2-amino-5-nitropyrimidine (1.0 g, 7.14 mmol) in pyridine (10 ml) and the reaction was heated at reflux for 4 hours under an inert atmosphere. The reaction mixture was cooled then stirred in 2N hydrochloric acid (100 ml) and the resulting solid collected by suction filtration. Purification by flash chromatography on silica gel, eluting with 2% methanol in dichloromethane, yielded 2-(N-cyclopentanoyl)amino-5-nitropyrimidine (812 mg, 48% yield) as an beige solid:

$^1$H-NMR (DMSO-d$_6$): 11.27 (s, 1H), 9.37 (s, 2H), 3.05 (m, 1H), 2.88 (m, 2H), 1.61 (m, 6H):

MS (+ve ESI): 237 (M+H)$^+$.

b) Platinum oxide (50 mg, 0.22 mmol) was added to a solution 2-(N-cyclopentanoyl)amino-5-nitropyrimidine (808 mg, 3.42 mmol) in ethanol (100 ml) at ambient temperature and the reaction stirred for 1 hour under an atmosphere of hydrogen. The reaction was filtered through a pad of celite and the solvents were evaporated in vacuo. Trituration with diethylether and drying yielded 2-(N-cyclopentanoyl)amino-5-aminopyrimidine (516 mg, 73% yield) as brown solid:

$^1$H-NMR (DMSO-d$_6$): 9.95 (s, 1H), 7.99 (s, 2H), 5.23 (s, 2H), 2.85 (m, 1H), 1.40–1.82 (m, 8H):

MS (+ve ESI): 207 (M+H)$^+$.

EXAMPLE 119

Preparation of Compound 119 in Table 4

An analogous reaction to that described in example 117, but starting with 2-(N-cyclohexanoyl)amino-5-aminopyrimidine (143 mg, 0.65 mmol), yielded the title compound (143 mg, 46% yield) as a white solid:

$^1$H-NMR (DMSO-d$_6$): 11.92 (s, 1H), 10.57 (s, 1H), 9.03 (s, 2H), 8.83 (s, 1H), 8.52 (s, 1H), 7.41 (s, 1H), 4.31 (t, 2H, J=7 Hz), 4.04 (s, 3H), 3.98 (m, 2H), 3.84 (t, 2H, J=7 Hz), 3.50 (m, 2H), 3.29 (m, 2H), 3.09 (m, 2H), 2.58 (m, 1H), 2.33 (m, 2H), 1.78 (m, 4H), 1.63 (m, 1H), 1.11–1.47 (m, 5H):

MS (−ve ESI): 520 (M−H)$^−$.

2-(N-cyclohexanoyl)amino-5-aminopyrimidine, used as the starting material was obtained as follows:

a) Cyclohexanoyl chloride (1.05 g, 7.14 mmol) was added dropwise to a stirred suspension of 2-amino-5-nitropyrimidine (1.0 g, 7.14 mmol) in pyridine (10 ml) and the reaction was heated at reflux for 4 hours under an inert atmosphere. The reaction mixture was cooled then stirred in 2N hydrochloric acid (100 ml) and extracted with ethyl acetate. Crystallisation from ethyl acetate/hexane, yielded 2-(N-cyclohexanoyl)amino-5-nitropyrimidine (1.15 g, 64% yield) as a beige solid:

$^1$H-NMR (DMSO-$d_6$): 11.22 (s, 1H), 9.38 (s, 2H), 2.63 (m, 1H), 1.12–1.91 (m, 10H).

b) Platinum oxide (50 mg, 0.22 mmol) was added to a solution 2-(N-cyclohexanoyl)amino-5-nitropyrimidine (1.15 g, 4.6 mmol) in ethanol (100 ml) at ambient temperature and the reaction stirred for 1 hour under an atmosphere of hydrogen. The reaction was filtered through a pad of celite and the solvents were evaporated in vacuo to give 2-(N-cyclohexanoyl)amino-5-aminopyrimidine (105 g, 100% yield) as brown solid:

$^1$H-NMR (DMSO-$d_6$): 9.80 (s, 1H), 7.98 (s, 2H), 5.21 (s, 2H), 2.40 (m, 1H), 1.71 (m, 6H), 1.32 (m, 4H):

MS (+ve ESI): 221 (M+H)$^+$.

EXAMPLE 120

Preparation of Compound 120 in Table 4

An analogous reaction to that described in example 117, but starting with 2-(N-2-chlorobenzoyl)amino-5-aminopyrimidine (110 mg, 0.44 mmol), yielded the title compound (110 mg, 45% yield) as a white solid:

$^1$H-NMR (DMSO-$d_6$): 11.14 (s, 1H), 9.67 (s, 1H), 9.02 (s, 2H), 8.47 (s, 1H), 7.78 (s, 1H), 7.35–7.55 (m, 4H), 7.20 (s, 1H), 4.18 (t, 2H), 3.95 (s, 3H), 3.57 (t, 4H), 2.45 (t, 2H), 2.35 (t, 4H), 1.95 (m, 2H):

MS (+ve ESI): 550 (M+H)$^+$.

2-(N-cyclohexanoyl)amino-5-aminopyrimidine, used as the starting material was obtained as follows:

a) 2-chlorobenzoyl chloride (577 mg, 3.3 mmol) was added dropwise to a stirred suspension of 2-amino-5-nitropyrimidine (420 mg, 3 mmol) in pyridine (5 ml) and the reaction was heated at reflux for 4 hours under an inert atmosphere followed by solvent removed in vacuo. Purification by flash chromatography on silica gel, eluting with 10–60% ethyl acetate in hexane yielded 2-(N-2-chlorobenzoyl)amino-5-nitropyrimidine (366 g, 44% yield) as a beige solid:

$^1$H-NMR (DMSO-$d_6$): 11.87 (s, 1H), 9.37 (s, 2H), 7.39–7.61 (m, 4H):

b) Platinum oxide (60 mg, 0.22 mmol) was added to a solution 2-(N-2-chlorobenzoyl)amino-5-nitropyrimidine (278 mg, 1.0 mmol) in ethanol (1 ml) and ethyl acetate (10 ml) at ambient temperature and the reaction stirred for 3 hours under an atmosphere of hydrogen. The reaction was filtered through a pad of celite and the solvents were evaporated in vacuo. Purification by flash chromatography on silica gel, eluting with 5% methanol in ethyl acetate yielded 2-(N-2-chlorobenzoyl)amino-5-aminopyrimidine (121 mg, 50% yield) as brown solid:

$^1$H-NMR (DMSO-$d_6$): 10.51 (s, 1H), 7.97 (s, 2H), 7.32–7.52 (m, 4H), 5.33 (s, 2H).

EXAMPLE 121

Preparation of Compound 121 in Table 4

An analogous reaction to that described in example 90, but starting with 4-((dipropylamino)-sulfenyl)benzoic acid (220 mg, 0.77 mmol), yielded the title compound (68 mg, 57% yield) as a white solid:

$^1$H-NMR (DMSO-$d_6$): 11.20 (s, 1H), 9.71 (s, 1H), 9.05 (s, 2H), 9.43 (s, 1H), 8.07 (d, 2H), 7.87 (d, 2H), 7.75 (s, 1H), 7.18 (s, 1H), 4.13 (t, 2H), 3.92 (s, 3H), 3.51 (m, 4H), 3.01 (t, 4H), 2.40 (m, 2H), 2.32 (m, 4H), 1.90 (m, 2H), 1.43 (m, 4H), 0.75 (t, 6H):

MS (–ve ESI): 677 (M–H)$^-$,

MS (+ve ESI): 679 (M+H)$^+$.

EXAMPLE 122

Preparation of Compound 122 in Table 4

An analogous reaction to that described in example 117, but starting with 2-(N-4-fluoro-2-trifluoromethylbenzoyl) amino-5-aminopyrimidine (147 mg, 0.49 mmol), yielded the title compound (188 mg, 57% yield) as a white solid:

$^1$H-NMR (DMSO-$d_6$): 12.01 (s, 1H), 11.41 (s, 1H), 9.04 (s, 2H), 8.84 (s, 1H), 8.54 (s, 1H), 7.74 (m, 2H), 7.62 (m, 1H), 7.42 (s, 1H), 4.31 (t, 2H), 4.04 (s, 3H), 3.98 (m, 2H), 3.82 (t, 2H), 3.47 (d, 2H), 3.28 (t, 2H), 3.09 (m, 2H), 2.33 (m, 2H):

MS (–ve ESI): 602 (M–H)$^-$.

2-(N-4-fluoro-2-trifluoromethylbenzoyl)amino-5-aminopyrimidine, used as starting material was obtained as follows:

a) Triphosgene (656 mg, 2.21 mmol) was added to an ice cold solution of 4-fluoro-2-trifluoromethylbenzoic acid (2.75 g, 13.2 mmol) and triethlamine (1.93 ml, 13.5 mmol) in ethyl acetate (15 ml), and the reaction was stirred for 1 hour at ambient temperature. The mixture was filtered to remove triethylamine hydrochloride and the filtrate was concentrated in vacuo. The residue was dissolved in pyridine (10 ml), 5-nitro-2-aminopyrimidine (420 mg, 3 mmol) was added and the reaction mixture was heated at 110° C. for 20 hours. The solvent was removed in vacuo and the residue was dissolved in dilute hydrochloric acid and extracted into ethyl acetate (3×100 ml). The organic solution was washed with water and brine, dried over magnesium sulphate and concentrated in vacuo. Purification by flash chromatography on silica, eluting with 25–50% ethyl acetate in hexane, yielded 2-(N-4-fluoro-2-trifluoromethylbenzoyl)amino-5-nitropyrimidine (474 mg, 48% yield) as a beige solid:

$^1$H-NMR (DMSO-$d_6$): 12.04 (s, 1H), 9.36 (s, 2H), 7.77 (m, 2H), 7.63 (m, 1H):

b) 10% Platinum on carbon (60 mg, 0.22 mmol) was added to a solution 2-(N-4-fluoro-2-trifluoromethylbenzoyl) amino-5-nitropyrimidine (330 mg, 1.0 mmol) in ethanol (1 ml) and ethyl acetate (10 ml) at ambient temperature and the reaction stirred for 20 hours under an atmosphere of hydrogen. The reaction was filtered through a pad of celite. Concentration in vacuo and trituration with ether, yielded 2-(N-4-fluoro-2-trifluoromethylbenzoyl)amino-5-aminopyrimidine (158 mg, 53% yield) as brown solid:

$^1$H-NMR (DMSO-$d_6$): 10.70 (s, 1H), 7.97 (s, 2H), 7.69 (d, 1H), 7.55 (m, 2H), 5.33 (s, 2H).

EXAMPLE 123

Preparation of Compound 123 in Table 4

An analogous reaction to that described in example 117, but starting with 2-(N-2-chloro-4,5-difluorobenzoyl)amino-5-aminopyrimidine (97 mg, 0.341 mmol), yielded the title compound (110 mg, 49% yield) as a white solid:

$^1$H-NMR (DMSO-$d_6$): 11.97 (s, 1H), 11.41 (s, 1H), 9.07 (s, 2H), 8.83 (s, 1H), 8.53 (s, 1H), 7.81 (m, 2H), 7.42 (s, 1H), 4.31 (t, 2H), 4.03 (s, 3H), 3.96 (m, 2H), 3.82 (t, 2H), 3.48 (d, 2H), 3.28 (t, 2H), 3.10 (m, 2H), 2.34 (m, 2H):

MS (−ve ESI): 586 (M−H)$^-$.

2-(N-2-chloro-4,5-difluorobenzoyl)amino-5-aminopyrimidine, used as starting material was obtained as follows:

a) An analogous reaction to that described in example 117 (part a), but starting with 2-chloro-4,5-difluorobenzoic acid (2.54 g, 13.2 mmol), yielded 2-(N-2-chloro-4,5-difluorobenzoyl)amino-5-nitropyrimidine (514 mg, 54.5% yield) as a beige solid:

$^1$H-NMR (DMSO-$d_6$): 12.02 (s, 1H), 9.38 (s, 2H), 7.72–7.95 (m, 2H).

b) An analogous reaction to that described in example 117 (part b), but starting with, 2-(N-2-chloro-4,5-difluorobenzoyl)amino-5-nitropyrimidine (314 mg, 1.0 mmol), yielded 2-(N-2-chloro-4,5-difluorobenzoyl)amino-5-aminopyrimidine (107 mg, 38% yield) as a brown solid:

$^1$H-NMR (DMSO-$d_6$): 10.70 (s, 1H), 7.96 (s, 2H), 7.63–7.76 (m, 2H), 5.35 (s, 2H).

Particular examples of compounds of formula (I) are set out in Table 5

EXAMPLE 124

Preparation of Compound 124 in Table 5

An analogous reaction to that described in example 87, but starting with 4-chloro-6-methoxy-7-(3-morpholinopropoxy)quinazoline (371 mg, 1.1 mmol) and 5-amino-2-pyrimidinecarboxylic acid (145 mg, 1.04 mmol), yielded the title compound (277 mg, 52% yield) as a light brown dihydrochloride salt:

$^1$H-NMR (DMSO-$d_6$): 9.46 (s, 2H), 8.88 (s, 1H), 8.40 (s, 1H), 8.12 (s, 1H), 7.40 (s, 1H), 4.30 (t, 2H), 4.04 (s, 3H), 3.00–4.05 (m, 10H), 2.20–2.40 (m, 2H):

MS (−ve ESI): 439 (M−H)$^-$,
MS (+ve ESI): 441 (M+H)$^+$.

5-Amino-2-pyrimidinecarboxylic acid, used as the starting material was obtained from literature procedures: Arnold et al, *Coll. Czech. Chem. Comm.* 1973, 38, 1371, Arnold et al, *Coll. Czech. Chem. Comm.* 1975, 40, 1384 and Arnold et al, *Coll. Czech. Chem. Comm.* 1975, 40, 1396 (NB)-due to safety concerns, the key trimethinium intermediate was isolated as the HPF$_6$ salt rather than the diperchlorate adduct reported in the above manuscript.

EXAMPLE 125

Preparation of Compound 125 in Table 5

4-(2-Carboxy-5-pyrimidinamino)-6-methoxy-7-(3-morpholinopropoxy)quinazoline (64 mg, 0.125 mmol) and aniline (12 mg, 0.131 mmol) were added to a solution of 1-(3-dimethylaminopropyl)-3-ethylcarbodiimide hydrochloride (26 mg, 0.138 mmol) and 4-dimethylaminopyridine (47 mg, 0.388 mmol) in N,N-dimethylacetamide (1 ml) and the reaction mixture stirred at ambient temperature for 20 hours then heated to 50° C. for 1 hour. The reaction was cooled, water (5 ml) was added and the resulting solid collected by suction filtration before being washed with water and diethyl ether. Drying in vacuo yielded the title compound (39 mg, 61% yield) as a pale yellow solid:

$^1$H-NMR (DMSO-$d_6$): 10.60 (s, 1H), 9.98 (s, 1H), 9.45 (s, 2H), 8.55 (s, 1H), 7.83 (d, 2H), 7.80 (s, 1H), 7.32 (t, 2H), 7.21 (s, 1H), 7.07 (t, 1H), 4.16 (t, 2H), 3.95 (s, 3H), 3.47–3.56 (m, 4H), 2.25–2.50 (m, 6H), 1.82–1.98 (m, 2H):

MS (−ve ESI): 514 (M−H)$^-$,
MS (+ve ESI): 516 (M+H)$^+$.

EXAMPLE 126

Preparation of Compound 126 in Table 5

An analogous reaction to that described in example 125, but starting with cyclohexylamine (13 mg, 0.131 mmol), yielded the title compound (40 mg, 61% yield) as an off-white solid:

$^1$H-NMR (DMSO-$d_6$): 9.96 (s, 1H), 9.40 (s, 2H), 8.57 (s, 1H), 8.45 (d, 1H), 7.83 (s, 1H), 7.25 (s, 1H), 4.20 (t, 2H), 3.99 (s, 3H), 3.68–3.84 (m, 1H), 3.52–3.60 (m, 4H), 2.30–2.40 (m, 6H), 1.90–2.02 (m, 2H), 1.00–1.89 (m, 10H):

MS (−ve ESI): 520 (M−H)$^-$,
MS (+ve ESI): 522 (M+H)$^+$.

EXAMPLE 127

Preparation of Compound 127 in Table 5

O-(7-azabenzotriazol-1-yl)-N,N,N',N'-tetramethyluronium hexafluorophosphate (HATU) (380 mg, 0.28 mmol) was added to a mixture of 4-chloroaniline (36 mg, 0.28 mmol), triethylamine (88 mg, 0.87 mmol) and 4-(2-carboxylate-5-pyrimidinamino)-6-methoxy-7-(3-morpholinopropoxy)quinazoline (128 mg, 0.25 mmol), in dimethylacetamide (1.25 ml) and dichloromethane (0.5 ml) and the mixture heated at 50° C. for 20 hours. The reaction was cooled and volatile solvents were removed in vacuo. Water (10 ml) was added, the resulting solid was collected by suction filtration and washed with water then ethyl acetate. Drying yielded the title compound (140 mg, 64% yield) as an off-white solid (di-hexafluorophosphate salt):

$^1$H-NMR (DMSO-$d_6$): 10.87 (s, 1H), 10.1 (s, 1H), 9.52 (m, 3H), 8.65 (s, 1H), 7.95 (d, 2H), 7.89 (s, 1H), 7.42 (d, 2H), 7.33 (s, 1H), 4.27 (t, 2H), 4.00 (m, 5H), 3.65 (m, 2H), 3.5 (m, 2H), 3.32 (m, 2H), 3.14 (m, 2H), 2.22 (m, 2H):

MS (+ve ESI): 550 (M+H)$^+$.

EXAMPLE 128

Preparation of Compound 128 in Table 5

An analogous reaction to that described in example 127, but starting with 4-methylaniline (30 mg, 0.28 mmol), yielded the title compound (132 mg, 62% yield) as an off-white solid (di-hexafluorophosphate salt):

$^1$H-NMR (DMSO-$d_6$): 10.62 (s, 1H), 10.08 (s, 1H), 9.50 (m, 3H), 8.63 (s, 1H), 7.88 (s, 1H), 7.78 (d, 2H), 7.32 (s, 1H), 7.18 (d, 2H), 4.25 (t, 2H), 3.99 (m, 5H), 3.67 (m, 1H), 3.46 (m, 2H), 3.31 (m, 2H), 3.14 (m, 2H), 2.27 (s, 3H), 2.23 (m, 2H):

MS (+ve ESI): 530 (M+H)$^+$.

EXAMPLE 129

Preparation of Compound No. 129 in Table 5

An analogous reaction to that described in example 127, but starting with 2-aminoquinoline (40.4 mg, 0.28 mmol), yielded the title compound (136.9 mg, 63% yield) as an off-white solid:
$^1$H-NMR (DMSO-$d_6$): 10.55 (s, 1H), 9.85 (s, 1H), 9.55 (s, 2H), 8.60 (s, 1H), 8.45 (m, 2H), 7.95 (d, 1H), 7.90 (m, 2H), 7.75 (m, 1H), 7.50 (m, 1H), 7.30 (s, 1H), 4.25 (t, 2H), 4.03 (s, 3H), 3.60 (m, 4H), 2.60 (m, 2H), 2.40 (m, 4H), 2.90 (m, 2H):
MS (+ve ESI): 567 (M+H)$^+$.

EXAMPLE 130

Preparation of Compound No. 130 in Table 5

An analogous reaction to that described in example 127, but starting with 2,3-difluoroaniline (36.2 mg, 0.28 mmol), yielded the title compound (120.8 mg, 57% yield) as an off-white solid:
$^1$H-NMR (DMSO-$d_6$): 9.55 (s, 2H), 8.65 (s, 1H), 7.88 (s, 1H), 7.80 (m, 1H), 7.30 (m, 3H), 4.25 (t, 2H), 4.00 (s, 3H), 3.65 (m, 4H), 2.65 (m, 6H), 2.05 (m, 2H):
MS (+ve ESI): 552 (M+H)$^+$.

EXAMPLE 131

Preparation of Compound No. 131 in Table 5

An analogous reaction to that described in example 127, but starting with 5-amino-1-methylpyrazole (27.2 mg, 0.28 mmol), yielded the title compound (127.7 mg, 63% yield) as an off-white solid:
$^1$H-NMR (DMSO-$d_6$): 9.52 (s, 2H), 8.63 (s, 1H), 7.88 (s, 1H), 7.40 (s, 1H), 7.30 (s, 1H), 6.30 (s, 1H), 4.25 (t, 2H), 4.01 (s, 3H), 3.75 (s, 3H), 3.65 (m, 4H), 2.60 (m, 6H), 2.05 (m, 2H):
MS (+ve ESI): 520 (M+H)$^+$.

EXAMPLE 132

Preparation of Compound No. 132 in Table 5

An analogous reaction to that described in example 127, but starting with 5-amino-3-methyl-4-nitroisoxazole (40.1 mg, 0.28 mmol), yielded the title compound (128 mg, 59% yield) as an off-white solid:
$^1$H-NMR (DMSO-$d_6$): 10.00 (s, 1H), 9.57 (s, 2H), 8.60 (s, 1H), 7.88 (s, 1H), 7.30 (s, 1H), 4.25 (t, 2H), 4.02 (s, 3H), 3.65 (m, 4H), 2.70 (t, 2H), 2.60 (m, 4H), 2.50 (s, 3H), 2.05 (m, 2H):
MS (+ve ESI): 566 (M+H)+.

EXAMPLE 133

Preparation of Compound No. 133 in Table 5

An analogous reaction to that described in example 127, but starting with 2-chloroaniline (35.7 mg, 0.28 mmol), yielded the title compound (121.7 mg, 58% yield) as an off-white solid:
$^1$H-NMR (DMSO-$d_6$): 9.58 (s, 2H), 8.65 (s, 1H), 8.35 (d, 1H), 7.92 (s, 1H), 7.60 (d, 1H), 7.50 (t, 1H), 7.30 (s, 1H), 7.23 (t, 1H), 4.27 (t, 2H), 4.02 (s, 3H), 3.70 (m, 4H), 2.70 (m, 4H), 2.52 (m, 2H), 2.10 (m, 2H):
MS (+ve ESI): 550 (M+H)+.

EXAMPLE 134

Preparation of Compound No. 134 in Table 5

An analogous reaction to that described in example 127, but starting with 2-chloro-5-nitroaniline (48.3 mg, 0.28 mmol), yielded the title compound (87.8 mg, 39% yield) as an off-white solid:
$^1$H-NMR (DMSO-$d_6$): 10.60 (s, 1H), 9.90 (s, 1H), 9.55 (s, 2H), 9.20 (s, 1H), 8.60 (s, 1H), 8.00 (dd, 1H), 7.88 (m, 2H), 7.28 (s, 1H), 4.22 (t, 2H), 4.01 (s, 3H), 3.60 (m, 4H), 2.45 (m, 2H), 2.38 (m, 4H), 1.95 (m, 2H):
MS (+ve ESI): 595 (M+H)+.

EXAMPLE 135

Preparation of Compound No. 135 in Table 5

An analogous reaction to that described in example 127, but starting with 2-nitroaniline (38.7 mg, 0.28 mmol), yielded the title compound (8.8 mg, 4% yield) as an off-white solid:
$^1$H-NMR (DMSO-$d_6$): 12.20 (s, 1H), 10.13 (s, 1H), 9.60 (s, 2H), 8.66 (m, 2H), 8.25 (d, 1H), 7.87 (m, 2H), 7.40 (t, 1H), 7.30 (s, 1H), 4.25 (m, 2H), 4.00 (s, 3H), 3.70 (m, 4H), 2.60 (m, 6H), 2.10 (m, 2H):
MS (+ve ESI): 561 (M+H)+.

EXAMPLE 136

Preparation of Compound No. 136 in Table 5

An analogous reaction to that described in example 127, but starting with 2-(methylthio)aniline (39 mg, 0.28 mmol), yielded the title compound (114.2 mg, 53% yield) as an off-white solid:
$^1$H-NMR (DMSO-$d_6$): 9.55 (s, 2H), 8.65 (s, 1H), 8.28 (d, 1H), 7.90 (s, 1H), 7.58 (d, 1H), 7.38 (t, 1H), 7.32 (s, 1H), 7.20 (t, 1H), 4.27 (m, 2H), 4.00 (s, 3H), 3.70 (m, 4H), 2.50 (m, 6H), 2.13 (m, 2H):
MS (+ve ESI): 562 (M+H)+.

EXAMPLE 137

Preparation of Compound No. 137 in Table 5

An analogous reaction to that described in example 127, but starting with 3-aminobenzonitrile (33.1 mg, 0.28 mmol), yielded the title compound (124.1 mg, 59% yield) as an off-white solid:
$^1$H-NMR (DMSO-$d_6$): 9.55 (s, 2H), 8.65 (s, 1H), 8.39 (s, 1H), 8.23 (m, 1H), 7.89 (s, 1H), 7.60 (m, 2H), 7.30 (s, 1H), 4.25 (t, 2H), 4.00 (s, 3H), 3.70 (m, 4H), 2.80 (s, 6H), 2.1 (m, 2H):
MS (+ve ESI): 541 (M+H)+.

EXAMPLE 138

Preparation of Compound No. 138 in Table 5

An analogous reaction to that described in example 127, but starting with 3-fluoroaniline (31.1 mg, 0.28 mmol), yielded the title compound (132.6 mg, 64% yield) as an off-white solid:

$^1$H-NMR (DMSO-$d_6$): 9.50 (s, 2H), 8.63 (s, 1H), 8.87 (m, 2H), 7.75 (d, 1H), 7.40 (dd, 1H), 7.3 (s, 1H), 6.97 (m, 1H), 4.25 (t, 2H), 4.02 (s, 3H), 3.65 (m, 4H), 2.70 (m, 6H), 2.05 (m, 2H):

MS (+ve ESI): 534 (M+H)+.

EXAMPLE 139

Preparation of Compound No. 139 in Table 5

An analogous reaction to that described in example 127, but starting with 3,4-dichloroaniline (45.4 mg, 0.28 mmol), yielded the title compound (106.4 mg, 48% yield) as an off-white solid:

$^1$H-NMR (DMSO-$d_6$): 9.52 (s, 2H), 8.62 (s, 1H), 8.30 (d, 1H), 7.93 (d, 1H), 7.88 (s, 1H), 7.62 (d, 1H), 7.28 (s, 1H), 4.22 (t, 2H), 4.00 (s, 3H), 3.60 (m, 4H), 2.45 (m, 6H), 2.00 (m, 2H):

MS (+ve ESI): 584 (M+H)+.

EXAMPLE 140

Preparation of Compound No. 140 in Table 5

An analogous reaction to that described in example 127, but starting with meta-anisidine (34.5 mg, 0.28 mmol), yielded the title compound (97.8 mg, 46% yield) as an off-white solid:

$^1$H-NMR (DMSO-$d_6$): 9.50 (s, 2H), 8.62 (s, 1H), 7.88 (s, 1H), 7.60 (m, 1H), 7.52 (d, 1H), 7.30 (m, 2H), 6.75 (d, 1H), 4.25 (t, 2H), 4.01 (s, 3H), 3.78 (s, 3H), 3.65 (m, 4H), 2.65 (m, 6H), 2.05 (m, 2H):

MS (+ve ESI): 546 (M+H)+.

EXAMPLE 141

Preparation of Compound No. 141 in Table 5

An analogous reaction to that described in example 127, but starting with 3-aminobenzotrifluoride (45.1 mg, 0.28 mmol), yielded the title compound (137.9 mg, 63% yield) as an off-white solid:

$^1$H-NMR (DMSO-$d_6$): 9.53 (s, 2H), 8.65 (s, 1H), 8.42 (s, 1H), 8.20 (d, 1H), 7.89 (s, 1H), 7.63 (t, 1H), 7.50 (d, 1H), 7.30 (s, 1H), 4.25 (t, 2H), 4.00 (s, 3H), 3.65 (m, 4H), 2.67 (m, 6H), 2.07 (m, 2H):

MS (+ve ESI): 584 (M+H)+.

EXAMPLE 142

Preparation of Compound No. 142 in Table 5

An analogous reaction to that described in example 127, but starting with 4-nitroaniline (38.7 mg, 0.28 mmol), yielded the title compound (63.2 mg, 29% yield) as an off-white solid:

$^1$H-NMR (DMSO-$d_6$): 10.90 (s, 1H), 9.87 (s, 1H), 9.50 (s, 2H), 8.60 (s, 1H), 8.21 (d, 2H), 8.15 (d, 2H), 7.90 (s, 1H), 7.30 (s, 1H), 4.27 (t, 2H), 4.03 (s, 3H), 3.65 (m, 4H), 2.70 (m, 2H), 2.60 (m, 4H), 2.05 (m, 2H):

MS (+ve ESI): 561 (M+H)+.

EXAMPLE 143

Preparation of Compound No. 143 in Table 5

An analogous reaction to that described in example 127, but starting with isoamylamine (24.4 mg, 0.28 mmol), yielded the title compound (53.1 mg, 26% yield) as an off-white solid:

$^1$H-NMR (DMSO-$d_6$): 9.95 (s, 1H), 9.40 (s, 2H), 8.76 (t, 1H), 8.60 (s, 1H), 7.85 (s, 1H), 7.29 (s, 1H), 4.23 (t, 2H), 4.00 (s, 3H), 3.63 (m, 4H), 3.32 (m, 2H), 2.62 (m, 2H), 2.57 (m, 4H), 2.05 (m, 2H), 1.64 (m, 1H), 1.46 (m, 2H), 0.92 (d, 6H):

MS (+ve ESI): 510 (M+H)+.

EXAMPLE 144

Preparation of Compound No. 144 in Table 5

An analogous reaction to that described in example 127, but starting with methyl 5-amino-2-furoate (39.5 mg, 0.28 mmol), yielded the title compound (24.7 mg, 11% yield) as an off-white solid:

$^1$H-NMR (DMSO-$d_6$): 11.89 (s, 1H), 10.05 (s, 1H), 9.50 (s, 2H), 8.63 (s, 1H), 7.90 (s, 1H), 7.40 (d, 1H), 7.30 (s, 1H), 6.62 (d, 1H), 4.25 (t, 2H), 4.00 (s, 3H), 3.80 (s, 3H), 3.70 (m, 4H), 2.65 (m, 6H), 2.10 (m, 2H):

MS (+ve ESI): 564 (M+H)+.

EXAMPLE 145

Preparation of Compound No. 145 in Table 5

An analogous reaction to that described in example 127, but starting with 3-(trifluoromethyl)benzylamine (49 mg, 0.28 mmol), yielded the title compound (31.1 mg, 14% yield) as an off-white solid:

$^1$H-NMR (DMSO-$d_6$): 10.00 (s, 1H), 9.52 (t, 1H), 9.50 (s, 2H), 8.62 (s, 1H), 7.88 (s, 1H), 7.72 (s, 1H), 7.68 (d, 1H), 7.6 (m, 2H), 7.30 (s, 1H), 4.60 (d, 2H), 4.25 (d, 2H), 4.00 (s, 3H), 3.65 (m, 4H), 2.50 (m, 6H), 2.10 (m, 2H):

MS (+ve ESI): 598 (M+H)+.

EXAMPLE 146

Preparation of Compound No. 146 in Table 5

An analogous reaction to that described in example 127, but starting with N-heptylamine (32.3 mg, 0.28 mmol), yielded the title compound (78.3 mg, 38% yield) as an off-white solid:

$^1$H-NMR (DMSO-$d_6$): 9.95 (s, 1H), 9.42 (s, 2H), 8.79 (t, 1H), 8.60 (s, 1H), 7.88 (s, 1H), 7.28 (s, 1H), 4.25 (t, 2H), 4.00 (s, 3H), 3.62 (m, 4H), 3.30 (m, 2H), 2.50 (m, 6H), 2.00 (m, 2H), 1.55 (m, 2H), 1.30 (m, 8H), 0.87 (t, 3H):

MS (+ve ESI): 538 (M+H)+.

EXAMPLE 147

Preparation of Compound No. 147 in Table 5

An analogous reaction to that described in example 127, but starting with 4-fluorobenzylamine (35 mg, 0.28 mmol), yielded the title compound (116.5 mg, 55% yield) as an off-white solid:
$^1$H-NMR (DMSO-$d_6$): 9.95 (s, 1H), 9.43 (s, 1H), 9.38 (t, 1H), 8.61 (s, 1H), 7.87 (s, 1H), 7.42 (m, 2H), 7.31 (s, 1H), 7.17 (m, 1H), 4.50 (d, 2H), 4.25 (t, 2H), 4.00 (s, 3H), 3.60 (m, 4H), 2.62 (m, 2H), 2.52 (m, 4H), 2.00 (m, 2H):
MS (+ve ESI): 548 (M+H)+.

EXAMPLE 148

Preparation of Compound No. 148 in Table 5

An analogous reaction to that described in example 127, but starting with methyl 3-amino-4-methylthiophene-2-carboxylate (47.9 mg, 0.28 mmol), yielded the title compound (14.3 mg, 6% yield) as an off-white solid:
$^1$H-NMR (DMSO-$d_6$): 10.75 (s, 1H), 10.08 (s, 1H), 9.55 (s, 2H), 8.65 (s, 1H), 7.90 (s, 1H), 7.62 (s, 1H), 7.31 (s, 1H), 4.25 (t, 2H), 4.02 (s, 3H), 3.80 (s, 3H), 3.60 (m, 4H), 2.51 (m, 6H), 2.22 (s, 3H), 2.00 (m, 2H):
MS (+ve ESI): 594 (M+H)+.

EXAMPLE 149

Preparation of Compound No. 149 in Table 5

An analogous reaction to that described in example 127, but starting with 2-(1-cyclohexenyl)ethylamine (35.1 mg, 0.28 mmol), yielded the title compound (119.4 mg, 57% yield) as an off-white solid:
$^1$H-NMR (DMSO-$d_6$): 9.71 (s, 1H), 9.38 (s, 2H), 8.57 (s, 1H), 8.32 (t, 1H), 7.85 (s, 1H), 7.27 (s, 1H), 5.45 (s, 1H), 4.25 (t, 2H), 4.01 (s, 3H), 3.65 (m, 4H), 3.41 (dd, 2H), 2.62 (m, 2H), 2.55 (m, 4H), 2.23 (t, 2H), 1.95 (m, 6H), 1.61 (m, 2H), 1.52 (m, 2H):
MS (+ve ESI): 548 (M+H)+.

EXAMPLE 150

Preparation of Compound No. 150 in Table 5

An analogous reaction to that described in example 127, but starting with 2-amino-3,5-dimethylpyrazine (34.5 mg, 0.28 mmol), yielded the title compound (65.6 mg, 31% yield) as an off-white solid:
$^1$H-NMR (DMSO-$d_6$): 9.50 (s, 2H), 8.65 (s, 1H), 8.33 (s, 1H), 7.88 (s, 1H), 7.32 (s, 1H), 4.27 (t, 2H), 4.00 (s, 3H), 3.71 (m, 4H), 2.81 (m, 6H), 2.52 (s, 3H), 2.45 (s, 3H), 2.10 (m, 2H):
MS (+ve ESI): 546 (M+H)+.

EXAMPLE 151

Preparation of Compound No. 151 in Table 5

An analogous reaction to that described in example 127, but starting with thiophene-2-ethylamine (35.6 mg, 0.28 mmol), yielded the title compound (118.4 mg, 56% yield) as an off-white solid:
$^1$H-NMR (DMSO-$d_6$): 9.95 (s, 1H), 9.42 (s, 2H), 8.96 (t, 1H), 8.61 (s, 1H), 7.85 (s, 1H), 7.35 (m, 1H), 7.29 (s, 1H), 6.95 (m, 2H), 4.22 (t, 2H), 4.00 (s, 3H), 3.65 (m, 4H), 3.62 (m, 2H), 3.11 (m, 2H), 2.55 (m, 6H), 2.03 (m, 2H):
MS (+ve ESI): 550 (M+H)+.

EXAMPLE 152

Preparation of Compound No. 152 in Table 5

An analogous reaction to that described in example 127, but starting with 2-fluoro-5-nitroaniline (43.7 mg, 0.28 mmol), yielded the title compound (89.4 mg, 41% yield) as an off-white solid:
$^1$H-NMR (DMSO-$d_6$): 9.55 (s, 2H), 9.02 (m, 1H), 8.65 (s, 1H), 8.15 (m, 1H), 7.88 (s, 1H), 7.66 (t, 1H), 7.27 (s, 1H), 4.23 (t, 2H), 4.02 (s, 3H), 3.61 (m, 4H), 2.55 (m, 6H), 2.00 (m, 2H):
MS (+ve ESI): 579 (M+H)+.

EXAMPLE 153

Preparation of Compound No. 153 in Table 5

An analogous reaction to that described in example 127, but starting with cyclopropylamine (16 mg, 0.28 mmol), yielded the title compound (42 mg, 35% yield) as an off-white solid:
$^1$H-NMR (DMSO-$d_6$): 9.97 (s, 1H), 9.41 (s, 2H), 8.77 (d, 1H), 8.61 (s, 1H), 7.88 (s, 1H), 7.29 (s, 1H), 4.25 (t, 2H), 4.00 (s, 3H), 3.72 (m, 4H), 2.92 (m, 1H), 2.51 (m, 6H), 2.13 (m, 2H), 0.72 (m, 4H):
MS (+ve ESI): 480 (M+H)+.

EXAMPLE 154

Preparation of Compound No. 154 in Table 5

An analogous reaction to that described in example 127, but starting with cyclopropanemethylamine (19.9 mg, 0.28 mmol), yielded the title compound (38 mg, 31% yield) as an off-white solid:
$^1$H-NMR (DMSO-$d_6$): 9.95 (s, 1H), 9.42 (s, 2H), 8.85 (t, 1H), 8.61 (s, 1H), 7.85 (s, 1H), 7.27 (s, 1H), 4.25 (t, 2H), 4.01 (s, 3H), 3.61 (m, 4H), 3.20 (t, 2H), 2.47 (m, 2H), 2.41 (m, 4H), 2.00 (m, 2H), 1.11 (m, 1H), 0.45 (m, 2H), 0.28 (m, 2H):
MS (+ve ESI): 494 (M+H)+.

EXAMPLE 155

Preparation of Compound No. 155 in Table 5

An analogous reaction to that described in example 127, but starting with cyclobutylamine (19.9 mg, 0.28 mmol), yielded the title compound (81.9 mg, 41% yield) as an off-white solid:
$^1$H-NMR (DMSO-$d_6$): 9.95 (s, 1H), 9.42 (s, 2H), 8.95 (d, 1H), 8.62 (s, 1H), 7.85 (s, 1H), 7.31 (s, 1H), 4.45 (m, 1H), 4.22 (t, 2H), 4.00 (s, 3H), 3.61 (m, 4H), 2.52 (m, 2H), 2.42 (m, 4H), 2.21 (m, 4H), 2.00 (m, 2H), 1.71 (m, 2H):
MS (+ve ESI): 493 (M+H)+.

EXAMPLE 156

Preparation of Compound No. 156 in Table 5

An analogous reaction to that described in example 127, but starting with cyclopentylamine (23.8 mg, 0.28 mmol), yielded the title compound (85.4 mg, 43% yield) as an off-white solid:

$^1$H-NMR (DMSO-$d_6$): 9.95 (s, 1H), 9.41 (s, 2H), 8.62 (s, 1H), 8.58 (d, 1H), 7.85 (s, 1H), 7.28 (s, 1H), 4.25 (m, 3H), 4.00 (m, 3H), 3.61 (m, 4H), 2.52 (m, 2H), 2.41 (m, 4H), 1.98 (m, 2H), 1.91 (m, 2H), 1.72 (m, 2H), 1.62 (m, 4H):

MS (+ve ESI): 508 (M+H)+.

EXAMPLE 157

Preparation of Compound No. 157 in Table 5

An analogous reaction to that described in example 127, but starting with 1-aminoindane (37.3 mg, 0.28 mmol), yielded the title compound (88.2 mg, 41% yield) as an off-white solid:

$^1$H-NMR (DMSO-$d_6$): 9.96 (s, 1H), 9.42 (s, 2H), 8.92 (d, 1H), 8.60 (s, 1H), 7.85 (s, 1H), 7.25 (m, 5H), 5.57 (dd, 1H), 4.22 (t, 2H), 4.00 (s, 3H), 3.61 (m, 4H), 3.01 (m, 1H), 2.88 (m, 1H), 2.55 (m, 2H), 2.45 (m, 4H), 2.12 (m, 1H), 2.00 (m, 2H):

MS (+ve ESI): 556 (M+H)+.

EXAMPLE 158

Preparation of Compound No. 158 in Table 6

An analogous reaction to that described in example 127, but starting with cyclohexane methylamine (31.7 mg, 0.28 mmol), yielded the title compound (82.6 mg, 40% yield) as an off-white solid:

$^1$H-NMR (DMSO-$d_6$): 9.95 (s, 1H), 9.40 (s, 2H), 8.75 (t, 1H), 8.59 (s, 1H), 7.85 (s, 1H), 7.27 (s, 1H), 4.20 (t, 2H), 4.00 (s, 3H), 3.60 (m, 4H), 3.17 (t, 2H), 2.48 (m, 2H), 2.40 (m, 4H), 1.98 (m, 2H), 1.70 (m, 4H), 1.60 (m, 2H), 1.20 (m, 3H), 0.95 (m, 2H);

MS (+ve ESI): 536 (M+H)+.

EXAMPLE 159

Preparation of Compound No. 159 in Table 5

An analogous reaction to that described in example 127, but starting with 5-amino-2-chloropyridine (36 mg, 0.28 mmol), yielded the title compound (122.1 mg, 58% yield) as an off-white solid:

$^1$H-NMR (DMSO-$d_6$): 10.72 (s, 1H), 9.81 (s, 1H), 9.52 (s, 2H), 8.88 (d, 1H), 8.61 (s, 1H), 8.33 (dd, 1H), 7.88 (s, 1H), 7.48 (d, 1H), 7.31 (s, 1H), 4.22 (t, 2H), 4.00 (s, 3H), 3.62 (m, 4H), 2.61 (m, 2H), 2.51 (m, 4H), 2.00 (m, 2H):

MS (+ve ESI): 551 (M+H)+.

EXAMPLE 160

Preparation of Compound No. 160 in Table 5

An analogous reaction to that described in example 127, but starting with 4-nitrobenzylamine hydrochloride (52.8 mg, 0.28 mmol), yielded the title compound (112.6 mg, 52% yield) as an off-white solid:

$^1$H-NMR (DMSO-$d_6$): 10.11 (s, 1H), 9.62 (t, 1H), 9.48 (s, 2H), 8.62 (s, 1H), 8.21 (d, 2H), 7.88 (s, 1H), 7.62 (d, 2H), 7.31 (s, 1H), 4.65 (d, 2H), 4.25 (t, 2H), 4.00 (s, 3H), 3.72 (m, 4H), 2.81 (m, 6H), 2.11 (m, 2H):

MS (+ve ESI): 575 (M+H)+.

EXAMPLE 161

Preparation of Compound No. 161 in Table 5

An analogous reaction to that described in example 127, but starting with tetrahydrofurfurylamine (28.3 mg, 0.28 mmol), yielded the title compound (40 mg, 31% yield) as an off-white solid:

$^1$H-NMR (DMSO-$d_6$): 9.43 (s, 2H), 8.68 (t, 1H), 8.62 (s, 1H), 7.91 (s, 1H), 7.31 (s, 1H), 4.31 (t, 2H), 4.05 (m, 2H), 4.01 (s, 3H), 3.81 (dd, 1H), 3.68 (m, 3H), 3.55 (m, 2H), 3.40 (m, 2H), 3.15 (m, 2H), 2.26 (m, 2H), 1.91 (m, 3H), 1.62 (m, 1H):

MS (+ve ESI): 524 (M+H)+.

EXAMPLE 162

Preparation of Compound No. 162 in Table 5

An analogous reaction to that described in example 127, but starting with 5-methyltryptamine hydrochloride (59 mg, 0.28 mmol), yielded the title compound (109 mg, 73% yield) as an off-white solid:

$^1$H-NMR (DMSO-$d_6$): 10.00 (s, 1H), 9.42 (s, 2H), 8.92 (t, 1H), 8.61 (s, 1H), 7.88 (s, 1H), 7.41 (s, 1H), 7.32 (s, 1H), 7.22 (d, 1H), 7.15 (s, 1H), 6.91 (d, 1H), 4.26 (t, 2H), 4.00 (s, 3H), 3.73 (m, 4H), 3.62 (dd, 2H), 2.95 (t, 2H), 2.91 (m, 6H), 2.38 (s, 3H), 2.12 (m, 2H):

MS (+ve ESI): 597 (M+H)+.

EXAMPLE 163

Preparation of Compound No. 163 in Table 5

An analogous reaction to that described in example 127, but starting with 2-aminopyridine (26.4 mg, 0.28 mmol), yielded the title compound (103.1 mg, 51% yield) as an off-white solid:

$^1$H-NMR (DMSO-$d_6$): 10.25 (s, 1H), 9.82 (s, 1H), 9.51 (s, 2H), 8.62 (s, 1H), 8.38 (m, 1H), 8.25 (m, 1H), 7.88 (m, 3H), 7.31 (s, 1H), 7.18 (m, 1H), 4.25 (t, 2H), 4.02 (s, 3H), 3.65 (m, 4H), 2.62 (m, 2H), 2.52 (m, 4H), 2.02 (m, 2H):

MS (+ve ESI): 517 (M+H)+.

EXAMPLE 164

Preparation of Compound No. 164 in Table 5

An analogous reaction to that described in example 127, but starting with 3-aminopyridine (26.4 mg, 0.28 mmol), yielded the title compound (112.3 mg, 55% yield) as an off-white solid:

$^1$H-NMR (DMSO-$d_6$): 10.52 (s, 1H), 9.80 (s, 1H), 9.50 (s, 2H), 9.00 (s, 1H), 8.61 (s, 1H), 8.32 (m, 1H), 8.27 (m, 1H), 7.87 (s, 1H), 7.42 (m, 1H), 7.30 (s, 1H), 4.28 (t, 2H), 4.01 (s, 3H), 3.65 (m, 4H), 2.70 (m, 2H), 2.62 (m, 4H), 2.08 (m, 2H):

MS (+ve ESI): 517 (M+H)+.

EXAMPLE 165

Preparation of Compound No. 165 in Table 5

An analogous reaction to that described in example 127, but starting with 4-aminopyridine (26.4 mg, 0.28 mmol), yielded the title compound (120.8 mg, 59% yield) as an off-white solid:
$^1$H-NMR (DMSO-d$_6$): 9.55 (s, 2H), 8.65 (s, 1H), 8.50 (m, 2H), 7.95 (m, 2H), 7.31 (s, 1H), 4.25 (t, 2H), 4.01 (s, 3H), 3.65 (m, 4H), 2.62 (m, 4H), 2.05 (m, 2H):
MS (+ve ESI): 517 (M+H)+.

EXAMPLE 166

Preparation of Compound No. 166 in Table 5

An analogous reaction to that described in example 127, but starting with 1-aminoisoquinoline (40.4 mg, 0.28 mmol), yielded the title compound (104.6 mg, 48% yield) as an off-white solid:
$^1$H-NMR (DMSO-d$_6$): 9.55 (s, 2H), 8.65 (s, 1H), 8.38 (d, 1H), 8.12 (d, 1H), 8.05 (d, 1H), 7.92 (s, 1H), 7.82 (m, 2H), 7.70 (t, 1H), 7.31 (s, 1H), 4.25 (t, 2H), 4.05 (s, 3H), 3.62 (m, 4H), 2.48 (m, 2H), 2.41 (m, 4H), 2.00 (m, 2H):
MS (+ve ESI): 567 (M+H)+.

EXAMPLE 167

Preparation of Compound No. 167 in Table 5

An analogous reaction to that described in example 127, but starting with 2,4-dinitroaniline (51.3 mg, 0.28 mmol), yielded the title compound (131.4 mg, 58% yield) as an off-white solid:
$^1$H-NMR (DMSO-d$_6$): 12.42 (s, 1H), 9.91 (s, 1H), 9.58 (s, 2H), 9.02 (d, 1H), 8.95 (s, 1H), 8.62 (m, 4H), 7.91 (s, 1H), 7.32 (s, 1H), 4.25 (t, 2H), 4.00 (s, 3H), 3.61 (m, 4H), 2.42 (m, 6H), 2.03 (m, 2H):
MS (+ve ESI): 606 (M+H)+.

EXAMPLE 168

Preparation of Compound No. 168 in Table 5

An analogous reaction to that described in example 127, but starting with 5-amino-2-nitrobenzotrifluoride (57.7 mg, 0.28 mmol), yielded the title compound (77.1 mg, 33% yield) as an off-white solid:
$^1$H-NMR (DMSO-d$_6$): 11.55 (s, 1H), 10.10 (s, 1H), 9.55 (s, 2H), 8.65 (m, 2H), 8.52 (d, 1H), 8.25 (d, 1H), 7.91 (s, 1H), 7.32 (s, 1H), 4.21 (t, 2H), 4.02 (s, 3H), 3.55 (m, 4H), 2.50 (m, 2H), 2.40 (m, 4H), 1.96 (m, 2H):
MS (+ve ESI): 629 (M+H)+.

EXAMPLE 169

Preparation of Compound No. 169 in Table 5

An analogous reaction to that described in example 127, but starting with anthranilonitrile (33.1 mg, 0.28 mmol), yielded the title compound (47.1 mg, 22% yield) as an off-white solid:
$^1$H-NMR (DMSO-d$_6$): 9.55 (s, 2H), 8.65 (s, 1H), 8.05 (d, 1H), 7.91 (m, 2H), 7.78 (t, 1H), 7.40 (t, 1H), 7.32 (s, 1H), 4.25 (t, 2H), 4.00 (s, 3H), 3.67 (m, 4H), 2.65 (m, 6H), 2.05 (m, 2H):
MS (+ve ESI): 541 (M+H)+.

EXAMPLE 170

Preparation of Compound No. 170 in Table 5

An analogous reaction to that described in example 127, but starting with 2-fluoroaniline (31.1 mg, 0.28 mmol), yielded the title compound (123.1 mg, 59% yield) as an off-white solid:
$^1$H-NMR (DMSO-d$_6$): 9.53 (s, 2H), 8.62 (s, 1H), 8.10 (t, 1H), 7.85 (s, 1H), 7.35 (m, 1H), 7.27 (m, 3H), 4.25 (t, 2H), 4.03 (s, 3H), 3.62 (m, 4H), 2.55 (m, 6H), 2.04 (m, 2H):
MS (+ve ESI): 534 (M+H)+.

EXAMPLE 171

Preparation of Compound No. 171 in Table 5

An analogous reaction to that described in example 127, but starting with 2,4-difluoroaniline (36.2 mg, 0.28 mmol), yielded the title compound (130.9 mg, 62% yield) as an off-white solid:
$^1$H-NMR (DMSO-d$_6$): 9.52 (s, 2H), 8.65 (s, 1H), 7.96 (m, 1H), 7.89 (s, 1H), 7.42 (m, 1H), 7.30 (s, 1H), 7.15 (m, 1H), 4.25 (t, 2H), 4.02 (s, 3H), 3.65 (m, 4H), 2.60 (m, 6H), 2.05 (m, 2H):
MS (+ve ESI): 552 (M+H)+.

EXAMPLE 172

Preparation of Compound 172 in Table 5

An analogous reaction to that described in example 127, but starting with 3-chloro-4-fluorobenzylamine (44.7 mg, 0.28 mmol), yielded the title compound (104 mg, 72% yield) as an off-white solid as the dihexafluorophosphate salt:
$^1$H-NMR (DMSO-d$_6$): 10.01 (s, 1H), 9.43–9.52 (m, 3H), 8.62 (s, 1H), 7.80 (s, 1H), 7.63 (d, 1H), 7.40 (d, 2H), 7.31 (s, 1H), 4.45 (d, 2H), 4.23 (t, 2H), 4.05 (s, 3H), 3.62 (m, 4H), 2.40–2.50 (m, 6H), 1.98–2.01 (m, 2H):
MS (+ve ESI): 582 (M+H)+.

EXAMPLE 173

Preparation of Compound 173 in Table 5

An analogous reaction to that described in example 127, but starting with 4-amino-2,2-dimethyltetrahydropyran (36 mg, 0.28 mmol), yielded the title compound (65 mg, 47% yield) as an off-white solid as the dihexafluorophosphate salt:
$^1$H-NMR (DMSO-d$_6$): 10.01 (s, 1H), 9.43 (s, 2H), 8.62 (m, 2H), 7.80 (s, 1H), 7.20 (s, 1H), 4.23 (m, 2H), 4.05 (s, 3H), 3.60–3.70 (m, 6H), 2.25–2.50 (m, 7H), 1.98–2.01 (m, 2H), 1.71–1.80 (m, 2H), 1.45–1.63 (m, 2H), 1.20 (s, 3H), 1.15 (s, 3H):
MS (+ve ESI): 552 (M+H)$^+$.

EXAMPLE 174

Preparation of Compound 174 in Table 5

An analogous reaction to that described in example 127, but starting 3-(methylthio)propylamine (29 mg, 0.28 mmol), yielded the title compound (74 mg, 56% yield) as an off-white solid as the dihexafluorophosphate salt:

$^1$H-NMR (DMSO-d$_6$): 10.01 (s, 1H), 9.43 (m, 2H), 8.90 (t, 1H), 8.62 (s, 1H), 7.80 (s, 1H), 7.23 (s, 1H), 4.23 (t, 2H), 4.05 (s, 3H), 3.62 (m, 4H), 3.33–3.40 (m, 2H), 2.20–2.50 (m, 8H), 2.10 (s, 3H), 1.98–2.10 (m, 2H), 1.85–1.98 (m, 2H):

MS (+ve ESI): 528 (M+H)$^+$.

EXAMPLE 175

Preparation of Compound 175 in Table 5

An analogous reaction to that described in example 127, but starting with 3-(5-methyl-1H-pyrazol-4-yl)propylamine (39 mg, 0.28 mmol), yielded the title compound (60 mg, 43% yield) as an off-white solid as the dihexafluorophosphate salt:

$^1$H-NMR (DMSO-d$_6$): 12.10 (s, 1H), 9.01 (s, 2H), 8.62 (m, 1H), 8.01 (s, 1H), 7.82 (s, 1H), 7.34 (s, 1H), 6.80 (s, 1H), 4.23 (t, 2H), 4.05 (s, 3H), 3.62 (m, 4H), 2.31–2.61 (m, 10H), 2.10 (s, 3H), 1.98–2.01 (m, 2H), 1.70–1.80 (m, 2H):

MS (+ve ESI): 562 (M+H)$^+$.

EXAMPLE 176

Preparation of Compound 176 in Table 5

An analogous reaction to that described in example 127, but starting with 2-amino-5-methyl-1,3,4-thiadiazole (32 mg, 0.28 mmol), yielded the title compound (102 mg, 76% yield) as an off-white solid as the dihexafluorophosphate salt:

$^1$H-NMR (DMSO-d$_6$): 12.50 (s, 1H), 10.01 (s, 1H), 9.51 (s, 2H), 8.62 (s, 1H), 7.90 (s, 1H), 7.34 (s, 1H), 4.23 (t, 2H), 4.05 (s, 3H), 3.62 (s, 4H), 2.81 (s, 3H), 2.50–2.90 (s, 6H), 2.01–2.20 (s, 2H):

MS (+ve ESI): 538 (M+H)$^+$.

EXAMPLE 177

Preparation of Compound 177 in Table 5

An analogous reaction to that described in example 127, but starting with 4-fluoroaniline (31 mg, 0.28 mmol), yielded the title compound (110 mg, 83% yield) as an off-white solid as the dihexafluorophosphate salt:

$^1$H-NMR (DMSO-d$_6$): 10.45 (s, 1H), 9.80 (s, 1H), 9.45 (s, 2H), 8.62 (s, 1H), 7.90 (m, 3H), 7.23 (s, 1H), 7.21 (m, 2H), 4.23 (t, 2H), 4.05 (s, 3H), 3.62 (s, 4H), 2.91–3.10 (s, 6H), 2.50 (s, 6H), 1.98–2.01 (m, 2H):

MS (+ve ESI): 534 (M+H)$^+$.

EXAMPLE 178

Preparation of Compound 178 in Table 5

An analogous reaction to that described in example 127, but starting with 4-(methylmercapto)aniline (39 mg, 0.28 mmol), yielded the title compound (89 mg, 64% yield) as an off-white solid as the dihexafluorophosphate salt:

$^1$H-NMR (DMSO-d$_6$): 10.45 (s, 1H), 9.80 (s, 1H), 9.45 (s, 2H), 8.62 (s, 1H), 7.90 (m, 3H), 7.23 (m, 3H), 4.23 (t, 2H), 4.05 (s, 3H), 3.62 (s, 4H), 2.91–3.10 (s, 6H), 2.41–2.80 (m, 9H), 1.98–2.01 (m, 2H):

MS (+ve ESI): 561 (M+H)$^+$.

EXAMPLE 179

Preparation of Compound 179 in Table 5

An analogous reaction to that described in example 127, but starting with benzylamine (30 mg, 0.28 mmol), yielded the title compound (85 mg, 64% yield) as an off-white solid as the dihexafluorophosphate salt:

$^1$H-NMR (DMSO-d$_6$): 10.01 (s, 1H), 9.43 (m, 2H), 9.40 (t, 1H), 8.62 (s, 1H), 7.80 (s, 1H), 7.15–7.20 (m, 6H), 4.55 (d, 1H), 4.23 (m, 2H), 4.05 (s, 3H), 3.62 (m, 4H), 2.40–2.50 (m, 6H), 1.98–2.01 (m, 2H):

MS (+ve ESI): 530 (M+H)$^+$.

EXAMPLE 180

Preparation of Compound 180 in Table 5

An analogous reaction to that described in example 127, but starting with 2-methylbenzylamine (33 mg, 0.28 mmol), yielded the title compound (111 mg, 82% yield) as an off-white solid as the dihexafluorophosphate salt:

$^1$H-NMR (DMSO-d$_6$): 10.01 (s, 1H), 9.43 (s, 2H), 9.20 (t, 1H), 8.62 (s, 1H), 7.80 (s, 1H), 7.00–7.40 (m, 5H), 4.45 (d, 2H), 4.23 (t, 2H), 4.05 (s, 3H), 3.62 (s, 4H), 2.40–2.50 (m, 6H), 2.35 (s, 3H), 1.98–2.01 (m, 2H):

MS (+ve ESI): 544 (M+H)$^+$.

EXAMPLE 181

Preparation of Compound 181 in Table 5

An analogous reaction to that described in example 127, but starting with 3,4-dichlorobenzylamine (49 mg, 0.28 mmol), yielded the title compound (69 mg, 46% yield) as an off-white solid as the dihexafluorophosphate salt:

$^1$H-NMR (DMSO-d$_6$): 10.01 (s, 1H), 9.43–9.51 (m, 3H), 8.62 (s, 1H), 7.82 (s, 1H), 7.62 (m, 2H), 7.43 (m, 2H), 7.40 (s, 1H), 4.62 (d, 2H), 4.23 (t, 2H), 4.05 (s, 3H), 3.62 (m, 4H), 2.40–2.50 (m, 6H), 1.98–2.01 (m, 2H):

MS (+ve ESI): 598 (M+H)$^+$.

EXAMPLE 182

Preparation of Compound 182 in Table 5

An analogous reaction to that described in example 127, but starting with 3-phenyl-1-propylamine (38 mg, 0.28 mmol), yielded the title compound (80 mg, 57% yield) as an off-white solid as the dihexafluorophosphate salt:

$^1$H-NMR (DMSO-d$_6$): 10.01 (s, 1H), 9.43 (s, 2H), 9.21 (t, 1H), 8.85 (t, 1H), 8.62 (s, 1H), 7.80 (s, 1H), 7.20 (s, 1H), 4.23 (t, 2H), 4.05 (s, 3H), 3.62 (m, 8H), 2.40–2.50 (m, 8H), 1.98–2.01 (m, 2H), 1.75–1.85 (m, 2H):

MS (+ve ESI): 526 (M+H)$^+$.

EXAMPLE 183

Preparation of Compound 183 in Table 5

An analogous reaction to that described in example 127, but starting with 1-(3-aminopropyl)imidazole (35 mg, 0.28 mmol), yielded the title compound (28 mg, 21% yield) as off-white solid as the dihexafluorophosphate salt:

$^1$H-NMR (DMSO-d$_6$): 10.01 (s, 1H), 9.43 (s, 2H), 9.01 (t, 1H), 8.62 (s, 1H), 7.89 (s, 1H), 7.80 (s, 1H), 7.40 (s, 1H), 7.20 (s, 1H), 6.85 (s, 1H), 4.23 (t, 2H), 3.95–4.10 (m, 5H), 3.62 (m, 4H), 2.41–2.62 (m, 8H), 1.98–2.01 (m, 4H):

MS (+ve ESI): 548 (M+H)$^+$.

EXAMPLE 184

Preparation of Compound 184 in Table 5

An analogous reaction to that described in example 127, but starting with 2,4-difluorobenzylamine (40 mg, 0.28 mmol), yielded the title compound 89 mg, 63% yield) as an off-white solid as the dihexafluorophosphate salt:

$^1$H-NMR (DMSO-d$_6$): 10.01 (s, 1H), 9.43 (s, 2H), 9.40 (t, 1H), 8.62 (s, 1H), 7.80 (s, 1H), 7.41–7.50 (m, 1H), 7.15–7.30 (m, 2H), 7.00 (m, 1H), 4.50 (d, 2H), 4.23 (t, 2H), 4.05 (s, 3H), 3.62 (m, 4H), 2.20–2.50 (m, 6H), 1.98–2.01 (m, 2H):

MS (+ve ESI): 566 (M+H)$^+$.

EXAMPLE 185

Preparation of Compound 185 in Table 5

An analogous reaction to that described in example 127, but starting with 3-pyrrolidinopropylamine (36 mg, 0.28 mmol), yielded the title compound (30 mg, 22% yield) as an off-white solid as the dihexafluorophosphate salt:

$^1$H-NMR (DMSO-d$_6$): 10.01 (s, 1H), 9.43 (s, 2H), 9.10 (t, 1H), 8.62 (s, 1H), 7.87 (s, 1H), 7.32 (m, 1H), 4.23 (t, 2H), 4.05 (s, 3H), 3.62 (m, 4H), 3.30–3.40 (m, 2H), 2.20–2.50 (m, 12H), 1.98–2.01 (m, 2H), 1.65–1.80 (m, 6H):

MS (+ve ESI): 551 (M+H)$^+$.

EXAMPLE 186

Preparation of Compound 186 in Table 5

An analogous reaction to that described in example 127, but starting with 3-aminomethylthiophene dihydrochloride (48 mg, 0.28 mmol), yielded the title compound (124 mg, 93% yield) as an off-white solid as the dihexafluorophosphate salt:

$^1$H-NMR (DMSO-d$_6$): 10.01 (s, 1H), 9.43 (s, 2H), 9.20 (t, 1H), 8.62 (s, 1H), 7.87 (s, 1H), 7.51 (m, 1H), 7.25 (m, 2H), 7.03 (d, 1H), 4.45 (d, 2H), 4.23 (t, 2H), 4.05 (s, 3H), 3.62 (m, 4H), 2.20–2.50 (m, 6H), 2.20–2.30 (m, 2H):

MS (+ve ESI): 536 (M+H)$^+$.

EXAMPLE 187

Preparation of Compound 187 in Table 5

An analogous reaction to that described in example 127, but starting with 3-aminotetrahydrothiophene-S,S-dioxide dihydrochloride (58 mg, 0.28 mmol), yielded the title compound (35 mg, 25% yield) as an off-white solid as the dihexafluorophosphate salt:

$^1$H-NMR (DMSO-d$_6$): 10.01 (s, 1H), 9.43 (s, 2H), 9.20 (d, 1H), 8.62 (s, 1H), 7.87 (s, 1H), 7.25 (s, 1H), 4.80 (m, 1H), 4.23 (t, 2H), 4.05 (s, 3H), 3.10–3.80 (m, 8H), 2.20–2.45 (m, 4H):

MS (+ve ESI): 558 (M+H)$^+$.

EXAMPLE 188

Preparation of Compound 188 in Table 5

An analogous reaction to that described in example 127, but starting with C-[1,4]dioxan-2-yl-methylamine (32 mg, 0.28 mmol), yielded the title compound (8 mg, 6% yield) as an off-white solid:

$^1$H-NMR (DMSO-d$_6$): 10.01 (bs, 1H), 9.43 (s, 2H), 8.80 (t, 1H), 8.62 (s, 1H), 7.80 (s, 1H), 7.20 (s, 1H), 4.23 (m, 2H), 4.05 (s, 3H), 3.21–3.81 (m, 13H), 2.25–2.50 (m, 8H), 1.98–2.01 (m, 2H):

MS (+ve ESI): 540 (M+H)$^+$.

EXAMPLE 189

Preparation of Compound 189 in Table 5

An analogous reaction to that described in example 127, but starting with 4-(dimethylamino)benzylamine dihydrochloride (63 mg, 0.28 mmol), yielded the title compound (92 mg, 64% yield) as an off-white solid as the dihexafluorophosphate salt:

$^1$H-NMR (DMSO-d$_6$): 10.01 (s, 1H), 9.43 (s, 2H), 9.20 (t, 1H), 8.62 (s, 1H), 7.87 (s, 1H), 7.25 (s, 1H), 7.20 (d, 2H), 6.70 (d, 2H), 4.45 (d, 2H), 4.23 (t, 2H), 4.10 (m, 5H), 3.10–3.80 (m, 8H), 2.98 (s, 6H), 2.20–2.45 (m, 2H):

MS (+ve ESI): 573 (M+H)$^+$.

EXAMPLE 190

Preparation of Compound 190 in Table 5

An analogous reaction to that described in example 127, but starting with 3-phenyl-1-propylamine (38 mg, 0.28 mmol), yielded the title compound (80 mg, 57% yield) as an off-white solid as the dihexafluorophosphate salt:

$^1$H-NMR (DMSO-d$_6$): 10.01 (s, 1H), 9.43 (s, 2H), 8.84 (t, 1H), 8.62 (s, 1H), 7.80 (s, 1H), 7.21–7.30 (m, 6H), 4.23 (t, 2H), 4.05 (s, 3H), 3.62 (m, 4H), 2.60–2.71 (m, 2H), 2.20–2.50 (m, 8H), 1.98–2.01 (m, 2H), 1.95 (m, 2H):

MS (+ve ESI): 558 (M+H)$^+$.

EXAMPLE 191

Preparation of Compound 191 in Table 5

An analogous reaction to that described in example 127, but starting with 4-(2-aminoethyl)pyridine (34 mg, 0.28 mmol), yielded the title compound (5 mg, 4% yield) as an off-white solid as the dihexafluorophosphate salt:

$^1$H-NMR (DMSO-d$_6$): 10.01 (s, 1H), 9.43 (s, 2H), 8.94 (t, 1H), 8.62 (s, 1H), 8.50 (d, 3H), 7.80 (s, 1H), 7.21–7.30 (m, 3H), 4.23 (t, 2H), 4.05 (s, 3H), 3.62 (m, 6H), 2.80 (m, 2H), 2.20–2.50 (m, 6H), 1.98–2.01 (m, 2H):

MS (+ve ESI): 545 (M+H)$^+$.

EXAMPLE 192

Preparation of Compound 192 in Table 5

An analogous reaction to that described in example 127, but starting with 3-chlorobenzylamine (40 mg, 0.28 mmol), yielded the title compound (88 mg, 62% yield) as an off-white solid as the dihexafluorophosphate salt:

$^1$H-NMR (DMSO-d$_6$): 10.01 (s, 1H), 9.43 (m, 3H), 8.62 (s, 1H), 7.80 (s, 1H), 7.10–7.20 (m, 5H), 4.45 (d, 2H), 4.23 (t, 2H), 4.05 (s, 3H), 3.60–3.70 (m, 4H), 2.25–2.50 (m, 6H), 1.98–2.01 (m, 2H):

MS (+ve ESI): 564 (M+H)$^+$.

EXAMPLE 193

Preparation of Compound 193 in Table 5

An analogous reaction to that described in example 127, but starting with 3-bromo-4-methylaniline (51 mg, 0.28 mmol), yielded the title compound (96 mg, 63% yield) as an off-white solid as the dihexafluorophosphate salt:

$^1$H-NMR (DMSO-d$_6$): 10.80 (s, 1H), 10.01 (s, 1H), 9.43 (s, 2H), 8.62 (s, 1H), 8.20 (s, 1H), 7.87 (s, 1H), 7.80 (d, 1H), 7.45 (d, 1H), 7.30 (s, 1H), 4.23 (t, 2H), 4.05 (s, 3H), 3.62 (m, 4H), 2.20–2.50 (m, 6H), 2.40 (s, 3H), 1.98–2.01 (s, 2H):

MS (+ve ESI): 609 (M+H)$^+$.

EXAMPLE 194

Preparation of Compound 194 in Table 5

An analogous reaction to that described in example 127, but starting with 2-amino-5-ethyl-1,3,4-thiadiazole (36 mg, 0.28 mmol), yielded the title compound (75 mg, 54% yield) as an off-white solid as the dihexafluorophosphate salt:

$^1$H-NMR (DMSO-d$_6$): 12.50 (s, 1H), 10.01 (s, 1H), 9.51 (s, 2H), 8.62 (s, 1H), 7.90 (s, 1H), 7.34 (s, 1H), 4.23 (t, 2H), 4.05 (s, 3H), 3.62 (m, 4H), 3.01 (q, 2H), 2.50–2.90 (m, 6H), 2.01–2.20 (m, 2H), 1.22 (t, 3H):

MS (+ve ESI): 552 (M+H)$^+$.

EXAMPLE 195

Preparation of Compound 195 in Table 5

An analogous reaction to that described in example 127, but starting with 2-aminopyrazine (27 mg, 0.28 mmol), yielded the title compound (6.5 mg, 5% yield) as an off-white solid as the dihexafluorophosphate salt:

$^1$H-NMR (DMSO-d$_6$): 11.81 (s, 1H), 10.01 (s, 1H), 9.51 (s, 2H), 9.50 (s, 1H), 8.62 (s, 1H), 8.45–8.50 (d, 1H), 7.90 (s, 1H), 7.34 (s, 1H), 4.23 (t, 2H), 4.05 (s, 3H), 3.62 (s, 4H), 2.50–2.90 (m, 6H), 2.01–2.20 (bs, 2H):

MS (+ve ESI): 518 (M+H)$^+$.

EXAMPLE 196

Preparation of Compound 196 in Table 5

An analogous reaction to that described in example 127, but starting with 3-chloroaniline (36 mg, 0.28 mmol), yielded the title compound (111 mg, 81% yield) as an off-white solid as the dihexafluorophosphate salt:

$^1$H-NMR (DMSO-d$_6$): 10.81 (s, 1H), 10.01 (s, 1H), 9.50 (s, 2H), 8.62 (s, 1H), 8.20 (s, 1H), 7.83 (m, 2H), 7.30–7.40 (t, 1H), 7.25 (s, 1H), 7.15–7.20 (m, 1H), 4.23 (t, 2H), 4.05 (s, 3H), 3.62 (s, 4H), 2.50–2.90 (m, 6H), 2.01–2.20 (m, 2H):

MS (+ve ESI): 550 (M+H)$^+$.

EXAMPLE 197

Preparation of Compound 197 in Table 5

An analogous reaction to that described in example 127, but starting with 3,5-dichloroaniline (45 mg, 0.28 mmol), yielded the title compound (118 mg, 81% yield) as an off-white solid as the dihexafluorophosphate salt:

$^1$H-NMR (DMSO-d$_6$): 11.01 (s, 1H), 10.01 (s, 1H), 9.50 (s, 2H), 8.62 (s, 1H), 8.01 (s, 2H), 7.85 (s, 1H), 7.40 (s, 1H), 7.30 (s, 1H), 7.15–7.20 (m, 1H), 4.23 (t, 2H), 4.05 (s, 3H), 3.62 (s, 4H), 2.50–2.90 (m, 6H), 1.98–2.01 (m, 2H):

MS (+ve ESI): 584 (M+H)$^+$.

EXAMPLE 198

Preparation of Compound 198 in Table 5

An analogous reaction to that described in example 127, but starting with 2-chlorobenzylamine (40 mg, 0.28 mmol), yielded the title compound (98 mg, 70% yield) as an off-white solid as the dihexafluorophosphate salt:

$^1$H-NMR (DMSO-d$_6$): 10.01 (s, 1H), 9.43 (s, 2H), 9.20 (t, 1H), 8.62 (s, 1H), 7.80 (s, 1H), 7.00–7.40 (m, 5H), 4.45 (d, 2H), 4.23 (t, 2H), 4.05 (s, 3H), 3.62 (bs, 4H), 2.40–2.50 (m, 6H), 1.98–2.01 (m, 2H):

MS (+ve ESI): 564 (M+H)$^+$.

EXAMPLE 199

Preparation of Compound 199 in Table 5

An analogous reaction to that described in example 127, but starting with 3-methylbenzylamine (34 mg, 0.28 mmol), yielded the title compound (91 mg, 67% yield) as an off-white solid as the dihexafluorophosphate salt:

$^1$H-NMR (DMSO-d$_6$): 10.01 (s, 1H), 9.43 (s, 2H), 9.20 (t, 1H), 8.62 (s, 1H), 7.80 (s, 1H), 7.05–7.40 (m, 5H), 4.45 (d, 2H), 4.23 (t, 2H), 4.05 (s, 3H), 3.62 (s, 4H), 2.30–2.50 (m, 6H), 2.29 (s, 3H), 1.98–2.01 (m, 2H):

MS (+ve ESI): 544 (M+H)$^+$.

EXAMPLE 200

Preparation of Compound 200 in Table 5

An analogous reaction to that described in example 127, but starting with phenethylamine (33 mg, 0.28 mmol), yielded the title compound (75 mg, 55% yield) as an off-white solid as the dihexafluorophosphate salt:

$^1$H-NMR (DMSO-d$_6$): 10.01 (s, 1H), 9.43 (s, 2H), 8.90 (t, 1H), 8.62 (s, 1H), 7.80 (s, 1H), 7.10–7.20 (m, 5H), 4.23 (t, 2H), 4.05 (s, 3H), 3.55–3.70 (m, 6H), 2.85 (t, 2H), 2.40–2.50 (m, 6H), 1.98–2.01 (m, 2H):

MS (+ve ESI): 544 (M+H)$^+$.

EXAMPLE 201

Preparation of Compound 201 in Table 5

An analogous reaction to that described in example 127, but starting with 2,5-difluorobenzylamine (40 mg, 0.28 mmol), yielded the title compound (112 mg, 790% yield) as an off-white solid as the dihexafluorophosphate salt:

$^1$H-NMR (DMSO-d$_6$): 10.01 (s, 1H), 9.43 (s, 2H), 9.40 (t, 1H), 8.62 (s, 1H), 7.80 (s, 1H), 7.01–7.25 (m, 4H), 4.50 (d, 2H), 4.23 (t, 2H), 4.05 (s, 3H), 3.62 (m, 4H), 2.20–2.50 (m, 6H), 1.98–2.01 (m, 2H):

MS (+ve ESI): 566 (M+H)$^+$.

EXAMPLE 202

Preparation of Compound 202 in Table 5

An analogous reaction to that described in example 127, but starting 3,4-difluorobenzylamine (40 mg, 0.28 mmol), yielded the title compound (80 mg, 57% yield) as an off-white solid as the dihexafluorophosphate salt:

$^1$H-NMR (DMSO-d$_6$): 9.98 (s, 1H), 9.43 (m, 3H), 8.62 (s, 1H), 7.80 (s, 1H), 7.10–7.41 (m, 2H), 4.50 (d, 2H), 4.23 (t, 2H), 4.05 (s, 3H), 3.62 (m, 4H), 2.20–2.50 (m, 6H), 1.98–2.01 (m, 2H):

MS (+ve ESI): 566 (M+H)$^+$.

EXAMPLE 203

Preparation of Compound 203 in Table 5

An analogous reaction to that described in example 127, but starting with 3-methoxybenzylamine (38 mg, 0.28 mmol), yielded the title compound (80 mg, 57% yield) as an off-white solid as the dihexafluorophosphate salt:

$^1$H-NMR (DMSO-d$_6$): 9.98 (s, 1H), 9.43 (s, 2H), 9.30 (t, 1H), 8.62 (s, 1H), 7.80 (s, 1H), 7.10–7.20 (m, 2H), 6.90 (m, 2H), 6.80 (d, 1H), 4.45 (d, 2H), 4.23 (t, 2H), 4.05 (s, 3H), 3.85 (s, 3H), 3.62 (m, 4H), 2.40–2.50 (m, 6H), 2.01–1.98 (m, 2H):

MS (+ve ESI): 560 (M+H)$^+$.

EXAMPLE 204

Preparation of Compound 204 in Table 5

An analogous reaction to that described in example 127, but starting with 5-aminobenzotriazole (37 mg, 0.28 mmol), yielded the title compound (71 mg, 51% yield) as an off-white solid as the dihexafluorophosphate salt:

$^1$H-NMR (DMSO-d$_6$): 15.53 (s 1H), 10.98 (bs, 1H), 9.98 (s, 1H), 9.43 (s, 2H), 8.80 (m, 1H), 8.62 (s, 1H), 8.53 (d, 1H), 7.80 (s, 1H), 7.45 (m, 1H), 7.32 (s, 1H), 4.23 (t, 2H), 4.05 (s, 3H), 3.62 (m, 4H), 2.20–2.50 (m, 6H), 1.98–2.01 (m, 2H):

MS (+ve ESI): 557 (M+H)$^+$.

EXAMPLE 205

Preparation of Compound 205 in Table 5

An analogous reaction to that described in example 127, but starting with furfurylamine (27 mg, 0.28 mmol), yielded the title compound (90 mg, 69% yield) as an off-white solid as the dihexafluorophosphate salt:

$^1$H-NMR (DMSO-d$_6$): 10.01 (s, 1H), 9.51 (s, 2H), 9.02 (t, 1H), 8.62 (s, 1H), 7.90 (s, 1H), 7.62 (s, 1H), 7.34 (s, 1H), 6.41 (d, 1H), 6.30 (d, 1H), 4.52 (d, 2H), 4.23 (t, 2H), 4.05 (s, 3H), 3.62 (m, 4H), 2.30–2.50 (m, 6H), 1.98–2.01 (m, 2H):

MS (+ve ESI): 520 (M+H)$^+$.

EXAMPLE 206

Preparation of Compound 206 in Table 5

An analogous reaction to that described in example 127, but starting with 3-chloro-4-fluoroaniline (41 mg, 0.28 mmol), yielded the title compound (116 mg, 82% yield) as an off-white solid as the dihexafluorophosphate salt $^1$H-NMR (DMSO-d$_6$): 10.81 (s, 1H), 10.01 (s, 1H), 9.50 (s, 2H), 8.62 (s, 1H), 8.23 (d, 1H), 7.80–7.92 (m, 2H), 7.35–7.43 (t, 1H), 7.30 (s, 1H), 7.15–7.20 (m, 1H), 4.23 (t, 2H), 4.05 (s, 3H), 3.62 (s, 4H), 2.50–2.90 (m, 6H), 2.01–2.20 (m, 2H):

MS (+ve ESI): 568 (M+H)$^+$.

EXAMPLE 207

Preparation of Compound 207 in Table 5

An analogous reaction to that described in example 127, but starting with 3,5-dimethylaniline (34 mg, 0.28 mmol), yielded the title compound (83 mg, 61% yield) as an off-white solid as the dihexafluorophosphate salt:

$^1$H-NMR (DMSO-d$_6$): 10.45 (s, 1H), 10.01 (s, 1H), 9.50 (s, 2H), 8.62 (s, 1H), 7.92 (s, 1H), 7.53 (s, 2H), 7.21 (s, 1H), 6.80 (s, 1H), 4.23 (t, 2H), 4.05 (s, 3H), 3.62 (s, 4H), 2.50–2.90 (m, 6H), 2.20 (s, 6H), 1.98–2.01 (m, 2H):

MS (+ve ESI): 544 (M+H)$^+$.

EXAMPLE 208

Preparation of Compound 208 in Table 5

An analogous reaction to that described in example 127, but starting with para-anisidine (34 mg, 0.28 mmol), yielded the title compound (62 mg, 46% yield) as an off-white solid as the dihexafluorophosphate salt:

$^1$H-NMR (DMSO-d$_6$): 10.45 (s, 1H), 9.80 (s, 1H), 9.45 (s, 2H), 8.62 (s, 1H), 7.90 (m, 3H), 7.23 (s, 1H), 6.80–6.89 (m, 2H), 4.23 (t, 2H), 4.05 (s, 3H), 3.85 (s, 3H), 3.62 (s, 4H), 2.91–3.10 (m, 6H), 2.50 (s, 6H), 1.98–2.01 (m, 2H):

MS (+ve ESI): 546 (M+H)$^+$.

EXAMPLE 209

Preparation of Compound 209 in Table 5

An analogous reaction to that described in example 127, but starting with 2-fluorobenzylamine (35 mg, 0.28 mmol), yielded the title compound (99 mg, 72% yield) as an off-white solid as the dihexafluorophosphate salt:

$^1$H-NMR (DMSO-d$_6$): 10.01 (s, 1H), 9.43 (s, 2H), 9.20 (t, 1H), 8.62 (s, 1H), 7.80 (s, 1H), 7.00–7.40 (m, 5H), 4.45 (d, 2H), 4.23 (t, 2H), 4.05 (s, 3H), 3.62 (bs, 4H), 2.40–2.50 (m, 6H), 1.98–2.01 (m, 2H):

MS (+ve ESI): 548 (M+H)$^+$.

EXAMPLE 210

Preparation of Compound 210 in Table 5

An analogous reaction to that described in example 127, but starting with 2-methoxybenzylamine (38 mg, 0.28 mmol), yielded the title compound (75 mg, 53% yield) as an off-white solid as the dihexafluorophosphate salt:

$^1$H-NMR (DMSO-d$_6$): 10.01 (s, 1H), 9.43 (s, 2H), 9.02 (t, 1H), 8.62 (s, 1H), 7.80 (s, 1H), 7.10–7.20 (m, 3H), 7.00 (d,

1H), 6.90 (t, 1H), 4.45 (d, 2H), 4.23 (t, 2H), 4.05 (s, 3H), 3.80 (s, 3H), 3.62 (m, 4H), 2.40–2.50 (m, 6H), 1.98–2.01 (m, 2H):
MS (+ve ESI): 560 (M+H)$^+$.

EXAMPLE 211

Preparation of Compound 211 in Table 5

An analogous reaction to that described in example 127, but starting with 3-fluorobenzylamine (35 mg, 0.28 mmol), yielded the title compound (90 mg, 66% yield) as an off-white solid as the dihexafluorophosphate salt:
$^1$H-NMR (DMSO-d$_6$): 10.01 (s, 1H), 9.43 (m, 3H), 8.62 (s, 1H), 7.80 (s, 1H), 7.05–7.45 (m, 5H), 4.55 (d, 2H), 4.23 (t, 2H), 4.05 (s, 3H), 3.62 (m, 4H), 2.40–2.50 (m, 6H), 1.98–2.01 (m, 2H):
MS (+ve ESI): 548 (M+H)$^+$.

EXAMPLE 212

Preparation of Compound 212 in Table 5

An analogous reaction to that described in example 127, but starting with 4-chlorobenzylamine (40 mg, 0.28 mmol), yielded the title compound (104 mg, 74% yield) as an off-white solid as the dihexafluorophosphate salt:
$^1$H-NMR (DMSO-d$_6$): 10.01 (s, 1H), 9.43 (m, 3H), 8.62 (s, 1H), 7.80 (s, 1H), 7.30–7.40 (m, 4H), 7.20 (s, 1H), 4.55 (d, 2H), 4.23 (t, 2H), 4.05 (s, 3H), 3.62 (m, 4H), 2.40–2.50 (m, 6H), 1.98–2.01 (m, 2H):
MS (+ve ESI): 564 (M+H)$^+$.

EXAMPLE 213

Preparation of Compound 213 in Table 5

An analogous reaction to that described in example 127, but starting with 4-methylbenzylamine (33 mg, 0.28 mmol), yielded the title compound (100 mg, 74% yield) as an off-white solid as the dihexafluorophosphate salt:
$^1$H-NMR (DMSO-d$_6$): 10.01 (s, 1H), 9.43 (s, 2H), 9.21 (t, 1H), 8.62 (s, 1H), 7.80 (s, 1H), 7.21–7.30 (m, 3H), 7.10 (d, 2H), 4.55 (d, 2H), 4.23 (t, 2H), 4.05 (s, 3H), 3.62 (m, 4H), 2.40–2.50 (m, 6H), 2.25 (s, 3H), 1.98–2.01 (m, 2H):
MS (+ve ESI): 544 (M+H)$^+$.

EXAMPLE 214

Preparation of Compound 214 in Table 5

An analogous reaction to that described in example 127, but starting with 4-bromoaniline (48 mg, 0.28 mmol), yielded the title compound (119 mg, 80% yield) as an off-white solid as the dihexafluorophosphate salt:
$^1$H-NMR (DMSO-d$_6$): 10.98 (s, 1H), 10.01 (s, 1H), 9.43–9.52 (m, 3H), 8.62 (s, 1H), 7.80–8.00 (m, 3H), 7.63 (d, 2H), 7.20 (s, 1H), 4.23 (m, 2H), 4.05 (s, 3H), 3.62 (m, 4H), 2.40–2.50 (m, 6H), 1.98–2.01 (m, 2H):
MS (+ve ESI): 594 (M+H)$^+$.

EXAMPLE 215

Preparation of Compound 215 in Table 5

An analogous reaction to that described in example 127, but starting with isopropylamine (16 mg, 0.28 mmol), yielded the title compound (52 mg, 44% yield) as an off-white solid as the dihexafluorophosphate salt:
$^1$H-NMR (DMSO-d$_6$): 10.01 (s, 1H), 9.43 (s, 2H), 8.62 (s, 1H), 8.45 (d, 1H), 7.80 (s, 1H), 7.20 (s, 1H), 4.23 (t, 2H), 4.10 (m, 1H), 4.05 (s, 3H), 3.62 (m, 4H), 2.40–2.50 (m, 6H), 1.98–2.01 (m, 2H), 1.20 (d, 6H):
MS (+ve ESI): 482 (M+H)$^+$.

EXAMPLE 216

Preparation of Compound 216 in Table 5

An analogous reaction to that described in example 127, but starting with (S)-(+)-sec-butylamine (20 mg, 0.28 mmol), yielded the title compound (49 mg, 39% yield) as an off-white solid as the dihexafluorophosphate salt:
$^1$H-NMR (DMSO-d$_6$): 10.01 (s, 1H), 9.43 (s, 2H), 8.62 (s, 1H), 8.40 (d, 1H), 7.80 (s, 1H), 7.20 (s, 1H), 4.23 (t, 2H), 4.05 (s, 3H), 3.91–4.00 (m, 1H), 3.60–3.70 (m, 4H), 2.25–2.50 (m, 6H), 1.98–2.01 (m, 2H), 1.50–1.70 (m 2H), 1.20 (d, 3H), 0.98 (t, 3H):
MS (+ve ESI): 496 (M+H)$^+$.

EXAMPLE 217

Preparation of Compound 217 in Table 5

An analogous reaction to that described in example 127, but starting with (R)-(−)-sec-butylamine (20 mg, 0.28 mmol), yielded the title compound (50 mg, 41% yield) as an off-white solid as the dihexafluorophosphate salt:
$^1$H-NMR (DMSO-d$_6$): 10.01 (s, 1H), 9.43 (s, 2H), 8.62 (s, 1H), 8.40 (d, 1H), 7.80 (s, 1H), 7.20 (s, 1H), 4.23 (t, 2H), 4.05 (s, 3H), 3.91–4.00 (m, 1H), 3.60–3.70 (m, 4H), 2.25–2.50 (m, 6H), 1.98–2.01 (m, 2H), 1.50–1.70 (m 2H), 1.20 (d, 3H), 0.98 (t, 3H):
MS (+ve ESI): 496 (M+H)$^+$.

EXAMPLE 218

Preparation of Compound 218 in Table 5

An analogous reaction to that described in example 127, but starting with 4-(N,N-dimethylamino)aniline (38 mg, 0.28 mmol) yielded a crude product after the reaction had been cooled and the solvents removed in vacuo. Dioxane/water 10:1 (10 ml), followed by water (20 ml) was added, the resulting solid was collected by suction filtration and then washed with water and ethyl acetate. Drying in vacuo yielded the title compound (70 mg, 45% yield) as a greenish solid as the dihexafluorophosphate salt:
$^1$H-NMR (DMSO-d$_6$): 9.97 (s, 1H), 9.45 (s, 2H), 8.58 (s, 1H), 7.83 (s, 1H), 7.69 (d, 2H), 7.26 (s, 1H), 6.72 (d, 2H), 4.19 (t, 1H), 3.98 (s, 3H), 3.57 (m, 4H), 2.86 (s, 6H), 2.42 (m, 2H), 2.38 (m, 4H), 1.94 (m, 2H):
MS (+ve ESI): 559 (M+H)$^+$.
MS (−ve ESI): 557 (M−H)$^-$.

EXAMPLE 219

Preparation of Compound 219 in Table 5

An analogous reaction to that described in example 127, but starting with cyclopropylethylamine (0.043 ml, 0.5 mmol—prepared according to *J. Med. Chem.* 1998, 41, 3515–3529.), yielded the title compound (59 mg, 30% yield) as an off-white solid as the dihexafluorophosphate salt:

¹H-NMR (DMSO-d₆): 9.87 (s, 1H), 9.35 (s, 2H), 8.72 (t, 1H), 8.54 (s, 1H), 7.78 (s, 1H), 7.21 (s, 1H), 4.16 (t, 2H), 3.95 (s, 3H), 3.53 (t, 4H), 3.33 (q, 2H), 2.42 (m, 2H), 2.32 (m, 4H), 1.91 (m, 2H), 1.42 (m, 2H), 0.69 (m, 1H), 0.37 (m, 2H), 0.03 (m, 2H):
MS (+ve ESI): 508 (M+H)⁺.
MS (−ve ESI): 506 (M−H)⁻.

EXAMPLE 220

Preparation of Compound 220 in Table 6

An analogous reaction to that described in example 127, but starting with 4-(2-carboxy-5-pyrimidinamino)-6-methoxy-7-(3-benzyloxy)quinazoline (220 mg, 0.5 mmol) and 3-chloro-4-fluoroaniline (80 mg, 0.55 mmol), yielded the title compound (230 mg, 87% yield) as an off-white solid:
¹H-NMR (DMSO-d₆): 10.92 (bs, 1H), 10.04 (bs, 1H), 9.50 (s, 2H), 8.58 (s, 1H), 8.20 (m, 1H), 7.86 (m, 2H), 7.50 (m, 2H), 7.38 (m, 5H), 5.30 (s, 2H), 3.98 (s, 3H):
MS (+ve ESI): 531 (M+H)⁺.
MS (−ve ESI): 529 (M−H)⁻.

4-(2-Carboxy-5-pyrimidinamino)-6-methoxy-7-(3-benzyloxy)quinazoline, used as starting material was obtained as follows:

An analogous reaction to that described in example 87, but starting with 4-chloro-6-methoxy-7-(3-benzyloxy)quinazoline (18.93 g, 63 mmol) and 5-amino-2-pyrimidinecarboxylic acid (9.42 g, 60 mmol), yielded the title compound 22.08 g, 80% yield) as a light brown hydrochloride salt:
¹H-NMR (DMSO-d₆): 12.06 (s, 1H), 10.46 (s, 2H), 8.92 (s, 1H), 8.52 (s, 1H), 7.48 (m, 6H), 5.33 (s, 2H), 4.04 (s, 3H):
MS (−ve ESI): 404 (M−H)⁻,
MS (+ve ESI): 402 (M+H)⁺.

EXAMPLE 221

Preparation of Compound 221 in Table 6

An analogous reaction to that described in example 127, but starting with 2,4-difluoroaniline (4.26 g, 33 mmol) and 4-(2-carboxy-5-pyrimidinamino)-6-methoxy-7-(3-benzyloxy)quinazoline (13.18 g, 30.0 mmol), yielded the title compound (14.55 g, 94% yield) as an off-white solid:
¹H-NMR (DMSO-d₆): 10.36 (s, 1H), 10.04 (s, 1H), 9.48 (s, 2H), 8.58 (s, 1H), 7.94 (m, 1H), 7.85 (s, 1H), 7.50 (m, 2H), 7.39 (m, 5H), 7.12 (m, 1H), 5.28 (s, 2H), 3.98 (s, 3H):
MS (+ve ESI): 515 (M+H)⁺.
MS (−ve ESI): 513 (M−H)⁻.

EXAMPLE 222

Preparation of Compound 2 in Table 6

An analogous reaction to that described in example 13, but starting with 4-(2-N-(2,4-difluorophenyl)carboxamide-5-aminopyrimidine)-6-methoxy-7-(3-benzyloxy)quinazoline (14.54 g, 28.3 mmol), yielded the title compound (15.22 g, 94% yield) as a pale yellow solid:
¹H-NMR (DMSO-d₆): 10.44 (s, 1H), 9.41 (s, 2H), 8.83 (s, 1H), 7.99 (s, 1H), 7.90 (m, 1H), 7.39 (m, 1H), 7.22 (s, 1H), 7.12 (m, 1H), 4.00 (s, 3H):
MS (+ve ESI): 425 (M+H)⁺.
MS (−ve ESI): 423 (M−H)⁻.

EXAMPLE 223

Preparation of Compound 223 in Table 6

An analogous reaction to that described in example 13, but starting with 4-(2-N-(3-chloro,4-fluorophenyl)carboxamide-5-aminopyrimidine)-6-methoxy-7-(3-benzyloxy)quinazoline (159 mg, 0.3 mmol), yielded the title compound (118 mg, 90% yield) as a pale yellow solid:
¹H-NMR (DMSO-d₆): 10.92 (s, 1H), 10.04 (s, 1H), 9.47 (s, 2H), 8.55 (s, 1H), 8.20 (m, 1H), 7.87 (m, 1H), 7.82 (s, 1H), 7.41 (t, 1H), 7.12 (s, 1H), 3.79 (s, 3H):
MS (+ve ESI): 441 (M+H)⁺.
MS (−ve ESI): 439 (M−H)⁻.

EXAMPLE 224

Preparation of Compound 224 in Table 6

An analogous reaction to that described in example 53, but starting with 4-(2-N-(3-chloro,4-fluorophenyl)carboxamide-5-aminopyrimidine)-6-methoxy-7-(3-hydroxy)quinazoline (1.73 g, 3.9 mmol) and potassium carbonate (1.62 g, 11.7 mmol) in dimethylacetamide. The reaction mixture was filtered through silica (10 g) in a sinter funnel before treatment with water (100 ml) and the resultant solid was collected by suction filtration and washed with ether (contained 50% of dialkylated material). Purification by recrystallisation from dimethylformamide/acetonitrile 1:1 afforded the title compound (397 mg, 19% yield) as an off-white solid:
¹H-NMR (DMSO-d₆): 10.97 (s, 1H), 10.09 (s, 1H), 9.53 (s, 2H), 8.64 (s, 1H), 8.23 (m, 1H), 8.16 (s, 1H), 7.87 (m, 1H), 7.45 (m, 1H), 7.32 (s, 1H), 4.33 (t, 2H), 4.03 (s, 3H), 3.85 (t, 2H), 2.29 (m, 2H):
MS (+ve ESI): 517 (M+H)⁺.
MS (−ve ESI): 515 (M−H)⁻.

EXAMPLE 225

Preparation of Compound 225 in Table 6

An analogous reaction to that described in example 53, but starting with 4-(2-N-(2,4-difluorophenyl)carboxamide-5-aminopyrimidine)-6-methoxy-7-(3-hydroxy)quinazoline (4.75 g, 8.8 mmol), yielded the title compound (3.79 g, 86% yield) as a pale yellow solid:
¹H-NMR (DMSO-d₆): 10.42 (s, 1H), 10.07 (s, 1H), 9.53 (s, 2H), 8.64 (s, 1H), 7.97 (m, 1H), 7.90 (s, 1H), 7.43 (m, 1H), 7.34 (s, 1H), 7.17 (m, 1H), 4.33 (t, 2H), 4.03 (s, 3H), 3.84 (t, 2H), 2.29 (m, 2H):
MS (+ve ESI): 501 (M+H)⁺.
MS (−ve ESI): 499 (M−H)⁻.

EXAMPLE 226

Preparation of Compound 226 in Table 6

An analogous reaction to that described in example 14, but starting with 4-(2-N-(3-chloro,4-fluorophenyl)carboxamide-5-aminopyrimidine)-6-methoxy-7-(3-hydroxy)quinazoline (3.44 g, 7.8 mmol) and (2S)-(+)-glycidyl tosylate (1.96 g, 8.6 mmol) yielded the title compound (1.86 g, 42% yield) as a pale yellow powder:
¹H-NMR (DMSO-d₆): 10.95 (s, 1H), 10.05 (s, 1H), 9.51 (s, 2H), 8.61 (s, 1H), 8.22 (m, 1H), 7.88 (m, 2H), 7.43 (t, 1H), 7.28 (s, 1H), 4.56 (m, 1H), 4.03 (m, 4H), 3.43 (m, 1H), 2.91 (m, 1H), 2.78 (m, 1H):

MS (+ve ESI): 497 (M+H)⁺.
MS (−ve ESI): 495 (M−H)⁻.

EXAMPLE 227

Preparation of Compound 227 in Table 6

An analogous reaction to that described in example 14, but starting with 4-(2-N-(2,4-difluorophenyl)carboxamide-5-aminopyrimidine)-6-methoxy-7-(3-hydroxy)quinazoline (9.47 g, 17.6 mmol) and (2S)-(+)-glycidyl tosylate (4.42 g, 19.4 mmol) yielded the title compound (1.84 g, 22% yield) as a pale yellow solid:

$^1$H-NMR (DMSO-d$_6$): 10.39 (s, 1H), 10.08 (s, 1H), 9.40 (s, 2H), 8.61 (s, 1H), 7.95 (m, 1H), 7.88 (s, 1H), 7.41 (m, 1H), 7.31 (s, 1H), 7.14 (m, 1H), 4.56 (m, 1H), 4.00 (m, 4H), 3.44 (m, 1H), 2.90 (m, 1H), 2.78 (m, 1H):
MS (+ve ESI): 481 (M+H)⁺.
MS (−ve ESI): 479 (M−H)⁻.

EXAMPLE 228

Preparation of Compound 228 in Table 6

An analogous reaction to that described in example 127, but starting with cyclopropylethylamine (580 mg, 6.8 mmol) and 4-(2-carboxy-5-pyrimidinamino)-6-methoxy-7-(3-benzyloxy)quinazoline (1.5 g, 3.4 mmol), yielded the title compound (1.59 g, 99% yield) as an off-white solid:

$^1$H-NMR (DMSO-d$_6$): 9.90 (bs, 1H), 9.35 (s, 2H), 8.62 (t, 1H), 8.53 (s, 1H), 7.85 (s, 1H), 7.46 (m, 2H), 7.37 (m, 4H), 5.25 (s, 2H), 3.95 (s, 3H), 3.33 (q, 2H), 1.42 (q, 2H), 0.69 (m, 1H), 0.38 (m, 2H), 0.02 (m, 2H):
MS (+ve ESI): 471 (M+H)⁺.
MS (−ve ESI): 469 (M−H)⁻.

EXAMPLE 229

Preparation of Compound 229 in Table 6

A mixture of N-(5-((6-methoxy-7-((2S)oxiranylmethoxy)-4-quinazolinyl)amino)-2-pyrimidinyl)benzamide (150 mg, 0.338 mmol) and (±) pyrrolidinol (44 mg, 0.507 mmol) in dimethylacetamide (1 ml) was heated at 60° C. for 2 days. The reaction mixture was cooled and brine (10 ml) was added; collection of the resulting solid by suction filtration yielded the title compound (82 mg, 56% yield) as an pale yellow solid:

$^1$H-NMR (DMSO-d$_6$): 10.95 (s, 1H), 10.04 (s, 1H), 9.50 (s, 2H), 8.61 (s, 1H), 8.20 (m, 1H), 7.89 (m, 2H), 7.41 (t, 1H), 7.30 (s, 1H), 4.83 (s, 1H), 4.19 (m, 1H), 4.00 (m, 5H), 3.30 (m, 2H), 2.40 (m, 4H), 1.47 (m, 4H), 1.35 (m, 2H):
MS (+ve ESI): 582 (M+H)⁺.
MS (−ve ESI): 580 (M−H)⁻.

EXAMPLE 230

Preparation of Compound 230 in Table 6

An analogous reaction to that described in example 16, but starting with 4-(2-N-(2,4-difluorophenyl)carboxamide-5-aminopyrimidine)-6-methoxy-7-((2S)oxiranylmethoxy) quinazoline (125 mg, 0.25 mmol), cyclopropylmethylamine (0.044 ml, 0.5 mmol) and tetrabutylammonium iodide (37 mg, 0.025 mmol), yielded the title compound (64 mg, 48% yield) as a pale yellow solid:

$^1$H-NMR (DMSO-d$_6$): 10.40 (s, 1H), 10.04 (bs, 1H), 9.50 (s, 2H), 8.61 (s, 1H), 7.92 (m, 1H), 7.87 (s, 1H), 7.41 (m, 1H), 7.28 (s, 1H), 7.13 (m, 1H), 4.19 (m, 1H), 4.00 (s, 3H), 2.71 (m, 2H), 2.40 (m, 4H), 1.92 (m, 2H), 0.85 (m, 1H), 0.40 (m, 2H), 0.10 (m, 2H):
MS (+ve ESI): 536 (M+H)⁺.
MS (−ve ESI): 534 (M−H)⁻.

EXAMPLE 231

Preparation of Compound 231 in Table 7

To a solution of 4-chloro-6-methoxy-7-(3-morpholinopropoxy)quinazoline (1.82 g, 5.38 mmol) in water (7.3 ml) was added 4M hydrochloric acid in dioxane (2.7 ml, 10.8 mmols) followed by a solution of 5-amino-2-cyanopyrimidine (783 mg, 3.59 mmol) in dioxane (10 ml) and water (5 ml) and the reaction mixture heated at 60° C. for 1 hour. A further equivalent of 4-chloro-6-methoxy-7-(3-morpholinopropoxy)quinazoline (1.2 g, 3.59 mmol) in water (5 ml) and 4N hydrochloric acid/dioxane (1.8 ml, 7.18 mmol) was added and the mixture heated at 70° C. for 2 hours. The mixture was cooled, diluted with water (15 ml) and extracted with ethyl acetate (3×30 ml). The organic solution was washed with a dilute solution of sodium bicarbonate, dried over magnesium sulphate and concentrated to a solid. Purification by flash chromatography on silica gel, eluting with 10% methanol in dichloromethane containing 2% concentrated ammonia yielded the title compound (730 mg, 48% yield) as a pale yellow solid:

$^1$H-NMR (DMSO-d$_6$): 9.45 (s, 2H), 8.61 (s, 1H), 7.81 (s, 1H), 7.27 (s, 1H), 4.23 (t, 2H), 3.96 (s, 3H), 3.59 (m, 4H), 2.40 (m, 6H), 1.98 (m, 2H):
MS (−ve ESI): 420 (M−H)⁻,
MS (+ve ESI): 422 (M+H)⁺.

5-Amino-2-cyanopyrimidine, used as starting material, was obtained as follows:

5-(dimethylaminomethyleneamino)-2-cyanopyrimidine (2.0 g, 10.6 mmol) obtained from the literature procedure described in Arnold et al, *Coll. Czech. Chem. Comm.* 1975, 40, 1384, was treated with 2N sulphuric acid (20 ml, 41.0 mmol) at 100° C. for 30 minutes. The reaction mixture was cooled and the resulting solid collected by suction filtration and washed with ether. The filtrate was seeded with the above solid and another crop of solid collected as before. Drying yielded the title compound (823 mg, 65% yield) as brown needles:

MS (+ve ESI): 120.9 (M+H)⁺.

EXAMPLE 232

Preparation of Compound 232 in Table 7

To a solution of 4-chloro-6-methoxy-7-(3-morpholinopropoxy)quinazoline (174 mg, 0.52 mmol) in water (1.0 ml) was added 4N hydrochloric acid in dioxane (0.26 ml, 1.04 mmol) followed by a solution of 5-amino-2-(4-pyridino) pyrimidine (77 mg, 0.45 mmol) in dioxane (1 ml) and water (1 ml) and the reaction mixture heated at 60° C. for 30 minutes. A further 2 equivalents of 5-amino-2-(4-pyridino) pyrimidine (154 mg, 0.90 mmol) was added and the mixture heated at 60° C. for 1 hour. The mixture was cooled, diluted with water (2 ml), an aqueous potassium carbonate solution (3 ml) was added and the resulting solid was collected by suction filtration and washed with water and a dilute sodium bicarbonate solution. Drying yielded the title compound (94 mg, 20% yield) as an off-white solid:

$^1$H-NMR (DMSO-d$_6$): 9.90 (s, 1H), 9.42 (s, 2H), 8.72 (d, 2H), 8.55 (s, 1H), 8.21 (d, 2H), 7.81 (s, 1H), 7.23 (s, 1H), 4.19 (t, 2H), 3.97 (s, 3H), 3.57 (m, 4H), 2.38 (m, 6H), 1.92 (m, 2H):

MS (−ve ESI): 472 (M−H)$^−$,

MS (+ve ESI): 474 (M+H)$^+$.

5-Amino-2-(4-pyridino)pyrimidine, used as starting material, was obtained as follows:

Following the literature procedure outlined in Arnold et al, *Coll. Czech. Chem. Comm.* 1975, 40, 1384, starting with 4-amidinopyridinium hydrochloride (173 mg, 1.10 mmol) yielded the title compound (79 mg, 46% yield) as an off-white solid:

MS (+ve ESI): 173 (M+H)$^+$.

EXAMPLE 233

Preparation of Compound 233 in Table 7

An analogous reaction to that described in example 232, but starting with 5-amino-2-(4-carboxamidophenyl)pyrimidine (129 mg, 0.60 mmol), yielded the title compound (40 mg, 8% yield) as an off-white solid:

$^1$H-NMR (DMSO-d$_6$): 9.41 (s, 2H), 8.84 (s, 1H), 8.54 (s, 1H), 8.42 (d, 2H), 8.06 (bs, 1H), 8.00 (d, 2H), 7.40 (m, 2H), 4.29 (d, 3H), 4.05 (s, 3H), 3.95 (m, 2H), 3.80 (m, 2H), 3.60–3.20 (m, 6H), 3.10 (m, 2H), 2.32 (m, 2H);

MS (−ve ESI): 514 (M−H)$^−$,

MS (+ve ESI): 516 (M+H)$^+$.

5-Amino-2-(4-carboxamidophenyl)pyrimidine, used as starting material, was obtained as follows: an analogous reaction to that described in example 232 for the synthesis of 5-amino-2-(4-pyridino)pyrimidine, but starting with 4-amidinobenzamide hydrochloride (219 mg, 1.10 mmol) yielded the title compound (133 mg, 62% yield) as an off-white solid:

MS (+ve ESI): 215 (M+H)$^+$.

EXAMPLE 234

Preparation of Compound 234 in Table 7

An analogous reaction to that described in example 232 but starting with 5-amino-2-((carboxybenzyl)aminomethyl) pyrimidine (133 mg, 0.51 mmol), yielded the title compound (154 mg, 54% yield) as an off-white solid:

$^1$H-NMR (DMSO-d$_6$): 9.70 (s, 1H), 9.01 (s, 2H), 8.46 (s, 1H), 7.77 (s, 1H), 7.72 (t, 1H), 7.36 (m, 4H), 7.21 (s, 1H), 5.05 (s, 2H), 4.39 (d, 2H), 4.18 (s, 2H), 3.96 (s, 3H), 3.55 (m, 6H), 3.10 (m, 2H), 2.38 (m, 6H), 1.85 (m, 2H):

MS (−ve ESI): 558 (M−H)$^−$,

MS (+ve ESI): 560 (M+H)$^+$.

5-Amino-2-((carboxybenzyl)aminomethyl)pyrimidine, used as starting material, was obtained in an analogous reaction to that described in example 232, but starting with carboxybenzyl-aminoacetamidine hydrochloride (267 mg, 1.10 mmol). This yielded the title compound (138 mg, 48% yield) as an off-white solid:

MS (+ve ESI): 259 (M+H)$^+$.

EXAMPLE 235

Preparation of Compound 235 in Table 7

To compound 4, prepared as described above (3.87 g, 6.92 mmol) in acetic acid (80 ml) was added 10% palladium on carbon (580 mg) and the mixture hydrogenated at atmospheric pressure for 18 hours. The reaction mixture was filtered through celite, evaporated, azeotroped with toluene and evaporated to dryness. Purification by filtration on silica gel, eluting with 10% methanol in dichloromethane containing 1% concentrated ammonia yielded the title compound (2.03 g, 69% yield) as a yellow powder after trituration with ether and ethyl acetate:

$^1$H-NMR (DMSO-d$_6$): 9.12 (s, 2H), 8.46 (s, 1H), 7.77 (s, 1H), 7.19 (s, 1H), 4.19 (t, 2H), 3.96 (s, 3H), 3.88 (s, 2H), 3.57 (m, 4H), 2.40 (m, 6H), 1.85 (m, 2H):

MS (+ve ESI): 426 (M+H)$^+$.

EXAMPLE 236

Preparation of Compound 236 in Table 7

4-(2-Carbaldehyde-5-aminopyrimidine)-6-methoxy-7-(3-morpholinopropoxy)quinazoline-di-trifluoroacetate (230 mg, 0.43 mmol) and 4-chloroaniline (30 mg, 0.23 mmol) were stirred together in methanol (4 ml) under an atmosphere of nitrogen for 5 minutes. Acetic acid (0.026 ml, 0.43 mmol) and sodium cyanoborohydride (30 mg, 0.43 mmol) were added and the reaction mixture stirred at room temperature for 3 hours. The reaction mixture was diluted with dichloromethane (10 ml) and loaded directly onto silica gel. Purification by flash chromatography on silica gel, eluting with 10% methanol in dichloromethane then increased polarity to 10% methanol, 1% ammonia in dichloromethane yielded the title compound (30 mg, 26% yield) as a white solid:

$^1$H-NMR (DMSO-d$_6$): 9.70 (s, 1H), 9.15 (s, 2H), 8.47 (s, 1H), 7.78 (s, 1H), 7.20 (s, 1H), 7.05 (d, 2H), 6.64 (d, 2H), 6.43 (t, 1H), 4.42 (d, 2H), 4.19 (t, 2H), 3.96 (s, 3H), 3.57 (m, 4H), 2.45 (m, 2H), 2.36 (m, 4H), 1.93 (m, 2H):

MS (+ve ESI): 536 (M+H)$^+$.

MS (−ve ESI): 534 (M−H)$^−$.

4-(2-Carbaldehyde-5-aminopyrimidine)-6-methoxy-7-(3-morpholinopropoxy)quinazoline, used as the starting material was obtained as follows:

a) To a solution of sodium methoxide (3.54 ml of a 25% wt. solution in methanol, 15.5 mmol) in methanol (80 ml) was added diethoxyacetonitrile (215 ml, 155 mmol) and the reaction mixture stirred for 4 hours at room temperature. Solid carbon dioxide was added and most of the methanol was removed in vacuo. Diethyl ether (30 ml) was added and the sodium carbonate removed by filtration. The residue was concentrated to afford methyl diethoxyacetimidate as a colourless oil (22 g, 92% yield) which was used with no further purification.

MS (+ve ESI): 162 (M+H)$^+$.

b) Ammonium chloride (7.3 g, 136 mmol) was added in one portion to a solution of methyl diethoxyacetimidate (22 g, 136 mmol) in methanol (25 ml) at room temperature and the resultant mixture stirred for 8 hours. The methanol was removed in vacuo and the resulting oil was cooled to −30° C. at which point a solid formed. Warming to ambient temperature followed by trituration with ether gave diethoxy-acetimidine hydrochloride as a cream solid (24.5 g, 98% yield):

¹H-NMR (DMSO-d₆): 9.11 (s, 4H), 5.32 (s, 1H), 3.60 (q, 4H), 1.21 (t, 6H):

MS (+ve ESI): 147 (M+H)⁺.

c) Diethoxy-acetamidine hydrochloride (12 g, 66 mmol) was reacted in an analogous procedure to that outlined in example 124 to yield 2-diethoxymethyl-5-(dimethylaminomethyleneamino)pyrimidine (13.5 g, 87% yield) as an orange oil:

¹H-NMR (DMSO-d₆): 8.42 (s, 2H), 7.95 (s, 1H), 5.40 (s, 1H), 3.65 (m, 2H), 3.51 (m, 2H), 3.05 (s, 3H), 2.95 (s, 3H), 1.21 (t, 6H).

d) 2-Diethoxymethyl-5-(dimethylaminomethyleneamino) pyrimidine (6.3 g, 25 mmol) and a 5% aqueous solution of potassium carbonate (69 ml) in dioxane (40 ml) were heated at reflux for 6 hours. The reaction mixture was concentrated to a yellow solid which was triturated with ether to 2-diethoxymethyl-5-aminopyrimidine as a cream solid (4.64 g, 92% yield):

¹H-NMR (DMSO-d₆): 8.01 (s, 2H), 5.61 (bs, 2H), 5.20 (s, 1H), 3.32–3.60 (m, 4H), 1.01 (t, 6H).

e) Sodium hydride (500 mg of a 60% suspension in mineral oil, 10 mmol) was added to a solution of with 4-chloro-6-methoxy-7-(3-morpholinopropoxy)quinazoline (2.02 g, 6.0 mmol) 2-diethyoxymethyl-5-aminopyrimidine (1.0 g, 5.0 mmol) in tetrahydrofuran (25 ml) and the reaction was heated at 70° C. for 2 hours. The reaction was cooled and excess sodium hydride quenched by the addition of methanol (1 ml) followed by concentration to dryness. The residue was dissolved in dichloromethane/methanol 20:1 (30 ml) and poured quickly through silica gel (20 g in a sinter funnel). Elution with dichloromethane/methanol 20:1 yielded 4-(2-diethoxymethyl-5-aminopyrimidine)-6-methoxy-7-(3-morpholinopropoxy)quinazoline after trituration with isohexane/ether (1:1) as an off-white solid (1.7 g, 70% yield):

¹H-NMR (DMSO-d₆): 9.80 (s, 1H), 9.21 (s, 2H), 8.53 (s, 1H), 7.82 (s, 1H), 7.20 (s, 1H), 5.44 (s, 1H), 4.20 (t, 2H), 3.95 (s, 3H), 3.62–3.81 (m, 4H), 3.60 (m, 4H), 2.42 (m, 6H), 1.98 (m, 2H), 1.21 (t, 6H):

MS (−ve ESI): 497 (M−H)⁻.

f) A solution of 4-(2-diethoxymethyl-5-aminopyrimidine)-6-methoxy-7-(3-morpholinopropoxy)quinazoline (1.63 g, 3.3 mmol) in trifluoroacetic acid (10 ml) was heated at 80° C. for 1 hour. The reaction mixture was cooled and diethyl ether (100 ml) was added very slowly with vigorous stirring. The resultant fine red solid was collected by filtration and dried in vacuo to yield 4-(2-carbaldehyde-5-aminopyrimidine)-6-methoxy-7-(3-morpholinopropoxy) quinazoline as the di-trifluoroacetate (1.9 g, 98% yield):

¹H-NMR (DMSO-d₆): 9.98 (s, 1H), 9.45 (s, 2H), 8.85 (s, 1H), 8.05 (s, 1H), 7.40 (s, 1H), 5.35 (m, 2H), 3.95 (s, 3H), 3.62–3.80 (m, 2H), 3.55–3.60 (m, 2H), 3.15–3.40 (m, 6H):

MS (+ve ESI): 425 (M+H)⁺.

EXAMPLE 237

Preparation of Compound 237 in Table 7

An analogous reaction to that described in example 236, but starting with 2-(methylthio)aniline (30 mg, 0.23 mmol), yielded the title compound (20 mg, 16% yield) as a white solid:

¹H-NMR (DMSO-d₆): 9.74 (s, 1H), 9.21 (s, 2H), 8.51 (s, 1H), 7.80 (s, 1H), 7.32 (m, 1H), 7.23 (s, 1H), 7.11 (m, 1H), 6.66 (m, 1H), 6.62 (m, 1H), 6.11 (t, 1H), 4.55 (d, 2H), 4.20 (t, 2H), 3.96 (s, 3H), 3.57 (m, 4H), 2.45 (m, 2H), 2.38 (m, 7H), 1.96 (m, 2H):

MS (+ve ESI): 548 (M+H)⁺.
MS (−ve ESI): 546 (M−H)⁻.

EXAMPLE 238

Preparation of Compound 238 in Table 7

An analogous reaction to that described in example 236, but starting with 2,3-difluoroaniline (30 mg, 0.23 mmol), yielded the title compound (11 mg, 9% yield) as a white solid:

¹H-NMR (DMSO-d₆): 9.72 (s, 1H), 9.18 (s, 2H), 8.48 (s, 1H), 7.79 (s, 1H), 7.22 (s, 1H), 6.89 (m, 1H), 6.52 (m, 2H), 6.35 (t, 1H), 4.54 (d, 2H), 4.20 (t, 2H), 3.96 (s, 3H), 3.56 (m, 4H), 2.43 (m, 2H), 2.36 (m, 4H), 1.95 (m, 2H):

MS (+ve ESI): 538 (M+H)⁺.
MS (−ve ESI): 536 (M−H)⁻.

EXAMPLE 239

Preparation of Compound 239 in Table 7

An analogous reaction to that described in example 236, but starting with 3-chloro-4-fluoroaniline (38 mg, 0.23 mmol), yielded the title compound (77 mg, 60% yield) as a white solid:

¹H-NMR (DMSO-d₆): 9.72 (s, 1H), 9.18 (s, 2H), 8.48 (s, 1H), 7.22 (s, 1H), 7.08 (t, 1H), 6.76 (m, 1H), 6.62 (m, 1H), 6.48 (m, 1H), 4.42 (d, 2H), 4.18 (t, 2H), 3.96 (s, 3H), 3.57 (m, 4H), 2.45 (m, 2H), 2.38 (m, 4H), 1.96 (m, 2H):

MS (+ve ESI): 554 (M+H)⁺.
MS (−ve ESI): 552 (M−H)⁻.

EXAMPLE 240

Preparation of Compound 240 in Table 7

To a solution of isovaleric acid (54 mg, 0.53 mmol) and O-(7-azabenzotriazol-1-yl)-N,N,N',N'-tetramethyluronium hexafluorophosphate (HATU) (570 mg, 0.75 mmol) in dimethylacetamide (5 ml), was added (4-(2-amino-5-(aminomethyl)pyrimidine)-6-methoxy-7-(3-morpholinopropoxy) quinazoline (212 mg, 0.5 mmol) and the reaction mixture stirred at ambient temperature for 18 hours. The reaction mixture was poured into an aqueous solution of potassium carbonate (10% solution) and extracted with dichloromethane/methanol (20:1). The organics were dried over magnesium sulphate and concentrated to an oil. Trituration with ether yielded the title compound (162 mg, 40% yield) as the dihexafluorophosphate salt:

¹H-NMR (DMSO-d₆): 9.67 (s, 1H), 9.11 (s, 2H), 8.48 (s, 1H), 8.28 (t, 1H), 7.78 (s, 1H), 7.20 (s, 1H), 4.42 (d, 2H), 4.18 (t, 2H), 3.95 (s, 3H), 3.56 (m, 4H), 2.43 (m, 2H), 2.35 (m, 4H), 2.00 (m, 5H), 0.89 (d, 6H):

MS (+ve ESI): 510 (M+H)⁺.
MS (−ve ESI): 508 (M−H)⁻.

EXAMPLE 241

Preparation of Compound 241 in Table 7

An analogous reaction to that described in example 240, but starting with 4-chlorobenzoic acid (83 mg, 0.53 mmol), yielded the title compound (168 mg, 39% yield) as the dihexafluorophosphate salt:

¹H-NMR (DMSO-d₆): 9.70 (s, 1H), 9.12 (s, 2H), 8.46 (s, 1H), 7.93 (d, 2H), 7.78 (s, 1H), 7.55 (d, 2H), 7.20 (s, 1H), 4.66 (d, 2H), 4.17 (t, 2H), 3.95 (s, 3H), 3.55 (m, 4H), 2.43 (m, 2H), 2.35 (m, 4H), 1.93 (m, 2H):
MS (+ve ESI): 564 (M+H)$^+$.
MS (−ve ESI): 562 (M−H)$^-$.

EXAMPLE 242

Preparation of Compound 242 in Table 7

An analogous reaction to that described in example 240, but starting with 4-chlorophenylacetic acid (91 mg, 0.53 mmol), yielded the title compound (211 mg, 48% yield) as the dihexafluorophosphate salt:
$^1$H-NMR (DMSO-d$_6$): 9.70 (s, 1H), 9.13 (s, 2H), 8.61 (s, 1H), 8.48 (s, 1H), 7.78 (s, 1H), 7.33 (m, 4H), 7.20 (s, 1H), 4.47 (d, 2H), 4.18 (t, 2H), 3.95 (s, 3H), 3.55 (m, 4H), 3.50 (s, 2H), 2.43 (m, 2H), 2.36 (m, 4H), 1.93 (m, 2H):
MS (+ve ESI): 578 (M+H)$^+$.
MS (−ve ESI): 576 (M−H)$^-$.

EXAMPLE 243

Preparation of Compound 243 in Table 7

An analogous reaction to that described in example 240, but starting with 3-(4-chlorophenyl)propanoic acid (98 mg, 0.53 mmol), yielded the title compound (225 mg, 51% yield) as the dihexafluorophosphate salt:
$^1$H-NMR (DMSO-d$_6$): 9.70 (s, 1H), 9.13 (s, 2H), 8.48 (s, 1H), 8.39 (t, 3H), 7.78 (s, 1H), 7.27 (m, 4H), 7.20 (s, 1H), 4.45 (d, 2H), 4.18 (t, 2H), 3.95 (s, 3H), 3.55 (m, 4H), 2.85 (t, 2H), 2.44 (m, 2H), 2.36 (m, 4H), 1.93 (m, 2H):
MS (+ve ESI): 592 (M+H)$^+$.
MS (−ve ESI): 590 (M−H)$^-$.

EXAMPLE 244

Preparation of Compound 244 in Table 7

An analogous reaction to that described in example 236, but starting with isopentylamine (20 mg, 0.23 mmol), yielded the title compound (5 mg, 4% yield) as a white solid:
$^1$H-NMR (DMSO-d$_6$): 9.73 (s, 1H), 9.17 (s, 2H), 8.50 (s, 1H), 7.81 (s, 1H), 7.74 (t, 1H), 7.21 (s, 1H), 4.19 (t, 1H), 3.97 (s, 3H), 3.88 (s, 2H), 3.57 (m, 4H), 2.58 (t, 2H), 2.47 (m, 2H), 2.37 (m, 4H), 1.94 (m, 2H), 1.62 (m, 1H), 1.36 (m, 2H), 0.86 (d, 6H):
MS (+ve ESI): 496 (M+H)$^+$.
MS (−ve ESI): 494 (M−H)$^-$.

EXAMPLE 245

Preparation of Compound 245 in Table 7

An analogous reaction to that described in example 236, but starting with 2-(1-cyclohexenyl)ethylamine (29 mg, 0.23 mmol), yielded the title compound (18 mg, 15% yield) as a white solid:
$^1$H-NMR (DMSO-d$_6$): 9.73 (s, 1H), 9.17 (s, 2H), 8.48 (s, 1H), 7.81 (s, 1H), 7.22 (s, 1H), 5.39 (s, 1H), 4.19 (t, 1H), 3.97 (s, 3H), 3.88 (s, 2H), 3.57 (m, 4H), 2.63 (m, 2H), 2.45 (m, 2H), 2.37 (m, 4H), 2.08 (m, 2H), 1.94 (m, 4H), 1.88 (m, 2H), 1.52 (m, 4H):
MS (+ve ESI): 534 (M+H)$^+$.
MS (−ve ESI): 532 (M−H)$^-$.

EXAMPLE 246

Preparation of Compound 246 in Table 7

An analogous reaction to that described in example 236, but starting with 2-bromo-5-nitropyridine (51 mg, 0.25 mmol) yielded the title compound (11 mg, 8% yield) as a white solid, after purification by flash chromatography on silica gel, eluting with 20% methanol in dichloromethane:
$^1$H-NMR (DMSO-d$_6$): 9.73 (s, 1H), 9.16 (s, 2H), 8.88 (s, 1H), 8.66 (s, 1H), 8.48 (s, 1H), 8.13 (m, 1H), 7.80 (s, 1H), 7.21 (s, 1H), 6.76 (m, 1H), 4.83 (m, 2H), 4.20 (t, 2H), 3.96 (s, 3H), 3.56 (m, 4H), 2.46 (m, 2H), 2.35 (m, 4H), 1.93 (m, 2H):
MS (+ve ESI): 548 (M+H)$^+$.
MS (−ve ESI): 546 (M−H)$^-$.

EXAMPLE 247

Preparation of Compound 247 in Table 7

An analogous reaction to that described in example 246, but starting with 2-chloro-3-nitropyridine (36 mg, 0.25 mmol), yielded the title compound (8 mg, 6% yield) as a white solid:
$^1$H-NMR (DMSO-d$_6$): 10.13 (s, 1H), 9.50 (bs, 1H), 9.20 (m, 3H), 8.60 (s, 1H); 8.50 (m, 2H); 7.90 (s, 1H), 7.31 (s, 1H), 6.81 (m, 1H), 5.03 (d, 2H), 4.30 (t, 2H), 4.00 (m, 5H), 3.45 (m, 6H), 3.13 (m, 2H), 2.23 (m, 2H):
MS (+ve ESI): 548 (M+H)$^+$.
MS (−ve ESI): 546 (M−H)$^-$.

EXAMPLE 248

Preparation of Compound 248 in Table 7

An analogous reaction to that described in example 236, but starting with 3,4-difluoroaniline (32 mg, 0.23 mmol), yielded the title compound (63 mg, 51% yield) as a white solid:
$^1$H-NMR (DMSO-d$_6$): 9.81 (s, 1H), 9.20 (s, 2H), 8.45 (s, 1H), 7.82 (s, 1H), 7.20 (s, 1H), 7.10 (q, 1H), 6.62 (m, 1H), 6.41 (m, 1H), 4.40 (d, 2H), 4.23 (t, 2H), 3.95 (s, 3H), 3.62 (m, 4H), 2.40–2.60 (m, 6H), 1.98–2.01 (m, 2H):
MS (+ve ESI): 538 (M+H)$^+$.

EXAMPLE 249

Preparation of Compound 249 in Table 7

An analogous reaction to that described in example 236, but starting with 2,4-difluoroaniline (32 mg, 0.23 mmol), yielded the title compound (55 mg, 44% yield) as a white solid:
$^1$H-NMR (DMSO-d$_6$): 9.78 (s, 1H), 9.20 (s, 2H), 8.45 (s, 1H), 7.82 (s, 1H), 7.20 (s, 1H), 7.10 (q, 1H), 6.62–6.83 (m, 2H), 5.80 (m, 1H), 4.50 (d, 2H), 4.23 (t, 2H), 3.95 (s, 3H), 3.62 (m, 4H), 2.40–2.60 (m, 6H), 1.98–2.01 (m, 2H):
MS (+ve ESI): 538 (M+H)$^+$.

EXAMPLE 250

Preparation of Compound 250 in Table 7

An analogous reaction to that described in example 236, but starting with 4-fluoroaniline (26 mg, 0.23 mmol), yielded the title compound (63 mg, 53% yield) as a white solid:
$^1$H-NMR (DMSO-$d_6$): 9.78 (s, 1H), 9.20 (m, 2H), 8.45 (s, 1H), 7.82 (s, 1H), 7.20 (s, 1H), 6.90 (t, 2H), 6.62 (m, 2H), 6.10 (m, 1H), 4.40 (d, 2H), 4.23 (t, 2H), 3.95 (s, 3H), 3.62 (m, 4H), 2.40–2.60 (m, 6H), 1.98–2.01 (m, 2H):
MS (+ve ESI): 520 (M+H)$^+$.

EXAMPLE 251

Preparation of Compound 251 in Table 7

An analogous reaction to that described in example 236, but starting with 2-chloro-4-fluoroaniline (34 mg, 0.23 mmol), yielded the title compound (57 mg, 45% yield) as a white solid:
$^1$H-NMR (DMSO-$d_6$): 9.78 (s, 1H), 9.20 (s, 2H), 8.45 (s, 1H), 7.82 (s, 1H), 7.25 (m, 1H), 7.20 (s, 1H), 7.00 (m, 1H), 6.75 (m, 1H), 5.90 (m, 1H), 4.50 (d, 2H), 4.23 (t, 2H), 3.95 (s, 3H), 3.62 (m, 4H), 2.40–2.60 (m, 6H), 1.98–2.01 (m, 2H):
MS (+ve ESI): 554 (M+H)$^+$.

EXAMPLE 252

Preparation of Compound 252 in Table 8

An analogous reaction to that described in example 236, but starting with 4-(2-carbaldehyde-5-aminopyrimidine)-6-methoxy-7-(3-benzyloxy)quinazoline di-trifluoroacetate (876 mg, 1.75 mmol), 3-chloro-4-fluoroaniline (1.27 g, 8.75 mmol) and sodium cyanoborohydride (110 mg, 3.5 mmol), yielded the title compound (955 mg, 90% yield) as an off-white solid:
$^1$H-NMR (DMSO-$d_6$): 9.70 (s, 1H), 9.20 (s, 2H), 8.50 (s, 1H), 7.82 (s, 1H), 7.30–7.55 (m, 6H), 7.00–7.10 (t, 1H), 6.80 (m, 1H), 6.61 (m, 1H), 6.45 (t, 1H), 5.32 (s, 2H), 4.45 (d, 2H), 3.95 (s, 3H):
MS (+ve ESI): 517 (M+H)$^+$.

4-(2-Carbaldehyde-5-aminopyrimidine)-6-methoxy-7-(3-benzyloxy)quinazoline di-trifluoroacetate, used as starting material was obtained in an analogous set of reactions to example 236e, (but utilising 4-chloro-6-methoxy-7-(3-benzyloxy)quinazoline (18.93 g, 63 mmol)) yielding the title compound (22.08 g, 80% yield) as a light brown solid as a hydrochloride salt:
$^1$H-NMR (DMSO-$d_6$): 10.00 (1H, s), 9.75 (s, 2H), 8.80 (s, 1H), 8.50 (bs, 1H), 7.44–7.62 (m, 7H), 5.31 (s, 2H), 4.05 (s, 3H):
MS (+ve ESI): 387 (M+H)$^+$.

EXAMPLE 253

Preparation of Compound 253 in Table 8

An analogous reaction to that described in example 13, but starting with 4-(5-amino-2-N-(3-chloro-4-fluorophenyl)pyrimidinemethanamine)-6-methoxy-7-(3-benzyloxy)quinazoline (400 mg, 0.76 mmol), yielded the title compound (301 mg, 93% yield) as an off-white solid:
$^1$H-NMR (DMSO-$d_6$): 9.80 (s, 1H), 9.18 (s, 2H), 8.40 (s, 1H), 7.82 (s, 1H), 7.00–7.10 (m, 2H), 6.80 (m, 1H), 6.61 (m, 1H), 6.45 (m, 1H), 4.40 (s, 2H), 3.95 (s, 3H):
MS (–ve ESI): 427 (M+H)$^+$.

EXAMPLE 254

Preparation of Compound 254 in Table 8

An analogous reaction to that described in example 229, but starting with 4-(5-amino-2-N-(3-chloro-4-fluorophenyl)pyrimidinemethanamine)-6-methoxy-7-((2S)-oxiranylmethoxy)quinazoline (100 mg, 0.21 mmol) and piperidine (0.1 ml 1.05 mmol), yielded the title compound (12 mg, 10% yield) as an off-white solid:
$^1$H-NMR (DMSO-$d_6$): 9.05 (s, 2H), 8.30 (s, 1H), 7.82 (s, 1H), 7.00–7.10 (m, 3H), 6.80 (m, 1H), 6.61 (m, 1H), 6.45 (m, 1H), 4.40 (d, 2H), 4.05 (m, 1H), 4.00 (m, 2H), 3.90 (s, 3H), 2.30–2.42 (m, 6H), 1.30–1.55 (m, 6H):
MS (+ve ESI): 567 (M+H)$^+$.

4-(5-amino-2-N-(3-chloro-4-fluorophenyl)pyrimidinemethanamine)-6-methoxy-7-((2S)-oxiranylmethoxy)quinazoline used as starting material was obtained in an analogous reaction to that described in example 14, but starting with 4-(5-amino-2-N-(3-chloro-4-fluorophenyl)pyrimidinemethanamine)-6-methoxy-7-(3-hydroxy)quinazoline (150 mg, 0.35 mmol) and (2S)-(+)-glycidyl tosylate (88 mg, 0.38 mmol) yielding the title compound (149 mg, 88% yield) as a pale green solid:
$^1$H-NMR (DMSO-$d_6$): 8.80 (s, 2H), 7.95 (s, 1H), 7.65 (s, 1H), 7.05 (t, 1H), 6.80 (m, 1H), 6.65 (m, 1H), 6.25 (m, 1H), 4.39 (m, 1H), 4.21 (d, 2H), 3.90 (m, 1H), 3.80 (s, 3H), 2.81 (m, 1H), 2.75 (m, 1H):
MS (+ve ESI): 488 (M+H)$^+$.
MS (–ve ESI): 481 (M–H)$^-$.

EXAMPLE 255

Preparation of Compound 255 in Table 8

A solution of 5-amino-2-[(4-fluoro-3-chlorophenyl)methoxy]-pyrimidine (76 mg, 0.3 mmol), 4-chloro-6-methoxy-7-(3-morpholinopropoxy)quinazoline (95 mg, 0.28 mmol) and a 4.0 N solution of hydrogen chloride in dioxane (80 ul, 0.32 mmol), in isopropanol (3 ml) was heated at reflux for 4 hours before the reaction was allowed to cool to ambient temperature. The isopropanol was removed in vacuo and the resultant slurry was dissolved in a saturated ammonia solution and extracted with ethyl acetetate (3×10 ml), dried (magnesium sulphate) and concentrated to dryness. Recrystallisation from acetonitrile afforded the title compound (56 mg, 36% yield) as an off-white solid:
$^1$H-NMR (DMSO-$d_6$): 9.60 (s, 1H), 8.93 (s, 2H), 8.41 (s, 1H), 7.76 (s, 1H), 7.70 (dd, 1H), 7.50 (m, 1H), 7.43 (t, 1H), 7.18 (s, 1H), 5.37 (s, 2H), 4.17 (t, 2H), 3.94 (s, 3H), 3.57 (t, 4H), 2.44 (t, 2H), 2.36 (t, 4H), 1.94 (m, 2H):
MS (+ve ESI): 555.5 (M+H)$^+$.

5-Amino-2-[(4-fluoro-3-chlorophenyl)methoxy]-pyrimidine used as the starting material above was obtained as follows:
a) Sodium hydride (60% dispersion in oil-50 mg, 1.25 mmol) was added to a solution of 3-chloro-4-fluorobenzyl alcohol (177 mg, 1.1 mmol) in tetrahydrofuran (5 ml) under an atmosphere of nitrogen. After 10 minutes, 2-chloro-5-nitropyrimidine (159 mg, 1 mmol) was added and the reaction heated at reflux for 2 hours before quenching by the addition of methanol (1 ml). Purification by flash chromatography on silica gel, eluting with 12% ethyl acetate in isohexane yielded the title compound (86 mg, 30% yield):
$^1$H-NMR (CDCl$_3$): 9.33 (s, 2H), 7.57 (dd, 1H), 7.38 (m, 1H), 7.16 (t, 1H), 5.51 (s, 2H).

b) An analogous reaction to that described in example 2 (part d), starting with 5-nitro-2-[(4-fluoro-3-chlorophenyl) methoxy]-pyrimidine (86 mg, 0.3 mmol) afforded the title compound (76 mg, 0.3 mmol) which was used without further purification.

EXAMPLE 256

Preparation of Compound 256 in Table 9

An analogous reaction to that described in example 255, but starting with 4-chloro-7-methoxy-6-(3-(4-morpholinyl) propoxy)quinazoline (100 mg, 0.30 mmol) and 5-amino-2-(N-4-fluoro-3-chlorobenzamide)pyrimidine (100 mg, 0.38 mmol). On completion, the reaction was cooled, the solid collected by suction filtration and washed with diethyl ether to yield the title compound (153 mg, 80% yield) as an off-white dihydrochloride salt:
$^1$H-NMR (DMSO-d$_6$+CD$_3$COOD): 9.16 (s, 2H), 8.73 (s, 1H), 8.39 (s, 1H), 8.17 (dd, 1H, J=8,2 Hz), 7.96–8.00 (m, 1H), 7.43 (t, 1H, J=8 Hz), 7.37 (s, 1H), 4.43 (t, 2H, J=8 Hz), 4.01 (s, 3H), 3.92 (m, 4H), 3.29–3.41 (m, 6H), 2.30–2.39 (m, 2H):
MS (–ve ESI): 566 (M–H)$^-$.

4-Chloro-7-methoxy-6-(3-(4-morpholinyl)propoxy)-quinazoline used as the starting material, was obtained according to the following procedure outlined in patent WO 9742187 A1.

5-Amino-2-(N-4-fluoro-3-chlorobenzamide)pyrimidine used as the starting material was obtained as follows:

a) A mixture of 2-amino-5-nitropyrimidine (1.00 g, 7.14 mmol) and 4-fluoro-3-chlorobenzoyl chloride (1.52 g, 7.88 mmol) was heated in pyridine (40 ml) at reflux for 7 hours under an inert atmosphere. The reaction was allowed to cool to ambient temperature and poured into water (400 ml). The reaction mixture was extracted with dichloromethane (3×300 ml), dried (magnesium sulphate) and concentrated to dryness. Purification by flash chromatography on silica gel, eluting with 2% methanol in dichloromethane yielded 5-nitro-2-(N-4-fluoro-3-chlorobenzamide)pyrimidine (970 mg, 65% yield):
$^1$H-NMR (DMSO-d$_6$): 9.45 (s, 2H), 8.20 (m, 1H), 8.05 (m, 1H), 7.60 (t, 1H):
MS (–ve ESI): 295 (M–H)$^-$.

b) An analogous reaction to that described in example 2 (part d), starting with 5-nitro-2-(N-4-fluoro-3-chlorobenzamide)pyrimidine (743 mg, 2.51 mmol). Purification by flash chromatography on silica gel, eluting with ethyl acetate afforded the title compound (413 mg, 62% yield) as a yellow solid:
$^1$H-NMR (DMSO-d$_6$): 8.20 (m, 1H), 8.10 (s, 2H), 7.05 (m, 1H), 7.60 (t, 1H), 5.45 (s, 2H):
MS (–ve ESI): 265 (M–H)$^-$.

EXAMPLE 257

Preparation of Compound 257 in Table 9

An analogous reaction to that described in example 232, but starting with 4-chloro-7-fluoro-6-nitro-quinazoline (610 mg, 2.67 mmol) and 5-amino-2-(N-4-fluoro-3-chlorobenzamide)pyrimidine (750 mg, 2.81 mmol) at ambient temperature. Isohexane (20 ml) was added and the solid collected by suction filtration, dissolved in methanol and a saturated solution of sodium bicarbonate added. The resultant solid was collected by suction filtration, washed with water and dried to yield 4-(5-amino-2-(N-4-fluoro-3-chlorobenzamide)pyrimidine)-7-fluoro-6-nitro-quinazoline (900 mg, 73% yield) as a brown solid:
$^1$H-NMR (DMSO-d$_6$): 8.95 (d, 2H, J=9 Hz), 8.71 (s, 2H), 8.14–8.21 (m, 1H), 7.94–8.03 (m, 1H), 7.99 (s, 1H), 7.54 (t, 1H, J=9 Hz), 7.06 (d, 1H, J=14 Hz):
MS (+ve ESI): 458 (M–H)$^+$.

4-Chloro-7-fluoro-6-nitro-quinazoline used as starting material was obtained according to patent EP 635498 A1.

EXAMPLE 258

Preparation of Compound 258 in Table 9

Sodium (45 mg, 1.96 mmol) was added to a solution of benzyl alcohol (0.226 ml, 2.18 mmol) in tetrahydrofuran (5 ml) at ambient temperature under an atmosphere of nitrogen. The resultant suspension was stirred for 3 hours before being added via cannula to a solution of 4-(5-amino-2-(N-4-fluoro-3-chlorobenzamide)pyrimidine)-7-fluoro-6-nitro-quinazoline (100 mg, 0.218 mmol) in tetrahydrofuran (5 ml) at –10° C. The deep red solution was stirred for 30 minutes at this temperature and allowed to warm to ambient temperature over 48 hours. The reaction mixture was poured into water (10 ml), acidified with a 1N solution of hydrochloric acid and the solid collected by filtration and purified by preparative LCMS to yield the title compound (8 mg, 7% yield):
$^1$H-NMR (DMSO-d$_6$): 11.16 (s, 1H), 9.10 (s, 1H), 9.05 (s, 2H), 8.62 (s, 1H), 8.20 (d, 1H), 7.94–8.03 (m, 1H), 7.33–7.60 (m, 7H), 5.42 (s, 2H):
MS (+ve ESI): 546.5 (M–H)$^+$.

EXAMPLE 259

Preparation of Compound 259 in Table 9

An analogous reaction to that described in example 258, but starting with 1-methyl-4-piperidinemethanol (282 mg, 2.18 mmol). Purification by flash chromatography on silica gel, eluting with 10% methanol in dichloromethane then increased polarity to 10% methanol in dichloromethane containing 5% conc. ammonia yielded the title compound (13 mg, 10% yield) as a yellow solid:
$^1$H-NMR (DMSO-d$_6$): 9.10 (s, 1H), 9.05 (s, 2H), 8.62 (s, 1H), 8.20 (d, 1H), 8.02 (m, 1H), 7.60 (t, 1H), 7.43 (s, 1H), 4.15 (d, 2H), 2.79 (d, 2H), 1.90 (t, 2H), 1.65 (m, 3H), 1.38 (m, 2H):
MS (+ve ESI): 567 (M–H)$^+$.

1-Methyl-4-piperdinemethanol used as starting material was obtained as follows:

a) A solution of 2N hydrochloric acid in dioxane (2.8 ml, 11.13 mmol) was added to 1-methyl-4-piperdine carboxylic acid (20 g, 111.33 mmol) and the mixture heated at reflux for 18 hours. The reaction was concentrated to dryness and the resultant solid dissolved in dichloromethane and washed with a saturated solution of sodium bicarbonate, dried (magnesium sulphate) and concentrated to afford 1-methyl-4-piperdine carboxylic acid ethyl ester as a white solid (9.52 g, 50% yield).

b) 1-Methyl-4-piperdine carboxylic acid ethyl ester (8.95 g, 53 mmol) was dissolved in ether (100 ml) and a 1N solution of lithium aluminium hydride in tetrahydrofuran (57 ml, 57.5 mmol) added at 0° C. and the reaction mixture allowed to warm to ambient temperature and stirred for 3 hours. Water (2 ml), 2N sodium hydroxide (4 ml) and a further portion of water (2 ml) was added and the precipitate collected by suction filtration. The filtrate was evaporated to afford the title compound (4.6 g, 68% yield) as a colourless oil:

$^1$H-NMR (DMSO-d$_6$): 4.39 (t, 1H), 3.20 (t, 2H), 2.65–2.80 (m, 2H), 2.10 (s, 3H), 1.65–1.80 (m, 2H), 1.55–1.60 (m, 2H), 1.00–1.20 (m, 2H):

MS (+ve ESI): 132 (M–H)$^+$.

EXAMPLE 260

Preparation of Compound 260 in Table 9

An analogous reaction to that described in example 2 (part d), starting with 4-(5-amino-2-(N-4-fluoro-3-chlorobenzamide)pyrimidine)-7-fluoro-6-nitro-quinazoline (50 mg, 0.109 mmol). Purification by flash chromatography on silica gel, eluting with 5% methanol in dichloromethane afforded the title compound (15 mg, 33% yield):

$^1$H-NMR (DMSO-d$_6$): 11.10 (s, 1H), 9.05 (s, 2H), 8.40 (s, 1H), 8.10 (m, 1H), 8.05 (m, 1H), 7.41–7.60 (m, 3H), 5.80 (s, 2H):

MS (+ve ESI): 428 (M–H)$^+$.

EXAMPLE 261

Preparation of Compound 261 in Table 9

An analogous reaction to that described in example 255, but starting with 4-chloro-6,7-bis(2-methoxyethoxy)-quinazoline (80 mg, 0.26 mmol) and 5-amino-2-(N-4-fluoro-3-chlorobenzamide)pyrimidine (76 mg, 0.26 mmol). On completion, the reaction was cooled, the solid collected by suction filtration and washed with ether to yield the title compound (74 mg, 46% yield) as an off-white dihydrochloride salt:

$^1$H-NMR (DMSO-d$_6$): 11.63 (s, 1H), 11.27 (s, 1H), 9.09 (s, 2H), 8.84 (s, 1H), 8.39 (s, 1H), 8.20 (dd, 1H, J=8, 2 Hz), 7.96–8.03 (m, 1H), 7.56 (t, 1H, J=8 Hz), 7.36 (s, 1H), 4.31–4.40 (m, 4H), 3.75–3.80 (m, 2H), 3.35 (s, 6H):

MS (+ve ESI): 543 (M+H)$^+$.

MS (–ve ESI): 541 (M–H)$^-$.

4-Chloro-6,7-bis(2-methoxyethoxy)-quinazoline used as the starting material was obtained according to the procedure outlined in patent: WO 9615118 A1.

EXAMPLE 262

Preparation of Compound 262 in Table 9

An analogous reaction to that described in example 2 (part d), starting with 4-(5-amino-2-(N-4-fluoro-3-chlorobenzamide)pyrimidine)-7-(1-methyl-4-piperdinemethoxy)-6-nitro-quinazoline (15 mg, 0.026 mmol), afforded the title compound (8 mg, 56% yield):

$^1$H-NMR (DMSO-d$_6$): 11.08 (s, 1H), 9.05 (s, 2H), 8.65 (s, 1H), 8.40 (s, 1H), 8.34 (s, 1H), 8.20 (d, 1H), 8.00 (m, 1H), 7.85 (s, 1H), 7.58 (m, 1H), 7.05 (s, 1H), 4.00 (m, 2H), 2.74 (m, 1H), 2.05 (s, 3H), 1.70–1.95 (m, 4H), 1.05–1.40 (m, 4H):

MS (+ve ESI): 553 (M–H)$^+$.

EXAMPLE 263

Preparation of Compound 263 in Table 10

An analogous reaction to that described in example 125, but starting with 4-((3-amino-6-pyridine)amino)-6,7-dimethoxyquinazoline (100 mg, 0.336 mmol) and benzoic acid (45 mg, 0.37 mmol), yielded the title compound (70 mg, 51% yield) as an off-white solid, after purification by flash chromatography on silica gel, eluting with 2% methanol in dichloromethane:

$^1$H-NMR (DMSO-d$_6$): 10.66 (s, 1H), 9.00 (d, 1H), 8.89 (s, 1H), 8.39 (s, 1H), 8.33 (dd, 1H), 8.17 (d, 1H), 8.01 (d, 2H), 7.59 (m, 3H), 7.40 (s, 1H), 4.01 (s, 3H), 3.99 (s, 3H):

MS (–ve ESI): 400 (M–H)$^-$,

MS (+ve ESI): 402 (M+H)$^+$.

4-((3-amino-6-pyridine)amino)-6,7-dimethoxyquinazoline, used as the starting material, was obtained as follows:

a) Sodium hydride (2.40 g of a 60% suspension in mineral oil, 60.0 mmol) was added to a solution of 4-chloro-6,7-dimethoxyquinazoline (4.48 g, 20.0 mmol) and 2-amino-5-nitropyridine (3.33 g, 24.0 mmol) in dimethylformamide (100 ml) and the reaction was heated at 70° C. for 16 hours. The reaction was cooled, poured into water (100 ml) and the pH was adjusted to neutrality. Collection of the resultant solid by suction filtration yielded the title compound (3.7 g, 57% yield) as a white solid:

MS (–ve ESI): 326 (M–H)$^-$,

MS (+ve ESI): 328 (M+H)$^+$.

b) 10% Platinum on carbon (50 mg, 0.026 mmol) was added to a solution of 4-((3-nitro-6-pyridine)amino)-6,7-dimethoxyquinazoline (3.5 g, 10.7 mmol) in ethanol (100 ml) at ambient temperature and the reaction stirred for 16 hours under an atmosphere of hydrogen (2 mbar). Filtration of the reaction through a pad of celite and solvent evaporation in vacuo yielded 4-((3-amino-6-pyridine)amino)-6,7-dimethoxyquinazoline (2.91 g, 91% yield) as white solid:

$^1$H-NMR (DMSO-d$_6$): 8.68 (s, 1H), 8.31 (s, 1H), 7.83 (d, 1H, J=8 Hz), 7.81 (s, 1H), 7.33 (s, 1H), 7.17 (d, 1H, J=8 Hz), 3.95 (s, 3H), 3.93 (s, 3H):

MS (+ve ESI): 298 (M+H)$^+$.

EXAMPLE 264

Preparation of Compound 264 in Table 10

An analogous reaction to that described in example 263, but starting with 5-methyl-2-pyrazinecarboxlic acid (51 mg, 0.37 mmol), yielded the title compound (32 mg, 23% yield) as an off-white solid:

$^1$H-NMR (DMSO-d$_6$): 10.87 (s, 1H), 10.25 (s, 1H), 9.18 (s, 1H), 8.95 (d, 1H), 8.70 (s, 1H), 8.57 (s, 1H), 8.42 (d, 1H), 8.25 (dd, 1H), 8.02 (s, 1H), 7.20 (s, 1H), 3.97 (s, 3H), 3.92 (s, 3H), 2.63 (s, 3H):

MS (+ve ESI): 418 (M+H)$^+$.

EXAMPLE 265

Preparation of Compound 265 in Table 10

An analogous reaction to that described in example 127, but starting with 4-((3-amino-6-pyridine)amino)-6,7-dimethoxyquinazoline (100 mg, 0.34 mmol) and picolinic acid (46 mg, 0.37 mmol), yielded the title compound (63 mg, 34% yield) as an off-white solid, after purification by flash chromatography on silica gel, eluting with 2% methanol in dichloromethane:

$^1$H-NMR (DMSO-d$_6$): 11.05 (s, 1H), 9.11 (d, 1H), 8.87 (s, 1H), 8.75 (m, 1H), 8.44 (m, 2H), 8.18 (m, 2H), 8.09 (t, 1H), 7.70 (m, 1H), 7.40 (s, 1H), 4.01 (s, 3H), 3.99 (s, 3H):

MS (+ve ESI): 403 (M+H)$^+$.

EXAMPLE 266

Preparation of Compound 266 in Table 10

An analogous reaction to that described in example 265, but starting with quinaldic acid (64 mg, 0.37 mmol), yielded the title compound (20 mg, 10% yield) as an off-white solid:

$^1$H-NMR (DMSO-d$_6$): 10.94 (s, 1H), 10.27 (s, 1H), 9.00 (d, 1H), 8.63 (d, 1H), 8.57 (s, 1H), 8.47 (d, 1H), 8.36 (dd, 1H), 8.25 (d, 2H), 8.12 (d, 1H), 8.06 (s, 1H), 7.90 (t, 1H), 7.76 (t, 1H), 7.20 (s, 1H), 3.96 (s, 3H), 3.93 (s, 3H):

MS (+ve ESI): 453 (M+H)$^+$.

EXAMPLE 267

Preparation of Compound 267 in Table 10

An analogous reaction to that described in example 265, but starting with 2-chloro-5-nitrobenzoic acid (75 mg, 0.37 mmol), yielded the title compound (4 mg, 2% yield) as an off-white solid:

$^1$H-NMR (DMSO-d$_6$): 8.70 (s, 1H), 8.60 (m, 3H), 8.25 (m, 3H), 8.08 (d, 1H), 7.65 (d, 1H), 7.2 (s, 1H), 7.20 (s, 1H), 4.05 (s, 3H), 4.01 (s, 3H):

MS (−ve ESI): 479 (M−H)$^−$,
MS (+ve ESI): 481 (M+H)$^+$.

EXAMPLE 268

Preparation of Compound 268 in Table 10

An analogous reaction to that described in example 263, but starting with 3-methoxy-2-nitrobenzoic acid (73 mg, 0.37 mmol), yielded the title compound (32 mg, 20% yield) as an off-white solid:

$^1$H-NMR (DMSO-d$_6$): 10.81 (s, 1H), 10.27 (s, 1H), 8.75 (d, 1H), 8.58 (s, 1H), 8.42 (d, 1H), 8.4 (s, 1H), 7.73 (t, 1H), 7.55 (m, 3H), 7.2 (s, 1H), 3.97 (s, 3H), 3.95 (s, 3H):

MS (−ve ESI): 475 (M−H)$^−$,
MS (+ve ESI): 477 (M+H)$^+$.

EXAMPLE 269

Preparation of Compound 269 in Table 10

An analogous reaction to that described in example 263, but starting with 2,4-dinitrobenzoic acid (79 mg, 0.37 mmol), yielded the title compound (13 mg, 8% yield) as an off-white solid:

$^1$H-NMR (DMSO-d$_6$): 11.04 (s, 1H), 10.3 (s, 1H), 8.83 (d, 1H), 8.75 (d, 1H), 8.65 (dd, 1H), 8.57 (s, 1H), 8.48 (d, 1H), 8.15 (d, 1H), 8.05 (s, 1H), 8.0 (dd, 1H), 7.2 (s, 1H), 3.98 (s, 3H), 3.95 (s, 3H):

MS (−ve ESI): 490 (M−H)$^−$,
MS (+ve ESI): 492 (M+H)$^+$.

EXAMPLE 270

Preparation of Compound 270 in Table 10

An analogous reaction to that described in example 263, but starting with 2-(methylthio)benzoic acid (62 mg, 0.37 mmol), yielded the title compound (41 mg, 27% yield) as an off-white solid:

$^1$H-NMR (DMSO-d$_6$): 10.46 (s, 1H), 10.25 (s, 1H), 8.80 (s, 1H), 8.55 (s, 1H), 8.40 (d, 1H), 8.05 (m, 2H), 7.50 (m, 3H), 7.28 (t, 1H), 7.20 (s, 1H), 3.98 (s, 3H), 3.95 (s, 3H), 2.43 (s, 3H):

MS (−ve ESI): 446 (M−H)$^−$,
MS (+ve ESI): 448 (M+H)$^+$.

EXAMPLE 271

Preparation of Compound 271 in Table 10

An analogous reaction to that described in example 263, but starting with cyclopentanecarboxylic acid (43 mg, 0.37 mmol), yielded the title compound (20 mg, 15% yield) as an off-white solid:

$^1$H-NMR (CDCl$_3$): 8.67 (s, 2H), 8.52 (s, 1H), 8.20 (s, 1H), 7.95 (d, 1H), 7.62 (s, 1H), 7.2 (s, 1H), 7.12 (s, 1H), 4.00 (s, 6H), 2.75 (m, 1H), 1.61–2.09 (m, 8H);

MS (−ve ESI): 392 (M−H)$^−$,
MS (+ve ESI): 394 (M+H)$^+$.

EXAMPLE 272

Preparation of Compound 272 in Table 10

An analogous reaction to that described in example 265, but starting with cinnamic acid (55 mg, 0.37 mmol), yielded the title compound (4 mg, 2% yield) as an off-white solid:

$^1$H-NMR (CDCl$_3$): 8.8 (s, 1H), 8.63 (s, 1H), 8.22 (s, 1H), 8.00 (d, 1H), 7.80 (d, 1H, J=16 Hz), 7.58 (s, 1H), 7.54 (m, 3H), 7.38 (m, 4H), 7.23 (s, 1H), 6.59 (d, 1H, J=16 Hz), 4.06 (s, 3H), 4.02 (s, 3H):

MS (−ve ESI): 426 (M−H)$^−$,
MS (+ve ESI): 428 (M+H)$^+$.

EXAMPLE 273

Preparation of Compound 273 in Table 10

An analogous reaction to that described in example 263, but starting with 4-methoxyphenyacetic acid (62 mg, 0.37 mmol), yielded the title compound (32 mg, 21% yield) as an off-white solid:

$^1$H-NMR (DMSO-d$_6$): 10.23 (s, 1H), 10.17 (s, 1H), 8.66 (d, 1H), 8.50 (s, 1H), 8.36 (d, 1H), 8.02 (s, 1H), 7.90 (dd, 1H), 7.24 (d, 2H), 7.18 (s, 1H), 6.88 (dd, 2H), 3.94 (s, 3H), 3.92 (s, 3H), 3.72 (s, 3H), 3.58 (s, 2H):

MS (−ve ESI): 444 (M−H)$^−$,
MS (+ve ESI): 446 (M+H)$^+$.

EXAMPLE 274

Preparation of Compound 274 in Table 10

An analogous reaction to that described in example 263, but starting thiophene-3-carboxylic acid (48 mg, 0.37 mmol), yielded the title compound (29 mg, 16% yield) as a white solid:

¹H-NMR (DMSO-d₆): 10.32 (bs, 1H), 8.90 (s, 1H), 8.81 (s, 1H), 8.39 (s, 1H), 8.15–8.30 (m, 3H), 7.60–7.70 (m, 2H), 7.29 (s, 1H), 4.05 (s, 6H), 3.80–3.91 (m, 4H), 3.23–3.45 (m, 6H), 2.20–2.30 (m, 2H):
MS (–ve ESI): 406 (M–H)⁻,
MS (+ve ESI): 408 (M+H)⁺.

EXAMPLE 275

Preparation of Compound 275 in Table 11

An analogous reaction to that described in example 263, but starting with 4-((3-amino-6-pyridine)amino)-6-methoxy-7-(3-morpholinopropoxy)quinazoline (100 mg, 0.24 mmol) and 2-thiophenecarboxylic acid (33 mg, 0.26 mol), yielded the title compound (5 mg, 3% yield) as an off-white solid:
¹H-NMR (DMSO-d₆): 10.38 (s, 1H), 10.23 (s, 1H), 8.77 (d, 1H), 8.57 (s, 1H), 8.10 (dd, 1H), 7.70 (s, 1H), 7.16 (m, 4H), 4.18 (t, 2H), 3.97 (s, 3H), 3.60 (m, 4H), 2.47 (m, 2H), 2.40 (m, 4H), 1.98 (m, 2H):
MS (–ve ESI): 519 (M–H)⁻,
MS (+ve ESI): 521 (M+H)⁺.

4-((3-amino-6-pyridine)amino)-6-methoxy-7-(3-morpholinopropoxy)quinazoline, used as the starting material, was obtained as follows:

a) A solution of 2-amino-5-nitropyridine (1.67 g, 12 mmol), 4-chloro-6-methoxy-7-(3-morpholinopropoxy) quinazoline (3.38 g, 10 mmol) and 1.0M solution of hydrogen chloride in diethylether (10 ml, 10 mmol), in isopropanol (125 ml) was heated and the diethylether allowed to evaporate then heated at reflux for 3 hours before the reaction was allowed to cool to ambient temperature. The solid which had precipitated was collected by suction filtration, washed with diethyl ether (2×50 ml), dissolved in water (200 ml) and neutralised with concentrated aqueous ammonia. The resulting solid was collected by suction filtration, washed with water then acetone. Drying in vacuo yielded 4-((3-nitro-6-pyridine)amino)-6-methoxy-7-(3-morpholinopropoxy)quinazoline (2.3 g, 53% yield) as a beige solid:
¹H-NMR (DMSO-d₆): 9.15 (s, 1H), 8.63 (s, 1H), 8.45 (s, 2H), 7.98 (s, 1H), 7.22 (s, 1H), 4.20 (t, 2H), 3.57 (m, 4H), 2.43 (t, 2H), 2.37 (m, 4H), 1.93 (m, 2H):
MS (–ve ESI): 439 (M–H)⁻.

b) 10% Palladium on carbon (50 mg, 0.047 mmol) was added to a stirred suspension on 4-((3-nitro-6-pyridine)amino)-6-methoxy-7-(3-morpholinopropoxy)-quinazoline (2.1 g, 4.78 mmol) in ethanol (100 ml) at ambient temperature and the reaction stirred for 36 hours under an atmosphere of hydrogen. The reaction was filtered through a pad of celite and the solvent evaporated in vacuo to yield crude 4-((3-amino-6-pyridine)amino)-6-methoxy-7-(3-morpholinopropoxy)quinazoline (1.89 g, 97% yield) as an off-white solid:
MS (+ve ESI): 411 (M+H)⁺.

EXAMPLE 276

Preparation of Compound 276 in Table 11

An analogous reaction to that described in example 275, but starting with 2-thiopheneacetic acid (19 mg, 0.12 mmol), yielded the title compound (9 mg, 14% yield) as an off-white solid:

¹H-NMR (CDCl₃): 8.70 (s, 2H), 8.40 (s, 1H), 8.05 (s, 1H), 7.80 (m, 1H), 7.45 (s, 1H), 7.20–7.25 (m, 1H), 7.00–7.15 (m, 3H), 4.21 (t, 3H), 4.00–4.05 (m, 5H), 3.75 (m, 4H), 2.45–2.61 (m, 6H), 2.20 (m, 2H):
MS (–ve ESI): 533 (M–H)⁻,
MS (+ve ESI): 535 (M+H)⁺.

EXAMPLE 277

Preparation of Compound No. 277 in Table 11

An analogous reaction to that described in example 8, but starting with 2-amino-5-chloropyridine (57 mg, 0.50 mmol) and 4-chloro-6-methoxy-7-(3-morpholinopropoxy)quinazoline, (187 mg, 0.50 mmol), yielded the title compound (87 mg, 37% yield) as a pale yellow solid:
¹H-NMR (DMSO-d₆): 8.85 (s, 1H), 8.58 (d, 1H), 8.30 (s, 1H), 8.29 (d, 1H), 8.05 (m, 1H), 7.42 (s, 1H), 4.32 (t, 2H), 4.00 (s, 3H), 3.98 (m, 2H), 3.80 (t, 2H), 3.01–3.30 (m, 6H), 2.35 (m, 2H):
MS (+ve ESI): 430 (M+H)⁺.

EXAMPLE 278

Preparation of Compound No. 278 in Table 11

An analogous reaction to that described in example 275, but starting with 3,5-dichlorobenzoic acid (42 mg, 0.22 mmol), yielded the title compound (33 mg, 24% yield) as an off-white solid:
¹H-NMR (DMSO-d₆): 10.50 (s, 1H), 8.80 (m, 1H), 8.61 (s, 1H), 8.30–8.36 (m, 1H), 8.15–8.20 (m, 1H), 8.10 (m, 1H), 8.00 (d, 2H), 7.81 (t, 1H), 7.29 (s, 1H), 4.25 (t, 2H), 4.05 (s, 3H), 3.80–3.91 (m, 4H), 3.23–3.45 (m, 6H), 2.20–2.30 (m, 2H):
MS (–ve ESI): 581 (M–H)⁻,
MS (+ve ESI): 583 (M+H)⁺.

EXAMPLE 279

Preparation of Compound No. 279 in Table 11

An analogous reaction to that described in example 275, but starting with benzoic acid (32 mg, 0.22 mmol), yielded the title compound (26 mg, 17% yield) as an off-white solid:
¹H-NMR (DMSO-d₆): 10.30 (s, 1H), 8.80 (s, 1H), 8.61 (s, 1H), 8.20–8.30 (m, 2H), 8.10 (s, 1H), 7.52–7.70 (m, 5H), 7.22 (s, 1H), 4.25 (t, 2H), 4.05 (s, 3H), 3.80–3.91 (m, 4H), 3.23–3.45 (m, 6H), 2.20–2.30 (m, 2H):
MS (–ve ESI): 513 (M–H)⁻,
MS (+ve ESI): 515 (M+H)⁺.

EXAMPLE 280

Preparation of Compound No. 280 in Table 11

An analogous reaction to that described in example 275, but starting with 4-chlorobenzoic acid (41 mg, 0.22 mmol), yielded the title compound (24 mg, 18% yield) as an off-white solid:
¹H-NMR (DMSO-d₆): 10.30 (s, 1H), 8.80 (s, 1H), 8.61 (s, 1H), 8.40 (d, 1H), 8.20 (d, 1H), 8.10 (s, 1H), 8.00 (d, 2H), 7.61 (d, 2H), 7.29 (s, 1H), 4.25 (t, 2H), 4.05 (s, 3H), 3.80–3.91 (m, 4H), 3.23–3.45 (m, 6H), 2.20–2.30 (m, 2H):
MS (–ve ESI): 547 (M–H)⁻,
MS (+ve ESI): 549 (M+H)⁺.

EXAMPLE 281

Preparation of Compound No. 281 in Table 11

An analogous reaction to that described in example 275, but starting with 3,4-dichlorobenzoic acid (27 mg, 0.14 mmol), yielded the title compound (11 mg, 12% yield) as an off-white solid:

$^1$H-NMR (DMSO-d$_6$): 10.30 (s, 1H), 8.80 (s, 1H), 8.61 (s, 1H), 8.43 (d, 1H), 8.25 (s, 1H), 8.20 (d, 1H), 8.10 (d, 2H), 8.05 (d, 1H), 7.81 (d, 1H), 7.29 (s, 1H), 4.25 (t, 2H), 4.05 (s, 3H), 3.80–3.91 (m, 4H), 3.23–3.45 (m, 6H), 2.20–2.30 (m, 2H):

MS (+ve ESI): 583 (M+H)$^+$.

EXAMPLE 282

Preparation of Compound No. 282 in Table 11

An analogous reaction to that described in example 275, but starting with 3-chloro-4-fluorobenzoic acid (24 mg, 0.14 mmol), yielded the title compound (19 mg, 21% yield) as an off-white solid:

$^1$H-NMR (DMSO-d$_6$): 10.30 (s, 1H), 8.80 (s, 1H), 8.61 (s, 1H), 8.30 (d, 1H), 8.15–8.25 (m, 2H), 8.10 (s, 1H), 8.05 (m, 1H), 7.62 (t, 1H), 7.29 (s, 1H), 4.25 (t, 2H), 4.05 (s, 3H), 3.80–3.91 (m, 4H), 3.23–3.45 (m, 6H), 2.20–2.30 (m, 2H):

MS (−ve ESI): 565 (M−H)$^-$,
MS (+ve ESI): 567 (M+H)$^+$.

EXAMPLE 283

Preparation of Compound No. 283 in Table 12

An analogous reaction to that described in example 6, but starting with 2-(N-benzoyl)-2,5-diaminopyridine (128 mg, 0.60 mmol) and 4-chloro-6,7-dimethoxy-quinazoline (135 mg, 0.60 mmol), yielded the title compound (182 mg, 69% yield) as a pale-yellow solid:

$^1$H-NMR (DMSO-d$_6$): 11.54 (s, 1H), 10.90 (s, 1H), 9.11 (s, 1H), 8.84 (s, 1H), 8.74 (d, 1H, J=2 Hz), 8.36 (s, 1H), 8.30 (d, 1H, J=8 Hz), 8.19 (dd, 1H, J=2,8 Hz), 8.05 (d, 1H, J=8 Hz), 7.48–7.63 (m, 3H), 7.35 (s, 1H), 4.03 (s, 3H), 4.00 (s, 3H):

MS (−ve ESI): 400 (M−H)$^-$,
MS (+ve ESI): 402 (M+H)$^+$.

2-(N-Benzoyl)-2,5-diaminopyridine, used as the starting material was obtained as follows:

a) A mixture of 2-amino-5-nitropyridine (2.00 g, 14.4 mmol) and benzoyl chloride (1.90 ml, 15.9 mmol) was heated in pyridine (40 ml) at reflux for 4 hours under an inert atmosphere. The reaction was allowed to cool to ambient temperature, was poured into water (400 ml) and the precipitated solid was collected by suction filtration. Washing of the solid with water (3×100 ml) and drying in vacuo yielded 2-(N-benzoyl)-2-amino-5-nitropyridine (3.16 g, 90% yield) as a white solid:

$^1$H-NMR (DMSO-d$_6$): 11.49 (s, 1H), 9.23 (d, 1H, J=2 Hz), 8.65 (dd, 1H, J=2,8 Hz), 8.43 (d, 1H, J=8 Hz), 8.03 (d, 1H, J=8 Hz), 7.50–7.65 (m, 3H):

MS (−ve ESI): 242 (M−H)$^-$,
MS (+ve ESI): 244 (M+H)$^+$.

b) Sodium hydrosulphite (1.18 g, 6.76 mmol) was added portion-wise to a solution 2-(N-benzoyl)-2-amino-5-nitropyridine (329 mg, 1.35 mmol) in a mixture of ethanol (25 ml) and water at reflux. The reaction was heated at reflux for 20 minutes, cooled to ambient temperature and the ethanol was removed in vacuo. The residue was partitioned between water (5 ml) and ethyl acetate (25 ml), the organic layer was separated and the aqueous phase was extracted with more ethyl acetate (2×25 ml). Drying of the combined organic layers over magnesium sulphate, followed by solvent evaporation in vacuo, yielded 2-(N-benzoyl)-2,5-diaminopyridine (128 mg, 44% yield) as a pale-yellow solid:

$^1$H-NMR (DMSO-d$_6$): 10.26 (s, 1H), 7.99 (d, 2H, J=8 Hz), 7.79 (d, 1H, J=8 Hz), 7.74 (d, 1H, J=2 Hz), 7.43–7.56 (m, 3H), 7.03 (dd, 1H, J=2,8 Hz), 5.20 (s, 1H):

MS (+ve ESI): 214 (M+H)$^+$.

EXAMPLE 284

Preparation of Compound No. 284 in Table 12

An analogous reaction to that described in example 283, but starting with 2-n-butoxy-5-aminopyridine (83 mg, 0.50 mmol), yielded the title compound (122 mg, 61% yield) as a yellow solid:

$^1$H-NMR (DMSO-d$_6$): 11.38 (s, 1H), 8.77 (s, 1H), 8.39 (d, 1H, J=7 Hz), 8.27 (s, 1H), 7.96 (dd, 1H, J=1,7 Hz), 7.31 (s, 1H), 6.91 (d, 1H, J=8 Hz), 4.27 (t, 1H, J=7 Hz), 4.00 (s, 3H), 3.98 (s, 3H), 1.71 (qu, 2H, J=7 Hz), 1.44 (qu, 2H, J=7 Hz), 0.93 (t, 3H, J=7 Hz):

MS (−ve ESI): 353 (M−H)$^-$,
MS (+ve ESI): 354 (M+H)$^+$.

EXAMPLE 285

Preparation of Compound 285 Table 12

An analogous reaction to that described in example 283, but starting with 5-amino-2-bromopyridine (790 mg, 4.56 mmol), yielded the title compound (1.7 g, 94% yield) as a white solid:

$^1$H-NMR (DMSO-d$_6$): 11.65 (bs, 1H), 8.85 (s, 1H), 8.80 (d, 1H, J=2 Hz), 8.40 (s, 1H), 8.17 (dd, 1H, J=8,2 Hz), 7.76 (d, 1H, J=8 Hz), 7.36 (s, 1H), 4.04 (s, 3H), 3.97 (s, 3H):

MS (+ve ESI): 361, 363 (M+H)$^+$.

EXAMPLE 286

Preparation of Compound 286 Table 12

A mixture of 4-(3-amino-6-bromopyridyle)-6,7-dimethoxyquinazoline (80 mg, 0.2 mmol) and silver carbonate (110 mg, 0.4 mmol) in pyrrolidine (0.5 ml) was heated at reflux for 20 hours. Silver carbonate (110 mg, 0.4 mmol) and pyrrolidine (0.5 ml) were added and heating continued for a further 24 hours. Solvent evaporation in vacuo yielded the title compound (57 mg, 81% yield) as a white foam, after purification by flash chromatography on silica gel, eluting with 2% methanol in dichloromethane:

$^1$H-NMR (DMSO-d$_6$): 9.31 (s, 1H), 8.3 (s, 1H), 8.24 (d, 1H), 7.78 (s, 1H), 7.73 (m, 2H), 7.13 (s, 1H), 6.47 (d, 1H), 3.92 (s, 3H), 3.9 (s, 3H), 3.38 (m, 4H), 1.95 (m, 4H):

MS (−ve ESI): 350 (M−H)$^-$,
MS (+ve ESI): 352 (M+H)$^+$.

EXAMPLE 287

Preparation of Compound 287 Table 12

10% palladium on carbon (25 mg) and cyclohexene (2 ml) were added to a solution of 2-N-n-hexylamino-5-nitropyridine (157 mg, 0.7 mmol) in propan-2-ol (10 ml), under an inert atmosphere and the mixture heated at 80° C. for 12 hours. The reaction was cooled, filtered through a pad of celite and 4-chloro-6,7-dimethoxyquinazoline (157 mg, 0.7 mmol) and a 4.0 N solution of hydrogen chloride in dioxan (0.195 ml, 0.77 mmol) were added to the filtrate. The reaction was heated at reflux for 3 hours, cooled and the resulting solid was collected by suction filtration and washed with diethyl ether (2×50 ml). Drying in vacuo yielded the title compound (23 mg, 8% yield) as a white solid:

$^1$H-NMR (DMSO-d$_6$): 11.75 (s, 1H), 8.82 (s, 1H), 8.45 (s, 1H), 8.34 (s, 1H), 8.20 (m, 1H), 7.36 (s, 1H), 7.09 (m, 1H), 4.01 (s, 3H), 3.98 (s, 3H), 3.35 (m, 2H), 1.60 (m, 2H), 1.3 (m, 6H), 0.87 (m, 3H):

MS (−ve ESI): 380 (M−H)$^-$,
MS (+ve ESI): 382 (M+H)$^+$.

2-N-n-hexylamino-5-nitropyridine, used as the starting material was obtained as follows;

a) n-Hexylamine (51 mg, 5.0 mmol) was added to a solution of 2-bromo-5-nitropyridine (203 mg, 1 mmol) in dichloromethane (10 ml) and stirred at ambient temperature for 24 hours. n-Hexylamine (51 mg, 5.0 mmol) was added and the reaction stirred for a further 24 hours before isolation of the product by flash chromatography on silica gel, eluting with dichloromethane yielded 2-N-n-hexylamino-5-nitropyridine (217 mg, 97% yield) as a yellow solid:

$^1$H-NMR (CDCl$_3$): 9.00 (d, 1H, J=2 Hz), 8.19 (dd, 1H, J=8,2 Hz), 6.33 (d, 1H, J=8 Hz), 5.35 (s, 1H) 3.33–3.41 (m, 2H), 1.60–1.71 (m, 2H), 1.29–1.47 (m, 6H), 0.85–0.92 (m, 3H):

MS (−ve ESI): 222 (M−H)$^-$,
MS (+ve ESI): 224 (M+H)$^+$.

EXAMPLE 288

Preparation of Compound 288 Table 12

An analogous reaction to that described in example 283, but starting with 1-(4-cyanophenyl)-4-(5-aminopyridin-2-yl)piperazine (30 mg, 0.11 mmol), yielded the title compound (27 mg, 49% yield) as a brown solid:

$^1$H-NMR (DMSO-d$_6$): 11.30 (s, 1H), 8.75 (s, 1H), 8.40 (d, 1H, J=2 Hz), 8.28 (s, 1H), 7.86 (dd, 1H, J=8,2 Hz), 7.60 (d, 2H, J=8 Hz), 7.32 (s, 1H), 7.07 (d, 2H, J=8 Hz), 7.00 (d, 1H, J=8 Hz), 4.00 (s, 3H), 3.98 (s, 3H), 3.69–3.75 (m, 4H), 3.48–3.55 (m, 4H):

MS (−ve ESI): 466 (M−H)$^-$,
MS (+ve ESI): 468 (M+H)$^+$.

1-(4-cyanophenyl)-4-(5-aminopyridin-2-yl)piperazine, used as starting material was obtained as follows, a) Potassium carbonate (20.7 g, 0.15 mol) was added to a solution of 4-fluorobenzonitrile (12.1 g, 0.1 mol) and piperazine (25.8 g, 0.3 mol) in dimethylsulfoxide (75 ml) and heated at 95° C. for 20 hours. The reaction was cooled and poured into water (1100 ml) and extracted into dichloromethane (4×400 ml). The organic solution was dried and the solvent removed in vacuo to yield 4-cyanophenylpiperazine (17.5 g, 93.6% yield):

$^1$H-NMR (CDCl$_3$): 7.50 (d, 2H), 6.80 (d, 2H), 3.25 (m, 4H), 3.00 (m, 4H);

MS (+ve ESI): 188 (M+H)$^+$.

b) Potassium carbonate (780 mg, 5.65 mmol) was added to a solution of 4-cyanophenylpiperazine (880 mg, 4.7 mmol) and 2-nitro-5-bromopyridine (860 mg, 4.24 mmol) in dimethylsulfoxide (6 ml) and heated at 95° C. for 20 hours. The reaction was cooled, poured into water (90 ml) and extracted into dichloromethane (3×50 ml). The organic solution was washed with water then dried and concentrated in vacuo. Purification by flash chromatography on alumina, eluting with dichloromethane, followed by recrystallisation from methanol/ethyl acetate yielded 1-(4-cyanophenyl)-4-(5-nitropyridin-2-yl)piperazine (160 mg, 12% yield) as a white solid:

$^1$H-NMR (CDCl$_3$): 9.05 (s, 1H), 8.25 (d, 1H), 7.55 (d, 2H), 6.85 (d, 2H), 6.60 (d, 1H), 3.97 (m, 4H), 3.50 (m, 4H):

MS (+ve ESI): 310 (M+H)$^+$.

c) 10% Palladium on carbon (25 mg, 0.024 mmol) was added to a stirred suspension of 1-(4-cyanophenyl)-4-(5-nitropyridin-2-yl)-piperazine (150 mg, 0.48 mmol) in ethanol (50 ml) at ambient temperature and the reaction stirred for 6 hours under an atmosphere of hydrogen. The reaction was filtered through a pad of celite and the solvent evaporated in vacuo. Purification by flash chromatography on alumina, eluting with 0.5% methanol in dichloromethane yielded 1-(4-cyanophenyl)-4-(5-aminopyridin-2-yl)piperazine (100 mg, 74% yield):

$^1$H-NMR (CDCl$_3$): 7.82 (s, 1H), 7.50 (d, 2H), 7.20 (d, 1H), 6.90 (d, 2H), 6.50 (d, 1H), 4.20 (s, 2H), 3.47 (m, 4H), 3.15 (m, 4H):

MS (+ve ESI): 280 (M+H)$^+$.

EXAMPLE 289

Preparation of Compound 289 in Table 12

An analogous reaction to that described in example 287, but starting with 2-N-pyrrolidylamino-5-nitropyridine (101 mg, 0.48 mmol), yielded the title compound (129 mg, 67% yield) as a yellow solid:

$^1$H-NMR (DMSO-d$_6$): 11.25 (s, 1H), 8.71 (s, 1H), 8.36 (d, 1H), 8.27 (s, 1H), 7.82 (m, 1H), 7.30 (s, 1H), 6.96 (d, 1H), 3.99 (s, 3H), 3.96 (s, 3H), 3.55 (m, 4H), 1.57 (m, 6H):

MS (−ve ESI): 364 (M−H)$^-$,
MS (+ve ESI): 366 (M+H)$^+$.

2-N-pyrrolidylamino-5-nitropyridine, used as the starting material was obtained in an analogous reaction to example 287a, but starting with pyrrolidine:

$^1$H-NMR (DMSO-d$_6$): 8.91 (d, 1H), 8.14 (dd, 1H), 6.89 (d, 1H), 3.74 (m, 4H), 1.60 (m, 6H).

EXAMPLE 290

Preparation of Compound 290 in Table 12

An analogous reaction to that described in example 287, but starting with 2-N-cyclopropylamino-5-nitropyridine (65 mg, 0.36 mmol). Purification by flash chromatography on silica gel, eluting with 2–5% methanol in dichloromethane, yielded the title compound (27 mg, 22% yield) as an off-white solid:

$^1$H-NMR (CDCl$_3$): 8.58 (s, 1H), 8.18 (d, 1H, J=3 Hz), 7.87 (dd, 1H, J=9,3 Hz), 7.24 (s, 1H), 7.08 (s, 1H), 7.05 (s, 1H), 6.83 (d, 1H, J=9 Hz), 4.02 (s, 3H), 4.01 (s, 3H), 2.52 (m, 1H), 0.77–0.81 (m 2H), 0.55–0.60 (m, 2H):

MS (−ve ESI): 336 (M−H)$^-$,
MS (+ve ESI): 338 (M+H)$^+$.

2-N-cyclopropylamino-5-nitropyridine, used as the starting material was obtained in an analogous reaction to example 287a, but starting with cyclopropylamine:

$^1$H-NMR (CDCl$_3$): 9.0 (d, 1H), 8.27 (m, 1H), 6.75 (d, 1H), 5.85 (s, 1H), 2.63 (m, 1H), 0.95 (m, 2H), 0.65 (m, 2H):

MS (−ve ESI): 178 (M−H)⁻,
MS (+ve ESI): 180 (M+H)⁺.

EXAMPLE 291

Preparation of Compound 291 in Table 12

An analogous reaction to that described in example 287, but starting with 2-N-cyclohexylamino-5-nitropyridine (141 mg, 0.64 mmol), yielded the title compound (125 mg, 47% yield) as a yellow solid:
$^1$H-NMR (DMSO-$d_6$): 10.79 (s, 1H), 8.62 (s, 1H), 8.29 (s, 1H), 8.16 (d, 1H), 7.90 (m, 1H), 7.50 (s, 1H), 7.26 (s, 1H), 6.78 (m, 1H), 3.97 (s, 3H), 3.95 (s, 3H), 3.70 (m, 1H), 1.92 (m, 2H), 1.72 (m, 2H), 1.58 (m, 1H), 1.20 (m, 5H):
MS (−ve ESI): 378 (M−H)⁻,
MS (+ve ESI): 380 (M+H)⁺.

2-N-cyclohexylamino-5-nitropyridine, used as the starting material was obtained in an analogous reaction to example 287a, but starting with cyclohexylamine:
$^1$H-NMR (CDCl$_3$): 9.0 (d, 1H), 8.19 (dd, 1H), 6.30 (d, 1H), 5.22 (s, 1H), 3.70 (m, 1H), 2.02 (m, 2H), 1.80 (m, 2H), 1.70 (m, 1H), 1.20–1.49 (m, 5H):
MS (−ve ESI): 220 (M−H)⁻,
MS (+ve ESI): 222 (M+H)⁺.

EXAMPLE 292

Preparation of Compound 292 in Table 12

An analogous reaction to that described in example 290, but starting with 2-N-n-propylamino-5-nitropyridine (65 mg, 0.36 mmol), yielded the title compound (95 mg, 70% yield) as a yellow solid:
$^1$H-NMR (DMSO-$d_6$): 10.71 (s, 1H), 8.62 (s, 1H), 8.28 (d, 1H, J=2 Hz), 8.11 (s, 1H), 7.83–7.93 (m, 1H), 7.25 (s, 1H), 6.76 (d, 1H, J=9 Hz), 3.97 (s, 3H), 3.95 (s, 3H), 3.20–3.29 (m, 2H), 1.51–1.63 (m, 2H), 0.93 (t, 3H, J=7 Hz):
MS (−ve ESI): 338 (M−H)⁻,
MS (+ve ESI): 340 (M+H)⁺.

2-N-n-propylamino-5-nitropyridine, used as the starting material was obtained in an analogous reaction to example 287a, but starting with propylamine:
$^1$H-NMR (CDCl$_3$): 9.0 (d, 1H), 8.19 (dd, 1H), 6.35 (d, 1H), 5.38 (s, 1H), 3.27 (m, 1H), 1.68 (m, 2H), 1.0 (t, 3H):
MS (−ve ESI): 180 (M−H)⁻,
MS (+ve ESI): 182 (M+H)⁺.

EXAMPLE 293

Preparation of Compound 293 in Table 12

An analogous reaction to that described in example 287, but starting with 2-N-benzylamino-5-nitropyridine (145 mg, 0.64 mmol), yielded the title compound (51 mg, 19% yield) as an off-white solid:
$^1$H-NMR (DMSO-$d_6$): 11.94 (s, 1H), 9.0 (s, 1H), 8.83 (s, 1H), 8.52 (s, 1H), 8.38 (s, 1H), 8.25 (m, 1H), 7.39 (m, 6H), 7.12 (d, 1H), 4.65 (s, 2H), 4.01 (s, 3H), 3.98 (s, 3H):
MS (−ve ESI): 386 (M−H)⁻,
MS (+ve ESI): 388 (M+H)⁺.

2-N-benzylamino-5-nitropyridine, used as the starting material was obtained in an analogous reaction to example 287a, but starting with benzylamine:
$^1$H-NMR (CDCl$_3$): 9.0 (d, 1H), 8.19 (dd, 1H), 7.38 (m, 5H), 6.38 (d, 1H), 5.6 (br s, 1H), 4.62 (d, 2H):
MS (−ve ESI): 228 (M−H)⁻,

EXAMPLE 294

Preparation of Compound 294 in Table 12

An analogous reaction to that described in example 290, but starting with 2-N-4-toluenesulphonamide-amino-5-nitropyridine (106 mg, 0.36 mmol), yielded the title compound (0.6 mg, 0.4% yield) as a yellow solid:
MS (−ve ESI): 450 (M−H)⁻,
MS (+ve ESI): 452 (M+H)⁺.

2-N-4-toluenesulphonamide-5-nitropyridine, used as the starting material was obtained in an analogous reaction to example 287a, but starting with 4-toluenesulphonamide:
$^1$H-NMR (DMSO-$d_6$): 8.95 (d, 1H), 8.4 (dd, 1H), 7.83 (d, 2H), 7.38 (m, 2H), 7.10 (d, 1H), 2.35 (s, 3H):
MS (−ve ESI): 292 (M−H)⁻,
MS (+ve ESI): 294 (M+H)⁺.

EXAMPLE 295

Preparation of Compound 295 in Table 12

Sodium hydride (100 mg, 2.5 mmol) was added to a solution of 4-chloro-6,7-dimethoxyquinazoline (225 mg, 1.0 mmol) and 6-(4-chlorophenoxy)-3-aminopyridine (221 mg, 1.0 mmol) in tetrahydrofuran (10 ml) under an inert atmosphere and heated at 75° C. for 4 hours. After cooling, methanol (0.25 ml) was added and the solvents were removed in vacuo. Purification by flash chromatography on silica gel, eluting with 2–5% methanol containing ammonia in dichloromethane, yielded the title compound (192 mg, 45% yield) as a pale yellow solid:
$^1$H-NMR (DMSO-$d_6$): 9.56 (s, 1H), 8.48 (d, 1H), 8.42 (s, 1H), 8.23 (dd, 1H), 7.80 (s, 1H), 7.45 (d, 2H), 7.19 (m, 2H), 7.11 (m, 2H), 3.94 (s, 3H), 3.90 (s, 3H);
MS (+ve ESI): 409 (M+H)⁺.

EXAMPLE 296

Preparation of Compound 296 in Table 12

An analogous reaction to that described in example 295, but starting with 2-benzyloxy-5-aminopyridine (197 mg, 0.98 mmol), yielded the title compound (121 mg, 32% yield) as a pale yellow solid:
$^1$H-NMR (DMSO-$d_6$): 9.48 (s, 1H), 8.44 (d, 1H), 8.38 (s, 1H), 8.04 (dd, 1H), 7.80 (s, 1H), 7.26–7.50 (m, 5H), 7.17 (s, 1H), 6.93 (d, 1H), 3.94 (s, 3H), 3.90 (s, 3H):
MS (+ve ESI): 388 (M+H)⁺.

EXAMPLE 297

Preparation of Compound 297 in Table 13

An analogous reaction to that described in example 295, but starting with 5-amino-2-trifluoromethylpyridine (810 mg, 5.0 mmol) and 4-chloro-6-methoxy-7-(3-morpholinopropoxy)quinazoline, (1.69 g, 5.0 mmol), yielded the title compound (763 mg, 33% yield) as a pale yellow solid:
$^1$H-NMR (DMSO-$d_6$): 9.87 (s, 1H), 9.15 (d, 1H), 8.60 (dd, 1H), 8.54 (s, 1H), 7.91 (d, 1H), 7.83 (s, 1H), 7.23 (s, 1H), 4.20 (t, 2H), 3.97 (s, 3H), 3.56 (t, 4H), 2.45 (t, 2H), 2.36 (t, 4H), 1.96 (m, 2H):

MS (−ve ESI): 462 (M−H)⁻.

EXAMPLE 298

Preparation of Compound 298 in Table 13

A solution of 1.0 N hydrochloric acid in diethyl ether (0.50 ml, 0.50 mmol) was added to a solution of 5-amino-2-(pyrid-3-yloxy)pyridine (94 mg, 0.50 mmol) and 4-chloro-6-methoxy-7-(3-morpholinopropoxy)quinazoline (168 mg, 0.50 mmol), in isopropanol (5.0 ml). The reaction was heated at 40° C. for 30 minutes and then at 83° C. for 12 hours. The reaction was allowed to cool to ambient temperature and the solid which had precipitated was collected by suction filtration and washed with diethyl ether (2×10 ml). Drying of this material yielded the title compound (253 mg, 96% yield) as a white solid:

$^1$H-NMR (DMSO-d$_6$): 11.77 (s, 1H), 11.08 (s, 1H), 8.83 (s, 1H), 8.55 (s, 1H), 8.48 (m, 3H), 8.27 (d, 1H), 7.75 (m, 1H), 7.56 (m, 1H), 7.43 (s, 1H), 7.30 (d, 1H), 4.32 (t, 2H), 4.05 (s, 3H), 3.95 (m, 2H), 3.82 (m, 2H), 3.5 (m, 2H), 3.3 (m, 2H), 3.1 (m, 2H), 2.35 (m, 2H):

MS (+ve ESI): 489 (M+H)⁺.

EXAMPLE 299

Preparation of Compound 299 in Table 13

An analogous reaction to that described in example 298, but starting with 5-amino-2-(4-chlorophenoxy)pyridine (110 mg, 0.50 mmol) yielded the title compound (261 mg, 94% yield) as a white solid:

$^1$H-NMR (DMSO-d$_6$): 11.7 (s, 1H), 11.02 (s, 1H), 8.82 (s, 1H), 8.5 (d, 2H), 8.22 (d, 1H), 7.52 (d, 2H), 7.45 (s, 1H), 7.25 (s, 1H), 7.22 (d, 2H), 4.35 (t, 2H), 4.05 (s, 3H), 3.98 (m, 2H), 3.85 (m, 2H), 3.50 (m, 2H), 3.35 (m, 2H), 3.10 (m, 2H), 2.35 (m, 2H):

MS (+ve ESI): 524 (M+H)⁺.

EXAMPLE 300

Preparation of Compound 300 in Table 13

An analogous reaction to that described in example 297, but starting with 3-amino-6-(3-pyridylmethoxy)pyridine (235 mg, 1.17 mmol), yielded the title compound (132 mg, 22% yield) as a pale yellow solid:

$^1$H-NMR (DMSO-d$_6$): 9.49 (s, 1H), 8.69 (d, 1H), 8.53 (m, 1H), 8.45 (d, 1H), 8.37 (s, 1H), 8.06 (m, 1H), 7.89 (m, 1H), 7.78 (s, 1H), 7.41 (m, 1H), 7.16 (s, 1H), 6.94 (d, 1H), 5.39 (s, 2H), 4.17 (t, 2H), 3.94 (s, 3H), 3.57 (t, 4H), 2.43 (t, 2H), 2.36 (t, 4H), 1.95 (m, 2H):

MS (−ve ESI): 502 (M−H)⁻, 3-amino-6-(3-pyridylmethoxy)pyridine, used as starting material was obtained as follows, a) Sodium hydride (144 mg, 3.6 mmol) was added to a solution of 2-pyridine-methanol (361 mg, 3.3 mmol) in dimethylformamide (5 ml) and stirred for 20 minutes. 2,5-Dibromopyridine (711 mg, 3.0 mmol) was added, the reaction was heated to 100° C. for 10 hours, before the reaction was cooled and the solvents removed in vacuo. 2.0 N aqueous sodium hydroxide solution (5 ml) was added, the aqueous layer was extracted with ethyl acetate which was washed with and concentrated in vacuo. Purification by flash chromatography on silica gel, eluting with 5% ethyl acetate in isohexane, yielded 3-bromo-6-(3-pyridylmethoxy)pyridine (366 mg, 46% yield) as an off-white solid:

$^1$H-NMR (DMSO-d$_6$): 8.69 (s, 1H), 8.57 (m, 1H), 8.19 (m, 1H), 7.76 (d, 1H), 7.68 (dd, 1H), 7.30 (dd, 1H), 6.72 (d, 1H), 5.37 (d, 2H).

b) 2,2'-Bis(diphenylphosphino-1,1,;-binaphthyl (25 mg, 0.04 mmol), tris-(dibenzylideneacetone) palladium (0) (12.3 mg) and sodium tert-butoxide (184 mg, 1.9 mmol) were added to a solution of 3-bromo-6-(3-pyridylmethoxy)pyridine (366 mg, 1.38 mmol) in toluene (3.7 ml) under an inert atmosphere and heated at 100° C. for 4 hours. The solvent was removed in vacuo and the residue dissolved in tetrahydrofuran (7 ml) and 2.0 N hydrochloric acid solution (7 ml) added and stirred at ambient temperature for 1 hour. The solution was diluted with 2.0 N hydrochloric acid solution (40 ml) and washed twice with diethyl ether (10 ml). The aqueous solution was made alkaline by addition of ammonia then extracted into dichloromethane. Drying and evaporation in vacuo yielded, 3-amino-6-(3-pyridylmethoxy)pyridine (235 mg, 56% yield) as a waxy solid.

EXAMPLE 301

Preparation of Compound 301 in Table 13

An analogous reaction to that described in example 300, but starting with 3-amino-6-(3,4-dichlorobenzyloxy)pyridine (120 mg, 0.45 mmol), yielded the title compound (77 mg, 33% yield) as a pale yellow solid:

$^1$H-NMR (DMSO-d$_6$): 9.49 (s, 1H), 8.43 (d, 1H), 8.38 (s, 1H), 8.08 (dd, 1H), 7.78 (s, 1H), 7.70 (s, 1H), 7.63 (d, 1H), 7.46 (dd, 1H), 7.15 (s, 1H), 6.96 (d, 1H), 5.35 (s, 2H), 4.17 (t, 2H), 3.93 (s, 3H), 3.57 (t, 4H), 2.44 (t, 2H), 2.37 (t, 4H), 1.94 (m, 2H):

MS (−ve ESI): 570 (M−H)⁻,

MS (+ve ESI): 572 (M+H)⁺.

3-amino-6-(3,4-dichlorobenzyloxy)pyridine, used as starting material was obtained as in example 300 (a, b) but starting with 3,4-dichlorobenzylalcohol.

$^1$H-NMR (DMSO-d$_6$): 7.63 (d, 1H), 7.53 (d, 1H), 7.41 (d, 1H), 7.25 (dd, 1H), 7.04 (dd, 1H), 6.66 (d, 1H), 5.24 (s, 2H), 3.38 (s, 2H).

EXAMPLE 302

Preparation of Compound 302 in Table 13

An analogous reaction to that described in example 300, but starting with 3-amino-6-(3,5-dichlorobenzyloxy)pyridine (307 mg, 1.14 mmol), yielded the title compound (227 mg, 40% yield) as a white solid:

$^1$H-NMR (DMSO-d$_6$): 9.49 (s, 1H), 8.43 (d, 1H), 8.36 (s, 1H), 8.08 (dd, 1H), 7.77 (s, 1H), 7.53 (d, 1H), 7.50 (s, 2H), 7.16 (s, 1H), 6.98 (d, 1H), 5.37 (s, 2H), 4.16 (t, 2H), 3.93 (s, 3H), 3.56 (t, 4H), 2.44 (t, 2H), 2.37 (t, 4H), 1.94 (m, 2H):

MS (−ve ESI): 570 (M−H)⁻,

MS (+ve ESI): 572 (M+H)⁺.

3-amino-6-(3,5-dichlorobenzyloxy)pyridine, used as starting material was obtained as in example 300 (a, b) but starting with 3,5-dichlorobenzylalcohol.

$^1$H-NMR (DMSO-d$_6$): 7.63 (d, 1H), 7.27–7.32 (m, 3H), 7.06 (dd, 1H), 6.68 (d, 1H), 5.25 (s, 2H), 3.4 (s, 2H).

EXAMPLE 303

Preparation of Compound 303 in Table 13

An analogous reaction to that described in example 300, but starting with 3-amino-6-(3-fluorobenzyloxy)pyridine (120 mg, 0.55 mmol), yielded the title compound (71 mg, 25% yield) as a white solid:

$^1$H-NMR (DMSO-$d_6$): 9.49 (s, 1H), 8.43 (d, 1H), 8.37 (s, 1H), 8.07 (dd, 1H), 7.77 (s, 1H), 7.42 (m, 1H), 7.29 (m, 2H), 7.10–7.18 (m, 2H), 6.95 (d, 1H), 5.37 (s, 2H), 4.17 (t, 2H), 3.93 (s, 3H), 3.56 (t, 4H), 2.45 (t, 2H), 2.36 (t, 4H), 1.95 (m, 2H):

MS (−ve ESI): 518 (M−H)$^-$, 3-amino-6-(3-fluorobenzyloxy)pyridine, used as starting material was obtained as in example 300 (a, b) but starting with 3-fluorobenzylalcohol.

$^1$H-NMR (DMSO-$d_6$): 7.66 (d, 1H), 7.32 (m, 1H), 7.17 (m, 2H), 7.07 (dd, 1H), 6.69 (m, 1H), 5.29 (s, 2H), 3.17 (s, 2H).

EXAMPLE 304

Preparation of Compound 304 in Table 13

An analogous reaction to that described in example 300, but starting with 3-amino-6-(4-trifluoromethylbenzyloxy)pyridine (221 mg, 0.55 mmol), yielded the title compound (80 mg, 17% yield) as a white solid:

$^1$H-NMR (DMSO-$d_6$): 9.48 (s, 1H), 8.43 (d, 1H), 8.37 (s, 1H), 8.07 (dd, 1H), 7.77 (s, 1H), 7.73 (d, 2H), 7.65 (d, 2H), 7.15 (s, 1H), 6.97 (d, 1H), 5.47 (s, 2H), 4.17 (t, 2H), 3.93 (s, 3H), 3.57 (t, 4H), 2.43 (t, 2H), 2.36 (t, 4H), 1.94 (m, 2H):

MS (−ve ESI): 568 (M−H)$^-$, 3-amino-6-(4-trifluoromethylbenzyloxy)pyridine, used as starting material was obtained as in example 300 (a, b) but starting with 4-trifluoromethylbenzylalcohol.

$^1$H-NMR (DMSO-$d_6$): 7.65 (d, 1H), 7.62 (d, 1H), 7.52 (d, 1H), 7.04 (dd, 1H), 6.67 (d, 1H), 5.35 (s, 2H), 3.36 (s, 2H).

EXAMPLE 305

Preparation of Compound 305 in Table 13

An analogous reaction to that described in example 300, but starting with 3-amino-6-(4-chlorobenzyloxy)pyridine (198 mg, 0.84 mmol), yielded the title compound (141 mg, 31% yield) as a pale yellow solid:

$^1$H-NMR (DMSO-$d_6$): 9.49 (s, 1H), 8.43 (d, 1H), 8.37 (s, 1H), 8.05 (dd, 1H), 7.78 (s, 1H), 7.46 (dd, 4H), 7.16 (s, 1H), 6.92 (d, 1H), 5.34 (s, 2H), 4.17 (t, 2H), 3.93 (s, 3H), 3.57 (t, 4H), 2.44 (t, 2H), 2.37 (t, 4H), 1.95 (m, 2H):

MS (+ve ESI): 536 (M+H)$^+$.

3-amino-6-(4-chlorobenzyloxy)pyridine, used as starting material was obtained as in example 300 (a, b) but starting with 4-chlorobenzylalcohol.

$^1$H-NMR (DMSO-$d_6$): 7.48 (d, 1H), 7.39 (s, 4H), 7.00 (dd, 1H), 6.58 (d, 1H), 5.17 (s, 2H), 4.74 (s, 2H).

EXAMPLE 306

Preparation of Compound 306 in Table 13

An analogous reaction to that described in example 300, but starting with 3-amino-6-(benzyloxy)pyridine (164 mg, 0.82 mmol), yielded the title compound (122 mg, 30% yield) as a white solid:

$^1$H-NMR (DMSO-$d_6$): 9.47 (s, 1H), 8.43 (d, 1H), 8.37 (s, 1H), 8.04 (dd, 1H), 7.77 (s, 1H), 7.45 (d, 2H), 7.31 (m, 3H), 7.14 (s, 1H), 6.92 (d, 1H), 5.35 (s, 2H), 4.16 (t, 2H), 3.93 (s, 3H), 3.56 (t, 4H), 2.43 (t, 2H), 2.36 (t, 4H), 1.93 (m, 2H):

MS (+ve ESI): 502.5 (M+H)$^+$.

3-amino-6-(4-chlorobenzyloxy)pyridine, used as starting material was obtained as in example 300 (a, b) but starting with benzylalcohol:

$^1$H-NMR (CDCl$_3$): 7.66 (d, 1H), 7.45 (d, 2H), 7.34 (m, 3H), 7.04 (dd, 1H), 6.65 (d, 1H), 5.29 (s, 2H), 3.34 (s, 2H).

EXAMPLE 307

Preparation of Compound 307 in Table 13

An analogous reaction to that described in example 300, but starting with 3-amino-6-(3-chloroenzyloxy)pyridine (287 mg, 1.22 mmol), yielded the title compound (41 mg, 7% yield) as a white solid:

$^1$H-NMR (DMSO-$d_6$): 9.48 (s, 1H), 8.43 (d, 1H), 8.38 (s, 1H), 8.05 (dd, 1H), 7.78 (s, 1H), 7.51 (s, 1H), 7.40 (m, 3H), 7.15 (s, 1H), 6.95 (d, 1H), 5.36 (s, 2H), 4.16 (t, 2H), 3.93 (s, 3H), 3.56 (t, 4H), 2.44 (t, 2H), 2.36 (t, 4H), 1.94 (m, 2H):

MS (+ve ESI): 536.5 (M+H)$^+$.

3-amino-6-(4-chlorobenzyloxy)pyridine, used as starting material was obtained as in example 300 (a, b) but starting with 3-chlorobenzylalcohol:

$^1$H-NMR (CDCl$_3$): 7.65 (d, 1H), 7.44 (s, 1H), 7.28 (m, 3H), 7.04 (dd, 1H), 6.67 (d, 1H), 5.28 (s, 2H), 3.37 (s, 2H).

EXAMPLE 308

Preparation of Compound 308 in Table 13

An analogous reaction to that described in example 300, but starting with 3-amino-6-(2,3-difluorobenzyloxy)pyridine (84 mg, 0.36 mmol), yielded the title compound (41 mg, 21% yield) as a white solid:

$^1$H-NMR (DMSO-$d_6$): 9.47 (s, 1H), 8.46 (d, 1H), 8.36 (s, 1H), 8.07 (dd, 1H), 7.78 (s, 1H), 7.33–7.48 (m, 2H), 7.22 (m, 1H), 7.15 (s, 1H), 6.94 (d, 1H), 5.43 (s, 2H), 4.16 (t, 2H), 3.94 (s, 3H), 3.55 (t, 4H), 2.45 (t, 2H), 2.35 (t, 4H), 1.93 (m, 2H):

MS (+ve ESI): 538.5 (M+H)$^+$.

3-amino-6-(4-chlorobenzyloxy)pyridine, used as starting material was obtained as in example 300 (a, b) but starting with 2,3-difluorobenzylalcohol:

$^1$H-NMR (CDCl$_3$): 7.66 (d, 1H), 7.25 (m, 1H), 7.05 (m, 3H), 6.66 (d, 1H), 5.38 (s, 2H), 3.39 (s, 2H).

EXAMPLE 309

Preparation of Compound 309 in Table 13

An analogous reaction to that described in example 300, but starting with 3-amino-6-(4-fluorobenzyloxy)pyridine (111 mg, 0.49 mmol), yielded the title compound (51 mg, 20% yield) as a white solid:

¹H-NMR (DMSO-d₆): 9.49 (s, 1H), 8.45 (d, 1H), 8.38 (s, 1H), 8.05 (dd, 1H), 7.78 (s, 1H), 7.50 (m, 2H), 7.18 (t, 2H), 7.15 (s, 1H), 6.91 (d, 1H), 5.33 (s, 2H), 4.16 (t, 2H), 3.94 (s, 3H), 3.56 (t, 4H), 2.43 (t, 2H), 2.35 (t, 4H), 1.94 (m, 2H):

MS (+ve ESI): 520.6 (M+H)⁺.

3-amino-6-(4-chlorobenzyloxy)pyridine, used as starting material was obtained as in example 300 (a, b) but starting with 4-fluorobenzylalcohol:

¹H-NMR (CDCl₃): 7.67 (d, 1H), 7.22 (m, 2H), 7.05 (m, 3H), 6.65 (d, 1H), 5.27 (s, 2H), 3.37 (s, 2H).

EXAMPLE 310

Preparation of Compound 310 in Table 13

An analogous reaction to that described in example 300, but starting with 3-amino-6-(2-chlorobenzyloxy)pyridine (202 mg, 0.86 mmol), yielded the title compound (121 mg, 26% yield) as a white solid:

¹H-NMR (DMSO-d₆): 9.49 (s, 1H), 8.45 (d, 1H), 8.36 (s, 1H), 8.06 (dd, 1H), 7.77 (s, 1H), 7.58 (m, 1H), 7.49 (m, 1H), 7.35 (m, 2H), 7.15 (s, 1H), 6.96 (d, 1H), 5.43 (s, 2H), 4.16 (t, 2H), 3.93 (s, 3H), 3.56 (t, 4H), 2.45 (t, 2H), 2.35 (t, 4H), 1.94 (m, 2H):

MS (+ve ESI): 536.5 (M+H)⁺.

3-amino-6-(4-chlorobenzyloxy)pyridine, used as starting material was obtained as in example 300 (a, b) but starting with 2-chlorobenzylalcohol:

¹H-NMR (CDCl₃): 7.76 (d, 1H), 7.53 (dd, 1H), 7.38 (dd, 1H), 7.25 (m, 2H), 7.06 (dd, 1H), 6.69 (d, 1H), 5.40 (s, 2H), 3.36 (s, 2H).

EXAMPLE 311

Preparation of Compound 311 in Table 13

An analogous reaction to that described in example 300, but starting with 3-amino-6-(2-chloro-4-fluorobenzyloxy) pyridine (250 mg, 1.0 mmol), yielded the title compound (72 mg, 13% yield) as a white solid:

¹H-NMR (DMSO-d₆): 9.49 (s, 1H), 8.45 (d, 1H), 8.37 (s, 1H), 8.07 (dd, 1H), 7.79 (s, 1H), 7.66 (m, 1H), 7.49 (dd, 1H), 7.26 (td, 1H), 7.16 (s, 1H), 6.93 (d, 1H), 5.39 (s, 2H), 4.17 (t, 2H), 3.92 (s, 3H), 3.56 (t, 4H), 2.45 (t, 2H), 2.35 (t, 4H), 1.93 (m, 2H):

MS (+ve ESI): 554.5 (M+H)⁺.

3-amino-6-(4-chlorobenzyloxy)pyridine, used as starting material was obtained as in example 300 (a, b) but starting with 2-chloro-4-fluorobenzylalcohol:

¹H-NMR (CDCl₃): 7.68 (d, 1H), 7.51 (m, 1H), 7.14 (dd, 1H), 7.04 (dd, 1H), 6.98 (m, 1H), 6.66 (d, 1H), 5.35 (s, 2H), 3.37 (s, 2H).

EXAMPLE 312

Preparation of Compound 312 in Table 13

An analogous reaction to that described in example 300, but starting with 3-amino-6-(3-chloro-4-fluorobenzyloxy) pyridine (172 mg, 0.68 mmol), yielded the title compound (77 mg, 20% yield) as a white solid:

¹H-NMR (DMSO-d₆): 9.47 (s, 1H), 8.44 (d, 1H), 8.37 (s, 1H), 8.06 (dd, 1H), 7.78 (s, 1H), 7.68 (dd, 1H), 7.48 (m, 1H), 7.41 (t, 1H), 7.15 (s, 1H), 6.94 (d, 1H), 5.34 (s, 2H), 4.16 (t, 2H), 3.93 (s, 3H), 3.57 (t, 4H), 2.43 (t, 2H), 2.36 (t, 4H), 1.94 (m, 2H):

MS (+ve ESI): 554.5 (M+H)⁺.

3-amino-6-(4-chlorobenzyloxy)pyridine, used as starting material was obtained as in example 300 (a, b) but starting with 3-chloro-4-fluorobenzylalcohol:

¹H-NMR (CDCl₃): 7.64 (d, 1H), 7.49 (dd, 1H), 7.29 (m, 1H), 7.10 (t, 1H), 7.04 (dd, 1H), 6.65 (d, 1H), 5.23 (s, 2H), 3.38 (s, 2H).

EXAMPLE 313

Preparation of Compound 313 in Table 13

An analogous reaction to that described in example 300, but starting with 2-(4-chlorobenzyloxy)-3-methyl-5-aminopyridine (170 mg, 0.68 mmol), yielded the title compound (47 mg, 13% yield) as an off-white solid, after chromatography on silica gel, eluting with 2–10% methanol in dichloromethane:

¹H-NMR (DMSO-d₆): 9.41 (s, 1H), 8.37 (s, 1H), 8.28 (d, 1H), 7.89 (d, 1H), 7.77 (s, 1H), 7.50 (d, 2H), 7.43 (d, 2H), 7.15 (s, 1H), 5.37 (s, 2H), 4.15 (t, 2H), 3.92 (s, 3H), 3.56 (t, 4H), 2.45 (t, 2H), 2.36 (t, 4H), 2.23 (s, 3H), 1.94 (m, 2H):

MS (+ve ESI): 550.5 (M+H)⁺.

2-(2-Chloro-4-fluorobenzyloxy)-3-methyl-5-aminopyridine, used as starting material was obtained as in example 300 (a, b) but starting with 2-chloro-3-methyl-5-nitropyridine and 4-chlorobenzyl alcohol:

¹H-NMR (CDCl₃): 7.49 (d, 1H), 7.38 (d, 2H), 7.31 (d, 2H), 6.90 (d, 1H), 5.29 (s, 2H), 3.30 (s, 2H), 2.17 (s, 3H).

EXAMPLE 314

Preparation of Compound 314 in Table 13

An analogous reaction to that described in example 313, but starting with 2-benzyloxy-3-methyl-5-aminopyridine (226 mg, 1.06 mmol), yielded the title compound (143 mg, 29% yield) as an off-white solid, after chromatography on silica gel, eluting with 2–10% methanol in dichloromethane:

¹H-NMR (DMSO-d₆): 9.41 (s, 1H), 8.37 (s, 1H), 8.27 (d, 1H), 7.89 (d, 1H), 7.78 (s, 1H), 7.46 (d, 2H), 7.27–7.41 (m, 3H), 7.15 (s, 1H), 5.38 (s, 2H), 4.16 (t, 2H), 3.94 (s, 3H), 3.55 (t, 4H), 2.44 (t, 2H), 2.36 (t, 4H), 2.23 (s, 3H), 1.95 (m, 2H):

MS (+ve ESI): 516.5 (M+H)⁺.

2-(2-Chloro-4-fluorobenzyloxy)-3-methyl-5-aminopyridine, used as starting material was obtained as in example 300 (a, b) but starting with 2-chloro-3-methyl-5-nitropyridine and benzyl alcohol:

¹H-NMR (CDCl₃): 7.51 (d, 1H), 7.29–7.48 (m, 5H), 6.89 (d, 1H), 5.32 (s, 2H), 3.29 (s, 2H), 2.18 (s, 3H).

EXAMPLE 315

Preparation of Compound 315 in Table 13

An analogous reaction to that described in example 313, but starting with 2-(4-fluorobenzyloxy)-3-methyl-5-aminopyridine (295 mg, 1.27 mmol), yielded the title compound (110 mg, 16% yield) as an off-white solid, after chromatography on silica gel, eluting with 2–10% methanol in dichloromethane:

¹H-NMR (DMSO-d₆): 9.42 (s, 1H), 8.36 (s, 1H), 8.27 (d, 1H), 7.89 (d, 1H), 7.77 (s, 1H), 7.51 (m, 2H), 7.19 (t, 2H), 7.12 (s, 1H), 5.35 (s, 2H), 4.15 (t, 2H), 3.91 (s, 3H), 3.57 (t, 4H), 2.43 (t, 2H), 2.35 (t, 4H), 2.21 (s, 3H), 1.95 (m, 2H):
MS (+ve ESI): 534.5 (M+H)⁺.

2-(2-Chloro-4-fluorobenzyloxy)-3-methyl-5-aminopyridine, used as starting material was obtained as in example 300 (a, b) but starting with 2-chloro-3-methyl-5-nitropyridine and 4-fluorobenzyl alcohol:
¹H-NMR (CDCl₃): 7.50 (d, 1H), 7.41 (m, 2H), 7.04 (t, 2H), 6.89 (d, 1H), 5.29 (s, 2H), 3.30 (bs, 2H), 2.18 (s, 3H).

EXAMPLE 316

Preparation of Compound 316 in Table 13

An analogous reaction to that described in example 313, but starting with 2-(4-methylbenzyloxy)-3-methyl-5-aminopyridine (124 mg, 0.54 mmol), yielded the title compound (69 mg, 24% yield) as an off-white solid, after chromatography on silica gel, eluting with 2–10% methanol in dichloromethane:
¹H-NMR (DMSO-d₆): 9.39 (s, 1H), 8.37 (s, 1H), 8.26 (d, 1H), 7.86 (d, 1H), 7.77 (s, 1H), 7.34 (d, 2H), 7.16 (d, 2H), 7.13 (s, 1H), 5.34 (s, 2H), 4.15 (t, 2H), 3.94 (s, 3H), 3.56 (t, 4H), 2.44 (t, 2H), 2.38 (t, 4H), 2.30 (s, 3H), 2.19 (s, 3H), 1.05 (m, 2H);
MS (+ve ESI): 530.6 (M+H)⁺.

2-(2-Chloro-4-fluorobenzyloxy)-3-methyl-5-aminopyridine, used as starting material was obtained as in example 300 (a, b) but starting with 2-chloro-3-methyl-5-nitropyridine and 4-methylbenzyl alcohol:
¹H-NMR (CDCl₃): 7.50 (d, 1H), 7.34 (d, 1H), 7.16 (d, 2H), 6.89 (d, 1H), 5.27 (s, 2H), 3.28 (s, 2H), 2.35 (s, 3H), 2.17 (s, 3H).

EXAMPLE 317

Preparation of Compound 317 in Table 13

An analogous reaction to that described in example 313, but starting with 2-(3-chlorobenzyloxy)-3-methyl-5-aminopyridine (232 mg, 0.93 mmol), yielded the title compound (88 mg, 17% yield) as an off-white solid, after chromatography on silica gel, eluting with 2–10% methanol in dichloromethane:
¹H-NMR (DMSO-d₆): 9.41 (s, 1H), 8.36 (s, 1H), 8.27 (d, 1H), 7.90 (d, 1H), 7.77 (s, 1H), 7.50 (s, 1H), 7.30–7.45 (m, 3H), 7.14 (s, 1H), 5.40 (s, 2H), 4.16 (t, 2H), 3.93 (s, 3H), 3.56 (t, 4H), 2.44 (t, 2H), 2.36 (t, 4H), 2.23 (s, 3H), 1.94 (m, 2H):
MS (+ve ESI): 550.5 (M+H)⁺.

2-(2-Chloro-4-fluorobenzyloxy)-3-methyl-5-aminopyridine, used as starting material was obtained as in example 300 (a, b) but starting with 2-chloro-3-methyl-5-nitropyridine and 3-chlorobenzyl alcohol:
¹H-NMR (CDCl₃): 7.50 (d, 1H), 7.43 (s, 1H), 7.29 (m, 3H), 6.90 (d, 1H), 5.30 (s, 2H), 3.31 (s, 2H), 2.21 (s, 3H).

EXAMPLE 318

Preparation of Compound 318 in Table 13

An analogous reaction to that described in example 313, but starting with 2-(2,3-difluorobenzyloxy)-3-methyl-5-aminopyridine (153 mg, 0.61 mmol), yielded the title compound (42 mg, 12% yield) as an off-white solid:
¹H-NMR (DMSO-d₆): 9.42 (s, 1H), 8.38 (s, 1H), 8.29 (d, 1H), 7.90 (d, 1H), 7.77 (s, 1H), 7.37 (m, 2H), 7.22 (m, 1H), 7.14 (s, 1H), 5.48 (s, 2H), 4.17 (t, 2H), 3.93 (s, 3H), 3.56 (t, 4H), 2.45 (t, 2H), 2.36 (t, 4H), 2.20 (s, 3H), 1.94 (m, 2H):
MS (+ve ESI): 552.5 (M+H)⁺.

2-(2-Chloro-4-fluorobenzyloxy)-3-methyl-5-aminopyridine, used as starting material was obtained as in example 300 (a, b) but starting with 2-chloro-3-methyl-5-nitropyridine and 2,3-difluorobenzyl alcohol:
¹H-NMR (CDCl₃): 7.49 (d, 1H), 7.26 (m, 1H), 7.06 (m, 2H), 6.90 (d, 1H), 5.41 (s, 2H), 3.31 (s, 2H), 2.18 (s, 3H).

EXAMPLE 319

Preparation of Compound 319 in Table 13

An analogous reaction to that described in example 313, but starting with 2-(2-chloro-4-fluorobenzyloxy)-3-methyl-5-aminopyridine (222 mg, 0.83 mmol), yielded the title compound (172 mg, 37% yield) as an off-white solid:
¹H-NMR (DMSO-d₆): 9.42 (s, 1H), 8.38 (s, 1H), 8.29 (d, 1H), 7.90 (d, 1H), 7.78 (s, 1H), 7.65 (m, 1H), 7.50 (m, 1H), 7.26 (m, 1H), 7.15 (s, 1H), 5.42 (s, 2H), 4.16 (t, 2H), 3.94 (s, 3H), 3.56 (t, 4H), 2.44 (t, 2H), 2.37 (t, 4H), 2.22 (s, 3H), 1.94 (m, 2H):
MS (+ve ESI): 568.5 (M+H)⁺.

2-(2-Chloro-4-fluorobenzyloxy)-3-methyl-5-aminopyridine, used as starting material was obtained as in example 300 (a, b) but starting with 2-chloro-3-methyl-5-nitropyridine and 2-chloro-4-fluorobenzyl alcohol:
¹H-NMR (CDCl₃): 7.50 (m, 2H), 7.14 (dd, 1H), 6.97 (m, 1H), 6.89 (d, 1H), 5.35 (s, 2H), 3.30 (s, 2H), 2.20 (s, 3H).

EXAMPLE 320

Preparation of Compound 320 in Table 13

An analogous reaction to that described in example 8, but starting with 2-phenylmethylthio-5-aminopyridine (60 mg, 0.28 mmol), yielded the title compound (24 mg, 16% yield) as an off-white solid:
¹H-NMR (DMSO-d₆): 8.95 (s, 1H), 8.71 (s, 1H), 8.00–8.10 (m, 2H), 7.20–7.45 (m, 7H), 4.45 (s, 2H), 4.30 (t, 2H), 4.05 (s, 3H), 3.85–3.91 (m, 4H), 3.23–3.45 (m, 6H), 2.40 (m, 2H):
MS (-ve ESI): 516 (M-H)⁻,
MS (+ve ESI): 518 (M+H)⁺.

2-(Phenylmethylthio)-5-aminopyridine, used as starting material was obtained as in example 300 (a, b) but starting with benzyl mercaptan:
¹H-NMR (CDCl₃): 9.25 (d, 1H, J=2 Hz), 8.20 (m, 1H), 7.22–7.42 (m, 6H), 4.50 (s, 2H):
MS (+ve ESI): 247 (M+H)⁺.

EXAMPLE 321

Preparation of Compound 321 in Table 13

An analogous reaction to that described in example 320, but starting with 2-(3,4-dichlororophenylmethylthio)-5-aminopyridine (195 mg, 0.68 mmol), yielded the title compound (350 mg, 78% yield) as a pale yellow solid:

¹H-NMR (DMSO-d₆): 10.50 (s, 1H), 8.95 (s, 1H), 8.61 (s, 1H), 8.30 (s, 1H), 8.15 (d, 1H), 7.70 (s, 1H), 7.55 (d, 1H), 7.35–7.50 (m, 3H), 4.55 (s, 2H), 4.25 (t, 2H), 4.05 (s, 3H), 3.80–3.91 (m, 4H), 3.23–3.45 (m, 6H), 2.20–2.30 (m, 2H):
MS (−ve ESI): 584 (M−H)⁻,
MS (+ve ESI): 586 (M+H)⁺.

2-(3,4-Dichlorophenylmethylthio)-5-aminopyridine, used as starting material was obtained as in example 300 (a, b) but starting with 3,4-dichlorobenzyl mercaptan:
¹H-NMR (DMSO-d₆): 7.85 (d, 1H, J=2 Hz), 7.52 (d, 1H, J=2 Hz), 7.48 (d, 1H, J=8 Hz), 7.25 (m, 1H), 6.93 (d, 1H, J=8 Hz), 6.83 (m, 1H), 5.23 (s, 2H), 4.23 (s, 2H):
MS (+ve ESI): 285 (M+H)⁺.

EXAMPLE 322

Preparation of Compound 322 in Table 13

An analogous reaction to that described in example 320, but starting with 2-(4-fluorophenylmethylthio)-5-aminopyridine (141 mg, 0.60 mmol), yielded the title compound (239 mg, 66% yield) as a pale yellow solid:
¹H-NMR (DMSO-d₆): 10.50 (s, 1H), 8.95 (s, 1H), 8.61 (s, 1H), 8.30 (s, 1H), 8.15 (d, 1H), 7.35–7.55 (m, 4H), 7.10 (t, 2H), 4.55 (s, 2H), 4.25 (t, 2H), 4.05 (s, 3H), 3.80–3.91 (m, 4H), 3.23–3.45 (m, 6H), 2.20–2.30 (m, 2H):
MS (−ve ESI): 534 (M−H)⁻,
MS (+ve ESI): 536 (M+H)⁺.

2-(4-Fluorophenylmethylthio)-5-aminopyridine, used as starting material was obtained as in example 300 (a, b) but starting with 4-fluororobenzyl mercaptan:
¹H-NMR (DMSO-d₆): 7.85 (d, 1H, J=2 Hz), 7.28–7.33 (m, 2H), 7.00–7.08 (m, 2H), 6.93 (d, 1H, J=8 Hz), 6.82 (m, 1H), 5.20 (2s, H), 4.20 (s, 2H):
MS (+ve ESI): 235 (M+H)⁺.

EXAMPLE 323

Preparation of Compound 323 in Table 13

An analogous reaction to that described in example 320, but starting with 2-(4-fluorobenzylamino)-5-aminopyridine (77 mg, 0.35 mmol), yielded the title compound (125 mg, 60% yield) as an off-white solid:
¹H-NMR (DMSO-d₆): 10.50 (s, 1H), 8.55 (s, 1H), 8.42 (s, 1H), 8.20 (s, 1H), 7.85 (d, 1H), 7.40–7.45 (m, 3H), 7.20 (t, 3H), 6.70 (d, 1H), 4.55 (s, 2H), 4.25 (t, 2H), 4.05 (s, 3H), 3.80–3.91 (m, 4H), 3.23–3.45 (m, 6H), 2.20–2.30 (m, 2H):
MS (+ve ESI): 519 (M+H)⁺.

2-(4-Fluorobenzylamino)-5-aminopyridine, used as starting material was obtained as in example 300 (a, b) but starting with 4-fluorobenzylamine:
¹H-NMR (CDCl₃): 7.69 (d, 1H, J=2 Hz), 7.27–7.33 (m, 2H), 6.88–7.03 (m, 3H), 6.28 (d, 1H, J=8 Hz), 4.33–4.47 (m, 3H), 3.20 (s, 2H):
MS (+ve ESI): 218 (M+H)⁺.

EXAMPLE 324

Preparation of Compound 324 in Table 13

An analogous reaction to that described in example 320, but starting with 2-(3,4-dichlorobenzylamino)-5-aminopyridine (119 mg, 0.44 mmol), yielded the title compound (209 mg, 74% yield) as an off-white solid:
¹H-NMR (DMSO-d₆): 10.50 (s, 1H), 8.55 (s, 1H), 8.42 (s, 1H), 8.20 (s, 1H), 7.85 (d, 1H), 7.40–7.45 (m, 3H), 7.40 (m, 2H), 6.70 (d, 1H), 4.55 (s, 2H), 4.25 (t, 2H), 4.05 (s, 3H), 3.80–3.91 (m, 4H), 3.23–3.45 (m, 6H), 2.20–2.30 (m, 2H):
MS (+ve ESI): 569 (M+H)⁺.

2-(3,4-dichlorobenzylamino)-5-aminopyridine, used as starting material was obtained as in example 300 (a, b) but starting with 3,4-dichlorobenzylamine:
¹H-NMR (CDCl₃): 7.68 (d, 1H, J=2 Hz), 7.43 (d, 1H, J=2 Hz), 7.36 (d, 1H, J=8 Hz), 7.17 (m, 1H), 6.27 (d, 1H, J=8 Hz), 4.40–4.52 (m, 3H), 3.23 (s, 2H):
MS (+ve ESI): 268 (M+H)⁺.

EXAMPLE 325

Preparation of Compound 325 in Table 13

An analogous reaction to that described in example 320, but starting with 2-(4-fluorobenzylamino)-5-aminopyridine (77 mg, 0.35 mmol), yielded the title compound (125 mg, 60% yield) as an off-white solid:
¹H-NMR (DMSO-d₆): 10.55 (s, 1H), 8.58 (s, 1H), 8.30 (s, 1H), 8.13 (s, 1H), 7.80 (m, 1H), 7.35–7.41 (m, 4H), 6.72 (d, 1H, J=8 Hz), 4.58 (s, 2H), 4.32 (t, 2H, J=5 Hz), 4.03 (s, 3H), 3.86–3.93 (m, 4H), 3.18–3.25 (m, 6H), 2.28–2.35 (m, 2H):
MS (+ve ESI): 569 (M+H)⁺,
MS (−ve ESI): 567 (M−H)⁻.

2-(3,5-dichlorobenzylamino)-5-aminopyridine, used as starting material was obtained as in example 300 (a, b) but starting with 3,5-dichlorobenzylamine:
¹H-NMR (CDCl₃): 7.68 (d, 1H, J=2 Hz), 7.16–7.25 (m, 3H), 6.93 (m, 1H), 6.25 (d, 1H, J=8 Hz), 4.40–4.57 (m, 3H), 3.23 (s, 2H):
MS (+ve ESI): 268 (M+H)⁺.

EXAMPLE 326

Preparation of Compound 326 in Table 13

An analogous reaction to that described in example 320, but starting with 2-(4-fluorobenzylamino)-3-methyl-5-aminopyridine (661 mg, 3.10 mmol), yielded the title compound (1.36 g, 85% yield) as an off-white solid:
¹H-NMR (DMSO-d₆): 10.80 (s, 1H), 8.61 (s, 1H), 8.25 (d, 2H), 7.70 (s, 1H), 7.20–7.45 (m, 6H), 4.65 (s, 2H), 4.35 (t, 2H), 4.05 (s, 3H), 3.80–3.91 (m, 4H), 3.23–3.45 (m, 6H), 2.20–2.30 (m, 2H):
MS (−ve ESI): 513 (M−H)⁻,
MS (+ve ESI): 515 (M+H)⁺.

2-(Benzylamino)-3-methyl-5-aminopyridine, used as starting material was obtained as in example 300 (a, b) but starting with 2-chloro-3-methyl-5-nitropyridine and 4-benzylamine:
¹H-NMR (CDCl₃): 7.63 (s, 1H), 7.28–7.41 (m, 5H), 6.81 (s, 1H), 4.60 (d, 2H, J=4 Hz), 4.00 (s, 1H), 3.16 (s, 2H), 2.05 (s, 3H):
MS (+ve ESI): 214 (M+H)⁺.

EXAMPLE 327

Preparation of Compound 327 in Table 14

An analogous reaction to that described in example 6, but starting with 5-amino-2-(4-chlorophenoxy)pyridine (110 mg, 0.50 mmol) and 4-chloro-6-methoxy-7-benzyloxyquinazoline (150 g, 0.50 mmol), yielded the title compound (242 mg, 93% yield) as a white solid:

$^1$H-NMR (DMSO-d$_6$): 11.60 (s, 1H), 8.81 (s, 1H), 8.50 (s, 1H), 8.40 (s, 1H), 8.20 (d, 1H), 7.36–7.59 (m, 8H), 7.18–7.30 (m, 3H), 5.35 (s, 2H), 4.04 (s, 3H):

MS (+ve ESI): 485 (M+H)$^+$.

EXAMPLE 328

Preparation of Compound 328 in Table 14

An analogous reaction to that described in example 6, but starting with 5-amino-2-(pyrid-3-yloxy)pyridine (94 mg, 0.50 mmol) yielded the title compound (224 mg, 92% yield) as a white solid:

$^1$H-NMR (DMSO-d$_6$): 11.55 (s, 1H), 8.80 (s, 1H), 8.55 (s, 1H), 8.45 (d, 2H), 8.38 (s, 1H), 8.25 (d, 1H), 7.75 (m, 1H), 7.51 (m, 3H), 7.40 (m, 4H), 7.30 (d, 1H), 5.35 (s, 2H), 4.05 (s, 3H):

MS (+ve ESI): 452 (M+H)$^+$.

EXAMPLE 329

Preparation of Compound 329 in Table 14

An analogous reaction to that described in example 32, but starting with 4-(3-aminopropyl)morpholine (144 mg, 1.0 mmol) and 4-(6-(3-chlorobenzyloxy)-3-pyridinoamino)-6-methoxy-7-(3-chloropropoxy)quinazoline (100 mg, 0.20 mmol), yielded the title compound (31 mg, 26% yield) as a white solid:

$^1$H-NMR (DMSO-d$_6$): 9.49 (s, 1H), 8.43 (d, 1H), 8.37 (s, 1H), 8.07 (dd, 1H), 7.79 (s, 1H), 7.51 (s, 1H), 7.40 (m, 3H), 7.15 (s, 1H), 6.96 (d, 1H), 5.36 (s, 2H), 4.18 (t, 2H), 3.94 (s, 3H), 3.52 (t, 4H), 2.67 (t, 2H), 2.53 (t, 2H), 2.28 (m, 6H), 1.91 (m, 2H), 1.55 (m, 2H):

MS (+ve ESI): 593.3 (M+H)$^+$.

4-(6-(3-chlorobenzyloxy)-3-pyridinoamino)-6-methoxy-7-(3-chloropropoxy)-quinazoline, used as starting material was obtained as follows:

a) Chloromethyl pivalate (225 ml, 1.56 mol) was added dropwise to a stirred mixture of 6-methoxy-7-benzyloxyquinazol-4-one (400 g, 1.42 mol) and potassium carbonate (783 g, 5.67 mol) in dimethylacetamide (5500 ml). The reaction was heated to 90° C. for 4 hours. The reaction was cooled and filtered to remove inorganic salts. The filtrate was concentrated in vacuo to yield, crude tert-butyl 2-[7-(benzyloxy)-6-methoxy-4-oxo-3(4H)-quinazolinyl]acetate (562 g, 100% yield):

$^1$H-NMR (DMSO-d$_6$): 8.33 (s, 1H), 7.30–7.50 (m, 6H), 7.25 (s, 1H), 5.90 (s, 2H), 5.25 (s, 2H), 3.88 (s, 3H), 1.10 (s, 9H):

MS (+ve ESI): 397 (M+H)$^+$.

b) 10% palladium on carbon (56 g, 53 mmol) was added to a solution of tert-butyl 2-[7-(benzyloxy)-6-methoxy-4-oxo-3(4H)-quinazolinyl]acetate (562 g, 1.42 mmol) in dimethylacetamide (3500 ml) at ambient temperature and stirred for 3 hours under an atmosphere of hydrogen (1 bar). The reaction was filtered through a pad of celite and the solvent evaporated in vacuo. The residual solid was dissolved in 20% methanol in dichloromethane and passed through a pad of silica gel. Evaporation of the solvent in vacuo followed by trituration with methanol yielded, tert-butyl 2-[7-hydroxy-6-methoxy-4-oxo-3(4H)-quinazolinyl]acetate (188 g, 43% yield):

$^1$H-NMR (DMSO-d$_6$): 8.25 (s, 1H), 7.45 (s, 1H), 6.97 (s, 1H), 5.85 (s, 2H), 4.04 (s, 1H), 3.87 (s, 3H), 1.10 (s, 9H):

MS (+ve ESI): 307 (M+H)$^+$.

c) A mixture of tert-butyl 2-[7-hydroxy-6-methoxy-4-oxo-3(4H)-quinazolinyl]-acetate (100 g, 0.327 mol), 3-bromopropanol (49.3 g, 0.355 mol) and potassium carbonate (133 g, 0.967 mol) in dimethylformamide (500 ml) was stirred at 80° C. for 20 hours. The reaction was cooled and concentrated to quarter volume in vacuo. The residue was poured into ice/water (1500 ml) and the resulting solid collected by suction filtration. Purification by crystallisation from ethanol, yielded crude tert-butyl 2-[7-(3-hydroxypropoxy)-6-methoxy-4-oxo-3(4H)-quinazolinyl]acetate (33.8 g, 41% yield) as a beige solid:

$^1$H-NMR (DMSO-d$_6$): 7.95 (s, 1H), 7.43 (s, 1H), 7.1 (s, 1H), 4.16 (t, 2H), 3.86 (m, 5H), 2.08 (t, 2H), 1.12 (s, 9H):

MS (+ve ESI): 365 (M+H)$^+$.

d) Aqueous sodium hydroxide solution (100 ml, 0.2 mol) was added to a solution of tert-butyl 2-[7-(3-hydroxypropoxy)-6-methoxy-4-oxo-3(4H)-quinazolinyl]acetate (33.8 g, 93 mmol) in methanol (300 ml) and the solution heated to reflux for 1 hour. The methanol was evaporated in vacuo and the aqueous residue acidified with aqueous hydrochloric acid then sodium bicarbonate was added. Collection of the solid by suction filtration, washing with water and drying yielded 7-(3-hydroxypropoxy)-6-methoxy-4-quinazolone (26 g, 95% yield):

$^1$H-NMR (DMSO-d$_6$): 7.96 (s, 1H), 7.41 (s, 1H), 7.07 (s, 1H), 4.14 (t, 2H), 3.84 (s, 3H), 3.55 (t, 2H), 1.90 (t, 2H):

MS (+ve ESI): 251 (M+H)$^+$.

e) 7-(3-hydroxypropoxy)-6-methoxy-4-quinazolone (25 g, 100 mmol) was added slowly to a solution of dimethylformamide (1 ml) in thionyl chloride (250 ml). The mixture was heated to reflux for 4 hours then cooled and the solvents evaporated in vacuo. The residue was dissolved in dichloromethane and washed with aqueous sodium bicarbonate, brine, dried over magnesium sulphate and evaporated. Trituration and collection of the solid by suction filtration yielded, 4-chloro-6-methoxy-7-(3-chloroxypropoxy)quinazoline (19.5 g, 68% yield) as a yellow solid:

$^1$H-NMR (CDCl$_3$): 8.85 (s, 1H), 7.40 (s, 1H), 7.38 (s, 1H), 4.38 (t, 2H), 4.03 (s, 3H), 3.8 (t, 2H), 2.40 (m, 2H):

MS (+ve ESI): 287 (M+H)$^+$.

f) An analogous reaction to that described in example 1, but starting with 4-chloro-6-methoxy-7-(3-chloroxypropoxy)quinazoline (574 mg, 2.0 mmol) and 5-amino-2-(3-chlorobenzyloxy)pyridine (468 mg, 2.0 mmol) yielded the title compound (640 mg, 66% yield) as a white solid:

$^1$H-NMR (DMSO-d$_6$): 11.60 (s, 1H), 8.78 (s, 1H), 8.46 (s, 1H), 8.37 (s, 1H), 8.04 (dd, 1H), 7.52 (s, 1H), 7.39 (s, 1H), 7.03 (d, 1H), 5.39 (s, 2H), 4.29 (t, 2H), 4.01 (s, 3H), 3.82 (t, 2H), 2.29 (m, 2H):

MS (+ve ESI): 485.5 (M+H)$^+$.

EXAMPLE 330

Preparation of Compound 330 in Table 14

An analogous reaction to that described in example 329, but starting with 1,1-dimethyl-1,3-diaminopropane (102 mg, 1.0 mmol) yielded the title compound (8 mg, 7% yield) as a white solid:

$^1$H-NMR (DMSO-d$_6$): 9.49 (s, 1H), 8.44 (d, 1H), 8.38 (s, 1H), 8.07 (dd, 1H), 7.79 (s, 1H), 7.52 (s, 1H), 7.40 (m, 3H), 7.17 (s, 1H), 6.96 (d, 1H), 5.38 (s, 2H), 4.19 (t, 2H), 3.95 (s,

3H), 2.66 (m, 2H), 2.49 (t, 2H), 2.22 (t, 2H), 2.09 (s, 6H), 1.91 (m, 2H), 1.52 (m, 2H):
MS (+ve ESI): 551.3 (M+H)+.

EXAMPLE 331

Preparation of Compound 331 in Table 14

An analogous reaction to that described in example 329, but starting with N-methyl ethanolamine (75 mg, 1.0 mmol) yielded the title compound (35 mg, 33% yield) as a white solid:
$^1$H-NMR (DMSO-$d_6$): 9.48 (s, 1H), 8.43 (d, 1H), 8.37 (s, 1H), 8.06 (dd, 1H), 7.79 (s, 1H), 7.51 (s, 1H), 7.40 (m, 3H), 7.15 (s, 1H), 6.96 (d, 1H), 5.37 (s, 2H), 4.31 (t, 1H), 4.17 (t, 2H), 3.94 (s, 3H), 3.45 (q, 2H), 2.49 (t, 2H), 2.41 (t, 2H), 2.19 (s, 3H), 1.91 (m, 2H):
MS (+ve ESI): 524.3 (M+H)+.

EXAMPLE 332

Preparation of Compound 332 in Table 14

An analogous reaction to that described in example 329, but starting with piperidine (85 mg, 1.0 mmol) yielded the title compound (57 mg, 53% yield) as a white solid:
$^1$H-NMR (DMSO-$d_6$): 9.48 (s, 1H), 8.43 (d, 1H), 8.37 (s, 1H), 8.06 (dd, 1H), 7.78 (s, 1H), 7.51 (s, 1H), 7.40 (m, 3H), 7.15 (s, 1H), 6.96 (d, 1H), 5.37 (s, 2H), 4.15 (t, 2H), 3.94 (s, 3H), 2.39 (t, 2H), 2.32 (t, 4H), 1.92 (m, 2H), 1.48 (m, 4H), 1.37 (m, 2H):
MS (+ve ESI): 551.3 (M+H)+.

EXAMPLE 333

Preparation of Compound 333 in Table 14

An analogous reaction to that described in example 329, but starting with piperazine (258 mg, 3.0 mmol) yielded the title compound (32 mg, 30% yield) as a white solid:
$^1$H-NMR (DMSO-$d_6$): 9.49 (s, 1H), 8.44 (d, 1H), 8.37 (s, 1H), 8.06 (dd, 1H), 7.78 (s, 1H), 7.51 (s, 1H), 7.40 (m, 3H), 7.15 (s, 1H), 6.96 (d, 1H), 5.37 (s, 2H), 4.15 (t, 2H), 3.94 (s, 3H), 2.68 (t, 4H), 2.40 (t, 2H), 2.30 (t, 4H), 1.92 (m, 2H):
MS (+ve ESI): 535.6 (M+H)+.

EXAMPLE 334

Preparation of Compound 334 in Table 14

An analogous reaction to that described in example 329, but starting with pyrrolidine (213 mg, 3.0 mmol) yielded the title compound (37 mg, 36% yield) as a white solid:
$^1$H-NMR (DMSO-$d_6$): 9.56 (s, 1H), 8.51 (d, 1H), 8.45 (s, 1H), 8.14 (dd, 1H), 7.86 (s, 1H), 7.59 (s, 1H), 7.48 (m, 3H), 7.22 (s, 1H), 7.03 (d, 1H), 5.44 (s, 2H), 4.24 (t, 2H), 4.01 (s, 3H), 2.47–2.71 (m, 6H), 2.02 (m, 2H), 1.75 (m, 4H):
MS (+ve ESI): 520.7 (M+H)+.

EXAMPLE 335

Preparation of Compound 335 in Table 14

An analogous reaction to that described in example 329, but starting with 2,2-dimethylethanolamine (267 mg, 3.0 mmol) yielded the title compound (24 mg, 26% yield) as a white solid:
$^1$H-NMR (DMSO-$d_6$): 9.55 (s, 1H), 8.51 (d, 1H), 8.45 (s, 1H), 8.13 (dd, 1H), 7.86 (s, 1H), 7.59 (s, 1H), 7.48 (m, 3H), 7.24 (s, 1H), 7.03 (d, 1H), 5.44 (s, 2H), 4.48 (bs, 1H), 4.26 (t, 2H), 4.01 (s, 3H), 3.22 (s, 2H), 2.69 (t, 2H), 1.94 (m, 2H), 1.00 (s, 6H):
MS (+ve ESI): 538.6 (M+H)+.

Biological Data

The compounds of the invention inhibit the serine/threonine kinase activity of the aurora2 kinase and thus inhibit the cell cycle and cell proliferation. These properties may be assessed, for example, using one or more of the procedures set out below:

(a) In Vitro aurora2 kinase inhibition test

This assay determines the ability of a test compound to inhibit serine/threonine kinase activity. DNA encoding aurora2 may be obtained by total gene synthesis or by cloning. This DNA may then be expressed in a suitable expression system to obtain polypeptide with serine/threonine kinase activity. In the case of aurora2, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5' PCR primer contained a recognition sequence for the restriction endonuclease BamH1 5' to the aurora2 coding sequence. This allowed the insertion of the aurora2 gene in frame with the 6 histidine residues, spacer region and rTEV protease cleavage site encoded by the pFastBac HTc vector. The 3' PCR primer replaced the aurora2 stop codon with additional coding sequence followed by a stop codon and a recognition sequence for the restriction endonuclease Not1. This additional coding sequence (5' TAC CCA TAC GAT GTT CCA GAT TAC GCT TCT TAA 3') encoded for the polypeptide sequence YPYDVPDYAS. This sequence, derived from the influenza hemagglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged aurora2 protein. Details of the methods for the assembly of recombinant DNA molecules can be found in standard texts, for example Sambrook et al. 1989, Molecular Cloning—A Laboratory Manual, 2$^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the aurora2 gene was transformed into *E. coli* DH10Bac cells containing the baculovirus genome (bacmid DNA) and via a transposition event in the cells, a region of the pFastBac vector containing gentamycin resistance gene and the aurora2 gene including the baculovirus polyhedrin promoter was transposed directly into the bacmid DNA. By selection on gentamycin, kanamycin, tetracycline and X-gal, resultant white colonies should contain recombinant bacmid DNA encoding aurora2. Bacmid DNA was extracted from a small scale culture of several BH10Bac white colonies and transfected into *Spodoptera frugiperda* Sf21 cells grown in TC100 medium (GibcoBRL) containing 10% serum using CellFECTIN reagent (GibcoBRL) following manufacturer's instructions. Virus particles were harvested by collecting cell culture medium 72 hrs post transfection. 0.5 mls of medium was used to infect 100 ml suspension culture of Sf21s containing $1\times10^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant aurora2 protein.

For the large scale expression of aurora2 kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2 \times 10^6$ cells ml$^{-1}$ they were infected with plaque-pure aurora2 recombinant virus at a multiplicity of infection of 1 and harvested 48 hours later. All subsequent purification steps were performed at 4° C. Frozen insect cell pellets containing a total of $2.0 \times 10^8$ cells were thawed and diluted with lysis buffer (25 mM HEPES (N-[2-hydroxyethyl]piperazine-N'-[2-ethanesulphonic acid]) pH7.4 at 4° C., 100 mM KCl, 25 mM NaF, 1 mM Na$_3$VO$_4$, 1 mM PMSF (phenylmethylsulphonyl fluoride), 2 mM 2-mercaptoethanol, 2 mM imidazole, 1 µg/ml aprotinin, 1 µg/ml pepstatin, 1 µg/ml leupeptin), using 1.0 ml per $3 \times 10^7$ cells. Lysis was achieved using a dounce homogeniser, following which the lysate was centrifuged at 41,000 g for 35 minutes. Aspirated supernatant was pumped onto a 5 mm diameter chromatography column containing 500 µl Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH7.4 at 4° C., 100 mM KCl, 20 mM imidazole, 2 mM 2-mercaptoethanol). Bound aurora2 protein was eluted from the column using elution buffer (25 mM HEPES pH7.4 at 4° C., 100 mM KCl, 400 mM imidazole, 2 mM 2-mercaptoethanol). An elution fraction (2.5 ml) corresponding to the peak in UV absorbance was collected. The elution fraction, containing active aurora2 kinase, was dialysed exhaustively against dialysis buffer (25 mM HEPES pH7.4 at 4° C., 45% glycerol (v/v), 100 mM KCl, 0.25% Nonidet P40 (v/v), 1 mM dithiothreitol).

Each new batch of aurora2 enzyme was titrated in the assay by dilution with enzyme diluent (25 mM Tris-HCl pH7.5, 12.5 mM KCl, 0.6 mM DTT). For a typical batch, stock enzyme is diluted 1 in 666 with enzyme diluent & 20 µl of dilute enzyme is used for each assay well. Test compounds (at 10 mM in dimethylsulphoxide (DMSO)) were diluted with water & 10 µl of diluted compound was transferred to wells in the assay plates. "Total" & "blank" control wells contained 2.5% DMSO instead of compound. Twenty microliters of freshly diluted enzyme was added to all wells, apart from "blank" wells. Twenty microliters of enzyme diluent was added to "blank" wells. Twenty microliters of reaction mix (25 mM Tris-HCl, 78.4 mM KCl, 2.5 mM NaF, 0.6 mM dithiothreitol, 6.25 mM MnCl$_2$, 6.25 mM ATP, 7.5 µM peptide substrate [biotin-LRRWSLGLRRWS-LGLRRWSLGLRRWSLG]) containing 0.2 µCi [$\gamma^{33}$P]ATP (Amersham Pharmacia, specific activity≧2500 Ci/mmol) was then added to all test wells to start the reaction. The plates were incubated at room temperature for 60 minutes. To stop the reaction 100 µl 20% v/v orthophosphoric acid was added to all wells. The peptide substrate was captured on positively-charged nitrocellulose P30 filternat (Whatman) using a 96-well plate harvester (TomTek) & then assayed for incorporation of $^{33}$P with a Beta plate counter. "Blank" (no enzyme) and "total" (no compound) control values were used to determine the dilution range of test compound which gave 50% inhibition of enzyme activity.

In this test, compound 6 in Table 2 gave 50% inhibition of enzyme activity at a concentration of 0.00785 µM.

(b) In Vitro cell proliferation assay

These and other assays can be used to determine the ability of a test compound to inhibit the growth of adherent mammalian cell lines, for example the human tumour cell line MCF7.

Assay 1

MCF-7 (ATCC HTB-22) or other adherent cells were typically seeded at $1 \times 10^3$ cells per well (excluding the peripheral wells) in DMEM (Sigma Aldrich) without phenol red, plus 10% foetal calf serum, 1% L-glutamine and 1% penicillin/streptomycin in 96 well tissue culture treated clear plates (Costar). The following day (day 1), the media was removed from a no treatment control plate and the plate stored at −80° C. The remaining plates were dosed with compound (diluted from 10 mM stock in DMSO using DMEM (without phenol red, 10% FCS, 1% L-glutamine, 1% penicillin/streptomycin). Untreated control wells were included on each plate. After 3 days in the presence/absence of compound (day 4) the media was removed and the plates stored at −80° C. Twenty four hours later the plates were thawed at room temperature and cell density determined using the CyQUANT cell proliferation assay kit (c-7026/c-7027 Molecular Probes Inc.) according to manufacturers directions. Briefly, 200 µl of cell lysis/dye mixture (10 µl of 20× cell lysis buffer B, 190 µl of sterile water, 0.25 µl of CYQUANT GR dye) was added to each well and the plates incubated at room temperature for 5 minutes in the dark. The fluorescence of the wells was then measured using a fluorescence microplate reader (gain 70, 2 reads per well, 1 cycle with excitation 485 nm and emission 530 nm using a CytoFluor plate reader (PerSeptive Biosystems Inc.)). The values from day 1 and day 4 (compound treated) together with the values from the untreated cells were used to determine the dilution range of a test compound that gave 50% inhibition of cell proliferation. Compound 6 in Table 2 was effective in this test at 1.7 µM.

These values could also be used to calculate the dilution range of a test compound at which the cell density dropped below the day 1 control value. This indicates the cytotoxicity of the compound.

Assay 2

This assay determines the ability of at test compound to inhibit the incorporation of the thymidine analogue, 5'-bromo-2'-deoxy-uridine (BrdU) into cellular DNA. MCF-7, or other adherent cells were typically seeded at $0.8 \times 10^4$ cells per well in DMEM (Sigma Aldrich) without phenol red, plus 10% foetal calf serum, 1% L-glutamine and 1% penicillin/streptomycin (50 µl/well) in 96 well tissue culture treated 96 well plates (Costar) and allowed to adhere overnight. The following day the cells were dosed with compound (diluted from 10 mM stock in DMSO using DMEM (without phenol ed, 10% FCS, 1% L-glutamine, 1% penicillin/streptomycin). Untreated control wells and wells containing a compound known to give 100% inhibition of BrdU incorporation were included on each plate. After 48 hours in the presence/absence of test compound the ability of the cells to incorporate BrdU over a 2 hour labelling period was determined using a Boehringer (Roche) Cell Proliferation BrdU ELISA kit (cat. No. 1 647 229) according to manufacturers directions. Briefly, 15 µl of BrdU labelling reagent (diluted 1:100 in media—DMEM no phenol red, 10% FCS, 1% L-glutamine, 1% penicillin/streptomycin) was added to each well and the plate returned to a humidified (+5% CO$_2$) 37° C. incubator for 2 hours. After 2 hours the labelling reagent was removed by decanting and tapping the plate on a paper towel. FixDenat solution (50 µl per well)

was added and the plates incubated at room temperature for 45 mins with shaking. The FixDenat solution was removed by decanting and tapping the inverted plate on a paper towel. The plate was then washed once with phosphate buffered saline (PBS) and 100 µl/well of Anti-BrdU-POD antibody solution (diluted 1:100 in antibody dilution buffer) added. The plate was then incubated at room temperature with shaking for 90 min. Unbound Anti-BrdU-POD antibody was removed by decanting and washing the plate 5 times with PBS before being blotted dry. TMB substrate solution was added (100 µl/well) and incubated for approximately 10 minutes at room temperature with shaking until a colour change was apparent. The optical density of the wells was then determined at 690 nm wavelength using a Titertek Multiscan plate reader. The values from compound treated, untreated and 100% inhibition controls were used to determine the dilution range of a test compound that gave 50% inhibition of BrdU incorporation. Compound 6 in Table 2 was effective in this test at from 1.92–2.848 µM (c) In Vitro cell cycle analysis assay This assay determines the ability of a test compound to arrest cells in specific phases of the cell cycle. Many different mammalian cell lines could be used in this assay and MCF7 cells are included here as an example. MCF-7 cells were seeded at $3 \times 10^5$ cells per T25 flask (Costar) in 5 ml DMEM (no phenol red 10% FCS, 1% L-glutamine 1% penicillin/streptomycin). Flasks were then incubated overnight in a humidified 37° C. incubator with 5% $CO_2$. The following day 1 ml of DMEM (no phenol red 10% FCS, 1% L-glutamine 1% penicillin/streptomycin) carrying the appropriate concentration of test compound solubilised in DMSO was added to the flask. A no compound control treatments was also included (0.5% DMSO). The cells were then incubated for a defined time (usually 24 hours) with compound. After this time the media was aspirated from the cells and they were washed with 5 ml of prewarmed (37° C.) sterile PBSA, then detached from the flask by brief incubation with trypsin and followed by resuspension in 10 ml of 1% Bovine Serum Albumin (BSA, Sigma-Aldrich Co.) in sterile PBSA. The samples were then centrifuged at 2200 rpm for 10 min. The supernatant was aspirated and the cell pellet was resuspended in 200 µl of 0.1% (w/v) Tris sodium citrate, 0.0564% (w/v) NaCl, 0.03% (v/v) Nonidet NP40, [pH 7.6]. Propridium Iodide (Sigma Aldrich Co.) was added to 40 µg/ml and RNAase A (Sigma Aldrich Co.) to 100 µg/ml. The cells were then incubated at 37° C. for 30 minutes. The samples were centrifuged at 2200 rpm for 10 min, the supernatant removed and the remaining pellet (nuclei) resuspended in 200 µl of sterile PBSA. Each sample was then syringed 10 times using 21 gauge needle. The samples were then transferred to LPS tubes and DNA content per cell analysed by Fluorescence activated cell sorting (FACS) using a FACScan flow cytometer (Becton Dickinson). Typically 25000 events were counted and recorded using CellQuest v1.1 software (Verity Software). Cell cycle distribution of the population was calculated using Modfit software (Verity Software) and expressed as percentage of cells in G0/G1, S and G2/M phases of the cell cycle.

Treating MCF7 cells with 10 µM Compound 6 in Table 2 for 24 hours produced the following changes in cell cycle distribution:

| Treatment | % Cells in G1 | % Cells in S | % Cells in G2/M |
| --- | --- | --- | --- |
| DMSO (control) | 74.29 | 20 | 5.97 |
| 10 µM Compound 6 | 43.22 | 18 | 30.38 |

The invention claimed is:
1. A compound of formula (I)

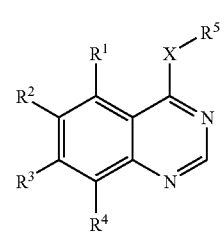

or a salt thereof;
where X is O, or S, S(O), $S(O)_2$ or $NR^6$ where $R^6$ is hydrogen or $C_{1-6}$alkyl;
$R^5$ is a group of sub-formula (iii) or (v)

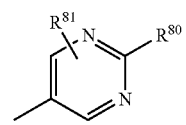

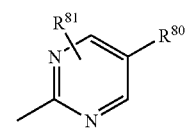

where $R^{80}$ is a group of sub-formula (II)

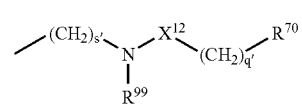

where q' is 0, 1, 2, 3 or 4;
s' is 0 or 1;
$X^{12}$ is C(O) or $S(O_2)$,
$R^{70}$ is $C_{3-7}$cycloalkyl,
or $R^{70}$ is of the Formula (III):

 (III)

wherein J is aryl, heteroaryl or heterocyclyl and K is a bond, oxy, imino, N-($C_{1-6}$alkyl)imino, oxy$C_{1-6}$alkylene, imino$C_{1-6}$alkylene, N-($C_{1-6}$alkyl)imino$C_{1-6}$alkylene, —NHC(O)—, —$SO_2$NH—, —$NHSO_2$— or —NHC(O)—$C_{1-6}$alkylene-, and any aryl, heteroaryl or heterocyclyl group in a $R^{70}$ group is optionally substituted by one or more groups selected from hydroxy, oxo, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)—O—, $C_{1-6}$alkylS$(O)_n$— wherein n is 0–2, N-$C_{1-6}$alkylamino, N,N-($C_{1-6}$ alkyl)$_2$amino, C$_{1-6}$alkoxycarbonyl, N-C$_{1-6}$ alkylcarbamoyl, N,N-(C$_{1-6}$alkyl)$_2$carbamoyl, C$_{2-6}$alkanoyl, C$_{1-6}$alkanoyloxy, C$_{1-6}$alkanoylamino, N-C$_{1-6}$alkylsulphamoyl, N,N-(C$_{1-6}$alkyl)$_2$sulphamoyl, C$_{1-6}$alkylsulphonylamino and C$_{1-6}$alkylsulphonyl-N-(C$_{1-6}$alkyl) amino, or any aryl, heteroaryl or heterocyclyl group in a R$^{70}$ group is optionally substituted with one or more groups of the Formula (IV):

—B$^1$—(CH$_2$)$_p$—A$^1$   (IV)

wherein A$^1$ is halo, hydroxy, C$_{1-6}$alkoxy, cyano, amino, N-C$_{1-6}$alkylamino, N,N-(C$_{1-6}$alkyl)$_2$amino, carboxy, C$_{1-6}$alkoxycarbonyl, carbamoyl, N-C$_{1-6}$alkylcarbamoyl or N,N-(C$_{1-6}$alkyl)$_2$carbamoyl, p is 1–6, and B$^1$ is a bond, oxy, imino, N-(C$_{1-6}$alkyl)imino or —NHC(O)—, with the proviso that p is 2 or more unless B$^1$ is a bond or —NHC(O)—;

or any aryl, heteroaryl or heterocyclyl group in a R$^{70}$ group is optionally substituted with one or more groups of the Formula (V):

—E$^1$—D$^1$   (V)

wherein D$^1$ is aryl, heteroaryl or heterocyclyl and E$^1$ is a bond, C$_{1-6}$alkylene, oxyC$_{1-6}$alkylene, oxy, imino, N-(C$_{1-6}$alkyl)imino, iminoC$_{1-6}$alkylene, N-(C$_{1-6}$alkyl)-iminoC$_{1-6}$alkylene, C$_{1-6}$alkylene-oxyC$_{1-6}$alkylene, C$_{1-6}$alkylene-iminoC$_{1-6}$alkylene, C$_{1-6}$alkylene-N-(C$_{1-6}$alkyl)-iminoC$_{1-6}$alkylene, —NHC(O)—, —NHSO$_2$—, —SO$_2$NH— or —NHC(O)—C$_{1-6}$alkylene-, and any aryl, heteroaryl or heterocyclyl group in a R$^{70}$ group is optionally substituted with one or more groups selected from hydroxy, halo, C$_{1-6}$alkyl, C$_{1-6}$alkoxy, carboxy, C$_{1-6}$alkoxycarbonyl, carbamoyl, N-C$_{1-6}$alkylcarbamoyl, N-(C$_{1-6}$alkyl)$_2$carbamoyl, C$_{2-6}$alkanoyl, amino, N-C$_{1-6}$alkylamino and N,N-(C$_{1-6}$ alkyl)$_2$amino, and any C$_{3-7}$cycloalkyl or heterocyclyl group in a R$^{70}$ group is optionally substituted with one or two oxo or thioxo substituents, and any of the R$^{70}$ groups defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, C$_{1-6}$alkoxy, N-C$_{1-6}$alkylamino, N,N-(C$_{1-6}$alkyl)$_2$amino and heterocyclyl;

or R$^{70}$ may be cycloalkenyl;

and R$^{99}$ is hydrogen or a group C(O)R$^{70}$ where R$^{70}$ is as defined above; and R$^{81}$ is hydrogen, halo, C$_{1-4}$alkoxy, cyano, trifluoromethyl, or phenyl, and R$^1$, R$^2$, R$^3$, R$^4$ are independently selected from halogeno, cyano, nitro, C$_{1-3}$alkylsulphanyl, —N(OH)R$^7$— wherein R$^7$ is hydrogen, or C$_{1-3}$alkyl, or R$^9$X$^1$— wherein X$^1$ represents a direct bond, —O—, —CH$_2$—, —OC(O)—, —C(O)—, —S—, —SO—, —SO$_2$—, —NR$^{10}$C(O)—, —C(O)NR$^{11}$—, —SO$_2$NR$^{12}$—, —NR$^{13}$SO$_2$— or —NR$^{14}$—, wherein R$^{10}$, R$^{11}$, R$^{12}$, R$^{13}$ and R$^{14}$ each independently represents hydrogen, C$_{1-3}$alkyl or C$_{1-3}$alkoxyC$_{2-3}$alkyl, provided that at least one of R$^1$, R$^2$, R$^3$ and R$^4$ is a group R$^9$X$^1$— and R$^9$ is selected from one of the following groups: provided that at least one of R$^2$ or R$^3$ is other than hydrogen;

1) hydrogen or C$_{1-5}$alkyl which may be unsubstituted or which may be substituted with one or more groups selected from hydroxy, oxiranyl, fluoro, chloro, bromo and amino;

2) —R$^a$X$^2$C(O)R$^{15}$ wherein X$^2$ represents —O— or —NR$^{16}$— in which R$^{16}$ represents hydrogen, C$_{1-3}$alkyl or C$_{1-3}$alkoxyC$_{2-3}$alkyl and R$^{15}$ represents C$_{1-3}$alkyl, —NR$^{17}$R$^{18}$ or —OR$^{19}$ wherein R$^{17}$, R$^{18}$ and R$^{19}$ which may be the same or different each represents hydrogen, C$_{1-5}$alkyl, hydroxyC$_{1-5}$alkyl or C$_{1-3}$alkoxyC$_{2-3}$alkyl;

3) —R$^b$X$^3$R$^{20}$ wherein X$^3$ represents —O—, —C(O)—S—, —SO—, —SO$_2$—, —OC(O)—, —NR$^{21}$C(O)$_s$—, —C(O)NR$^{22}$—, —SO$_2$NR$^{23}$—, —NR$^{24}$SO$_2$— or —NR$^{25}$— wherein R$^{21}$, R$^{22}$, R$^{23}$, R$^{24}$ and R$^{25}$ each independently represents hydrogen, C$_{1-3}$alkyl, hydroxy C$_{1-4}$alkyl or C$_{1-3}$alkoxyC$_{2-3}$alkyl and s is 1 or 2 and R$^{20}$ represents hydrogen, C$_{1-6}$alkyl, C$_{2-6}$alkenyl, cyclopropyl, cyclobutyl, cyclopentyl, cyclohexyl, phenyl or a 5–6-membered saturated heterocyclic group with 1–2 heteroatoms, selected independently form O, S, and N, which C$_{1-6}$alkyl group may bear 1, 2 or 3 substituents selected from oxo, hydroxy, halogeno, cyclopropyl, amino, C$_{1-4}$alkylamino, C$_{1-4}$alkanoyldi-C$_{1-4}$alkylamino, C$_{1-4}$alkylthio, C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(R$^{b'}$)$_g$D$^2$ wherein f is 0 or 1, g is 0 or 1 and D$^2$ is a C$_{3-6}$cycloalkyl group or a 5–6-membered saturated heterocyclic group with 1–2 heteroatoms, selected independently from O, S and N, which cyclic group may bear one or more substituents selected from C$_{1-4}$alkyl;

4) —R$^c$X$^4$R$^{c'}$X$^5$R$^{26}$ wherein X$^4$ and X$^5$ which may be the same or different are each —O—, —C(O), —S—, —SO—, —SO$_2$—, —NR$^{27}$C(O)$_s$—, —C(O)$_s$NR$^{28}$—, —SO$_2$NR$^{29}$—, —NR$^{30}$SO$_2$— or —NR$^{31}$— wherein R$^{27}$, R$^{28}$, R$^{29}$, R$^{30}$ and R$^{31}$ each independently represents hydrogen, C$_{1-3}$alkyl or C$_{1-3}$alkoxyC$_{2-3}$alkyl and s is 1 or 2 and R$^{26}$ represents hydrogen, C$_{1-3}$alkyl, hydroxyC$_{1-3}$alkyl or C$_{1-3}$alkoxyC$_{2-3}$alkyl;

5) R$^{32}$ wherein R$^{32}$ is a 4–6-membered cycloalkyl or saturated heterocyclic ring, linked via carbon or nitrogen, with 1–2 heteroatoms, selected independently from O, S and N, which cycloalkyl or heterocyclic group may bear 1 or 2 substituents selected from oxo, hydroxy, halogeno, cyano, C$_{1-4}$alkyl, hydroxyC$_{1-4}$alkyl, cyanoC$_{1-4}$alkyl, cyclopropyl, C$_{1-4}$alkylsulphonylC$_{1-4}$alkyl, C$_{1-4}$alkoxycarbonyl, carboxamido, C$_{1-4}$aminoalkyl, C$_{1-4}$alkylamino, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy, nitro, amino, C$_{1-4}$alkoxy, C$_{1-4}$hydroxyalkoxy, carboxy, trifluoromethyl, —C(O)NR$^{38}$R$^{39}$, —NR$^{40}$C(O)R$^{41}$, wherein R$^{38}$, R$^{39}$, R$^{40}$ and R$^{41}$, which may be the same or different, each represents hydrogen, C$_{1-4}$alkyl, hydroxyC$_{1-4}$alkyl or C$_{1-3}$alkoxyC$_{2-3}$alkyl, and a group —(—O—)$_f$(C$_{1-4}$alkyl)$_g$ringD wherein f is 0 or 1, g is 0 or 1 and ring D is a cyclic group selected from C$_{3-6}$cycloalkyl, aryl or 5–6-membered saturated or unsaturated heterocyclic group with 1–2 heteroatoms, selected independently from O, S and N, which cyclic group may bear one or more substituents selected from halo and C$_{1-4}$alkyl;

6) —R$^d$R$^{32}$ wherein R$^{32}$ is as defined hereinbefore;

7) —R$^e$R$^{32}$ wherein R$^{32}$ is as defined hereinbefore;

8) —R$^f$R$^{32}$ wherein R$^{32}$ is as defined hereinbefore;

9) $R^{33}$ wherein $R^{33}$ represents a pyridone group, a phenyl group or a 5–6-membered aromatic heterocyclic group, linked via carbon or nitrogen, with 1–3 heteroatoms selected from O, N and S, which pyridone, phenyl or aromatic heterocyclic group may carry up to 5 substituents selected from hydroxy, nitro, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, oxo, cyano$C_{1-4}$alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy, carboxy, carboxamido, trifluoromethyl, cyano, —C(O)NR$^{38}$R$^{39}$, —NR$^{40}$C(O)R$^{41}$, wherein R$^{38}$, R$^{39}$, R$^{40}$ and R$^{41}$, which may be the same or different, each represents hydrogen, $C_{1-4}$alkyl, hydroxy$C_{1-4}$alkyl or $C_{1-3}$alkoxy$C_{2-3}$alkyl, and a group —(—O—)$_f$($C_{1-4}$alkyl)$_g$ringD wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl;

10) —R$^g$R$^{33}$ wherein R$^{33}$ is as defined hereinbefore;

11) —R$^h$R$^{33}$ wherein R$^{33}$ is as defined hereinbefore;

12) —R$^i$R$^{33}$ wherein R$^{33}$ is as defined hereinbefore;

13) —R$^j$X$^6$R$^{33}$ wherein X$^6$ represents —O—, —C(O)—, —S—, —SO—, —SO$_2$—, —OC(O)—, —NR$^{38'}$C(O)—, —C(O)NR$^{39'}$—, —SO$_2$NR$^{40'}$—, —NR$^{41'}$SO$_2$— or —NR$^{42'}$—, wherein R$^{38'}$, R$^{39'}$, R$^{40'}$, R$^{41'}$ and R$^{42'}$ each independently represents hydrogen, $C_{1-3}$alkyl, hydroxy$C_{1-3}$alkyl or $C_{1-3}$alkoxy$C_{2-3}$alkyl, or alkyl optionally substituted and R$^{33}$ is as defined hereinbefore;

14) —R$^k$X$^7$R$^{33}$ wherein X$^7$ represents —O—, —C(O), —S—, —SO—, —SO$_2$—, —NR$^{43}$C(O)—, —C(O)NR$^{44}$—, —SO$_2$NR$^{45}$—, —NR$^{46}$SO$_2$— or —NR$^{47}$—, wherein R$^{43}$, R$^{44}$, R$^{45}$, R$^{46}$ and R$^{47}$ each independently represents hydrogen, $C_{1-3}$alkyl, hydroxy$C_{1-3}$alkyl or $C_{1-3}$alkoxy$C_{2-3}$alkyl, and R$^{33}$ is as defined hereinbefore;

15) —R$^m$X$^8$R$^{33}$ wherein X$^8$ represents —O—, —C(O)—, —S—, —SO—, —SO$_2$—, —NR$^{48}$C(O)—, —C(O)NR$^{49}$—, —SO$_2$NR$^{50}$—, —NR$^{51}$SO$_2$— or —NR$^{52}$—, wherein R$^{48}$, R$^{49}$, R$^{50}$, R$^{51}$ and R$^{52}$ each independently represents hydrogen, $C_{1-3}$alkyl, hydroxy$C_{1-3}$alkyl or $C_{1-3}$alkoxy$C_{2-3}$alkyl, and R$^{33}$ is as defined hereinbefore;

16) —R$^n$X$^9$R$^{n'}$R$^{33}$ wherein X$^9$ represents —O—, —C(O)—, —S—, —SO—, —SO$_2$—, —NR$^{53}$C(O)—, —C(O)NR$^{54}$—, —SO$_2$NR$^{55}$—, —NR$^{56}$SO$_2$— or —NR$^{57}$—, wherein R$^{53}$, R$^{54}$, R$^{55}$, R$^{56}$ and R$^{57}$ each independently represents hydrogen, $C_{1-3}$alkyl, hydroxy$C_{1-3}$alkyl or $C_{1-3}$alkoxy$C_{2-3}$alkyl, and R$^{33}$ is as defined hereinbefore;

17) —R$^p$X$^9$—R$^{p'}$R$^{32}$ wherein X$^9$ and R$^{32}$ are as defined hereinbefore;

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N-$C_{1-4}$alkylaminosulphonyl and N,N-di($C_{1-4}$alkyl)aminosulphonyl;

20) —R$^r$X$^9$R$^{r'}$R$^{32}$ wherein X$^9$ and R$^{32}$ are as defined hereinbefore;

21) —R$^u$X$^9$R$^{u''}$R$^{32}$ wherein X$^9$ and R$^{32}$ are as defined hereinbefore; and 22) —R$^v$R$^{58}$(R$^{v'}$)$_q$(X$^9$)$_r$R$^{59}$ wherein X$^9$ is as defined hereinbefore, q is 0 or 1, r is 0 or 1, and R$^{58}$ is a $C_{1-3}$alkylene group or a cyclic group selected from cyclopropyl, cyclobutyl, cyclopentylene, cyclohexylene or a 5–6-membered saturated heterocyclic group with 1–2 heteroatoms, selected independently from O, S and N, which $C_{1-3}$alkylene group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD, wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl; and R$^{59}$ is hydrogen, $C_{1-3}$alkyl, or a cyclic group selected from cyclopropyl, cyclobutyl, cyclopentyl, cyclohexyl and a 5–6-membered saturated heterocyclic group with 1–2 heteroatoms, selected independently from O, S and N, which $C_{1-3}$alkyl group may bear 1 or 2 substituents selected from oxo, hydroxy, halogeno, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD wherein f is 0 or 1, g is 0 or 1 and D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl;

and wherein R$^a$, R$^b$, R$^{b'}$, R$^c$, R$^{c'}$, R$^d$, R$^g$, R$^j$, R$^n$, R$^{n'}$, R$^p$, R$^{p'}$, R$^r$, R$^{u'}$, R$^v$ and R$^{v'}$ are independently selected from $C_{1-6}$alkylene groups optionally substituted by one or more substituents selected from hydroxy, halogeno, amino, R$^e$ R$^h$, R$^k$ and R$^t$ are independently selected from $C_{2-8}$alkenylene groups optionally substituted by one or more substituents selected from hydroxy, halogeno, amino, and R$^t$ may additionally be a bond; and R$^f$, R$^i$, R$^m$ and R$^u$ are independently selected from by $C_{2-8}$alkynylene groups optionally substituted by one or more substituents selected from hydroxy, halogeno, amino; and where a functional group is selected from nitro, cyano, halo, oxo, =CR$^{78}$R$^{79}$, C(O)$_x$R$^{77}$, OR$^{77}$, S(O)$_y$R$^{77}$, NR$^{78}$R$^{79}$, C(O)NR$^{78}$R$^{79}$, OC(O)NR$^{78}$R$^{79}$, =NOR$^{77}$, —NR$^{77}$C(O)$_x$R$^{78}$, —NR$^{77}$CONR$^{78}$R$^{79}$, —N=CR$^{78}$R$^{79}$, S(O)$_y$NR$^{78}$R$^{79}$ or —NR$^{77}$S(O)$_y$R$^{78}$ where $R^{77}$, $R^{78}$ and $R^{79}$ are independently selected from hydrogen, optionally substituted hydrocarbyl, optionally substituted heterocyclyl or optionally substituted alkoxy, or $R^{78}$ and $R^{79}$ together form an optionally substituted ring which optionally contains further heteroatoms such as oxygen, nitrogen, S, S(O) or $S(O)_2$, where x is an integer of 1 or 2, y is 0 or an integer of 1–3 and where hydrocarbyl, heterocyclyl or alkoxy groups $R^{77}$, $R^{78}$ and $R^{79}$ as well as rings formed by $R^{78}$ and $R^{79}$ are optionally substituted by halo, perhaloalkyl, mercapto, alkylthio, hydroxy, carboxy, alkoxy, heteroaryl, heteroaryloxy, cycloalkyl, cycloalkenyl, cycloalkynyl, alkenyloxy, alkynyloxy, alkoxyalkyl, aryloxy where the aryl group may be substituted by halo, nitro, or hydroxy, cyano, nitro, amino, mono- or di-alkyl amino, oximino or $S(O)_y R^{90}$ where y is 0 or an integer of 1–3 and $R^{90}$ is a alkyl; and wherein hydrocarbyl is selected from alkyl, alkenyl, alkynyl, aryl, aralkyl, cycloalkyl, cycloalkenyl, or combinations thereof.

2. A compound according to claim 1 wherein $R^1$, $R^2$, $R^3$, $R^4$ are independently selected from, halo, cyano, nitro, trifluoromethyl, $C_{1-3}$alkyl, or other groups from formula $-X^1 R^9$ wherein $X^1$ represents a direct bond, $-O-$, $-CH_2-$, $-OCO-$, carbonyl, $-S-$, $-SO-$, $-SO_2-$, $-NR^{10}CO-$, $-CONR^{11}-$, $-SO_2 NR^{12}-$, $-NR^{13}SO_2-$ or $-NR^{14}-$, wherein $R^{10}$, $R^{11}$, $R^{12}$, $R^{13}$ and $R^{14}$ each independently represents hydrogen, $C_{1-3}$alkyl or $C_{1-3}$alkoxy$C_{2-3}$alkyl, and $R^9$ is selected from one of the following groups:

1') hydrogen or $C_{1-5}$alkyl which may be unsubstituted or which may be substituted with one or more groups selected from hydroxy, fluoro or amino, 2') $C_{1-5}$-alkyl$X^2 C(O)R^{15}$ wherein $X^2$ represents $-O-$ or $-NR^{16}-$ in which $R^{16}$ represents hydrogen, $C_{1-3}$alkyl or $C_{1-3}$alkoxy$C_{2-3}$alkyl and $R^{15}$ represents $C_{1-3}$alkyl, $-NR^{17}R^{18}$ or $-OR^{19}$ wherein $R^{17}$, $R^{18}$ and $R^{19}$ which may be the same or different each represents hydrogen, $C_{1-3}$alkyl or $C_{1-3}$alkoxy$C_{2-3}$alkyl;

3') $C_{1-5}$alkyl$X^3 R^{20}$ wherein $X^3$ represents $-O-$, $-S-$, $-SO-$, $-SO_2-$, $-OCO-$, $-NR^{21}CO-$, $-CONR^{22}-$, $-SO_2 NR^{23}-$, $-NR^{24}SO_2-$ or $-NR^{25}-$, wherein $R^{21}$, $R^{22}$, $R^{23}$, $R^{24}$ and $R^{25}$ each independently represents hydrogen, $C_{1-3}$alkyl or $C_{1-3}$alkoxy$C_{2-3}$alkyl and $R^{20}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy;

4') $C_{1-5}$alkyl$X^4 C_{1-5}$alkyl$X^5 R^{26}$ wherein $X^4$ and $X^5$ which may be the same or different are each $-O-$, $-S-$, $-SO-$, $-SO_2-$, $-NR^{27}CO-$, $-CONR^{28}-$, $-SO_2 NR^{29}-$, $-NR^{30}SO_2-$ or $-NR^{31}-$, wherein $R^{27}$, $R^{28}$, $R^{29}$, $R^{30}$ and $R^{31}$ each independently represents hydrogen, $C_{1-3}$alkyl or $C_{1-3}$alkoxy$C_{2-3}$alkyl and $R^{26}$ represents hydrogen or $C_{1-3}$alkyl;

5') $R^{32}$ wherein $R^{32}$ is a 5–6-membered saturated heterocyclic group, linked via carbon or nitrogen, with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy and $C_{1-4}$alkylsulphonyl$C_{1-4}$alkyl;

6') $C_{1-5}$alkyl$R^{32}$ wherein $R^{32}$ is as defined in (5') above;

7') $C_{2-5}$alkenyl$R^{32}$ wherein $R^{32}$ is as defined in (5') above;

8') $C_{2-5}$alkynyl$R^{32}$ wherein $R^{32}$ is as defined in (5') above;

9') $R^{33}$ wherein $R^{33}$ represents a pyridone group, a phenyl group or a 5–6-membered aromatic heterocyclic group, linked via carbon or nitrogen, with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, $-CONR^{38}R^{39}$ and $-NR^{40}COR^{41}$, wherein $R^{38}$, $R^{39}$, $R^{40}$ and $R^{41}$, which may be the same or different, each represents hydrogen, $C_{1-4}$alkyl or $C_{1-3}$alkoxy$C_{2-3}$alkyl;

10') $C_{1-5}$alkyl$R^{33}$ wherein $R^{33}$ is as defined in (9') above;

11') $C_{2-5}$alkenyl$R^{33}$ wherein $R^{33}$ is as defined in (9') above;

12') $C_{2-5}$alkynyl$R^{33}$ wherein $R^{33}$ is as defined in (9') above;

13') $C_{1-5}$alkyl$X^6 R^{33}$ wherein $X^6$ represents $-O-$, $-S-$, $-SO-$, $-SO_2-$, $-NR^{38'}CO-$, $-CONR^{39'}-$, $-SO_2 NR^{40'}-$, $-NR^{41'}SO_2-$ or $-NR^{42'}-$, wherein $R^{38'}$, $R^{39'}$, $R^{40'}$, $R^{41'}$ and $R^{42'}$ each independently represents hydrogen, $C_{1-3}$alkyl or $C_{1-3}$alkoxy$C_{2-3}$alkyl, and $R^{33}$ is as defined hereinbefore;

14') $C_{2-5}$alkenyl$X^7 R^{33}$ wherein $X^7$ represents $-O-$, $-S-$, $-SO-$, $-SO_2-$, $-NR^{43}CO-$, $-CONR^{44}-$, $-SO_2 NR^{45}-$, $-NR^{46}SO_2-$ or $-NR^{47}-$, wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl, and $R^{33}$ is as defined hereinbefore;

15') $C_{2-5}$alkynyl$X^8 R^{33}$ wherein $X^8$ represents $-O-$, $-S-$, $-SO-$, $-SO_2-$, $-NR^{48}CO-$, $-C(O)NR^{49}-$, $-SO_2 NR^{50}-$, $-NR^{51}SO_2-$ or $-NR^{52}-$, wherein $R^{48}$, $R^{49}$, $R^{50}$, $R^{51}$ and $R^{52}$ each independently represents hydrogen, $C_{1-3}$alkyl or $C_{1-3}$alkoxy$C_{2-3}$alkyl, and $R^{33}$ is as defined hereinbefore;

16') $C_{1-3}$alkyl$X^9 C_{1-3}$alkyl$R^{33}$ wherein $X^9$ represents $-O-$, $-S-$, $-SO-$, $-SO_2-$, $-NR^{53}CO-$, $-C(O)NR^{54}-$, $-SO_2 NR^{55}-$, $-NR^{56}SO_2-$ or $-NR^{57}-$, wherein $R^{53}$, $R^{54}$, $R^{55}$, $R^{56}$ and $R^{57}$ each independently represents hydrogen, $C_{1-3}$alkyl or $C_{1-3}$alkoxy$C_{2-3}$alkyl, and $R^{33}$ is as defined hereinbefore; and 17') $C_{1-3}$alkyl$X^9 C_{1-3}$alkyl$R^{32}$ wherein $X^9$ and $R^{32}$ are as defined in (5') above, provided that at least one of $R^2$ or $R^3$ is other than hydrogen.

3. A compound according to claim 1, where $R^1$ is hydrogen and $R^4$ is hydrogen, halo, $C_{1-4}$alkyl or $C_{1-4}$alkoxy.

4. A compound according to claim 1 or claim 3 wherein $R^3$ is a group $X^1 R^9$ where $X^1$ is oxygen.

5. A compound according to claim 3 wherein $R^9$ is selected from a group (1), (3), (6) or (10).

6. A compound according to claim 5 wherein X is NH or O.

7. A compound according to claim 6 wherein $R^5$ is a group of formula (iii).

8. A compound according to claim 6 wherein $R^{80}$ is a group of sub formula (II) which is a group of formula (IIA)

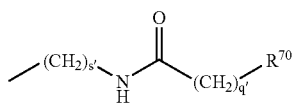
(IIA)

where q' is 0, 1, 2, 3 or 4;
s' is 0 or 1;
$R^{70}$ is $C_{3-7}$cycloalkyl,
or $R^{70}$ is of the Formula (III):

—K—J (III)

wherein J is aryl, heteroaryl or heterocyclyl and K is a bond, oxy, imino, N-($C_{1-6}$alkyl)imino, oxy$C_{1-6}$alkylene, imino$C_{1-6}$alkylene, N-($C_{1-6}$alkyl)imino$C_{1-6}$alkylene, —NHC(O)—, —SO$_2$NH—, —NHSO$_2$— or —NHC(O)—$C_{1-6}$alkylene-,
and any aryl, heteroaryl or heterocyclyl group in a $R^{70}$ group is optionally substituted by one or more groups selected from hydroxy, oxo, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)—O—, $C_{1-6}$alkylS(O)$_n$— wherein n is 0–2, N-$C_{1-6}$alkylamino, N,N-($C_{1-6}$ alkyl)$_2$amino, $C_{1-6}$alkoxycarbonyl, N-$C_{1-6}$ alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N-$C_{1-6}$alkylsulphamoyl, N,N-($C_{1-6}$alkyl)$_2$sulphamoyl, $C_{1-6}$alkylsulphonylamino and $C_{1-6}$alkylsulphonyl-N-($C_{1-6}$alkyl)amino,
or any aryl, heteroaryl or heterocyclyl group in a $R^{70}$ group is optionally substituted with one or more groups of the Formula (IV):

—B$^1$—(CH$_2$)$_p$—A$^1$ (IV)

wherein A$^1$ is halo, hydroxy, $C_{1-6}$alkoxy, cyano, amino, N-$C_{1-6}$alkylamino, N,N-($C_{1-6}$alkyl)$_2$amino, carboxy, $C_{1-6}$alkoxycarbonyl, carbamoyl, N-$C_{1-6}$alkylcarbamoyl or N,N-($C_{1-6}$alkyl)$_2$carbamoyl, p is 1–6, and B$^1$ is a bond, oxy, imino, N-($C_{1-6}$alkyl)imino or —NHC(O)—, with the proviso that p is 2 or more unless B$^1$ is a bond or —NHC(O)—;
or any aryl, heteroaryl or heterocyclyl group in a $R^{70}$ group is optionally substituted with one or more groups of the Formula (V):

—E$^1$—D$^1$ (V)

wherein D$^1$ is aryl, heteroaryl or heterocyclyl and E$^1$ is a bond, $C_{1-6}$alkylene, oxy$C_{1-6}$alkylene, oxy, imino, N-($C_{1-6}$alkyl)imino, imino$C_{1-6}$alkylene, N-($C_{1-6}$alkyl)-imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N-($C_{1-6}$ alkyl)-imino$C_{1-6}$alkylene, —NHC(O)—, —NHSO$_2$—, —SO$_2$NH— or —NHC(O)—$C_{1-6}$alkylene-, and any aryl, heteroaryl or heterocyclyl group in a $R^{70}$ group is optionally substituted with one or more groups selected from hydroxy, halo, $C_{1-6}$alkyl, $C_{1-6}$alkoxy, carboxy, $C_{1-6}$alkoxycarbonyl, carbamoyl, N-$C_{1-6}$alkylcarbamoyl, N-($C_{1-6}$alkyl)$_2$carbamoyl, $C_{2-6}$alkanoyl, amino, N-$C_{1-6}$alkylamino and N,N-($C_{1-6}$ alkyl)$_2$amino, and any $C_{3-7}$cycloalkyl or heterocyclyl group in a $R^{70}$ group is optionally substituted with one or two oxo or thioxo substituents, and any of the $R^{70}$ groups defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, $C_{1-6}$alkoxy, N-$C_{1-6}$alkylamino, N,N-($C_{1-6}$alkyl)$_2$amino and heterocyclyl;

or $R^{70}$ may be cycloalkenyl.

9. A compound according to claim 1 or claim 8 wherein $R^{80}$ includes a group $R^{70}$ and said group is phenyl optionally substituted by halo.

10. A compound according to claim 1 wherein both $R^1$ and $R^4$ are hydrogen.

11. A compound according to claim 5 wherein one of $R^2$ or $R^3$ is 3-morpholinopropoxy.

12. A method for preparing a compound of formula (I) as defined in claim 1, which method comprises reacting a compound of formula (VII)

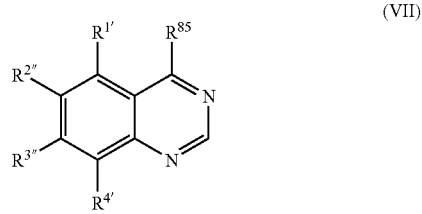
(VII)

where $R^{1'}$, $R^{2''}$, $R^{3'''}$, and $R^{4'}$ are equivalent to a group $R^1$, $R^2$, $R^3$ and $R^4$ as defined in relation to formula (I), and $R^{85}$ is a leaving group, with a compound of formula (VIII)

H—X—R$^5$ (VIII)

where X and R$^5$ are as defined in relation to formula (I).

13. A pharmaceutical composition comprising a compound according to any one of claims 1, 3, 5, 7, 8 or 11 or salt thereof, in combination with a pharmaceutically acceptable carrier.

14. A method for treating colorectal or breast cancer in a warm blooded animal, such as man, in need of such treatment, which comprises administering to said animal an effective amount of a compound according to claim 1, or salt thereof.

* * * * *